US006180383B1

(12) United States Patent
Grieve et al.

(10) Patent No.: US 6,180,383 B1
(45) Date of Patent: *Jan. 30, 2001

(54) FLEA LEUCINE AMINOPEPTIDASE PROTEINS AND USES THEREOF

(75) Inventors: Robert B. Grieve, Windsor; Keith E. Rushlow; Shirley Wu Hunter, both of Ft. Collins; Glenn R. Frank, Wellington; Gary L. Stiegler, Ft. Collins, all of CO (US)

(73) Assignee: Heska Corporation, Ft. Collins, CO (US)

( * ) Notice: Under 35 U.S.C. 154(b), the term of this patent shall be extended for 0 days.

This patent is subject to a terminal disclaimer.

(21) Appl. No.: 09/012,431

(22) Filed: Jan. 23, 1998

Related U.S. Application Data

(63) Continuation of application No. 08/639,075, filed on Apr. 24, 1996, which is a continuation-in-part of application No. 08/484,211, filed on Jun. 7, 1995, now Pat. No. 5,972,645, and a continuation-in-part of application No. 08/482,130, filed on Jun. 7, 1995, now Pat. No. 5,962,257, and a continuation-in-part of application No. 08/485,443, filed on Jun. 7, 1995, and a continuation-in-part of application No. 08/485,455, filed on Jun. 7, 1995, now Pat. No. 5,712,143, which is a continuation-in-part of application No. 08/326,773, filed on Oct. 18, 1994, now Pat. No. 5,766,609, which is a continuation-in-part of application No. 07/806,482, filed on Dec. 13, 1991, now Pat. No. 5,356,622, and a continuation-in-part of application No. PCT/US95/14442, filed on Oct. 18, 1995.

(51) Int. Cl.[7] .................................................... C12N 9/48
(52) U.S. Cl. ...................... 435/212; 435/219; 530/329; 530/350
(58) Field of Search .................................. 530/350, 329; 514/12; 435/212, 219

(56) References Cited

U.S. PATENT DOCUMENTS

| | | |
|---|---|---|
| 4,800,159 | 1/1989 | Mullis et al. . |
| 5,288,612 | 2/1994 | Griffin et al. . |
| 5,304,482 | 4/1994 | Sambrook et al. . |
| 5,356,622 | 10/1994 | Heatlh et al. . |
| 5,712,143 | * 1/1998 | Grieve et al. . |

FOREIGN PATENT DOCUMENTS

| | | |
|---|---|---|
| 0571911 | 12/1993 | (EP) . |
| WO 90/03433 | 9/1990 | (WO) . |
| WO 93/23542 | 11/1993 | (WO) . |

OTHER PUBLICATIONS

Azad et al., 1987, *Am. J. Trop. Med. Hyg.*, 37:629–635.
Billingsley, 1990 *Annu. Rev. Entomol.*, 35:219–248.
Borovsky et al., 1990 *FASEB J.*, 4:3015–3020.
Borovsky, 1988 *Arch. Insect Biochem. Physiol.*, 7:187–210.
Casu et al, 1994 *Insect. Mol. Biol.*, 3(4):201–211.
Casu et al., 1994 *Insect Mol. Biol.*, 3(3):159–170.
Chaikau, 1982 *Entomol. Obozor* 61(4):746–754.
Cherney et al., 1939 *Am J. Trop. Med.*, 19:327–332.
Chinzel et al., 1987 *Med. Vet. Entomol.*, 1:409–416.
Cuypers, et al., 1982, *J. Biol. Chem.*, 257(12):7077–7085.
Eldridge et al., 1993 *Seminars in Hemotology*, 30(4)(Supp.4):16–25.
Elvin et al., 1993 *Mol. Gen. Genet.*, 240:132–139.
Halliwell, 1973 *J. Immunol.*, 110:422–430.
Halliwell, et al., 1978 *J. Allerg. Clin. Immunol.*, 62:236–242.
Halliwell et al., 1985 *Vet. Immunol. Immunopathol.*, 8:215–223.
Hatfield, 1988 *Med. Vet. Entomol.*, 2:331–338.
Hatfield, 1988 *Med. Vet. Entomol.*, 2:339–345.
Houk et al., 1986 *Archives of Insect Biochemistry and Physiology*, 3:135–146.
Jany et al., 1983, *Biochem. & Biophys. Res. Comm.*, 110(1):1–7.
Johnson et al., 1986 *Int. J. Parasitol.*, 16(1):27–34.
Kalhok et al., 1993 *Insect Mol. Biol.*, 2(2):71–79.
Kay et al., 1994 *Am. J. Trop. Med. Hyg.*, 50(6) Suppl.:87–96.
Kemp et al., 1986 *Internat. J. Parasitol.*, 16, 155–120.
Kwochka, 1987 *Vet. Clin. North Am.*, 17:1235–1262.
Law et al., 1992 *Annu. Rev. Biochem.*, 61:87–111.
Matsushima, et al., 1991, *Biochem. & Biophys. Res. Comm.*, 178(3):1459–1464.
McFarlane, 1985 *Fundamentals of Insect Physiology*, 59–89.
Muller et al., 1993 *EMBO J.*, 12(7):2891–2900.
Nesbitt et al., 1978 *J. Am. Vet. Med. Assoc.*, 173:282–288.
Opdebeeck et al., 1988 *Immunol.*, 63:363–367.
Opdebeeck et al., 1988 *Parasite Immunol.*, 10:405–410.
Opdebeeck et al., 1989 *Immunol.*, 67:388.
Otieno et al., 1984 *Insect Sci. Applic.*, 5(4):297–302.
Ramos et al., 1993 *Insect Mol. Biol.*, 1(3):149–163.
Rand et al., 1989 *Proc. Natl. Acad. Sci. (USA)*, 86:9657–9661.
Reeves et al. 1993 *Insect Biochem. & Mol. Biol.* 23(7):809–14.
Ribiero, 1987 *Ann. Rev. Entomol.*, 32:463–478.
Roitt et al., 1985, *Immunology*, pp. 5.4–5.5.
Sandeman et al., 1990 *Int. J. Parasitol.*, 20(8):1019–1023.
Sarkar et al., 1990, *Genomics*, 6(1):133–143.

(List continued on next page.)

Primary Examiner—Marianne P. Allen
(74) Attorney, Agent, or Firm—Sheridan Ross, P.C.

(57) ABSTRACT

The present invention relates to flea serine protease proteins, aminopeptidase proteins and flea cysteine protease proteins; to flea serine protease, aminopeptidase and cysteine protease nucleic acid molecules, including those that encode such proteins; to antibodies raised against such proteins; and to compounds that inhibit flea serine protease, aminopeptidase and/or cysteine protease activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

5 Claims, 12 Drawing Sheets

OTHER PUBLICATIONS

Schedrin et al. 1978 *Med. Parazitol. Parazit Bolezni* 47(1):89–91.
Schein et al., 1976 *Physiolog. Entomol.*, 1:55–59.
Soulsby, 1982, *Helminths, Arthopods and Protozoa of Domesticated Animals*, 7th ed., 378–384.
Vaughn et al., 1988 *J. Med. Entomol.*, 25:472–474.
Wikel, 1984 *Vet. Parasitol.*, 14:321–329.
Wikel, 1988 *Vet. Parasitol.*, 29:235–264.
Willadsen et al., 1989 *J. Immunol.*, 143:1346–1351.
Wong et al., 1989 *Immunol.*, 66:149–155.
Young et al., 1963 *Exp. Parasitol*, 13:155–166.
Zwilling et al., 1975, *Febs Letters*, 60(2):247–249.

* cited by examiner

```
                              SEQUENCE LISTING (1) GENERAL INFORMATION:

(iii) NUMBER OF SEQUENCES: 190

(2) INFORMATION FOR SEQ ID NO: 1:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 1:

Ile Ile Gly Gly Glu Val Ala Gly Glu Gly Ser Ala Pro Tyr Gln Va
1               5                   10                  15

Ser Leu Arg Thr Lys Glu Gly Asn His Phe Ser Gly Gly Ser Ile Le
            20                  25                  30

(2) INFORMATION FOR SEQ ID NO: 2:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 2:

Xaa Val Gly Gly His Asp Thr Ser Ile Asp Xaa His Pro His Gln Va
1               5                   10                  15

Thr (2) INFORMATION FOR SEQ ID NO: 3:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 3:

Ile Val Gly Gly Ala Asp Ala Ala Pro Gly Asn Ala Pro Phe Gln Va
1               5                   10                  15

Ser Leu Arg Asp Lys Gly
            20
```

```
(2) INFORMATION FOR SEQ ID NO: 4:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 4:

Ile Val Gly Gly Gln Asp Ala Asp Ile Ala Lys Tyr Gly Tyr Gln Al
1               5                   10                  15

Ser Leu Gln Val Phe Asn Glu His Phe Xaa Gly Ala Xaa Ile Leu As
            20                  25                  30

Asn Tyr (2) INFORMATION FOR SEQ ID NO: 5:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 5:

Ile Val Gly Gly Thr Asp Val Asn Ile Glu Asn Phe Gly Trp Gln Va
1               5                   10                  15

Ser Leu Phe Asp Arg Asn Gly His Phe
            20                  25

(2) INFORMATION FOR SEQ ID NO: 6:

(i) SEQUENCE CHARACTERISTICS:
        (A) LENGTH: 22 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 6:

Ile Val Gly Gly His Asp Thr Ser Ile Asp Lys His Pro Phe Gln Va
1               5                   10                  15

Ser Leu Ile Asp Lys Asn
            20

(2) INFORMATION FOR SEQ ID NO: 7:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 7:

Val Val Gly Gly Leu Glu Ala Ala Glu Gly Ser Ala Pro Tyr Gln Va
1               5                   10                  15

Xaa Leu Gln Trp Gly Asn Phe
            20
```

(2) INFORMATION FOR SEQ ID NO: 8:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 8:

Ile Val Gly Gly Glu Asp Ala Glu Leu Gly Glu Xaa Pro Thr Gln
1               5                   10                  15

(2) INFORMATION FOR SEQ ID NO: 9:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 9:

Asp Glu Asp Gly Lys Asp Asp Ser Ala Pro Gly Glu Ile
1               5                   10

(2) INFORMATION FOR SEQ ID NO: 10:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: protein (ix) FEATURE:
        (A) NAME/KEY: Protein
        (B) LOCATION: 1..9
        (D) OTHER INFORMATION: /note= "At pos. aa 2, Xaa = Gln or
            Asn"

(xi) SEQUENCE DESCRIPTION: SEQ ID NO: 10:

Cys Xaa Gly Asp Ser Gly Gly Pro Leu
1               5

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 11:

TAAWGGWCCW CCYGAATCTC CCTGGCA                                              27

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear

```
    (ii) MOLECULE TYPE: other nucleic acid
        (A) DESCRIPTION: /desc = "primer"

(xi) SEQUENCE DESCRIPTION: SEQ ID NO: 12:

TAAWGGWCCA GARTCTCCTT GACA                                              24

(2) INFORMATION FOR SEQ ID NO: 13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 13:

GGAAACAGCT ATGACCATG                                                    19

(2) INFORMATION FOR SEQ ID NO: 14:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 14:

ATTAACCCTC ACTAAAG                                                      17

(2) INFORMATION FOR SEQ ID NO: 15:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "probe"

(xi) SEQUENCE DESCRIPTION: SEQ ID NO: 15:

TGGGTWGTWA CWGCWGCWCA TTG                                               23

(2) INFORMATION FOR SEQ ID NO: 16:

(i) SEQUENCE CHARACTERISTICS:
        (A) LENGTH: 672 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..672
        (D) OTHER INFORMATION: /note= "At pos. aa 224, substitute
            Xaa."

(xi) SEQUENCE DESCRIPTION: SEQ ID NO: 16:

GCA CGA GAT CGC ATT GTT GGA GGA TTG GAG GCG AAA AAT GGA TCA GCC         48
Ala Arg Asp Arg Ile Val Gly Gly Leu Glu Ala Lys Asn Gly Ser Ala
 1               5                  10                  15
```

```
CCA TTC ATG GTT TCT TTG CAA GCG GAA GAC TAT TTT CAT TTT TGT GGA      96
Pro Phe Met Val Ser Leu Gln Ala Glu Asp Tyr Phe His Phe Cys Gly
             20                  25                  30

TCC TCT ATT CTG AAT GAG AGA TGG GTT CTT ACT GCT GCT CAC TGT ATC     144
Ser Ser Ile Leu Asn Glu Arg Trp Val Leu Thr Ala Ala His Cys Ile
         35                  40                  45

CAA CCA AAT GTA CAC AAG TAC GTT TAC GTC GGT TCG AAC AAC GTA GAA     192
Gln Pro Asn Val His Lys Tyr Val Tyr Val Gly Ser Asn Asn Val Glu
 50                  55                  60

GTA GGC GGA ACA CAC TAC GAA ATC GAA AAA GCT TTC TAT CAC GAA GAA     240
Val Gly Gly Thr His Tyr Glu Ile Glu Lys Ala Phe Tyr His Glu Glu
 65                  70                  75                  80

TAT GAT GGA GTA GAT CTT GTA GAT CAT GAT GTG ATT GAT CAA AGT GAG     288
Tyr Asp Gly Val Asp Leu Val Asp His Asp Val Ile Asp Gln Ser Glu
             85                  90                  95

ACA AAC ATT GAT TTA ATG AAG TGT CAA CCC ATT AAA TTA CGA AGA AAG     336
Thr Asn Ile Asp Leu Met Lys Cys Gln Pro Ile Lys Leu Arg Arg Lys
            100                 105                 110

CCA CTC GTT GGT GGT GAG GAA TTG AGA GCA GTA GGC TGG GGA AAT ACA     384
Pro Leu Val Gly Gly Glu Glu Leu Arg Ala Val Gly Trp Gly Asn Thr
        115                 120                 125

AAT TCA GCA GGG GAA AAT TTT CCA TTG AAA CTT CAA GAA TTG TAC GTG     432
Asn Ser Ala Gly Glu Asn Phe Pro Leu Lys Leu Gln Glu Leu Tyr Val
130                 135                 140

AAA GCT TTG ACT AAT GAG GAG TGC AAA GCT AAA TCA CCA ATT CCA CCA     480
Lys Ala Leu Thr Asn Glu Glu Cys Lys Ala Lys Ser Pro Ile Pro Pro
145                 150                 155                 160

ACG ACC CAA GTC TGC ACA CTT TTG GAA AAG AAT CAT GGT GTA TGC TCG     528
Thr Thr Gln Val Cys Thr Leu Leu Glu Lys Asn His Gly Val Cys Ser
                165                 170                 175

GGA GAT TCT GGT GGT CCA TTG CTT TTG GAT GGC GAG CAA GTT GGC ATT     576
Gly Asp Ser Gly Gly Pro Leu Leu Leu Asp Gly Glu Gln Val Gly Ile
            180                 185                 190

GCC TCA TTT GTT ATC TTC AAA TGC GCA ATG GGG TAC CCT GAC TAT TTC     624
Ala Ser Phe Val Ile Phe Lys Cys Ala Met Gly Tyr Pro Asp Tyr Phe
        195                 200                 205

ACA AGA TTG TCT CTA TAT GTA GAT TGG ATT GAA CAA CAC ATG GAT TAA     672
Thr Arg Leu Ser Leu Tyr Val Asp Trp Ile Glu Gln His Met Asp Xaa
    210                 215                 220
```

(2) INFORMATION FOR SEQ ID NO: 17:

(i) SEQUENCE CHARACTERISTICS:
        (A) LENGTH: 224 amino acids
        (B) TYPE: amino acid
        (D) TOPOLOGY: linear (ii) MOLECULE TYPE: protein (xi) SEQUENCE DESCRIPTION: SEQ ID NO: 17:

```
Ala Arg Asp Arg Ile Val Gly Gly Leu Glu Ala Lys Asn Gly Ser Ala
 1               5                  10                  15

Pro Phe Met Val Ser Leu Gln Ala Glu Asp Tyr Phe His Phe Cys Gly
             20                  25                  30

Ser Ser Ile Leu Asn Glu Arg Trp Val Leu Thr Ala Ala His Cys Ile
         35                  40                  45

Gln Pro Asn Val His Lys Tyr Val Tyr Val Gly Ser Asn Asn Val Glu
 50                  55                  60

Val Gly Gly Thr His Tyr Glu Ile Glu Lys Ala Phe Tyr His Glu Glu
 65                  70                  75                  80
```

```
Tyr Asp Gly Val Asp Leu Val Asp His Asp Val Ile Asp Gln Ser Glu
                85                  90                  95

Thr Asn Ile Asp Leu Met Lys Cys Gln Pro Ile Lys Leu Arg Arg Lys
            100                 105                 110

Pro Leu Val Gly Gly Glu Glu Leu Arg Ala Val Gly Trp Gly Asn Thr
            115                 120                 125

Asn Ser Ala Gly Glu Asn Phe Pro Leu Lys Leu Gln Glu Leu Tyr Val
130                 135                 140

Lys Ala Leu Thr Asn Glu Glu Cys Lys Ala Lys Ser Pro Ile Pro Pro
145                 150                 155                 160

Thr Thr Gln Val Cys Thr Leu Leu Glu Lys Asn His Gly Val Cys Ser
            165                 170                 175

Gly Asp Ser Gly Gly Pro Leu Leu Leu Asp Gly Glu Gln Val Gly Ile
            180                 185                 190

Ala Ser Phe Val Ile Phe Lys Cys Ala Met Gly Tyr Pro Asp Tyr Phe
            195                 200                 205

Thr Arg Leu Ser Leu Tyr Val Asp Trp Ile Glu Gln His Met Asp Xaa
            210                 215                 220

(2) INFORMATION FOR SEQ ID NO: 18:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

(xi) SEQUENCE DESCRIPTION: SEQ ID NO: 18:

GGG TGG GGA AGA CTT GGA GCT AAC TTG AAT GGA CCG AAT GAA CTC CAA       48
Gly Trp Gly Arg Leu Gly Ala Asn Leu Asn Gly Pro Asn Glu Leu Gln
 1               5                  10                  15

GAA CTT AAC ACT GTC ACA TTA AGC CAC CAG CAA TGT GTA AGA CAA CAA       96
Glu Leu Asn Thr Val Thr Leu Ser His Gln Gln Cys Val Arg Gln Gln
            20                  25                  30

ATT TAT CCA GTA TAC GAC AGC CAA CTT TGC ACA TTT GTT GGC AGT GGA      144
Ile Tyr Pro Val Tyr Asp Ser Gln Leu Cys Thr Phe Val Gly Ser Gly
            35                  40                  45

CGA GGC GCC TGC                                                      156
Arg Gly Ala Cys
    50

(2) INFORMATION FOR SEQ ID NO: 19:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 19:

Gly Trp Gly Arg Leu Gly Ala Asn Leu Asn Gly Pro Asn Glu Leu Gln
 1               5                  10                  15

Glu Leu Asn Thr Val Thr Leu Ser His Gln Gln Cys Val Arg Gln Gln
            20                  25                  30
```

```
Ile Tyr Pro Val Tyr Asp Ser Gln Leu Cys Thr Phe Val Gly Ser Gly
        35                  40                  45

Arg Gly Ala Cys
        50
```

(2) INFORMATION FOR SEQ ID NO: 20:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO: 20:

```
GGA TGG GGC AAA TTA AGT GAA TCA GGA CCC AAG CCA GTA AAT CTA CAA     48
Gly Trp Gly Lys Leu Ser Glu Ser Gly Pro Lys Pro Val Asn Leu Gln
 1               5                  10                  15

GGA GTA AAA GTG CCT TAT GTG ACC AAG ATA CAT GCT CTG ACA GCT ACG     96
Gly Val Lys Val Pro Tyr Val Thr Lys Ile His Ala Leu Thr Ala Thr
             20                  25                  30

TCT TTG CAG GTA AAA GAT ATC ACC GAA AAC ATG TTG TGT GCC GGA GTT    144
Ser Leu Gln Val Lys Asp Ile Thr Glu Asn Met Leu Cys Ala Gly Val
         35                  40                  45

AGA AGA GGT GGC AAG GAC TCC TGC                                    168
Arg Arg Gly Gly Lys Asp Ser Cys
     50                  55
```

(2) INFORMATION FOR SEQ ID NO: 21:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 21:

```
Gly Trp Gly Lys Leu Ser Glu Ser Gly Pro Lys Pro Val Asn Leu Gln
 1               5                  10                  15

Gly Val Lys Val Pro Tyr Val Thr Lys Ile His Ala Leu Thr Ala Thr
             20                  25                  30

Ser Leu Gln Val Lys Asp Ile Thr Glu Asn Met Leu Cys Ala Gly Val
         35                  40                  45

Arg Arg Gly Gly Lys Asp Ser Cys
     50                  55
```

(2) INFORMATION FOR SEQ ID NO: 22:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO: 22:

```
GGA TGG GGA TCA AGA TCT ACT TCC AAT TTC CCA TCT TAC CCC AAC CTT         48
Gly Trp Gly Ser Arg Ser Thr Ser Asn Phe Pro Ser Tyr Pro Asn Leu
 1               5                  10                  15

TTA CAG ACC GTT GAC AAA CCA ATT GTA TCT TAT GCC GAA TGT GAG AAA         96
Leu Gln Thr Val Asp Lys Pro Ile Val Ser Tyr Ala Glu Cys Glu Lys
                20                  25                  30

GTA TTG GGA GGT CCT GGA GCC TCA CCA CTT CAC CCC TTG AAC CTC TGC        144
Val Leu Gly Gly Pro Gly Ala Ser Pro Leu His Pro Leu Asn Leu Cys
             35                  40                  45

ACT GGA CCC TTG ACC GGT GGA GTA AGC GCT TGT                            177
Thr Gly Pro Leu Thr Gly Gly Val Ser Ala Cys
         50                  55
```

(2) INFORMATION FOR SEQ ID NO: 23:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 23:

```
Gly Trp Gly Ser Arg Ser Thr Ser Asn Phe Pro Ser Tyr Pro Asn Leu
 1               5                  10                  15

Leu Gln Thr Val Asp Lys Pro Ile Val Ser Tyr Ala Glu Cys Glu Lys
                20                  25                  30

Val Leu Gly Gly Pro Gly Ala Ser Pro Leu His Pro Leu Asn Leu Cys
             35                  40                  45

Thr Gly Pro Leu Thr Gly Gly Val Ser Ala Cys
         50                  55
```

(2) INFORMATION FOR SEQ ID NO: 24:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

(xi) SEQUENCE DESCRIPTION: SEQ ID NO: 24:

```
GGC TGG GGA AAT ACA AAT TCA GCA GGG GAA AAT TTT CCA TTG AAA CTT         48
Gly Trp Gly Asn Thr Asn Ser Ala Gly Glu Asn Phe Pro Leu Lys Leu
 1               5                  10                  15

CAA GAA TTG TAC GTG AAA GCT TTG ACT AAT GAG GAG TGC AAA GCT AAA         96
Gln Glu Leu Tyr Val Lys Ala Leu Thr Asn Glu Glu Cys Lys Ala Lys
                20                  25                  30

TCA CCA ATT CCA CCA ACG ACC CAA GTC TGC ACA CTT TTG GAA AAG AAT        144
Ser Pro Ile Pro Pro Thr Thr Gln Val Cys Thr Leu Leu Glu Lys Asn
             35                  40                  45

CAT GGT GTA TGC                                                        156
His Gly Val Cys
         50
```

```
(2) INFORMATION FOR SEQ ID NO: 25:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 25:

Gly Trp Gly Asn Thr Asn Ser Ala Gly Glu Asn Phe Pro Leu Lys Leu
 1               5                  10                  15

Gln Glu Leu Tyr Val Lys Ala Leu Thr Asn Glu Glu Cys Lys Ala Lys
            20                  25                  30

Ser Pro Ile Pro Pro Thr Thr Gln Val Cys Thr Leu Leu Glu Lys Asn
        35                  40                  45

His Gly Val Cys
    50

(2) INFORMATION FOR SEQ ID NO: 26:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 26:

GGA TGG GGA TCA ACT GGA TCT GGT GGT CCA ATT ACA AAT GTT CTA CAA       48
Gly Trp Gly Ser Thr Gly Ser Gly Gly Pro Ile Thr Asn Val Leu Gln
 1               5                  10                  15

GAA GTC GAA GTT CCA TTT ATC GAC TTC AAC ACC TGC CGA AAA TCC TAC       96
Glu Val Glu Val Pro Phe Ile Asp Phe Asn Thr Cys Arg Lys Ser Tyr
            20                  25                  30

TCA ACC AGC TTA ACC GAC CGT ATG TTC TGC GCT GGA TTT TTG GGA ATT      144
Ser Thr Ser Leu Thr Asp Arg Met Phe Cys Ala Gly Phe Leu Gly Ile
        35                  40                  45

GGT GGT AAG GCT TGC                                                  159
Gly Gly Lys Ala Cys
    50

(2) INFORMATION FOR SEQ ID NO: 27:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 27:

Gly Trp Gly Ser Thr Gly Ser Gly Gly Pro Ile Thr Asn Val Leu Gln
 1               5                  10                  15

Glu Val Glu Val Pro Phe Ile Asp Phe Asn Thr Cys Arg Lys Ser Tyr
            20                  25                  30

Ser Thr Ser Leu Thr Asp Arg Met Phe Cys Ala Gly Phe Leu Gly Ile
        35                  40                  45

Gly Gly Lys Ala Cys
    50
```

(2) INFORMATION FOR SEQ ID NO: 28:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO: 28:

```
GGC TGG GGA AAT TTA GGG GAA GAT GAG GAC GAC CCC GAA CAA CTG CAA      48
Gly Trp Gly Asn Leu Gly Glu Asp Glu Asp Asp Pro Glu Gln Leu Gln
 1               5                  10                  15

TAT GTA AAG GTA CCT ATT GTT AAC TGG ACT CAG TGC AAA ACT ATA TAT      96
Tyr Val Lys Val Pro Ile Val Asn Trp Thr Gln Cys Lys Thr Ile Tyr
                20                  25                  30

GGA AAT GAA GGA CTA ATA ATT ACC CAA AAT ATG ATT TGT GCT GGT TAT     144
Gly Asn Glu Gly Leu Ile Ile Thr Gln Asn Met Ile Cys Ala Gly Tyr
            35                  40                  45

CCT GAT GGC GGT AAG GAC TCT TGC                                     168
Pro Asp Gly Gly Lys Asp Ser Cys
    50                  55
```

(2) INFORMATION FOR SEQ ID NO: 29:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 29:

```
Gly Trp Gly Asn Leu Gly Glu Asp Glu Asp Asp Pro Glu Gln Leu Gln
 1               5                  10                  15

Tyr Val Lys Val Pro Ile Val Asn Trp Thr Gln Cys Lys Thr Ile Tyr
                20                  25                  30

Gly Asn Glu Gly Leu Ile Ile Thr Gln Asn Met Ile Cys Ala Gly Tyr
            35                  40                  45

Pro Asp Gly Gly Lys Asp Ser Cys
    50                  55
```

(2) INFORMATION FOR SEQ ID NO: 30:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..159

(xi) SEQUENCE DESCRIPTION: SEQ ID NO: 30:

```
GGA TGG GCA TCT CCA AAG ATT TCC CCT GCT TTC GAA TTG CCT GAC AAA      48
Gly Trp Ala Ser Pro Lys Ile Ser Pro Ala Phe Glu Leu Pro Asp Lys
 1               5                  10                  15
```

-continued

```
CTA CAG TAC ACA ACT TTG GAA GTC CAA CCA AGT GAA GAC TGC AAA AAA        96
Leu Gln Tyr Thr Thr Leu Glu Val Gln Pro Ser Glu Asp Cys Lys Lys
            20                  25                  30

GTA TGG GCC CCT TAC ATG CGC GAC TAC ATC CTT TGT GCC AAA TTT GAA        144
Val Trp Ala Pro Tyr Met Arg Asp Tyr Ile Leu Cys Ala Lys Phe Glu
        35                  40                  45

AAA CAA AAC ATT TGC                                                    159
Lys Gln Asn Ile Cys
    50
```

(2) INFORMATION FOR SEQ ID NO: 31:

(i) SEQUENCE CHARACTERISTICS:
        (A) LENGTH: 53 amino acids
        (B) TYPE: amino acid
        (D) TOPOLOGY: linear (ii) MOLECULE TYPE: protein (xi) SEQUENCE DESCRIPTION: SEQ ID NO: 31:

```
Gly Trp Ala Ser Pro Lys Ile Ser Pro Ala Phe Glu Leu Pro Asp Lys
 1               5                  10                  15

Leu Gln Tyr Thr Thr Leu Glu Val Gln Pro Ser Glu Asp Cys Lys Lys
            20                  25                  30

Val Trp Ala Pro Tyr Met Arg Asp Tyr Ile Leu Cys Ala Lys Phe Glu
        35                  40                  45

Lys Gln Asn Ile Cys
    50
```

(2) INFORMATION FOR SEQ ID NO: 32:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..186
        (D) OTHER INFORMATION: /note= "At pos. bp 86/87, change
            A/A to V/Y; at pos. aa 29, change Glu to Xaa and define
            Xaa = Val, Ala, Asp, Glu or Gly. "

(xi) SEQUENCE DESCRIPTION: SEQ ID NO: 32:

```
GGT TGG GGA AAG ATA GAC TAT TCT GAG AGC AGA AGT GAT GAC CTA CTG        48
Gly Trp Gly Lys Ile Asp Tyr Ser Glu Ser Arg Ser Asp Asp Leu Leu
 1               5                  10                  15

AAA GTA GTA CTG AAA ATT ATT GAT AAT AGG CAA TGC GVY CCC TTA TAC        96
Lys Val Val Leu Lys Ile Ile Asp Asn Arg Gln Cys Xaa Pro Leu Tyr
            20                  25                  30

GTT GAT CAG ATT AAT AGA AGA AGA TTG AGA AAT GGA ATT GTA GAA ACA        144
Val Asp Gln Ile Asn Arg Arg Arg Leu Arg Asn Gly Ile Val Glu Thr
        35                  40                  45

CAG ATG TGT GCA GGA GAA TTG GAT GGT GGA AAA GAC ACT TGC                186
Gln Met Cys Ala Gly Glu Leu Asp Gly Gly Lys Asp Thr Cys
    50                  55                  60
```

(2) INFORMATION FOR SEQ ID NO: 33:

(i) SEQUENCE CHARACTERISTICS:
        (A) LENGTH: 62 amino acids
        (B) TYPE: amino acid
        (D) TOPOLOGY: linear

```
    (ii) MOLECULE TYPE: protein (ix) FEATURE:
         (A) NAME/KEY: Xaa = Val, Ala, Asp Glu or Gly
         (B) LOCATION: 29

(xi) SEQUENCE DESCRIPTION: SEQ ID NO: 33:

Gly Trp Gly Lys Ile Asp Tyr Ser Glu Ser Arg Ser Asp Asp Leu Leu
1               5                   10                  15

Lys Val Val Leu Lys Ile Ile Asp Asn Arg Gln Cys Xaa Pro Leu Tyr
                20                  25                  30

Val Asp Gln Ile Asn Arg Arg Arg Leu Arg Asn Gly Ile Val Glu Thr
            35                  40                  45

Gln Met Cys Ala Gly Glu Leu Asp Gly Gly Lys Asp Thr Cys
        50                  55                  60

(2) INFORMATION FOR SEQ ID NO: 34:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 1..168

(xi) SEQUENCE DESCRIPTION: SEQ ID NO: 34:

GGA TGG GGA AGA ACA TCG TTC GGT GGC CAA TTG TCT AAA AAT CTG CGA        48
Gly Trp Gly Arg Thr Ser Phe Gly Gly Gln Leu Ser Lys Asn Leu Arg
1               5                   10                  15

GGA GTC GAG TTG GAA ATA ATA GAT CTA TTC GAT TGT TTC CTT TCC TAC        96
Gly Val Glu Leu Glu Ile Ile Asp Leu Phe Asp Cys Phe Leu Ser Tyr
                20                  25                  30

ATG GAT AAA GTA AAC GTG TCC GAA AGG CAA GTT TGC GCT GGA ATC CCC       144
Met Asp Lys Val Asn Val Ser Glu Arg Gln Val Cys Ala Gly Ile Pro
            35                  40                  45

GTT GTA GGT GGT AAA GAT TCT TGC                                       168
Val Val Gly Gly Lys Asp Ser Cys
        50                  55

(2) INFORMATION FOR SEQ ID NO: 35:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 35:

Gly Trp Gly Arg Thr Ser Phe Gly Gly Gln Leu Ser Lys Asn Leu Arg
1               5                   10                  15

Gly Val Glu Leu Glu Ile Ile Asp Leu Phe Asp Cys Phe Leu Ser Tyr
                20                  25                  30

Met Asp Lys Val Asn Val Ser Glu Arg Gln Val Cys Ala Gly Ile Pro
            35                  40                  45

Val Val Gly Gly Lys Asp Ser Cys
        50                  55
```

(2) INFORMATION FOR SEQ ID NO: 36:

(i) SEQUENCE CHARACTERISTICS:
        (A) LENGTH: 120 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..120

(xi) SEQUENCE DESCRIPTION: SEQ ID NO: 36:

```
GGA TGG GGT GCA GTC TAC GAA GGA GGT GCA GGA TCC ACC CAA TTA CTA      48
Gly Trp Gly Ala Val Tyr Glu Gly Gly Ala Gly Ser Thr Gln Leu Leu
 1               5                  10                  15

TAC TCC CAA TTT GGC GGT GTT GCT CCT AGC ATG ATC TGC GCT GGA TTT      96
Tyr Ser Gln Phe Gly Gly Val Ala Pro Ser Met Ile Cys Ala Gly Phe
                20                  25                  30

GAC CAA GGC GGT AAG GAC GCT TGT                                     120
Asp Gln Gly Gly Lys Asp Ala Cys
            35                  40
```

(2) INFORMATION FOR SEQ ID NO: 37:

(i) SEQUENCE CHARACTERISTICS:
        (A) LENGTH: 40 amino acids
        (B) TYPE: amino acid
        (D) TOPOLOGY: linear (ii) MOLECULE TYPE: protein (xi) SEQUENCE DESCRIPTION: SEQ ID NO: 37:

```
Gly Trp Gly Ala Val Tyr Glu Gly Gly Ala Gly Ser Thr Gln Leu Leu
 1               5                  10                  15

Tyr Ser Gln Phe Gly Gly Val Ala Pro Ser Met Ile Cys Ala Gly Phe
                20                  25                  30

Asp Gln Gly Gly Lys Asp Ala Cys
            35                  40
```

(2) INFORMATION FOR SEQ ID NO: 38:

(i) SEQUENCE CHARACTERISTICS:
        (A) LENGTH: 162 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..162

(xi) SEQUENCE DESCRIPTION: SEQ ID NO: 38:

```
GGT TGG GGA ACT ACA GAG AGT ACT GAA TCA TCA CAC CAC CTG AAA GAA      48
Gly Trp Gly Thr Thr Glu Ser Thr Glu Ser Ser His His Leu Lys Glu
 1               5                  10                  15

GTT GAA GTG AAC GCT GTA TCT AAT AGT GAA TGT CAA AGG CCT AAT GAA      96
Val Glu Val Asn Ala Val Ser Asn Ser Glu Cys Gln Arg Pro Asn Glu
                20                  25                  30

GAT CTT GCT ACT ATA TCA TCA CAT GAG ATA TGT GCA AGC GTT CCT GGT     144
Asp Leu Ala Thr Ile Ser Ser His Glu Ile Cys Ala Ser Val Pro Gly
            35                  40                  45
```

```
GGC GGC AAA GAT TCT TGT                                              162
Gly Gly Lys Asp Ser Cys
    50
```

(2) INFORMATION FOR SEQ ID NO: 39:

(i) SEQUENCE CHARACTERISTICS:
        (A) LENGTH: 54 amino acids
        (B) TYPE: amino acid
        (D) TOPOLOGY: linear (ii) MOLECULE TYPE: protein (xi) SEQUENCE DESCRIPTION: SEQ ID NO: 39:

```
Gly Trp Gly Thr Thr Glu Ser Thr Glu Ser Ser His His Leu Lys Glu
  1               5                  10                  15

Val Glu Val Asn Ala Val Ser Asn Ser Glu Cys Gln Arg Pro Asn Glu
                 20                  25                  30

Asp Leu Ala Thr Ile Ser Ser His Glu Ile Cys Ala Ser Val Pro Gly
             35                  40                  45

Gly Gly Lys Asp Ser Cys
    50
```

(2) INFORMATION FOR SEQ ID NO: 40:

(i) SEQUENCE CHARACTERISTICS:
        (A) LENGTH: 40 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 40:

```
Ile Val Gly Gly Glu Asn Ala Lys Glu Lys Ser Asp Val Pro Tyr Gl
  1               5                  10                  15

Val Ser Leu Arg Asn Ala Glu Asn Lys His Phe Cys Gly Gly Ala Il
                 20                  25                  30

Ile Asp Asp Tyr Trp Val Leu Thr
             35                  40
```

(2) INFORMATION FOR SEQ ID NO: 41:

(i) SEQUENCE CHARACTERISTICS:
        (A) LENGTH: 25 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 41:

```
Ile Val Gly Gly Leu Glu Ala Lys Asn Gly Ser Ala Pro Phe Met Va
  1               5                  10                  15

Ser Leu Gln Ala Glu Asp Tyr Phe His
                 20                  25
```

(2) INFORMATION FOR SEQ ID NO: 42:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 42:

Ile Ile Gly Gly Glu Val Ala Gly Glu Gly Ser Ala Pro Tyr Gln Va
1               5                   10                  15

Ser Leu Arg Thr Lys Glu Gly Asn His Phe
                20                  25

(2) INFORMATION FOR SEQ ID NO: 43:

(i) SEQUENCE CHARACTERISTICS:
        (A) LENGTH: 29 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 43:

Ile Val Gly Gly Thr Ala Val Asp Ile Arg Gly Phe Pro Gly Arg Ty
1               5                   10                  15

Gln Phe Lys Pro Lys Pro Ser Phe Leu Trp Trp Phe Tyr
                20                  25

(2) INFORMATION FOR SEQ ID NO: 44:

(i) SEQUENCE CHARACTERISTICS:
        (A) LENGTH: 35 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 44:

Ile Val Asn Gly Leu Glu Ala Gly Val Gly Gln Phe Pro Ile Gln Va
1               5                   10                  15

Phe Leu Asp Leu Thr Asn Ile Arg Asp Glu Lys Ser Arg Cys Gly Gl
                20                  25                  30

Ala Leu Phe
        35

(2) INFORMATION FOR SEQ ID NO: 45:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 45:

Ile Val Gly Gly Leu Glu Ala Lys Asn Gly Ile Thr Pro Phe Ile Gl
1               5                   10                  15

Phe Phe Ala Ser Gly Arg Leu Phe
                20

(2) INFORMATION FOR SEQ ID NO: 46:

(i) SEQUENCE CHARACTERISTICS:
        (A) LENGTH: 26 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 46:

Ile Val Gly Gly Asn Asp Val Ser Xaa Lys Ile Phe Trp Gln Val Se
1               5                   10                  15

Ile Gln Ser Asn Xaa Gln His Phe Cys Gly
            20                  25

(2) INFORMATION FOR SEQ ID NO: 47:

(i) SEQUENCE CHARACTERISTICS:
        (A) LENGTH: 31 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 47:

Ile Ile Gly Gly Glu Asp Ala Pro Glu Gly Ser Ala Pro Tyr Gln Va
1               5                   10                  15

Ser Leu Arg Asn Gln Asn Leu Glu His Phe Cys Gly Gly Ser Ile
            20                  25                  30

(2) INFORMATION FOR SEQ ID NO: 48:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 48:

GTWGGWAAAG GWWTWACWTT YGATTCWGGW GG                              32

(2) INFORMATION FOR SEQ ID NO: 49:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 49:

CGWCCTTCWG CATCWGTATT                                            20

(2) INFORMATION FOR SEQ ID NO: 50:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..453

(xi) SEQUENCE DESCRIPTION: SEQ ID NO: 50:

CAC GAG TTT TGT GCG AGT GTC AGA TAT TGC AGC TCT ATG AGT AAC AAG     48
His Glu Phe Cys Ala Ser Val Arg Tyr Cys Ser Ser Met Ser Asn Lys
1               5                   10                  15

```
AAA GGA TTA GTA CTG GGC ATC TAC GAC AAT GAA TTC GAT AAA AAA ATA         96
Lys Gly Leu Val Leu Gly Ile Tyr Asp Asn Glu Phe Asp Lys Lys Ile
            20                  25                  30

AGG TTA ACG CCA ACT GCT GAA CAA TTC AAT CGG CGA TTG CAG GGG CGT        144
Arg Leu Thr Pro Thr Ala Glu Gln Phe Asn Arg Arg Leu Gln Gly Arg
        35                  40                  45

TTA CTA GAT CTA ATT CAT TTG AGT GGA CCC ATT AAA TTG GGC AAG AGC        192
Leu Leu Asp Leu Ile His Leu Ser Gly Pro Ile Lys Leu Gly Lys Ser
    50                  55                  60

CGT ATT TTC TGG GAT CTC GAT GAA TTC GGC GCA GTT GCA GTT GCA GGT        240
Arg Ile Phe Trp Asp Leu Asp Glu Phe Gly Ala Val Ala Val Ala Gly
65                  70                  75                  80

TTG GGA AAT CAC TCC CCC TGC GAA CTC CTG GAA GAA CTC GAT GTT TTG        288
Leu Gly Asn His Ser Pro Cys Glu Leu Leu Glu Glu Leu Asp Val Leu
                85                  90                  95

CGC GAA AAT GCC AGA ATA GCT GCC GGT GCT GGT TGC CAA GCT CTT GCC        336
Arg Glu Asn Ala Arg Ile Ala Ala Gly Ala Gly Cys Gln Ala Leu Ala
            100                 105                 110

GCC GAT GGA ATC ACT ACC ATT AGC GTT GAA GTA TGG AGC ACC CGG AGG        384
Ala Asp Gly Ile Thr Thr Ile Ser Val Glu Val Trp Ser Thr Arg Arg
        115                 120                 125

CGG CCA TGC GAA GGT GCA ATA CTA TCG ACG TTC AAA TTC AGG TCA ACA        432
Arg Pro Cys Glu Gly Ala Ile Leu Ser Thr Phe Lys Phe Arg Ser Thr
    130                 135                 140

GAA GTA GTC CAG TGT AGC GGT                                            453
Glu Val Val Gln Cys Ser Gly
145                 150

(2) INFORMATION FOR SEQ ID NO: 51:

(i) SEQUENCE CHARACTERISTICS:
        (A) LENGTH: 151 amino acids
        (B) TYPE: amino acid
        (D) TOPOLOGY: linear (ii) MOLECULE TYPE: protein (xi) SEQUENCE DESCRIPTION: SEQ ID NO: 51:

His Glu Phe Cys Ala Ser Val Arg Tyr Cys Ser Ser Met Ser Asn Lys
1               5                   10                  15

Lys Gly Leu Val Leu Gly Ile Tyr Asp Asn Glu Phe Asp Lys Lys Ile
            20                  25                  30

Arg Leu Thr Pro Thr Ala Glu Gln Phe Asn Arg Arg Leu Gln Gly Arg
        35                  40                  45

Leu Leu Asp Leu Ile His Leu Ser Gly Pro Ile Lys Leu Gly Lys Ser
    50                  55                  60

Arg Ile Phe Trp Asp Leu Asp Glu Phe Gly Ala Val Ala Val Ala Gly
65                  70                  75                  80

Leu Gly Asn His Ser Pro Cys Glu Leu Leu Glu Glu Leu Asp Val Leu
                85                  90                  95

Arg Glu Asn Ala Arg Ile Ala Ala Gly Ala Gly Cys Gln Ala Leu Ala
            100                 105                 110

Ala Asp Gly Ile Thr Thr Ile Ser Val Glu Val Trp Ser Thr Arg Arg
        115                 120                 125

Arg Pro Cys Glu Gly Ala Ile Leu Ser Thr Phe Lys Phe Arg Ser Thr
    130                 135                 140

Glu Val Val Gln Cys Ser Gly
145                 150
```

(2) INFORMATION FOR SEQ ID NO: 52:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..258

(xi) SEQUENCE DESCRIPTION: SEQ ID NO: 52:

```
TCA GCA CTC GTT GCC TTG TCT GCA GCT ATT CCT CAC TCC AAC AGA GTC      48
Ser Ala Leu Val Ala Leu Ser Ala Ala Ile Pro His Ser Asn Arg Val
 1               5                  10                  15

GTT GGA GGA CTG GAA GCT GCA GAG GGT TCT GCA CCT TAT CAA GTA TCC      96
Val Gly Gly Leu Glu Ala Ala Glu Gly Ser Ala Pro Tyr Gln Val Ser
                20                  25                  30

TTG CAA GTT GGC AAC TTC CAC TTC TGT GGT GGT TCA ATT CTG AAC GAA     144
Leu Gln Val Gly Asn Phe His Phe Cys Gly Gly Ser Ile Leu Asn Glu
        35                  40                  45

TAT TGG GTT TTG ACT GCT GCT CAC TGT TTG GGT TAT GAC TTC GAC GTG     192
Tyr Trp Val Leu Thr Ala Ala His Cys Leu Gly Tyr Asp Phe Asp Val
    50                  55                  60

GTA GTT GGA ACA AAC AAA CTT GAT CAA CCA GGT GAA AGA TAC CTC GTA     240
Val Val Gly Thr Asn Lys Leu Asp Gln Pro Gly Glu Arg Tyr Leu Val
65                  70                  75                  80

GAA CAA ACT TTT GTT CAC                                             258
Glu Gln Thr Phe Val His
            85
```

(2) INFORMATION FOR SEQ ID NO: 53:

(i) SEQUENCE CHARACTERISTICS:
        (A) LENGTH: 86 amino acids
        (B) TYPE: amino acid
        (D) TOPOLOGY: linear (ii) MOLECULE TYPE: protein (xi) SEQUENCE DESCRIPTION: SEQ ID NO: 53:

```
Ser Ala Leu Val Ala Leu Ser Ala Ala Ile Pro His Ser Asn Arg Val
 1               5                  10                  15

Val Gly Gly Leu Glu Ala Ala Glu Gly Ser Ala Pro Tyr Gln Val Ser
                20                  25                  30

Leu Gln Val Gly Asn Phe His Phe Cys Gly Gly Ser Ile Leu Asn Glu
        35                  40                  45

Tyr Trp Val Leu Thr Ala Ala His Cys Leu Gly Tyr Asp Phe Asp Val
    50                  55                  60

Val Val Gly Thr Asn Lys Leu Asp Gln Pro Gly Glu Arg Tyr Leu Val
65                  70                  75                  80

Glu Gln Thr Phe Val His
            85
```

(2) INFORMATION FOR SEQ ID NO: 54:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
              (A) NAME/KEY: CDS
              (B) LOCATION: 1..240

(xi) SEQUENCE DESCRIPTION: SEQ ID NO: 54:

```
TTA GAT GGG CGC ATT GTT GGA GGA CAA GAT GCT GAT ATT GCC AAA TAT        48
Leu Asp Gly Arg Ile Val Gly Gly Gln Asp Ala Asp Ile Ala Lys Tyr
 1               5                  10                  15

GGC TAT CAA GCT TCA CTC CAA GTA TTT AAC GAA CAT TTC TGT GGA GCT        96
Gly Tyr Gln Ala Ser Leu Gln Val Phe Asn Glu His Phe Cys Gly Ala
                20                  25                  30

TCA ATA TTG AAT AAT TAT TGG ATT GTC ACA GCA GCT CAT TGC ATA TAT       144
Ser Ile Leu Asn Asn Tyr Trp Ile Val Thr Ala Ala His Cys Ile Tyr
            35                  40                  45

GAT GAA TTC ACG TAT TCA GTT CGA GTC GGC ACC AGT TTC CAA GGA AGA       192
Asp Glu Phe Thr Tyr Ser Val Arg Val Gly Thr Ser Phe Gln Gly Arg
        50                  55                  60

CGT GGT TCC GTT CAT CCT GTG GCA CAA ATT ATC AAG CAT CCT GCA TAC       240
Arg Gly Ser Val His Pro Val Ala Gln Ile Ile Lys His Pro Ala Tyr
65                  70                  75                  80
```

(2) INFORMATION FOR SEQ ID NO: 55:

(i) SEQUENCE CHARACTERISTICS:
              (A) LENGTH: 80 amino acids
              (B) TYPE: amino acid
              (D) TOPOLOGY: linear (ii) MOLECULE TYPE: protein (xi) SEQUENCE DESCRIPTION: SEQ ID NO: 55:

```
Leu Asp Gly Arg Ile Val Gly Gly Gln Asp Ala Asp Ile Ala Lys Tyr
 1               5                  10                  15

Gly Tyr Gln Ala Ser Leu Gln Val Phe Asn Glu His Phe Cys Gly Ala
                20                  25                  30

Ser Ile Leu Asn Asn Tyr Trp Ile Val Thr Ala Ala His Cys Ile Tyr
            35                  40                  45

Asp Glu Phe Thr Tyr Ser Val Arg Val Gly Thr Ser Phe Gln Gly Arg
        50                  55                  60

Arg Gly Ser Val His Pro Val Ala Gln Ile Ile Lys His Pro Ala Tyr
65                  70                  75                  80
```

(2) INFORMATION FOR SEQ ID NO: 56:

(i) SEQUENCE CHARACTERISTICS:
              (A) LENGTH: 218 base pairs
              (B) TYPE: nucleic acid
              (C) STRANDEDNESS: single
              (D) TOPOLOGY: linear (ii) MOLECULE TYPE: cDNA (ix) FEATURE:
              (A) NAME/KEY: CDS
              (B) LOCATION: 1..216

(xi) SEQUENCE DESCRIPTION: SEQ ID NO: 56:

```
AGG GAA CAA AAG CTG GAG CTC CAC CGC GGT GCG CCG GCT CTA GAA CTA        48
Arg Glu Gln Lys Leu Glu Leu His Arg Gly Ala Pro Ala Leu Glu Leu
 1               5                  10                  15

GTG GAT CCC CCG GGT CTG CAG GAA TTG GCA CGA GGA TGT TCT TGG CTG        96
Val Asp Pro Pro Gly Leu Gln Glu Leu Ala Arg Gly Cys Ser Trp Leu
                20                  25                  30
```

```
TGT TTA GTA GCT ATT CTT TGT GCA GTG GCT GCT GGG CCT ACT AAT CGC      144
Cys Leu Val Ala Ile Leu Cys Ala Val Ala Ala Gly Pro Thr Asn Arg
         35                  40                  45

ATT GTT GGA GGA TTG GAG GCG AAA AAT GGA ATC ACC CCA TTC ATC GGT      192
Ile Val Gly Gly Leu Glu Ala Lys Asn Gly Ile Thr Pro Phe Ile Gly
 50                  55                  60

TTC TTT GCA AGC GGA AGA CTA TTT CA                                   218
Phe Phe Ala Ser Gly Arg Leu Phe
 65                  70

(2) INFORMATION FOR SEQ ID NO: 57:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 57:

Arg Glu Gln Lys Leu Glu Leu His Arg Gly Ala Pro Ala Leu Glu Leu
 1               5                  10                  15

Val Asp Pro Pro Gly Leu Gln Glu Leu Ala Arg Gly Cys Ser Trp Leu
                 20                  25                  30

Cys Leu Val Ala Ile Leu Cys Ala Val Ala Ala Gly Pro Thr Asn Arg
         35                  40                  45

Ile Val Gly Gly Leu Glu Ala Lys Asn Gly Ile Thr Pro Phe Ile Gly
 50                  55                  60

Phe Phe Ala Ser Gly Arg Leu Phe
 65                  70

(2) INFORMATION FOR SEQ ID NO: 58:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..240

(xi) SEQUENCE DESCRIPTION: SEQ ID NO: 58:

ACG AGG TTT CGC TTA GCA ATT GTA TGT GCT CTC GCT GTC TGC ACA TTC       48
Thr Arg Phe Arg Leu Ala Ile Val Cys Ala Leu Ala Val Cys Thr Phe
 1               5                  10                  15

GGT GCC AGT GTT CCA GAA CCA TGG AAA AGA TTA GAT GGT AGA ATC GTA       96
Gly Ala Ser Val Pro Glu Pro Trp Lys Arg Leu Asp Gly Arg Ile Val
                 20                  25                  30

GGA GGA CAC GAT ACC AGC ATC GAT AAA CAC CCT CAT CAA GTA TCT TTA      144
Gly Gly His Asp Thr Ser Ile Asp Lys His Pro His Gln Val Ser Leu
         35                  40                  45

TTG TAC TCC AGC CAC AAT TGT GGT GGT TCC TTG ATT GCC AAA AAC TGG      192
Leu Tyr Ser Ser His Asn Cys Gly Gly Ser Leu Ile Ala Lys Asn Trp
 50                  55                  60

GTT TTG ACT GCA GCT CAT TGC ATT GGA GTT AAC AAA TAC AAT GTC CGT      240
Val Leu Thr Ala Ala His Cys Ile Gly Val Asn Lys Tyr Asn Val Arg
 65                  70                  75                  80
```

(2) INFORMATION FOR SEQ ID NO: 59:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 59:

Thr Arg Phe Arg Leu Ala Ile Val Cys Ala Leu Ala Val Cys Thr Phe
 1               5                  10                  15

Gly Ala Ser Val Pro Glu Pro Trp Lys Arg Leu Asp Gly Arg Ile Val
                20                  25                  30

Gly Gly His Asp Thr Ser Ile Asp Lys His Pro His Gln Val Ser Leu
            35                  40                  45

Leu Tyr Ser Ser His Asn Cys Gly Gly Ser Leu Ile Ala Lys Asn Trp
        50                  55                  60

Val Leu Thr Ala Ala His Cys Ile Gly Val Asn Lys Tyr Asn Val Arg
 65                  70                  75                  80

(2) INFORMATION FOR SEQ ID NO: 60:

(i) SEQUENCE CHARACTERISTICS:
        (A) LENGTH: 234 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..234

(xi) SEQUENCE DESCRIPTION: SEQ ID NO: 60:

CCC TCA CTA AAG GGA ACA AAA GCT GGA GCT CCA CCG CGG TGC GCC GCT       48
Pro Ser Leu Lys Gly Thr Lys Ala Gly Ala Pro Pro Arg Cys Ala Ala
 1               5                  10                  15

CTA GAA CTA GTG GAT CCC CCG GGC TGC AGG AAT TCG GCA CGA GCG TTT       96
Leu Glu Leu Val Asp Pro Pro Gly Cys Arg Asn Ser Ala Arg Ala Phe
                20                  25                  30

GGT TGG ATT GAG CGC GTC TCA TCT TAC AAG ATA AAG GAT AGA TTA GAT      144
Gly Trp Ile Glu Arg Val Ser Ser Tyr Lys Ile Lys Asp Arg Leu Asp
            35                  40                  45

GGG CGC ATT GTT GGA GGA CAA GAT GCT GAT ATT GCC AAA TAT GGC TAT      192
Gly Arg Ile Val Gly Gly Gln Asp Ala Asp Ile Ala Lys Tyr Gly Tyr
        50                  55                  60

CAA GCT TCA CTC CAA GTA CTT AAC GAA CAT TTC TGT GGA GCT              234
Gln Ala Ser Leu Gln Val Leu Asn Glu His Phe Cys Gly Ala
 65                  70                  75

(2) INFORMATION FOR SEQ ID NO: 61:

(i) SEQUENCE CHARACTERISTICS:
        (A) LENGTH: 78 amino acids
        (B) TYPE: amino acid
        (D) TOPOLOGY: linear (ii) MOLECULE TYPE: protein (xi) SEQUENCE DESCRIPTION: SEQ ID NO: 61:

Pro Ser Leu Lys Gly Thr Lys Ala Gly Ala Pro Pro Arg Cys Ala Ala
 1               5                  10                  15

```
Leu Glu Leu Val Asp Pro Pro Gly Cys Arg Asn Ser Ala Arg Ala Phe
             20                  25                  30

Gly Trp Ile Glu Arg Val Ser Ser Tyr Lys Ile Lys Asp Arg Leu Asp
         35                  40                  45

Gly Arg Ile Val Gly Gly Gln Asp Ala Asp Ile Ala Lys Tyr Gly Tyr
     50                  55                  60

Gln Ala Ser Leu Gln Val Leu Asn Glu His Phe Cys Gly Ala
 65                  70                  75
```

(2) INFORMATION FOR SEQ ID NO: 62:

(i) SEQUENCE CHARACTERISTICS:
        (A) LENGTH: 291 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..291

(xi) SEQUENCE DESCRIPTION: SEQ ID NO: 62:

```
GCG GTG ATT GTG TCA TTT GTT CTG GCT TGT GCA TTT TCT GTA CAG GCT     48
Ala Val Ile Val Ser Phe Val Leu Ala Cys Ala Phe Ser Val Gln Ala
 1               5                  10                  15

CTT CCA TCA AGC AGA ATT GTC AAT GGA CTT GAA GCA GGA GTT GGA CAA     96
Leu Pro Ser Ser Arg Ile Val Asn Gly Leu Glu Ala Gly Val Gly Gln
             20                  25                  30

TTT CCA ATT CAG GTT TTC TTA GAC TTG ACA AAT ATC AGA GAC GAA AAA    144
Phe Pro Ile Gln Val Phe Leu Asp Leu Thr Asn Ile Arg Asp Glu Lys
         35                  40                  45

TCC AGA TGT GGT GGT GCT TTG TTA TCA GAT TCA TGG GTT TTG ACT GCT    192
Ser Arg Cys Gly Gly Ala Leu Leu Ser Asp Ser Trp Val Leu Thr Ala
 50                  55                  60

GCT CAT TGT TTT GAT GAT TTG AAG TCT ATG GTA GTG TCC GTT GGT GCT    240
Ala His Cys Phe Asp Asp Leu Lys Ser Met Val Val Ser Val Gly Ala
 65                  70                  75                  80

CAT GAT GTC AGC AAA TCT GAA GAA CCT CAC AGG CAA ACC AGG AAA CCT    288
His Asp Val Ser Lys Ser Glu Glu Pro His Arg Gln Thr Arg Lys Pro
             85                  90                  95

GAA                                                                 291
Glu
```

(2) INFORMATION FOR SEQ ID NO: 63:

(i) SEQUENCE CHARACTERISTICS:
        (A) LENGTH: 97 amino acids
        (B) TYPE: amino acid
        (D) TOPOLOGY: linear (ii) MOLECULE TYPE: protein (xi) SEQUENCE DESCRIPTION: SEQ ID NO: 63:

```
Ala Val Ile Val Ser Phe Val Leu Ala Cys Ala Phe Ser Val Gln Ala
 1               5                  10                  15

Leu Pro Ser Ser Arg Ile Val Asn Gly Leu Glu Ala Gly Val Gly Gln
             20                  25                  30

Phe Pro Ile Gln Val Phe Leu Asp Leu Thr Asn Ile Arg Asp Glu Lys
         35                  40                  45

Ser Arg Cys Gly Gly Ala Leu Leu Ser Asp Ser Trp Val Leu Thr Ala
 50                  55                  60
```

```
Ala His Cys Phe Asp Asp Leu Lys Ser Met Val Val Ser Val Gly Ala
 65                  70                  75                  80

His Asp Val Ser Lys Ser Glu Glu Pro His Arg Gln Thr Arg Lys Pro
                 85                  90                  95

Glu
```

(2) INFORMATION FOR SEQ ID NO: 64:

(i) SEQUENCE CHARACTERISTICS:
        (A) LENGTH: 144 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..144
        (D) OTHER INFORMATION: /note= "At pos. bp 108, change A to
            M; at pos. 135, change C to Y; at pos. 141, change A to
            R; at pos. 144, change A to R."

(xi) SEQUENCE DESCRIPTION: SEQ ID NO: 64:

```
GTA CTG ATC GTT TTA GCA GTC ATT GAA TTC GCA TCA GCG TCT TCA ATC      48
Val Leu Ile Val Leu Ala Val Ile Glu Phe Ala Ser Ala Ser Ser Ile
  1               5                  10                  15

GGC TGG AGA ATC GTG GGT GGT GAA AAT GCT AAA GAA AAA TCG GTG CCC      96
Gly Trp Arg Ile Val Gly Gly Glu Asn Ala Lys Glu Lys Ser Val Pro
                 20                  25                  30

TAT CAA GTT TCM CTT CGA AAT GCT GAA AAC AAA CAT TTY TGT GGR GGR     144
Tyr Gln Val Ser Leu Arg Asn Ala Glu Asn Lys His Phe Cys Gly Gly
                 35                  40                  45
```

(2) INFORMATION FOR SEQ ID NO: 65:

(i) SEQUENCE CHARACTERISTICS:
        (A) LENGTH: 48 amino acids
        (B) TYPE: amino acid
        (D) TOPOLOGY: linear (ii) MOLECULE TYPE: protein (xi) SEQUENCE DESCRIPTION: SEQ ID NO: 65:

```
Val Leu Ile Val Leu Ala Val Ile Glu Phe Ala Ser Ala Ser Ser Ile
  1               5                  10                  15

Gly Trp Arg Ile Val Gly Gly Glu Asn Ala Lys Glu Lys Ser Val Pro
                 20                  25                  30

Tyr Gln Val Ser Leu Arg Asn Ala Glu Asn Lys His Phe Cys Gly Gly
                 35                  40                  45
```

(2) INFORMATION FOR SEQ ID NO: 66:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..390

(xi) SEQUENCE DESCRIPTION: SEQ ID NO: 66:

```
TTC GGC TTC AAG CTA AGT CAT TTG GTA AGT AAG TAC TGT GCT TGT GCA        48
Phe Gly Phe Lys Leu Ser His Leu Val Ser Lys Tyr Cys Ala Cys Ala
 1               5                  10                  15

TTA GCA TCG GCA CTG AAG TAC TCC ATC GAT CAT GGT CCT CGT ATC ATC        96
Leu Ala Ser Ala Leu Lys Tyr Ser Ile Asp His Gly Pro Arg Ile Ile
            20                  25                  30

GGA GGT GAA GTT GCA GGT GAA GGA TCA GCA CCT TAC CAG GTG TCC TTA       144
Gly Gly Glu Val Ala Gly Glu Gly Ser Ala Pro Tyr Gln Val Ser Leu
        35                  40                  45

AGA ACC AAG GAA GGA AAT CAT TTT TGC GGT GGA TCA ATA CTA AAT AAG       192
Arg Thr Lys Glu Gly Asn His Phe Cys Gly Gly Ser Ile Leu Asn Lys
    50                  55                  60

CGA TGG GTT GTA ACT GCA GCA CAT TGT CTT GAA CCG GAA ATA TTA GAT       240
Arg Trp Val Val Thr Ala Ala His Cys Leu Glu Pro Glu Ile Leu Asp
65                  70                  75                  80

TCG GTA TAC GTC GGA TCC AAT CAC TTA GAC CGA AAA GGC AGA TAT TAC       288
Ser Val Tyr Val Gly Ser Asn His Leu Asp Arg Lys Gly Arg Tyr Tyr
                85                  90                  95

GAC GTA GAA CGG TAT ATA ATT CAT GAA AAA TAT ATA GGA GAA CTA AAT       336
Asp Val Glu Arg Tyr Ile Ile His Glu Lys Tyr Ile Gly Glu Leu Asn
            100                 105                 110

AAT TTT TAT GCT GAC ATC GGT CTA ATA AAA CTT GAT GGA AGA CTT AGA       384
Asn Phe Tyr Ala Asp Ile Gly Leu Ile Lys Leu Asp Gly Arg Leu Arg
        115                 120                 125

ATT CAA                                                                390
Ile Gln
    130
```

(2) INFORMATION FOR SEQ ID NO: 67:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 67:

```
Phe Gly Phe Lys Leu Ser His Leu Val Ser Lys Tyr Cys Ala Cys Ala
 1               5                  10                  15

Leu Ala Ser Ala Leu Lys Tyr Ser Ile Asp His Gly Pro Arg Ile Ile
            20                  25                  30

Gly Gly Glu Val Ala Gly Glu Gly Ser Ala Pro Tyr Gln Val Ser Leu
        35                  40                  45

Arg Thr Lys Glu Gly Asn His Phe Cys Gly Gly Ser Ile Leu Asn Lys
    50                  55                  60

Arg Trp Val Val Thr Ala Ala His Cys Leu Glu Pro Glu Ile Leu Asp
65                  70                  75                  80

Ser Val Tyr Val Gly Ser Asn His Leu Asp Arg Lys Gly Arg Tyr Tyr
                85                  90                  95

Asp Val Glu Arg Tyr Ile Ile His Glu Lys Tyr Ile Gly Glu Leu Asn
            100                 105                 110

Asn Phe Tyr Ala Asp Ile Gly Leu Ile Lys Leu Asp Gly Arg Leu Arg
        115                 120                 125

Ile Gln
    130
```

(2) INFORMATION FOR SEQ ID NO: 68:

(i) SEQUENCE CHARACTERISTICS:
        (A) LENGTH: 240 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..240
        (D) OTHER INFORMATION: /note= "At pos. bp 218, change A to
            M. At pos. aa 73, substitute Xaa."

(xi) SEQUENCE DESCRIPTION: SEQ ID NO: 68:

```
CGG GCT GCA GGA ATT CGG CAC GAG AAG AAA CTG CCA ATA TTA ATC GCC      48
Arg Ala Ala Gly Ile Arg His Glu Lys Lys Leu Pro Ile Leu Ile Ala
 1               5                  10                  15

TTG ATC GGA TGC GTT CTT TCT GAA GAA ATA GAG GAT CGC ATT GTC GGC      96
Leu Ile Gly Cys Val Leu Ser Glu Glu Ile Glu Asp Arg Ile Val Gly
             20                  25                  30

GGA ACG GCA GTT GAT ATA AGA GGT TTT CCC TGG CAG GTA TCA ATT CAA     144
Gly Thr Ala Val Asp Ile Arg Gly Phe Pro Trp Gln Val Ser Ile Gln
         35                  40                  45

ACC GAA AAC CGT CAT TTT TGT GGT GGT TCT ATT ATC GAT AAA AGC TGG     192
Thr Glu Asn Arg His Phe Cys Gly Gly Ser Ile Ile Asp Lys Ser Trp
     50                  55                  60

ATA TTA ACT GCC GCA CAT TGT GTA CMC GAT ATG AAG ATG TCG AAC TGG     240
Ile Leu Thr Ala Ala His Cys Val Xaa Asp Met Lys Met Ser Asn Trp
 65                  70                  75                  80
```

(2) INFORMATION FOR SEQ ID NO: 69:

(i) SEQUENCE CHARACTERISTICS:
        (A) LENGTH: 80 amino acids
        (B) TYPE: amino acid
        (D) TOPOLOGY: linear (ii) MOLECULE TYPE: protein (xi) SEQUENCE DESCRIPTION: SEQ ID NO: 69:

```
Arg Ala Ala Gly Ile Arg His Glu Lys Lys Leu Pro Ile Leu Ile Ala
 1               5                  10                  15

Leu Ile Gly Cys Val Leu Ser Glu Glu Ile Glu Asp Arg Ile Val Gly
             20                  25                  30

Gly Thr Ala Val Asp Ile Arg Gly Phe Pro Trp Gln Val Ser Ile Gln
         35                  40                  45

Thr Glu Asn Arg His Phe Cys Gly Gly Ser Ile Ile Asp Lys Ser Trp
     50                  55                  60

Ile Leu Thr Ala Ala His Cys Val Xaa Asp Met Lys Met Ser Asn Trp
 65                  70                  75                  80
```

(2) INFORMATION FOR SEQ ID NO: 70:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..177

(xi) SEQUENCE DESCRIPTION: SEQ ID NO: 70:

| | | | | | | | | | | | | | | | | |
|---|---|---|---|---|---|---|---|---|---|---|---|---|---|---|---|---|
| CAC | GAG | ATT | TTA | TTA | AGC | GCA | TTA | TTT | GCA | AGT | GTA | ATT | TGC | TCC | TTT | 48 |
| His | Glu | Ile | Leu | Leu | Ser | Ala | Leu | Phe | Ala | Ser | Val | Ile | Cys | Ser | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| AAC | GCG | GAA | GTA | CAA | AAT | CGA | ATC | GTT | GGT | GGC | AAT | GAT | GTA | AGT | ATT | 96 |
| Asn | Ala | Glu | Val | Gln | Asn | Arg | Ile | Val | Gly | Gly | Asn | Asp | Val | Ser | Ile | |
| | | 20 | | | | | 25 | | | | | 30 | | | | |

| | | | | | | | | | | | | | | | | |
|---|---|---|---|---|---|---|---|---|---|---|---|---|---|---|---|---|
| TCA | AAA | ATT | GGG | TGG | CAA | GTA | TCT | ATT | CAA | AGT | AAT | AAA | CAA | CAT | TTC | 144 |
| Ser | Lys | Ile | Gly | Trp | Gln | Val | Ser | Ile | Gln | Ser | Asn | Lys | Gln | His | Phe | |
| | | | 35 | | | | | 40 | | | | | 45 | | | |

| | | | | | | | | | |
|---|---|---|---|---|---|---|---|---|---|
| TGT | GGT | GGT | TCA | ATC | ATT | GCT | AAA | GAT | GGG | TCC | 177 |
| Cys | Gly | Gly | Ser | Ile | Ile | Ala | Lys | Asp | Gly | Ser | |
| 50 | | | | | 55 | | | | | | |

(2) INFORMATION FOR SEQ ID NO: 71:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO: 71:

His Glu Ile Leu Leu Ser Ala Leu Phe Ala Ser Val Ile Cys Ser Phe
 1               5                  10                  15

Asn Ala Glu Val Gln Asn Arg Ile Val Gly Gly Asn Asp Val Ser Ile
            20                  25                  30

Ser Lys Ile Gly Trp Gln Val Ser Ile Gln Ser Asn Lys Gln His Phe
        35                  40                  45

Cys Gly Gly Ser Ile Ile Ala Lys Asp Gly Ser
        50                  55

(2) INFORMATION FOR SEQ ID NO: 72:

(i) SEQUENCE CHARACTERISTICS:
        (A) LENGTH: 168 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..168

(xi) SEQUENCE DESCRIPTION: SEQ ID NO: 72:

| | | | | | | | | | | | | | | | | |
|---|---|---|---|---|---|---|---|---|---|---|---|---|---|---|---|---|
| ATC | ATG | GCA | AAT | TTT | AGG | CTA | TTC | ACC | TTA | CTA | GCC | TTG | GTT | TCA | GTA | 48 |
| Ile | Met | Ala | Asn | Phe | Arg | Leu | Phe | Thr | Leu | Leu | Ala | Leu | Val | Ser | Val | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| GCA | ACT | TCC | AAA | TAT | ATT | GAT | CCA | AGA | ATA | ATT | GGA | GGC | GAA | GAT | GCT | 96 |
| Ala | Thr | Ser | Lys | Tyr | Ile | Asp | Pro | Arg | Ile | Ile | Gly | Gly | Glu | Asp | Ala | |
| | | 20 | | | | | 25 | | | | | 30 | | | | |

| | | | | | | | | | | | | | | | | |
|---|---|---|---|---|---|---|---|---|---|---|---|---|---|---|---|---|
| CCT | GAA | GGC | TCG | GCT | CCG | TAC | CAA | GTT | TCA | TTG | AGA | AAT | CAG | AAT | CTG | 144 |
| Pro | Glu | Gly | Ser | Ala | Pro | Tyr | Gln | Val | Ser | Leu | Arg | Asn | Gln | Asn | Leu | |
| | | | 35 | | | | | 40 | | | | | 45 | | | |

| | | | | | | | |
|---|---|---|---|---|---|---|---|
| GAG | CAT | TTC | TGT | GGT | GGT | TCC | ATT | 168 |
| Glu | His | Phe | Cys | Gly | Gly | Ser | Ile | |
| 50 | | | | | 55 | | | |

(2) INFORMATION FOR SEQ ID NO: 73:

(i) SEQUENCE CHARACTERISTICS:
        (A) LENGTH: 56 amino acids
        (B) TYPE: amino acid
        (D) TOPOLOGY: linear (ii) MOLECULE TYPE: protein (xi) SEQUENCE DESCRIPTION: SEQ ID NO: 73:

```
Ile Met Ala Asn Phe Arg Leu Phe Thr Leu Leu Ala Leu Val Ser Val
 1               5                  10                  15

Ala Thr Ser Lys Tyr Ile Asp Pro Arg Ile Ile Gly Gly Glu Asp Ala
             20                  25                  30

Pro Glu Gly Ser Ala Pro Tyr Gln Val Ser Leu Arg Asn Gln Asn Leu
         35                  40                  45

Glu His Phe Cys Gly Gly Ser Ile
     50                  55
```

(2) INFORMATION FOR SEQ ID NO: 74:

(i) SEQUENCE CHARACTERISTICS:
        (A) LENGTH: 192 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..192

(xi) SEQUENCE DESCRIPTION: SEQ ID NO: 74:

```
GCA CGA GAT CGC ATT GTT GGA GGA TTG GAG GCG AAA AAT GGA TCA GCC      48
Ala Arg Asp Arg Ile Val Gly Gly Leu Glu Ala Lys Asn Gly Ser Ala
 1               5                  10                  15

CCA TTC ATG GTT TCT TTG CAA GCG GAA GAC TAT TTT CAT TTT TGT GGA      96
Pro Phe Met Val Ser Leu Gln Ala Glu Asp Tyr Phe His Phe Cys Gly
             20                  25                  30

TCC TCT ATT CTG AAT GAG AGA TGG GTT CTT ACT GCT GCT CAC TGT ATC     144
Ser Ser Ile Leu Asn Glu Arg Trp Val Leu Thr Ala Ala His Cys Ile
         35                  40                  45

CAA CCA AAT GTA CAC AAG TAC GTT TAC GTC GGT TCG AAC AAC GTA GAA     192
Gln Pro Asn Val His Lys Tyr Val Tyr Val Gly Ser Asn Asn Val Glu
     50                  55                  60
```

(2) INFORMATION FOR SEQ ID NO: 75:

(i) SEQUENCE CHARACTERISTICS:
        (A) LENGTH: 64 amino acids
        (B) TYPE: amino acid
        (D) TOPOLOGY: linear (ii) MOLECULE TYPE: protein (xi) SEQUENCE DESCRIPTION: SEQ ID NO: 75:

```
Ala Arg Asp Arg Ile Val Gly Gly Leu Glu Ala Lys Asn Gly Ser Ala
 1               5                  10                  15

Pro Phe Met Val Ser Leu Gln Ala Glu Asp Tyr Phe His Phe Cys Gly
             20                  25                  30

Ser Ser Ile Leu Asn Glu Arg Trp Val Leu Thr Ala Ala His Cys Ile
         35                  40                  45

Gln Pro Asn Val His Lys Tyr Val Tyr Val Gly Ser Asn Asn Val Glu
     50                  55                  60
```

(2) INFORMATION FOR SEQ ID NO: 76:

(i) SEQUENCE CHARACTERISTICS:
        (A) LENGTH: 207 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..204

(xi) SEQUENCE DESCRIPTION: SEQ ID NO: 76:

```
CCA ATC CAC GAT AGC CAA TAT GCA CTT TTG CAG ATA TGG GTC AAG GGT       48
Pro Ile His Asp Ser Gln Tyr Ala Leu Leu Gln Ile Trp Val Lys Gly
 1               5                  10                  15

GCA TGT AAG GGT GAT TCC GGT GGC CCC TTA GTC ATC AAT GGA CAA CTT       96
Ala Cys Lys Gly Asp Ser Gly Gly Pro Leu Val Ile Asn Gly Gln Leu
                20                  25                  30

CAT GGA ATT GTT TCC TGG GGC ATT CCT TGC GCT GTC GCA AGC CTG ATG      144
His Gly Ile Val Ser Trp Gly Ile Pro Cys Ala Val Ala Ser Leu Met
         35                  40                  45

TAT TCA CAA GAG TTT CTC ATT ATG TCG ATT GGA TTA AAT CCA AAA TTG      192
Tyr Ser Gln Glu Phe Leu Ile Met Ser Ile Gly Leu Asn Pro Lys Leu
 50                  55                  60

AAT AAA ATT GTT TAG                                                  207
Asn Lys Ile Val
 65
```

(2) INFORMATION FOR SEQ ID NO: 77:

(i) SEQUENCE CHARACTERISTICS:
        (A) LENGTH: 68 amino acids
        (B) TYPE: amino acid
        (D) TOPOLOGY: linear (ii) MOLECULE TYPE: protein (xi) SEQUENCE DESCRIPTION: SEQ ID NO: 77:

```
Pro Ile His Asp Ser Gln Tyr Ala Leu Leu Gln Ile Trp Val Lys Gly
 1               5                  10                  15

Ala Cys Lys Gly Asp Ser Gly Gly Pro Leu Val Ile Asn Gly Gln Leu
                20                  25                  30

His Gly Ile Val Ser Trp Gly Ile Pro Cys Ala Val Ala Ser Leu Met
         35                  40                  45

Tyr Ser Gln Glu Phe Leu Ile Met Ser Ile Gly Leu Asn Pro Lys Leu
 50                  55                  60

Asn Lys Ile Val
 65
```

(2) INFORMATION FOR SEQ ID NO: 78:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..156

```
    (xi) SEQUENCE DESCRIPTION: SEQ ID NO: 78:

GGA GGT CCT TTG GCA ATC AAT GGT GAA CTT GTT GGT GTT ACT TCA TTC        48
Gly Gly Pro Leu Ala Ile Asn Gly Glu Leu Val Gly Val Thr Ser Phe
  1               5                  10                  15

ATT ATG GGG ACA TGT GGA GGA GGA CAT CCT GAT GTC TTC GGT CGA GTC        96
Ile Met Gly Thr Cys Gly Gly Gly His Pro Asp Val Phe Gly Arg Val
                 20                  25                  30

CTT GAC TTC AAA CCA TGG ATT GAT TCT CAT ATG GCA AAT GAC GGC GCT       144
Leu Asp Phe Lys Pro Trp Ile Asp Ser His Met Ala Asn Asp Gly Ala
             35                  40                  45

AAT TCT TTT ATT TAA                                                   159
Asn Ser Phe Ile
    50

(2) INFORMATION FOR SEQ ID NO: 79:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 79:

Gly Gly Pro Leu Ala Ile Asn Gly Glu Leu Val Gly Val Thr Ser Phe
  1               5                  10                  15

Ile Met Gly Thr Cys Gly Gly Gly His Pro Asp Val Phe Gly Arg Val
                 20                  25                  30

Leu Asp Phe Lys Pro Trp Ile Asp Ser His Met Ala Asn Asp Gly Ala
             35                  40                  45

Asn Ser Phe Ile
    50

(2) INFORMATION FOR SEQ ID NO: 80:

(i) SEQUENCE CHARACTERISTICS:
        (A) LENGTH: 779 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..699
        (D) OTHER INFORMATION: /note= "At pos. bp 371, change G to
            B. At pos. aa 123, substitute Xaa."

(xi) SEQUENCE DESCRIPTION: SEQ ID NO: 80:

TT TTC TCA GCA CTC GTT GCC TTG TCT GCA GCT ATT CCT CAC TCC AAC         47
   Phe Ser Ala Leu Val Ala Leu Ser Ala Ala Ile Pro His Ser Asn
     1               5                  10                  15

AGA GTC GTT GGA GGA CTG GAA GCT GCA GAA GGT TCT GCA CCT TAC CAA        95
Arg Val Val Gly Gly Leu Glu Ala Ala Glu Gly Ser Ala Pro Tyr Gln
                 20                  25                  30

GTA TCC TTG CAA GTT GGT AAC TTC CAC TTC TGT GGT GGT TCA ATT TTG       143
Val Ser Leu Gln Val Gly Asn Phe His Phe Cys Gly Gly Ser Ile Leu
             35                  40                  45

AAC GAA TAT TGG GTT TTG ACT GCT GCT CAC TGT TTG GGT TAT GAC TTC       191
Asn Glu Tyr Trp Val Leu Thr Ala Ala His Cys Leu Gly Tyr Asp Phe
         50                  55                  60
```

```
GAC GTG GTA GTG GGA ACA AAC AAA CTT GAT CAA CCA GGT GAA AGA TAC       239
Asp Val Val Val Gly Thr Asn Lys Leu Asp Gln Pro Gly Glu Arg Tyr
     65                  70                  75

CTC GTA GAA CAA ACT TTT GTT CAC CAA TTC GAC CAG GAA TCT TTA AGA       287
Leu Val Glu Gln Thr Phe Val His Gln Phe Asp Gln Glu Ser Leu Arg
 80                  85                  90                  95

CAC GAT CTT GCT TTG GTA AAA GTG TCC AGC CCT ATC GAA TTC AAT GAT       335
His Asp Leu Ala Leu Val Lys Val Ser Ser Pro Ile Glu Phe Asn Asp
                100                 105                 110

TAT GTT CAA CCA ATT CCA TTG GGC GAA ACT TAT GTB GGC GGT GAA GTT       383
Tyr Val Gln Pro Ile Pro Leu Gly Glu Thr Tyr Xaa Gly Gly Glu Val
             115                 120                 125

GCT CGT CTT ACT GGA TGG GGA AGA CTT GGA GCT AAC TTG AAT GGA CCG       431
Ala Arg Leu Thr Gly Trp Gly Arg Leu Gly Ala Asn Leu Asn Gly Pro
         130                 135                 140

AAT GAA CTC CAA GAA CTT AAC ACT GTC ACA TTA AGC CAC CAG CAA TGT       479
Asn Glu Leu Gln Glu Leu Asn Thr Val Thr Leu Ser His Gln Gln Cys
     145                 150                 155

GTA AGA CAA CAA ATT TAT CCA GTA TAC GAC AGC CAA CTT TGC ACA TTT       527
Val Arg Gln Gln Ile Tyr Pro Val Tyr Asp Ser Gln Leu Cys Thr Phe
160                 165                 170                 175

GTT GGC AGT GGA CGA GGC GCC TGC AAC GGT GAC TCT GGT GGT CCA TTG       575
Val Gly Ser Gly Arg Gly Ala Cys Asn Gly Asp Ser Gly Gly Pro Leu
                180                 185                 190

GTC GTC AAT GGA GAA CTT CAC GGA GTC GTC TCC TGG GGA ATC CCC TGC       623
Val Val Asn Gly Glu Leu His Gly Val Val Ser Trp Gly Ile Pro Cys
             195                 200                 205

GCC GTT GGA TTA CCC GAT GTC TTC ACA AGA GTT TCA CAC TAC GCT GAC       671
Ala Val Gly Leu Pro Asp Val Phe Thr Arg Val Ser His Tyr Ala Asp
         210                 215                 220

TGG ATT AGA GAG ACC ATG GAA AAT AAC T AATTTTTAAT GGCATATTAT           719
Trp Ile Arg Glu Thr Met Glu Asn Asn
     225                 230

TGTATTGTCT GTGATGAAAA TTAATAAAAA CGTGATAGAT TAAAAAAAAA AAAAAAAA       779

(2) INFORMATION FOR SEQ ID NO: 81:

(i) SEQUENCE CHARACTERISTICS:
        (A) LENGTH: 232 amino acids
        (B) TYPE: amino acid
        (D) TOPOLOGY: linear (ii) MOLECULE TYPE: protein (xi) SEQUENCE DESCRIPTION: SEQ ID NO: 81:

Phe Ser Ala Leu Val Ala Leu Ser Ala Ala Ile Pro His Ser Asn Arg
 1               5                  10                  15

Val Val Gly Gly Leu Glu Ala Ala Glu Gly Ser Ala Pro Tyr Gln Val
                 20                  25                  30

Ser Leu Gln Val Gly Asn Phe His Phe Cys Gly Gly Ser Ile Leu Asn
             35                  40                  45

Glu Tyr Trp Val Leu Thr Ala Ala His Cys Leu Gly Tyr Asp Phe Asp
         50                  55                  60

Val Val Val Gly Thr Asn Lys Leu Asp Gln Pro Gly Glu Arg Tyr Leu
 65                  70                  75                  80

Val Glu Gln Thr Phe Val His Gln Phe Asp Gln Glu Ser Leu Arg His
                 85                  90                  95

Asp Leu Ala Leu Val Lys Val Ser Ser Pro Ile Glu Phe Asn Asp Tyr
            100                 105                 110
```

```
Val Gln Pro Ile Pro Leu Gly Glu Thr Tyr Xaa Gly Gly Glu Val Ala
    115                 120                 125

Arg Leu Thr Gly Trp Gly Arg Leu Gly Ala Asn Leu Asn Gly Pro Asn
    130                 135                 140

Glu Leu Gln Glu Leu Asn Thr Val Thr Leu Ser His Gln Gln Cys Val
145                 150                 155                 160

Arg Gln Gln Ile Tyr Pro Val Tyr Asp Ser Gln Leu Cys Thr Phe Val
                165                 170                 175

Gly Ser Gly Arg Gly Ala Cys Asn Gly Asp Ser Gly Gly Pro Leu Val
            180                 185                 190

Val Asn Gly Glu Leu His Gly Val Val Ser Trp Gly Ile Pro Cys Ala
        195                 200                 205

Val Gly Leu Pro Asp Val Phe Thr Arg Val Ser His Tyr Ala Asp Trp
    210                 215                 220

Ile Arg Glu Thr Met Glu Asn Asn
225                 230
```

(2) INFORMATION FOR SEQ ID NO: 82:

(i) SEQUENCE CHARACTERISTICS:
        (A) LENGTH: 944 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..768

(xi) SEQUENCE DESCRIPTION: SEQ ID NO: 82:

```
CT GAA GTG TGG ATT CAT CGT TGT TTT CCT TGT GGC GGC AGC TTG GGT        47
   Glu Val Trp Ile His Arg Cys Phe Pro Cys Gly Gly Ser Leu Gly
   1               5                   10                  15

GAA GAT TCG GTC GTC GAC CGC ATC GTC GGC GGC ACC AGT GTT AAA ATT       95
Glu Asp Ser Val Val Asp Arg Ile Val Gly Gly Thr Ser Val Lys Ile
                20                  25                  30

GAG AAC TTC GGA TGG CAA GTG TCC TTA TTC GAT CGT AAG GGT CAC TTT      143
Glu Asn Phe Gly Trp Gln Val Ser Leu Phe Asp Arg Lys Gly His Phe
            35                  40                  45

TGC GGT GGT TCT ATA ATC AGC GAC GAA TGG GTC TTG ACT GCT GCA CAT      191
Cys Gly Gly Ser Ile Ile Ser Asp Glu Trp Val Leu Thr Ala Ala His
        50                  55                  60

TGC GTA TAC GAT TAT TTC TCG CCA AAG CAA TAT GGA GTG CGT GTC GGA      239
Cys Val Tyr Asp Tyr Phe Ser Pro Lys Gln Tyr Gly Val Arg Val Gly
    65                  70                  75

AGC AGT TTA CGC AAC AAA GGT GGA GTC CTT CAC AGA ATT TCC AGG GTA      287
Ser Ser Leu Arg Asn Lys Gly Gly Val Leu His Arg Ile Ser Arg Val
80                  85                  90                  95

CAC ATT CAC CCA GAC TAC GAC ACG GTC AGC TAC GAC AAT GAC GTC GCG      335
His Ile His Pro Asp Tyr Asp Thr Val Ser Tyr Asp Asn Asp Val Ala
                100                 105                 110

CTC CTG AAA GTT GAA ACC AAA TTT AAA CTA AAC GGC AGG AGC GTT CGC      383
Leu Leu Lys Val Glu Thr Lys Phe Lys Leu Asn Gly Arg Ser Val Arg
            115                 120                 125

AAA GTT AAA TTG GTT GAC GAA GAT CAC GAG GTT GAT GAT GGT GCC CGG      431
Lys Val Lys Leu Val Asp Glu Asp His Glu Val Asp Asp Gly Ala Arg
        130                 135                 140
```

-continued

```
CTC ACC GTC ACT GGA TGG GGC AAA TTA AGT GAA TCA GGA CCC AAG CCA        479
Leu Thr Val Thr Gly Trp Gly Lys Leu Ser Glu Ser Gly Pro Lys Pro
    145                 150                 155

GTA AAT CTA CAA GGA GTA AAA GTG CCT TAT GTG GAC CAA GAT ACA TGC        527
Val Asn Leu Gln Gly Val Lys Val Pro Tyr Val Asp Gln Asp Thr Cys
160                 165                 170                 175

TCT GAC AGC TAC GTC TTT GCA GGA AAA GAT ATC ACC GAA AAC ATG TTG        575
Ser Asp Ser Tyr Val Phe Ala Gly Lys Asp Ile Thr Glu Asn Met Leu
                180                 185                 190

TGT GCC GGA GTT AGA AGA GGT GGC AAG GAC TCC TGC CAG GGT GAC AGC        623
Cys Ala Gly Val Arg Arg Gly Gly Lys Asp Ser Cys Gln Gly Asp Ser
            195                 200                 205

GGT GGT CCA CTT GTG GAC GAA AAC AAA AAT CTG GTC GGA GTC GTC TCT        671
Gly Gly Pro Leu Val Asp Glu Asn Lys Asn Leu Val Gly Val Val Ser
        210                 215                 220

TGG GGA AAT GGT TGT GCC AGA CCA AAC ATG CCA GGA GTA TAC GCT AAA        719
Trp Gly Asn Gly Cys Ala Arg Pro Asn Met Pro Gly Val Tyr Ala Lys
    225                 230                 235

GTT GCT GCT TCT AGC ATT AGA GAG TTC ATT CGC AAA AAA ACT GGT CTT        768
Val Ala Ala Ser Ser Ile Arg Glu Phe Ile Arg Lys Lys Thr Gly Leu
240                 245                 250                 255

AATTTCCTTA TATGAACAAA TGTTCCACCA AAAATATAGT TTAGATTTTA GTATAATAA       828

TCCTTTGTGA TTCATGCAAA TATTTTGTTT TATTTATTTA TTTACTTTAT TCAAACGAA       888

GTATAAAGTG AATTAACAAT AAAAATGTTA GTGTTGCCAA AAAAAAAAAA AAAAAA          944
```

(2) INFORMATION FOR SEQ ID NO: 83:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO: 83:

```
Glu Val Trp Ile His Arg Cys Phe Pro Cys Gly Gly Ser Leu Gly Glu
1               5                   10                  15

Asp Ser Val Val Asp Arg Ile Val Gly Gly Thr Ser Val Lys Ile Glu
            20                  25                  30

Asn Phe Gly Trp Gln Val Ser Leu Phe Asp Arg Lys Gly His Phe Cys
        35                  40                  45

Gly Gly Ser Ile Ile Ser Asp Glu Trp Val Leu Thr Ala Ala His Cys
    50                  55                  60

Val Tyr Asp Tyr Phe Ser Pro Lys Gln Tyr Gly Val Arg Val Gly Ser
65                  70                  75                  80

Ser Leu Arg Asn Lys Gly Gly Val Leu His Arg Ile Ser Arg Val His
                85                  90                  95

Ile His Pro Asp Tyr Asp Thr Val Ser Tyr Asp Asn Asp Val Ala Leu
            100                 105                 110

Leu Lys Val Glu Thr Lys Phe Lys Leu Asn Gly Arg Ser Val Arg Lys
        115                 120                 125

Val Lys Leu Val Asp Glu Asp His Glu Val Asp Gly Ala Arg Leu
    130                 135                 140

Thr Val Thr Gly Trp Gly Lys Leu Ser Glu Ser Gly Pro Lys Pro Val
145                 150                 155                 160

Asn Leu Gln Gly Val Lys Val Pro Tyr Val Asp Gln Asp Thr Cys Ser
                165                 170                 175
```

```
Asp Ser Tyr Val Phe Ala Gly Lys Asp Ile Thr Glu Asn Met Leu Cys
            180                 185                 190

Ala Gly Val Arg Arg Gly Gly Lys Asp Ser Cys Gln Gly Asp Ser Gly
            195                 200                 205

Gly Pro Leu Val Asp Glu Asn Lys Asn Leu Val Gly Val Val Ser Trp
210                 215                 220

Gly Asn Gly Cys Ala Arg Pro Asn Met Pro Gly Val Tyr Ala Lys Val
225                 230                 235                 240

Ala Ala Ser Ser Ile Arg Glu Phe Ile Arg Lys Lys Thr Gly Leu
                245                 250                 255
```

(2) INFORMATION FOR SEQ ID NO: 84:

(i) SEQUENCE CHARACTERISTICS:
        (A) LENGTH: 157 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..157

(xi) SEQUENCE DESCRIPTION: SEQ ID NO: 84:

```
GGA ATT CGG CAC GAG TAT CTG TGC CCT CGC AGT CTG CAC CCT TGG CGT      48
Gly Ile Arg His Glu Tyr Leu Cys Pro Arg Ser Leu His Pro Trp Arg
 1               5                  10                  15

AGC GTT CCT GAC TTT TGG AAC AGG TTA GAT GGC AGA ATC GTT GGA GGA      96
Ser Val Pro Asp Phe Trp Asn Arg Leu Asp Gly Arg Ile Val Gly Gly
             20                  25                  30

CAC GAT ACT AGC ATT GAT AAC ATC CTC ATG CAA GTA TCT TTG AGT TTA     144
His Asp Thr Ser Ile Asp Asn Ile Leu Met Gln Val Ser Leu Ser Leu
         35                  40                  45

CAC AAA CCA CAA  T                                                  157
His Lys Pro Gln
     50
```

(2) INFORMATION FOR SEQ ID NO: 85:

(i) SEQUENCE CHARACTERISTICS:
        (A) LENGTH: 52 amino acids
        (B) TYPE: amino acid
        (D) TOPOLOGY: linear (ii) MOLECULE TYPE: protein (xi) SEQUENCE DESCRIPTION: SEQ ID NO: 85:

```
Gly Ile Arg His Glu Tyr Leu Cys Pro Arg Ser Leu His Pro Trp Arg
 1               5                  10                  15

Ser Val Pro Asp Phe Trp Asn Arg Leu Asp Gly Arg Ile Val Gly Gly
             20                  25                  30

His Asp Thr Ser Ile Asp Asn Ile Leu Met Gln Val Ser Leu Ser Leu
         35                  40                  45

His Lys Pro Gln
     50
```

(2) INFORMATION FOR SEQ ID NO: 86:

(i) SEQUENCE CHARACTERISTICS:
        (A) LENGTH: 218 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..218

(xi) SEQUENCE DESCRIPTION: SEQ ID NO: 86:

```
AA GAT GTA GAA TTA ACA CCT GGA ACT ATG TGC ACT GTT ACT GGA TGG        47
   Asp Val Glu Leu Thr Pro Gly Thr Met Cys Thr Val Thr Gly Trp
    1               5                  10                  15

GGA TCA ACT GGA TCT GGT GGT CCA ATT ACA AAT GTT CTA CAA GAA GTC        95
Gly Ser Thr Gly Ser Gly Gly Pro Ile Thr Asn Val Leu Gln Glu Val
             20                  25                  30

GAA GTT CCA TTT ATC GAC TTC AAC ACC TGC CGA AAA TCC TAC TCA ACC       143
Glu Val Pro Phe Ile Asp Phe Asn Thr Cys Arg Lys Ser Tyr Ser Thr
         35                  40                  45

AGC TTA ACC GAC CGT ATG TTC TGC GCT GGA TTT TTG GGA ATT GGT GGT       191
Ser Leu Thr Asp Arg Met Phe Cys Ala Gly Phe Leu Gly Ile Gly Gly
     50                  55                  60

AAG GAC GCT TGC CAA GGC GAC TCC GGA                                   218
Lys Asp Ala Cys Gln Gly Asp Ser Gly
 65                  70
```

(2) INFORMATION FOR SEQ ID NO: 87:

(i) SEQUENCE CHARACTERISTICS:
        (A) LENGTH: 72 amino acids
        (B) TYPE: amino acid
        (D) TOPOLOGY: linear (ii) MOLECULE TYPE: protein (xi) SEQUENCE DESCRIPTION: SEQ ID NO: 87:

```
Asp Val Glu Leu Thr Pro Gly Thr Met Cys Thr Val Thr Gly Trp Gly
 1               5                  10                  15

Ser Thr Gly Ser Gly Gly Pro Ile Thr Asn Val Leu Gln Glu Val Glu
             20                  25                  30

Val Pro Phe Ile Asp Phe Asn Thr Cys Arg Lys Ser Tyr Ser Thr Ser
         35                  40                  45

Leu Thr Asp Arg Met Phe Cys Ala Gly Phe Leu Gly Ile Gly Gly Lys
     50                  55                  60

Asp Ala Cys Gln Gly Asp Ser Gly
 65                  70
```

(2) INFORMATION FOR SEQ ID NO: 88:

(i) SEQUENCE CHARACTERISTICS:
        (A) LENGTH: 932 base pairs
        (B) TYPE: nucleic acid
        (C) STRANDEDNESS: single
        (D) TOPOLOGY: linear (ii) MOLECULE TYPE: cDNA -continued (ix) FEATURE:
    (A) NAME/KEY: CDS
    (B) LOCATION: 2..770
    (D) OTHER INFORMATION: /note= "At pos. bp 276, change G to
        K. At pos. bp 332, change G to K. At pos. aa 92 and aa
        111, substitute Xaa."

(xi) SEQUENCE DESCRIPTION: SEQ ID NO: 88:

```
G TTC ATA TTT GTG CTC GTT TGC GTT GGA TTG AGC GCC GTC TCA TCT         46
  Phe Ile Phe Val Leu Val Cys Val Gly Leu Ser Ala Val Ser Ser
   1               5                  10                  15

TAC AAG ATA AAG GAT GGA TTA GAT GGG CGC ATT GTT GGA GGA CAA GAT       94
Tyr Lys Ile Lys Asp Gly Leu Asp Gly Arg Ile Val Gly Gly Gln Asp
                 20                  25                  30

GCT GAT ATT GCC AAA TAT GGC TAT CAA GCT TCA CTC CAA GTA TTT AAC      142
Ala Asp Ile Ala Lys Tyr Gly Tyr Gln Ala Ser Leu Gln Val Phe Asn
             35                  40                  45

GAA CAT TTC TGT GGA GCT TCA ATA TTG AAT AAT TAT TGG ATT GTC ACA      190
Glu His Phe Cys Gly Ala Ser Ile Leu Asn Asn Tyr Trp Ile Val Thr
         50                  55                  60

GCA GCT CAT TGC ATA TAT GAT GAA TTC ACG TAT TCA GTT CGA GTC GGC      238
Ala Ala His Cys Ile Tyr Asp Glu Phe Thr Tyr Ser Val Arg Val Gly
     65                  70                  75

ACC AGT TTC CAA GGA AGA CGT GGT TCC GTT CAT CCT GKG GCA CAA ATT      286
Thr Ser Phe Gln Gly Arg Arg Gly Ser Val His Pro Xaa Ala Gln Ile
 80                  85                  90                  95

ATC AAG CAT CCT GCA TAC GGT AAT GTA ACT GAC ATC GAT ATG GAA KGC      334
Ile Lys His Pro Ala Tyr Gly Asn Val Thr Asp Ile Asp Met Glu Xaa
                100                 105                 110

GCC CTC ATC AAG GTT CGA AGA CCA TTC CGG TTG AAT AAC AGA ACT GTT      382
Ala Leu Ile Lys Val Arg Arg Pro Phe Arg Leu Asn Asn Arg Thr Val
            115                 120                 125

AGA ACA GTC AAA CTT ACT GAT GTT GGA AAA GAC ATG CCA TCA GGA GAA      430
Arg Thr Val Lys Leu Thr Asp Val Gly Lys Asp Met Pro Ser Gly Glu
        130                 135                 140

TTA GCC ACT GTT ACT GGC TGG GGA AAT TTA GGG GAA GAT GAA GAC GAC      478
Leu Ala Thr Val Thr Gly Trp Gly Asn Leu Gly Glu Asp Glu Asp Asp
    145                 150                 155

CCC GAA CAA CTG CAA TAT GTA AAG GTA CCT ATT GTT AAC TGG ACT CAG      526
Pro Glu Gln Leu Gln Tyr Val Lys Val Pro Ile Val Asn Trp Thr Gln
160                 165                 170                 175

TGC AAA ACT ATA TAT GGA AAT GAA GGA CTA ATA ATT ACC CAA AAT ATG      574
Cys Lys Thr Ile Tyr Gly Asn Glu Gly Leu Ile Ile Thr Gln Asn Met
                180                 185                 190

ATT TGT GCT GGT TAT CCT GAA GGC GGT AAG GAC TCT TGC CAA GGA GAT      622
Ile Cys Ala Gly Tyr Pro Glu Gly Gly Lys Asp Ser Cys Gln Gly Asp
            195                 200                 205

AGC GGT GGC CCA CTC GTC AAC TCT AAG GGA GTT CTG CAT GGA ATA GTG      670
Ser Gly Gly Pro Leu Val Asn Ser Lys Gly Val Leu His Gly Ile Val
        210                 215                 220

TCT TGG GGA ATA GGA TGT GCA CGA CCC GAA ATC CCA GGA GTA TAT ACC      718
Ser Trp Gly Ile Gly Cys Ala Arg Pro Glu Ile Pro Gly Val Tyr Thr
    225                 230                 235

CGA GTG GCT TCA AAA CCA ATA AGA GAA TTT ATC AAA ATG CAC ACT GGA      766
Arg Val Ala Ser Lys Pro Ile Arg Glu Phe Ile Lys Met His Thr Gly
240                 245                 250                 255

ATA T AAGAGTTTTA ACTTATAATA TTACAAATAT TTTTTGATAT TCCTTAATTT         820
Ile

CAATGATATA CTAAGACGAG ATGTTTTACA AAATTTTGAT ACTCAACTAA CAAATTAAA     880

CATATTACTA CTCAAATAAA TATCACTAAT AATCAAAAAA AAAAAAAAA AA             932
```

(2) INFORMATION FOR SEQ ID NO: 89:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO: 89:

```
Phe Ile Phe Val Leu Val Cys Val Gly Leu Ser Ala Val Ser Ser Tyr
 1               5                  10                  15

Lys Ile Lys Asp Gly Leu Asp Gly Arg Ile Val Gly Gly Gln Asp Ala
                20                  25                  30

Asp Ile Ala Lys Tyr Gly Tyr Gln Ala Ser Leu Gln Val Phe Asn Glu
            35                  40                  45

His Phe Cys Gly Ala Ser Ile Leu Asn Asn Tyr Trp Ile Val Thr Ala
        50                  55                  60

Ala His Cys Ile Tyr Asp Glu Phe Thr Tyr Ser Val Arg Val Gly Thr
65                  70                  75                  80

Ser Phe Gln Gly Arg Arg Gly Ser Val His Pro Xaa Ala Gln Ile Ile
                85                  90                  95

Lys His Pro Ala Tyr Gly Asn Val Thr Asp Ile Asp Met Glu Xaa Ala
                100                 105                 110

Leu Ile Lys Val Arg Arg Pro Phe Arg Leu Asn Asn Arg Thr Val Arg
                115                 120                 125

Thr Val Lys Leu Thr Asp Val Gly Lys Asp Met Pro Ser Gly Glu Leu
            130                 135                 140

Ala Thr Val Thr Gly Trp Gly Asn Leu Gly Glu Asp Glu Asp Asp Pro
145                 150                 155                 160

Glu Gln Leu Gln Tyr Val Lys Val Pro Ile Val Asn Trp Thr Gln Cys
                165                 170                 175

Lys Thr Ile Tyr Gly Asn Glu Gly Leu Ile Ile Thr Gln Asn Met Ile
                180                 185                 190

Cys Ala Gly Tyr Pro Glu Gly Gly Lys Asp Ser Cys Gln Gly Asp Ser
                195                 200                 205

Gly Gly Pro Leu Val Asn Ser Lys Gly Val Leu His Gly Ile Val Ser
            210                 215                 220

Trp Gly Ile Gly Cys Ala Arg Pro Glu Ile Pro Gly Val Tyr Thr Arg
225                 230                 235                 240

Val Ala Ser Lys Pro Ile Arg Glu Phe Ile Lys Met His Thr Gly Ile
                245                 250                 255
```

(2) INFORMATION FOR SEQ ID NO: 90:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..766
        (D) OTHER INFORMATION: /note= "At pos. bp 560, change G to
            N. At pos. aa 187, substitute Xaa."

(xi) SEQUENCE DESCRIPTION: SEQ ID NO: 90:

```
CCG GCG GTG ATT GTG TCA TTT GTT CTG GCT TGT GCA TTT TCT GTA CAG        48
Pro Ala Val Ile Val Ser Phe Val Leu Ala Cys Ala Phe Ser Val Gln
 1               5                  10                  15

GCT CTT CCA TCA AGC AGA ATT GTC AAT GGA CTT GAA GCA GGA GTT GGA        96
Ala Leu Pro Ser Ser Arg Ile Val Asn Gly Leu Glu Ala Gly Val Gly
            20                  25                  30

CAA TTT CCA ATT CAG GTT TTC TTA GAC TTG ACA AAT ATC AGA GAC GAA       144
Gln Phe Pro Ile Gln Val Phe Leu Asp Leu Thr Asn Ile Arg Asp Glu
        35                  40                  45

AAA TCC AGA TGT GGT GGT GCT TTG TTA TCA GAT TCA TGG GTT TTG ACT       192
Lys Ser Arg Cys Gly Gly Ala Leu Leu Ser Asp Ser Trp Val Leu Thr
50                  55                  60

GCT GCT CAT TGT TTT GAT GAT TTG AAG TCT ATG GTA GTG TCC GTT GGT       240
Ala Ala His Cys Phe Asp Asp Leu Lys Ser Met Val Val Ser Val Gly
65                  70                  75                  80

GCT CAT GAT GTC AGC AAA TCT GAA GAA CCT CAC AGG CAA ACC AGG AAA       288
Ala His Asp Val Ser Lys Ser Glu Glu Pro His Arg Gln Thr Arg Lys
                85                  90                  95

CCT GAA AGG TAC TTC CAG CAT GAA AAA TAC GAC AGG GCA AAT CTT GCA       336
Pro Glu Arg Tyr Phe Gln His Glu Lys Tyr Asp Arg Ala Asn Leu Ala
            100                 105                 110

TAT GAT CTT GGT TTG TTG AAA TTG GAC AAA CCA GTG GAA TTG AAT GAT       384
Tyr Asp Leu Gly Leu Leu Lys Leu Asp Lys Pro Val Glu Leu Asn Asp
        115                 120                 125

TTC GTG AAA CTC ACA AAA TTG AAC AAA GAC AAA ACT GAA ACT TTT GTC       432
Phe Val Lys Leu Thr Lys Leu Asn Lys Asp Lys Thr Glu Thr Phe Val
130                 135                 140

GGC AAA ACT GCA ACT GTT AGT GGA TGG GCA TCT CCA AAG ATT TCC CCT       480
Gly Lys Thr Ala Thr Val Ser Gly Trp Ala Ser Pro Lys Ile Ser Pro
145                 150                 155                 160

GCT TTC GAA TTG CCT GAC AAA CTA CAG TAC ACA ACT TTG GAA GTC CAA       528
Ala Phe Glu Leu Pro Asp Lys Leu Gln Tyr Thr Thr Leu Glu Val Gln
                165                 170                 175

CCA AGT GAA GAC TGC AAA AAA GTA TGG GCC CNT TAC ATG CGC GAC TAC       576
Pro Ser Glu Asp Cys Lys Lys Val Trp Ala Xaa Tyr Met Arg Asp Tyr
            180                 185                 190

ATC CTT TGT GCC AAA TTT GAA AAA CAA AAC ATT TGC ACT GGT GAC AGT       624
Ile Leu Cys Ala Lys Phe Glu Lys Gln Asn Ile Cys Thr Gly Asp Ser
        195                 200                 205

GGC GGT CCA TTG ACC ATT GAT GGT GTC CAA GTT GGT GTG GTG AGT TTT       672
Gly Gly Pro Leu Thr Ile Asp Gly Val Gln Val Gly Val Val Ser Phe
    210                 215                 220

GGA AGT GTT CCT TGT GCC AGA GGA AAT CCT TCA GGA TTT ACC AAT GTT       720
Gly Ser Val Pro Cys Ala Arg Gly Asn Pro Ser Gly Phe Thr Asn Val
225                 230                 235                 240

GCT CAT TTT GTG GAT TGG ATT CAA GAA CAT ACT GGA TTG GAA TTG T         766
Ala His Phe Val Asp Trp Ile Gln Glu His Thr Gly Leu Glu Leu
                245                 250                 255

AAAAATAAAA CTCAAACTAA AAAAAAAATA ATTTAATTGC ACTGAAAAAT TTTTCAAGA      826

AAGTTTGGAT CGTTTTGTAA TTGAATGACA ATAAAAGCGT AAATTAGAAA AAAAAAAA       886

AAAAACTC                                                              894
```

(2) INFORMATION FOR SEQ ID NO: 91:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO: 91:

```
Pro Ala Val Ile Val Ser Phe Val Leu Ala Cys Ala Phe Ser Val Gln
 1               5                  10                  15

Ala Leu Pro Ser Ser Arg Ile Val Asn Gly Leu Glu Ala Gly Val Gly
                20                  25                  30

Gln Phe Pro Ile Gln Val Phe Leu Asp Leu Thr Asn Ile Arg Asp Glu
            35                  40                  45

Lys Ser Arg Cys Gly Gly Ala Leu Leu Ser Asp Ser Trp Val Leu Thr
        50                  55                  60

Ala Ala His Cys Phe Asp Asp Leu Lys Ser Met Val Val Ser Val Gly
 65                 70                  75                  80

Ala His Asp Val Ser Lys Ser Glu Glu Pro His Arg Gln Thr Arg Lys
                85                  90                  95

Pro Glu Arg Tyr Phe Gln His Glu Lys Tyr Asp Arg Ala Asn Leu Ala
            100                 105                 110

Tyr Asp Leu Gly Leu Leu Lys Leu Asp Lys Pro Val Glu Leu Asn Asp
        115                 120                 125

Phe Val Lys Leu Thr Lys Leu Asn Lys Asp Lys Thr Glu Thr Phe Val
130                 135                 140

Gly Lys Thr Ala Thr Val Ser Gly Trp Ala Ser Pro Lys Ile Ser Pro
145                 150                 155                 160

Ala Phe Glu Leu Pro Asp Lys Leu Gln Tyr Thr Thr Leu Glu Val Gln
                165                 170                 175

Pro Ser Glu Asp Cys Lys Lys Val Trp Ala Xaa Tyr Met Arg Asp Tyr
            180                 185                 190

Ile Leu Cys Ala Lys Phe Glu Lys Gln Asn Ile Cys Thr Gly Asp Ser
        195                 200                 205

Gly Gly Pro Leu Thr Ile Asp Gly Val Gln Val Gly Val Val Ser Phe
    210                 215                 220

Gly Ser Val Pro Cys Ala Arg Gly Asn Pro Ser Gly Phe Thr Asn Val
225                 230                 235                 240

Ala His Phe Val Asp Trp Ile Gln Glu His Thr Gly Leu Glu Leu
                245                 250                 255
```

(2) INFORMATION FOR SEQ ID NO: 92:

(i) SEQUENCE CHARACTERISTICS:
        (A) LENGTH: 299 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..299
        (D) OTHER INFORMATION: /note= "At pos. bp 178/179, change
           G/C to V/Y. At pos. aa 59, substitue Xaa."

(xi) SEQUENCE DESCRIPTION: SEQ ID NO: 92:

```
AA TTC GGC ACG AGA GTT AGT CTT TCC AAT TCG ATC AGA CCT TCT TGT        47
   Phe Gly Thr Arg Val Ser Leu Ser Asn Ser Ile Arg Pro Ser Cys
    1               5                  10                  15

TTA TGG GCC AAT GAC GAG TTC GAC ACA GAT AGT TCA ATT GCT ACT GGT       95
Leu Trp Ala Asn Asp Glu Phe Asp Thr Asp Ser Ser Ile Ala Thr Gly
                20                  25                  30
```

```
TGG GGA AAG ATA GAC TAT GCT GAG AGC AGA AGT GAT GAC CTA CTG AAA      143
Trp Gly Lys Ile Asp Tyr Ala Glu Ser Arg Ser Asp Asp Leu Leu Lys
            35                  40                  45

GTA GTA CTG AAA ATT ATT GAT AAT AGG CAA TGC GVY CCC TTA TAC GTT      191
Val Val Leu Lys Ile Ile Asp Asn Arg Gln Cys Xaa Pro Leu Tyr Val
        50                  55                  60

GAT CAG ATT AAT AGA AGA AGA TTG AGA AAT GGA ATT GTA GAT ACA CAG      239
Asp Gln Ile Asn Arg Arg Arg Leu Arg Asn Gly Ile Val Asp Thr Gln
            65                  70                  75

ATG TGT GCA GGA GAA TTG GAT GGT GGC AAA GAC ACT TGC CAG GGA GAT      287
Met Cys Ala Gly Glu Leu Asp Gly Gly Lys Asp Thr Cys Gln Gly Asp
 80                  85                  90                  95

TCA GGT GGT CCT                                                      299
Ser Gly Gly Pro
```

(2) INFORMATION FOR SEQ ID NO: 93:

(i) SEQUENCE CHARACTERISTICS:
        (A) LENGTH: 99 amino acids
        (B) TYPE: amino acid
        (D) TOPOLOGY: linear (ii) MOLECULE TYPE: protein (xi) SEQUENCE DESCRIPTION: SEQ ID NO: 93:

```
Phe Gly Thr Arg Val Ser Leu Ser Asn Ser Ile Arg Pro Ser Cys Leu
 1               5                  10                  15

Trp Ala Asn Asp Glu Phe Asp Thr Asp Ser Ser Ile Ala Thr Gly Trp
            20                  25                  30

Gly Lys Ile Asp Tyr Ala Glu Ser Arg Ser Asp Asp Leu Leu Lys Val
            35                  40                  45

Val Leu Lys Ile Ile Asp Asn Arg Gln Cys Xaa Pro Leu Tyr Val Asp
        50                  55                  60

Gln Ile Asn Arg Arg Arg Leu Arg Asn Gly Ile Val Asp Thr Gln Met
 65                  70                  75                  80

Cys Ala Gly Glu Leu Asp Gly Gly Lys Asp Thr Cys Gln Gly Asp Ser
                85                  90                  95

Gly Gly Pro
```

(2) INFORMATION FOR SEQ ID NO: 94:

(i) SEQUENCE CHARACTERISTICS:
        (A) LENGTH: 266 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..266

(xi) SEQUENCE DESCRIPTION: SEQ ID NO: 94:

```
CTT GCA TAT CCG CTC AAG TTT AGC GAA GAC ATC CAA CCG ATC ATG ATG       48
Leu Ala Tyr Pro Leu Lys Phe Ser Glu Asp Ile Gln Pro Ile Met Met
 1               5                  10                  15

GCC GAA AAG GAC TAC GAA CCA CCA GCA GGA ACC AAG GCT TAT GTG TCT       96
Ala Glu Lys Asp Tyr Glu Pro Pro Ala Gly Thr Lys Ala Tyr Val Ser
            20                  25                  30

GGA TGG GGA AGA ACA TCG TTC GGT GGC CAA TTG TCT AAA AAT CTG CGA      144
Gly Trp Gly Arg Thr Ser Phe Gly Gly Gln Leu Ser Lys Asn Leu Arg
            35                  40                  45
```

-continued

```
GGA GTC GAG TTG GAA ATA ATA GAT CTA TTC GAT TGT TTC CTT TCC TAC     192
Gly Val Glu Leu Glu Ile Ile Asp Leu Phe Asp Cys Phe Leu Ser Tyr
     50                  55                  60

ATG GAT AAA GTA AAC GTG TCC GAA AGG CAA GTT TGC GCT GGA ATC CCC     240
Met Asp Lys Val Asn Val Ser Glu Arg Gln Val Cys Ala Gly Ile Pro
 65                  70                  75                  80

GTT GTA GGT GGT AAA GAT TCT TGC  CA                                 266
Val Val Gly Gly Lys Asp Ser Cys
             85
```

(2) INFORMATION FOR SEQ ID NO: 95:

(i) SEQUENCE CHARACTERISTICS:
        (A) LENGTH: 88 amino acids
        (B) TYPE: amino acid
        (D) TOPOLOGY: linear (ii) MOLECULE TYPE: protein (xi) SEQUENCE DESCRIPTION: SEQ ID NO: 95:

```
Leu Ala Tyr Pro Leu Lys Phe Ser Glu Asp Ile Gln Pro Ile Met Met
 1               5                  10                  15

Ala Glu Lys Asp Tyr Glu Pro Pro Ala Gly Thr Lys Ala Tyr Val Ser
                 20                  25                  30

Gly Trp Gly Arg Thr Ser Phe Gly Gln Leu Ser Lys Asn Leu Arg
             35                  40                  45

Gly Val Glu Leu Glu Ile Ile Asp Leu Phe Asp Cys Phe Leu Ser Tyr
     50                  55                  60

Met Asp Lys Val Asn Val Ser Glu Arg Gln Val Cys Ala Gly Ile Pro
 65                  70                  75                  80

Val Val Gly Gly Lys Asp Ser Cys
             85
```

(2) INFORMATION FOR SEQ ID NO: 96:

(i) SEQUENCE CHARACTERISTICS:
        (A) LENGTH: 378 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..376
        (D) OTHER INFORMATION: /note= "At pos. bp 3, change G to
           S. At pos. bp 270, change A to W. At pos. aa 1 and aa
           90, substitute Xaa."

(xi) SEQUENCE DESCRIPTION: SEQ ID NO: 96:

```
GGS GGT ACT TCC CAC CGT GTT GCC CAA ATC GTC GTC CAC CCA CAA TAC      48
Xaa Gly Thr Ser His Arg Val Ala Gln Ile Val Val His Pro Gln Tyr
 1               5                  10                  15

AAC GGC AAC ACC AAC ATC AAC GAT GTT GCT GTT CTC CGT GTT CAA GAC      96
Asn Gly Asn Thr Asn Ile Asn Asp Val Ala Val Leu Arg Val Gln Asp
                 20                  25                  30

AAA TTC GTA TTA AAC GGC AGA TCA GTT CGC CCC GTT GAC ATG ATC GCT     144
Lys Phe Val Leu Asn Gly Arg Ser Val Arg Pro Val Asp Met Ile Ala
             35                  40                  45

TCT GGT GTT GAC ACT CCA GCT GGA GCT CCC CTT TAC GTC ACT GGA TGG     192
Ser Gly Val Asp Thr Pro Ala Gly Ala Pro Leu Tyr Val Thr Gly Trp
     50                  55                  60
```

```
GGT GCA GTC TAC GAA GGA GGT GCA GGA TCC ACC CAA TTA CTA GGA GTA      240
Gly Ala Val Tyr Glu Gly Gly Ala Gly Ser Thr Gln Leu Leu Gly Val
 65                  70                  75                  80

GGT GTA CCC ATG CGT AGC CAC AAA AAC ACW TGT AAC AGC AAA TAC TCC      288
Gly Val Pro Met Arg Ser His Lys Asn Xaa Cys Asn Ser Lys Tyr Ser
                 85                  90                  95

CAA TTT GGC GGT GTT GCT CCT AGC ATG ATC TGC GCT GGA TTT GAC CAA      336
Gln Phe Gly Gly Val Ala Pro Ser Met Ile Cys Ala Gly Phe Asp Gln
            100                 105                 110

GGC GGT AAG GAC GCT TGT CAA GGA GAC TCT GGT GGT CCT    T TA          378
Gly Gly Lys Asp Ala Cys Gln Gly Asp Ser Gly Gly Pro
        115                 120                 125
```

(2) INFORMATION FOR SEQ ID NO: 97:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO: 97:

```
Xaa Gly Thr Ser His Arg Val Ala Gln Ile Val Val His Pro Gln Tyr
 1                   5                  10                  15

Asn Gly Asn Thr Asn Ile Asn Asp Val Ala Val Leu Arg Val Gln Asp
                 20                  25                  30

Lys Phe Val Leu Asn Gly Arg Ser Val Arg Pro Val Asp Met Ile Ala
             35                  40                  45

Ser Gly Val Asp Thr Pro Ala Gly Ala Pro Leu Tyr Val Thr Gly Trp
 50                  55                  60

Gly Ala Val Tyr Glu Gly Gly Ala Gly Ser Thr Gln Leu Leu Gly Val
 65                  70                  75                  80

Gly Val Pro Met Arg Ser His Lys Asn Xaa Cys Asn Ser Lys Tyr Ser
                 85                  90                  95

Gln Phe Gly Gly Val Ala Pro Ser Met Ile Cys Ala Gly Phe Asp Gln
            100                 105                 110

Gly Gly Lys Asp Ala Cys Gln Gly Asp Ser Gly Gly Pro
        115                 120                 125
```

(2) INFORMATION FOR SEQ ID NO: 98:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..252

(xi) SEQUENCE DESCRIPTION: SEQ ID NO: 98:

```
CGC GCG CCC TGT TGC CCT ACC AGC AGA GAA CGA GGA AAC CGA AAC AGG       48
Arg Ala Pro Cys Cys Pro Thr Ser Arg Glu Arg Gly Asn Arg Asn Arg
 1                   5                  10                  15

GTC ACA CTC ACG GTG ACG GGT TGG GGA ACT ACA GAG AGT ACT GAA TCA       96
Val Thr Leu Thr Val Thr Gly Trp Gly Thr Thr Glu Ser Thr Glu Ser
                 20                  25                  30
```

```
TCA CAC CAC CTG AAA GAA GTT GAA GTG AAC GCT GTA TCT AAT AGT GAA        144
Ser His His Leu Lys Glu Val Glu Val Asn Ala Val Ser Asn Ser Glu
         35                  40                  45

TGT CAA AGG CCT AAT GAA GAT CTT GCT ACT ATA TCA TCA CAT GAG ATA        192
Cys Gln Arg Pro Asn Glu Asp Leu Ala Thr Ile Ser Ser His Glu Ile
 50                  55                  60

TGT GCA AGC GTT CCT GGT GGC GGC AAA GAT TCT TGT CAA GGA GAC TCT        240
Cys Ala Ser Val Pro Gly Gly Gly Lys Asp Ser Cys Gln Gly Asp Ser
 65                  70                  75                  80

GGT GGT CCT TTA                                                        252
Gly Gly Pro Leu
```

(2) INFORMATION FOR SEQ ID NO: 99:

(i) SEQUENCE CHARACTERISTICS:
        (A) LENGTH: 84 amino acids
        (B) TYPE: amino acid
        (D) TOPOLOGY: linear (ii) MOLECULE TYPE: protein (xi) SEQUENCE DESCRIPTION: SEQ ID NO: 99:

```
Arg Ala Pro Cys Cys Pro Thr Ser Arg Glu Arg Gly Asn Arg Asn Arg
 1               5                  10                  15

Val Thr Leu Thr Val Thr Gly Trp Gly Thr Thr Glu Ser Thr Glu Ser
             20                  25                  30

Ser His His Leu Lys Glu Val Glu Val Asn Ala Val Ser Asn Ser Glu
         35                  40                  45

Cys Gln Arg Pro Asn Glu Asp Leu Ala Thr Ile Ser Ser His Glu Ile
 50                  55                  60

Cys Ala Ser Val Pro Gly Gly Gly Lys Asp Ser Cys Gln Gly Asp Ser
 65                  70                  75                  80

Gly Gly Pro Leu
```

(2) INFORMATION FOR SEQ ID NO: 100:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..208

(xi) SEQUENCE DESCRIPTION: SEQ ID NO: 100:

```
CCA ATC CAC GAT AGC CAA TAT GCA CTT TTG CAG ATA TGG GTC AAG GGT         48
Pro Ile His Asp Ser Gln Tyr Ala Leu Leu Gln Ile Trp Val Lys Gly
 1               5                  10                  15

GCA TGT AAG GGT GAT TCC GGT GGC CCC TTA GTC ATC AAT GGA CAA CTT         96
Ala Cys Lys Gly Asp Ser Gly Gly Pro Leu Val Ile Asn Gly Gln Leu
             20                  25                  30

CAT GGA ATT GTT TCC TGG GGC ATT CCT TGC GCT GTC GCA AGC CTG ATG        144
His Gly Ile Val Ser Trp Gly Ile Pro Cys Ala Val Ala Ser Leu Met
         35                  40                  45

TAT TCA CAA GAG TTT CTC ATT ATG TCG ATT GGA TTA AAT CCA AAA TTG        192
Tyr Ser Gln Glu Phe Leu Ile Met Ser Ile Gly Leu Asn Pro Lys Leu
 50                  55                  60
```

```
CCA AAT AAA ATT GTT  T AGAGTATTAA AAAAAAA                            225
Pro Asn Lys Ile Val
65
```

(2) INFORMATION FOR SEQ ID NO: 101:

(i) SEQUENCE CHARACTERISTICS:
        (A) LENGTH: 69 amino acids
        (B) TYPE: amino acid
        (D) TOPOLOGY: linear (ii) MOLECULE TYPE: protein (xi) SEQUENCE DESCRIPTION: SEQ ID NO: 101:

```
Pro Ile His Asp Ser Gln Tyr Ala Leu Leu Gln Ile Trp Val Lys Gly
1               5                   10                  15

Ala Cys Lys Gly Asp Ser Gly Gly Pro Leu Val Ile Asn Gly Gln Leu
            20                  25                  30

His Gly Ile Val Ser Trp Gly Ile Pro Cys Ala Val Ala Ser Leu Met
        35                  40                  45

Tyr Ser Gln Glu Phe Leu Ile Met Ser Ile Gly Leu Asn Pro Lys Leu
    50                  55                  60

Pro Asn Lys Ile Val
65
```

(2) INFORMATION FOR SEQ ID NO: 102:

(i) SEQUENCE CHARACTERISTICS:
        (A) LENGTH: 850 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..758

(xi) SEQUENCE DESCRIPTION: SEQ ID NO: 102:

```
C CTG GTG AAA CTT TTC TTT GTA ATG TAC TGT GCT TGT GCA TTA GCA         46
  Leu Val Lys Leu Phe Phe Val Met Tyr Cys Ala Cys Ala Leu Ala
  1               5                   10                  15

TCG GCA CTG AAG TAC TCC ATC GAT CAT GGT CCT CGT ATC ATC GGA GGT       94
Ser Ala Leu Lys Tyr Ser Ile Asp His Gly Pro Arg Ile Ile Gly Gly
                20                  25                  30

GAA GTT GCA GGT GAA GGA TCA GCA CCT TAC CAG GTG TCC TTA AGA ACC      142
Glu Val Ala Gly Glu Gly Ser Ala Pro Tyr Gln Val Ser Leu Arg Thr
            35                  40                  45

AAG GAA GGA AAT CAT TTT TGC GGT GGA TCA ATA CTA AAT AAG CGA TGG      190
Lys Glu Gly Asn His Phe Cys Gly Gly Ser Ile Leu Asn Lys Arg Trp
        50                  55                  60

GTT GTA ACT GCA GCA CAT TGT CTT GAA CCG GAA ATA TTA GAT TCG GTA      238
Val Val Thr Ala Ala His Cys Leu Glu Pro Glu Ile Leu Asp Ser Val
    65                  70                  75

TAC GTC GGA TCC AAT CAC TTA GAC CGA AAA GGC AGA TAT TAC GAC GTA      286
Tyr Val Gly Ser Asn His Leu Asp Arg Lys Gly Arg Tyr Tyr Asp Val
80                  85                  90                  95

GAA CGG TAT ATA ATT CAT GAA AAA TAT ATA GGA GAA CTA AAT AAT TTT      334
Glu Arg Tyr Ile Ile His Glu Lys Tyr Ile Gly Glu Leu Asn Asn Phe
                100                 105                 110

TAT GCT GAC ATC GGT CTA ATA AAA CTT GAT GAA GAC TTA GAA TTC AAT      382
Tyr Ala Asp Ile Gly Leu Ile Lys Leu Asp Glu Asp Leu Glu Phe Asn
            115                 120                 125
```

-continued

```
GAC AAA GTC AAG CCA ATA AAA ATT CAT GAA AAC ACA ATT CAA GGT GGT        430
Asp Lys Val Lys Pro Ile Lys Ile His Glu Asn Thr Ile Gln Gly Gly
            130                 135                 140

GAA GGG CTT AGA GCA ACA GGT TGG GGA CGT CTT GGT GCT GGT CGC CCA        478
Glu Gly Leu Arg Ala Thr Gly Trp Gly Arg Leu Gly Ala Gly Arg Pro
145                 150                 155

ATT CCT AAT AAA TTG CAG GAG CTA CAA ACA TTT GCT TTA AGT GAT AAA        526
Ile Pro Asn Lys Leu Gln Glu Leu Gln Thr Phe Ala Leu Ser Asp Lys
160                 165                 170                 175

GAT TGT ACA GTA AAA ACT GGT CTT GTA CCA AAG TCA CAA CTT TGT GTT        574
Asp Cys Thr Val Lys Thr Gly Leu Val Pro Lys Ser Gln Leu Cys Val
                180                 185                 190

TTC CGT GCA TCG GAA AAA GGA GTT TGC TTT GGT GAT TCG GGA GGT CCT        622
Phe Arg Ala Ser Glu Lys Gly Val Cys Phe Gly Asp Ser Gly Gly Pro
                195                 200                 205

TTG GCA ATC AAT GGT GAA CTT GTT GGT GTT ACT TCA TTC ATT ATG GGA        670
Leu Ala Ile Asn Gly Glu Leu Val Gly Val Thr Ser Phe Ile Met Gly
            210                 215                 220

ACA TGT GGA GGA GGA CAT CCT GAT GTC TTC GGT CGA GTC CTT GAC TTC        718
Thr Cys Gly Gly Gly His Pro Asp Val Phe Gly Arg Val Leu Asp Phe
225                 230                 235

AAA CCA TGG ATT GAT TCT CAT ATG GCA AAT GAC GGC GCA T AATTCTTTTA       768
Lys Pro Trp Ile Asp Ser His Met Ala Asn Asp Gly Ala
240                 245                 250

TTTAATAATG ATTGAATGTA AAATTATAAA CAAATTGTAA ATTGCATAAA TGATATAAA       828

GCAGGAAATT CGAAAAAAAA AA                                               850
```

(2) INFORMATION FOR SEQ ID NO: 103:

(i) SEQUENCE CHARACTERISTICS:
        (A) LENGTH: 252 amino acids
        (B) TYPE: amino acid
        (D) TOPOLOGY: linear (ii) MOLECULE TYPE: protein (xi) SEQUENCE DESCRIPTION: SEQ ID NO: 103:

```
Leu Val Lys Leu Phe Phe Val Met Tyr Cys Ala Cys Ala Leu Ala Ser
1               5                   10                  15

Ala Leu Lys Tyr Ser Ile Asp His Gly Pro Arg Ile Ile Gly Gly Glu
            20                  25                  30

Val Ala Gly Glu Gly Ser Ala Pro Tyr Gln Val Ser Leu Arg Thr Lys
        35                  40                  45

Glu Gly Asn His Phe Cys Gly Gly Ser Ile Leu Asn Lys Arg Trp Val
    50                  55                  60

Val Thr Ala Ala His Cys Leu Glu Pro Glu Ile Leu Asp Ser Val Tyr
65                  70                  75                  80

Val Gly Ser Asn His Leu Asp Arg Lys Gly Arg Tyr Tyr Asp Val Glu
                85                  90                  95

Arg Tyr Ile Ile His Glu Lys Tyr Ile Gly Glu Leu Asn Asn Phe Tyr
            100                 105                 110

Ala Asp Ile Gly Leu Ile Lys Leu Asp Glu Asp Leu Glu Phe Asn Asp
        115                 120                 125

Lys Val Lys Pro Ile Lys Ile His Glu Asn Thr Ile Gln Gly Gly Glu
    130                 135                 140

Gly Leu Arg Ala Thr Gly Trp Gly Arg Leu Gly Ala Gly Arg Pro Ile
145                 150                 155                 160
```

```
Pro Asn Lys Leu Gln Glu Leu Gln Thr Phe Ala Leu Ser Asp Lys Asp
            165                 170                 175

Cys Thr Val Lys Thr Gly Leu Val Pro Lys Ser Gln Leu Cys Val Phe
            180                 185                 190

Arg Ala Ser Glu Lys Gly Val Cys Phe Gly Asp Ser Gly Gly Pro Leu
            195                 200                 205

Ala Ile Asn Gly Glu Leu Val Gly Val Thr Ser Phe Ile Met Gly Thr
    210                 215                 220

Cys Gly Gly Gly His Pro Asp Val Phe Gly Arg Val Leu Asp Phe Lys
225                 230                 235                 240

Pro Trp Ile Asp Ser His Met Ala Asn Asp Gly Ala
            245                 250
```

(2) INFORMATION FOR SEQ ID NO: 104:

(i) SEQUENCE CHARACTERISTICS:
        (A) LENGTH: 252 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..251
        (D) OTHER INFORMATION: /note= "At pos. bp 4, change A to
            R. At pos. aa 2, substitute Xaa."

(xi) SEQUENCE DESCRIPTION: SEQ ID NO: 104:

```
GCA RGG ATT CGG CAC GAG AAT TTA TTA AGC GCA TTA TTT GCA AGT GTA      48
Ala Xaa Ile Arg His Glu Asn Leu Leu Ser Ala Leu Phe Ala Ser Val
 1               5                  10                  15

ATT TGC TCC TTT AAC GCG GAA GTA CAA AAT CGA ATC GTT GGT GGC AAT      96
Ile Cys Ser Phe Asn Ala Glu Val Gln Asn Arg Ile Val Gly Gly Asn
                20                  25                  30

GAT GTA AGT ATT TCA AAA ATT GGG TGG CAA GTA TCT ATT CAA AGT AAT     144
Asp Val Ser Ile Ser Lys Ile Gly Trp Gln Val Ser Ile Gln Ser Asn
            35                  40                  45

AAC CAA CAT TTC TGT GGT GGT TCA ATC ATT GCT AAA GAT TGG GTA CTG     192
Asn Gln His Phe Cys Gly Gly Ser Ile Ile Ala Lys Asp Trp Val Leu
        50                  55                  60

ACT TCT TCT CAA TGC GTC GTG GAC AAA CAA AGT CCA CCG AAG GAT TTA     240
Thr Ser Ser Gln Cys Val Val Asp Lys Gln Ser Pro Pro Lys Asp Leu
 65                 70                  75                  80

ACT GTT CGT  GT T                                                   252
Thr Val Arg
```

(2) INFORMATION FOR SEQ ID NO: 105:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO: 105:

```
Ala Xaa Ile Arg His Glu Asn Leu Leu Ser Ala Leu Phe Ala Ser Val
 1               5                  10                  15

Ile Cys Ser Phe Asn Ala Glu Val Gln Asn Arg Ile Val Gly Gly Asn
                20                  25                  30
```

```
Asp Val Ser Ile Ser Lys Ile Gly Trp Gln Val Ser Ile Gln Ser Asn
         35                  40                  45

Asn Gln His Phe Cys Gly Gly Ser Ile Ile Ala Lys Asp Trp Val Leu
         50                  55                  60

Thr Ser Ser Gln Cys Val Val Asp Lys Gln Ser Pro Pro Lys Asp Leu
 65                  70                  75                  80

Thr Val Arg (2) INFORMATION FOR SEQ ID NO: 106:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..534

(xi) SEQUENCE DESCRIPTION: SEQ ID NO: 106:

TCA AAT CGG ATT GTT AAT GGA GTT AAT GCC AAA AAC GGT TCT GCT CCA        48
Ser Asn Arg Ile Val Asn Gly Val Asn Ala Lys Asn Gly Ser Ala Pro
 1               5                  10                  15

TAT ATG GCT TCT CTA AGA GAT GTT ATG GAA ACC ATT TCT GTG GAG CAT        96
Tyr Met Ala Ser Leu Arg Asp Val Met Glu Thr Ile Ser Val Glu His
                 20                  25                  30

CGA TAT TGG ATG AAC CGC TGG ATT CTT ACT GCT GCC CAT TGC CTT ACT       144
Arg Tyr Trp Met Asn Arg Trp Ile Leu Thr Ala Ala His Cys Leu Thr
             35                  40                  45

GAC GGT TAT CTA GAT ACA GTC TAC GTT GGT TCA AAT CAT CTT TCT GGC       192
Asp Gly Tyr Leu Asp Thr Val Tyr Val Gly Ser Asn His Leu Ser Gly
         50                  55                  60

GAC GGA GAG TAC TAC AAT GTA GAA GAA CAA GTC ATC CAT GAT AAA TAT       240
Asp Gly Glu Tyr Tyr Asn Val Glu Glu Gln Val Ile His Asp Lys Tyr
 65                  70                  75                  80

TTT GGT CAA ACA ACC GGC TTC AAA AAT GAT ATT GCT CTC GTC AAA GTT       288
Phe Gly Gln Thr Thr Gly Phe Lys Asn Asp Ile Ala Leu Val Lys Val
                 85                  90                  95

TCT AGT GCT ATA AAA CTT AGC AAA AAT GTT CGT CCC ATC AAA TTG CAC       336
Ser Ser Ala Ile Lys Leu Ser Lys Asn Val Arg Pro Ile Lys Leu His
                100                 105                 110

AAA GAT TTT ATA CGC GGA GGT GAA AAA TTG AAA ATT ACT GGA TGG GGA       384
Lys Asp Phe Ile Arg Gly Gly Glu Lys Leu Lys Ile Thr Gly Trp Gly
            115                 120                 125

TTG ACC AAT CAA ACT CAT GGT GAA GTT CCT GAT GCT CTT CAA GAG TTA       432
Leu Thr Asn Gln Thr His Gly Glu Val Pro Asp Ala Leu Gln Glu Leu
130                 135                 140

CAG GTA GAA GCA CTT TCT AAC TCT AAA TGC AAG GCA ATT ACT GGT GTC       480
Gln Val Glu Ala Leu Ser Asn Ser Lys Cys Lys Ala Ile Thr Gly Val
145                 150                 155                 160

CAT CTT CCT GCT CAT CTC TGC ACC TTC AGA GCT CCT CAA AAG GGT GTA       528
His Leu Pro Ala His Leu Cys Thr Phe Arg Ala Pro Gln Lys Gly Val
                165                 170                 175

TGC CAG                                                                534
Cys Gln
```

-continued (2) INFORMATION FOR SEQ ID NO: 107:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO: 107:

```
Ser Asn Arg Ile Val Asn Gly Val Asn Ala Lys Asn Gly Ser Ala Pro
 1               5                  10                  15

Tyr Met Ala Ser Leu Arg Asp Val Met Glu Thr Ile Ser Val Glu His
            20                  25                  30

Arg Tyr Trp Met Asn Arg Trp Ile Leu Thr Ala Ala His Cys Leu Thr
        35                  40                  45

Asp Gly Tyr Leu Asp Thr Val Tyr Val Gly Ser Asn His Leu Ser Gly
    50                  55                  60

Asp Gly Glu Tyr Tyr Asn Val Glu Glu Gln Val Ile His Asp Lys Tyr
65                  70                  75                  80

Phe Gly Gln Thr Thr Gly Phe Lys Asn Asp Ile Ala Leu Val Lys Val
                85                  90                  95

Ser Ser Ala Ile Lys Leu Ser Lys Asn Val Arg Pro Ile Lys Leu His
                100                 105                 110

Lys Asp Phe Ile Arg Gly Gly Glu Lys Leu Lys Ile Thr Gly Trp Gly
            115                 120                 125

Leu Thr Asn Gln Thr His Gly Glu Val Pro Asp Ala Leu Gln Glu Leu
130                 135                 140

Gln Val Glu Ala Leu Ser Asn Ser Lys Cys Lys Ala Ile Thr Gly Val
145                 150                 155                 160

His Leu Pro Ala His Leu Cys Thr Phe Arg Ala Pro Gln Lys Gly Val
                165                 170                 175

Cys Gln
```

(2) INFORMATION FOR SEQ ID NO: 108:

(i) SEQUENCE CHARACTERISTICS:
        (A) LENGTH: 359 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..359

(xi) SEQUENCE DESCRIPTION: SEQ ID NO: 108:

```
GGG TTC GAA TTT GTG GAT CGA AAA GGC AGA TAT TAC GAT GTA GAA AGA    48
Gly Phe Glu Phe Val Asp Arg Lys Gly Arg Tyr Tyr Asp Val Glu Arg
 1               5                  10                  15

TTT GTG ATG CAC CAT AAT TAT ACT GGA AAG ATA GTT GCC AAT GTC GCT    96
Phe Val Met His His Asn Tyr Thr Gly Lys Ile Val Ala Asn Val Ala
            20                  25                  30

GAT ATA GGT CTA ATA AAA CTA GCA GAA GAT ATA AAA TTC AGT GAC AAG   144
Asp Ile Gly Leu Ile Lys Leu Ala Glu Asp Ile Lys Phe Ser Asp Lys
        35                  40                  45

GTA CAA CCT GTA AAA ATT CAT CAA ACT CAA ATC AAG GGC GGA GAG ATT   192
Val Gln Pro Val Lys Ile His Gln Thr Gln Ile Lys Gly Gly Glu Ile
    50                  55                  60
```

```
TGC AAA GCT ACT GGA TGG GGC AGG TTG GGT GCT GAT CAG CCT GTA CCA     240
Cys Lys Ala Thr Gly Trp Gly Arg Leu Gly Ala Asp Gln Pro Val Pro
 65              70                  75                  80

AAT AAA TTA CAA CAA TTG GAG ACA ATT GCT ATT AGT GAT GAG AAA TGT     288
Asn Lys Leu Gln Gln Leu Glu Thr Ile Ala Ile Ser Asp Glu Lys Cys
                 85                  90                  95

TAT GCA GAT ACA GGG TTT TTA GAA CCT ACA TCT CAA ATA TGT GTA TTC     336
Tyr Ala Asp Thr Gly Phe Leu Glu Pro Thr Ser Gln Ile Cys Val Phe
            100                 105                 110

AGT GCA TTT GGA AAA GGA GTT  GT                                     359
Ser Ala Phe Gly Lys Gly Val
        115
```

(2) INFORMATION FOR SEQ ID NO: 109:

(i) SEQUENCE CHARACTERISTICS:
        (A) LENGTH: 119 amino acids
        (B) TYPE: amino acid
        (D) TOPOLOGY: linear (ii) MOLECULE TYPE: protein (xi) SEQUENCE DESCRIPTION: SEQ ID NO: 109:

```
Gly Phe Glu Phe Val Asp Arg Lys Gly Arg Tyr Tyr Asp Val Glu Arg
 1               5                  10                  15

Phe Val Met His His Asn Tyr Thr Gly Lys Ile Val Ala Asn Val Ala
                20                  25                  30

Asp Ile Gly Leu Ile Lys Leu Ala Glu Asp Ile Lys Phe Ser Asp Lys
            35                  40                  45

Val Gln Pro Val Lys Ile His Gln Thr Gln Ile Lys Gly Gly Glu Ile
        50                  55                  60

Cys Lys Ala Thr Gly Trp Gly Arg Leu Gly Ala Asp Gln Pro Val Pro
 65              70                  75                  80

Asn Lys Leu Gln Gln Leu Glu Thr Ile Ala Ile Ser Asp Glu Lys Cys
                 85                  90                  95

Tyr Ala Asp Thr Gly Phe Leu Glu Pro Thr Ser Gln Ile Cys Val Phe
            100                 105                 110

Ser Ala Phe Gly Lys Gly Val
        115
```

(2) INFORMATION FOR SEQ ID NO: 110:

(i) SEQUENCE CHARACTERISTICS:
        (A) LENGTH: 841 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..746
        (D) OTHER INFORMATION: /note= "At pos. bp 306, change A to
           M. At pos. bp 382, change A to M. At pos. bp. 394,
           change G to S. At pos. aa 102, 127 and 131, substitute
           Xaa."

(xi) SEQUENCE DESCRIPTION: SEQ ID NO: 110:

```
C TTA GCA ATT GTA TGT GCT CTC GCT GTC TGC ACA TTC GGT GCC AGT       46
  Leu Ala Ile Val Cys Ala Leu Ala Val Cys Thr Phe Gly Ala Ser
   1               5                  10                  15
```

```
GTT CCA GAA TCA TGG AAA AGA TTA GAT AGT AGA ATC GTA GGA GGA CAC      94
Val Pro Glu Ser Trp Lys Arg Leu Asp Ser Arg Ile Val Gly Gly His
             20                  25                  30

GAT ACC AGC ATC GAT AAA CAC CCT CAT CAA GTA TCT TTA TTG TAC TCC     142
Asp Thr Ser Ile Asp Lys His Pro His Gln Val Ser Leu Leu Tyr Ser
             35                  40                  45

AGC CAC AAT TGT GGT GGT TCC TTG ATT GCC AAA AAC TGG TGG GTT TTG     190
Ser His Asn Cys Gly Gly Ser Leu Ile Ala Lys Asn Trp Trp Val Leu
             50                  55                  60

ACT GCA GCT CAT TGC ATT GGA GTT AAC AAA TAC AAT GTC CGT GTA GGA     238
Thr Ala Ala His Cys Ile Gly Val Asn Lys Tyr Asn Val Arg Val Gly
             65                  70                  75

AGT TCC ATC GTA AAC AGC GGT GGT ATC TTG CAT AAA GTT AAA AAC CAT     286
Ser Ser Ile Val Asn Ser Gly Gly Ile Leu His Lys Val Lys Asn His
         80                  85                  90                  95

TAC AGA CAT CCA AAA TAC AMC GCA GCT GCT ATT GAC TTT GAT TAC GCA     334
Tyr Arg His Pro Lys Tyr Xaa Ala Ala Ala Ile Asp Phe Asp Tyr Ala
                     100                 105                 110

CTC TTA GAA CTC GAA ACT CCT GTT CAA CTC ACA AAT GAT GTG TCC ATM     382
Leu Leu Glu Leu Glu Thr Pro Val Gln Leu Thr Asn Asp Val Ser Xaa
             115                 120                 125

ATA AAA TTG GTS GAT GAA GGA GTA GAT CTT AAA CCT GGT ACC TTG TTA     430
Ile Lys Leu Xaa Asp Glu Gly Val Asp Leu Lys Pro Gly Thr Leu Leu
             130                 135                 140

ACT GTT ACT GGA TGG GGA TCA ACT GGA AAT GGA CCT TCA ACC AAT GTT     478
Thr Val Thr Gly Trp Gly Ser Thr Gly Asn Gly Pro Ser Thr Asn Val
         145                 150                 155

TTG CAA GAA GTT CAA GTA CCA CAT GTC GAC CAA ACC ACT TGC TCC AAA     526
Leu Gln Glu Val Gln Val Pro His Val Asp Gln Thr Thr Cys Ser Lys
160                 165                 170                 175

TCT TAC CCA GGA AGT TTG ACT GAT CGT ATG TTC TGC GCT GGT TAT TTG     574
Ser Tyr Pro Gly Ser Leu Thr Asp Arg Met Phe Cys Ala Gly Tyr Leu
                 180                 185                 190

GGA CAA GGA GGC AAG GAC TCA TGC CAA GGT GAT TCT GGT GGC CCA GTT     622
Gly Gln Gly Gly Lys Asp Ser Cys Gln Gly Asp Ser Gly Gly Pro Val
             195                 200                 205

GTT GTC AAT GGT GTT CAA CAT GGA ATT GTC TCA TGG GGT CGT GGT TGT     670
Val Val Asn Gly Val Gln His Gly Ile Val Ser Trp Gly Arg Gly Cys
         210                 215                 220

GCA CTT CCT GAT TAT CCT GGA GTT TAC TCT AAA ATC TCT ACC GCT CGC     718
Ala Leu Pro Asp Tyr Pro Gly Val Tyr Ser Lys Ile Ser Thr Ala Arg
225                 230                 235

AGC TGG ATC AAG GAA GTG TCT GGT GTT T AATTTATTCT TGAAATCTCT         766
Ser Trp Ile Lys Glu Val Ser Gly Val
240                 245

ATTTTGTATT ATTTATGTAT ATAGTAAGAG TTGTAAATAT AAATAGTTAC ATCTAAAAA    826

AAAAAAAAAA AAAAA                                                    841

(2) INFORMATION FOR SEQ ID NO: 111:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO: 111:

Leu Ala Ile Val Cys Ala Leu Ala Val Cys Thr Phe Gly Ala Ser Val
1               5                   10                  15
```

```
Pro Glu Ser Trp Lys Arg Leu Asp Ser Arg Ile Val Gly Gly His Asp
          20                  25                  30

Thr Ser Ile Asp Lys His Pro His Gln Val Ser Leu Leu Tyr Ser Ser
        35                  40                  45

His Asn Cys Gly Gly Ser Leu Ile Ala Lys Asn Trp Trp Val Leu Thr
 50                  55                  60

Ala Ala His Cys Ile Gly Val Asn Lys Tyr Asn Val Arg Val Gly Ser
 65                  70                  75                  80

Ser Ile Val Asn Ser Gly Gly Ile Leu His Lys Val Lys Asn His Tyr
                85                  90                  95

Arg His Pro Lys Tyr Xaa Ala Ala Ile Asp Phe Asp Tyr Ala Leu
            100                 105                 110

Leu Glu Leu Glu Thr Pro Val Gln Leu Thr Asn Asp Val Ser Xaa Ile
        115                 120                 125

Lys Leu Xaa Asp Glu Gly Val Asp Leu Lys Pro Gly Thr Leu Leu Thr
    130                 135                 140

Val Thr Gly Trp Gly Ser Thr Gly Asn Gly Pro Ser Thr Asn Val Leu
145                 150                 155                 160

Gln Glu Val Gln Val Pro His Val Asp Gln Thr Thr Cys Ser Lys Ser
                165                 170                 175

Tyr Pro Gly Ser Leu Thr Asp Arg Met Phe Cys Ala Gly Tyr Leu Gly
            180                 185                 190

Gln Gly Gly Lys Asp Ser Cys Gln Gly Asp Ser Gly Pro Val Val
        195                 200                 205

Val Asn Gly Val Gln His Gly Ile Val Ser Trp Gly Arg Gly Cys Ala
    210                 215                 220

Leu Pro Asp Tyr Pro Gly Val Tyr Ser Lys Ile Ser Thr Ala Arg Ser
225                 230                 235                 240

Trp Ile Lys Glu Val Ser Gly Val
                245
```

(2) INFORMATION FOR SEQ ID NO: 112:

(i) SEQUENCE CHARACTERISTICS:
        (A) LENGTH: 1580 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..1491

(xi) SEQUENCE DESCRIPTION: SEQ ID NO: 112:

```
GG CAC GAG TTT TGT GCG AGT GTC AGA TAT TGC AGC TCT ATG AGT AAC         47
   His Glu Phe Cys Ala Ser Val Arg Tyr Cys Ser Ser Met Ser Asn
    1               5                  10                  15

AAG AAA GGA TTA GTA CTG GGC ATC TAC GAC AAT GAA TTC GAT AAA AAA        95
Lys Lys Gly Leu Val Leu Gly Ile Tyr Asp Asn Glu Phe Asp Lys Lys
                20                  25                  30

ATA AGG TTA ACG CCA ACT GCT GAA CAA TTC AAT CGG CGA TTG CAG GGG       143
Ile Arg Leu Thr Pro Thr Ala Glu Gln Phe Asn Arg Arg Leu Gln Gly
            35                  40                  45

CGT TTA CTA GAT CTA ATT CAT TTG AGT GGA CCC ATT AAA TTG GGC AAG       191
Arg Leu Leu Asp Leu Ile His Leu Ser Gly Pro Ile Lys Leu Gly Lys
        50                  55                  60
```

```
AGC CGT ATT TTC TGG GAT CTC GAT GAA TTC GGC GCA GTT GCA GTT GCA       239
Ser Arg Ile Phe Trp Asp Leu Asp Glu Phe Gly Ala Val Ala Val Ala
    65                  70                  75

GGT TTG GGA AAT CAC TCC CCC TGC GAA CTC CTG GAA GAA CTC GAT GTT       287
Gly Leu Gly Asn His Ser Pro Cys Glu Leu Leu Glu Glu Leu Asp Val
80                  85                  90                  95

TTG CGC GAA AAT GCC AGA ATA GCT GCC GGT GCT GGT TGC CAA GCT CTT       335
Leu Arg Glu Asn Ala Arg Ile Ala Ala Gly Ala Gly Cys Gln Ala Leu
                100                 105                 110

GCC GCC GAT GGA ATC ACT ACC ATT AGC GTT GAA GTA TGG AGC ACC CGG       383
Ala Ala Asp Gly Ile Thr Thr Ile Ser Val Glu Val Trp Ser Thr Arg
            115                 120                 125

AGG CGG CCA TGC GAA GGT GCA ATA CTA TCG ACG TTC AAA TTC AGG TCA       431
Arg Arg Pro Cys Glu Gly Ala Ile Leu Ser Thr Phe Lys Phe Arg Ser
        130                 135                 140

ACA GAA GAA GAG TCC AAG TGT AAG CCG ATA CCT ACC ATA ACC CCT TAC       479
Thr Glu Glu Glu Ser Lys Cys Lys Pro Ile Pro Thr Ile Thr Pro Tyr
    145                 150                 155

TGC CTT CAA GAT AAA GAT GCT CCA TTA TGG GAA CTT GGC CAA GTA TCA       527
Cys Leu Gln Asp Lys Asp Ala Pro Leu Trp Glu Leu Gly Gln Val Ser
160                 165                 170                 175

GCA GCA GCT CAA AAC TGG GCT CGT ACA TTG ATG GAT ACA CCA GCA AAT       575
Ala Ala Ala Gln Asn Trp Ala Arg Thr Leu Met Asp Thr Pro Ala Asn
                180                 185                 190

CAA ATG ACA CCA TTT TTG TTC GCC GAA GCC GCC AAA GAA AAT TTA GTG       623
Gln Met Thr Pro Phe Leu Phe Ala Glu Ala Ala Lys Glu Asn Leu Val
            195                 200                 205

CCA TTA GGA GTG AAA GTT GAA GCT AGA GAT CGG AAA TGG GCG GTA AGC       671
Pro Leu Gly Val Lys Val Glu Ala Arg Asp Arg Lys Trp Ala Val Ser
        210                 215                 220

ATG AAA ATG GGA TCC TTC TTG TCT GTC GCT CGT GGC TCC AAT GAA CCA       719
Met Lys Met Gly Ser Phe Leu Ser Val Ala Arg Gly Ser Asn Glu Pro
    225                 230                 235

CCA GTT TTT CTT GAA ATT TCT TAT TGT GGT GGT CCA AAA GAT GAG GCA       767
Pro Val Phe Leu Glu Ile Ser Tyr Cys Gly Gly Pro Lys Asp Glu Ala
240                 245                 250                 255

CCG TTC GCA CTT GTT GGA AAG GGT GTC ACT TTC GAT ACT GGC GGT ATT       815
Pro Phe Ala Leu Val Gly Lys Gly Val Thr Phe Asp Thr Gly Gly Ile
                260                 265                 270

AGC ATC AAA CCG AGT GCA TCC ATG GAC GAA ATG CGT GGA GAT ATG GGA       863
Ser Ile Lys Pro Ser Ala Ser Met Asp Glu Met Arg Gly Asp Met Gly
            275                 280                 285

GGA GCT GCT TGC GTT GTT TCT ACA TTG GCA CAA TTG AAA GCA CCA GTC       911
Gly Ala Ala Cys Val Val Ser Thr Leu Ala Gln Leu Lys Ala Pro Val
        290                 295                 300

AAC GTC GTC GGT CTT ATC CCC TTA ACC GAG AAT ATG CCA GGT GGT AAA       959
Asn Val Val Gly Leu Ile Pro Leu Thr Glu Asn Met Pro Gly Gly Lys
    305                 310                 315

GCA ACA AAA CCT GGT GAC GTC GTT GTT GCG ATG AAT GGG AAA TCG ATT      1007
Ala Thr Lys Pro Gly Asp Val Val Val Ala Met Asn Gly Lys Ser Ile
320                 325                 330                 335

TGC GTG GAC AAT ACA GAT GCT GAA GGC CGT TTG ATT TTA GCT GAC GCT      1055
Cys Val Asp Asn Thr Asp Ala Glu Gly Arg Leu Ile Leu Ala Asp Ala
                340                 345                 350

TTA TGT TAC TCG GCA CAC TTC AAG CCA AAA TGG GTT CTA GAT ATA GCT      1103
Leu Cys Tyr Ser Ala His Phe Lys Pro Lys Trp Val Leu Asp Ile Ala
            355                 360                 365

ACA TTG ACT GGA GCT ATG AGA GTT GCT CTA GGT GAT TGT GCT ACT GGT      1151
Thr Leu Thr Gly Ala Met Arg Val Ala Leu Gly Asp Cys Ala Thr Gly
        370                 375                 380
```

```
GTA TTT TCT TCA TGC GAT AAT CTC TGG AAC ACA CTG CAC GAA GCT GGT      1199
Val Phe Ser Ser Cys Asp Asn Leu Trp Asn Thr Leu His Glu Ala Gly
    385                 390                 395

AGA GTA ACT GGA GAT AGA ATG TGG AGA TTC CCT CTT TTT AAG CAC TAC      1247
Arg Val Thr Gly Asp Arg Met Trp Arg Phe Pro Leu Phe Lys His Tyr
400                 405                 410                 415

GCG AAT CGT GTA ACA GAA TAT TCC GGT TAC GAT GTG AAC AAC ATA GGA      1295
Ala Asn Arg Val Thr Glu Tyr Ser Gly Tyr Asp Val Asn Asn Ile Gly
                420                 425                 430

AAG GGC AAA GGG GGA GGC AGT TGC CTA GCA GCT GCT TTC CTT AAT CAG      1343
Lys Gly Lys Gly Gly Gly Ser Cys Leu Ala Ala Ala Phe Leu Asn Gln
            435                 440                 445

TTT AGA CCT GAG GAC GTA CCC TGG ATG CAC TTG GAC ATT GCT GGA GTA      1391
Phe Arg Pro Glu Asp Val Pro Trp Met His Leu Asp Ile Ala Gly Val
        450                 455                 460

ATG AGC GAT TGC TCT GAT CAG TCC TAT CTT CCT AAG GGA ATG ACA GGG      1439
Met Ser Asp Cys Ser Asp Gln Ser Tyr Leu Pro Lys Gly Met Thr Gly
    465                 470                 475

CGA CCT ACC AGA ACT CTT GTT CAA TTT ATT CAA AGC CAA AAG CGT CAT      1487
Arg Pro Thr Arg Thr Leu Val Gln Phe Ile Gln Ser Gln Lys Arg His
480                 485                 490                 495

TCT T GAATGCATTT AAGAAACATA TGTCACCTAA CACCTTTACA TGCGCACCTC         1541
Ser

TGCTTAGCCA AACCACTTTT GTACAAAACC ATATTTTTA                           1580

(2) INFORMATION FOR SEQ ID NO: 113:

(i) SEQUENCE CHARACTERISTICS:
        (A) LENGTH: 496 amino acids
        (B) TYPE: amino acid
        (D) TOPOLOGY: linear (ii) MOLECULE TYPE: protein (xi) SEQUENCE DESCRIPTION: SEQ ID NO: 113:

His Glu Phe Cys Ala Ser Val Arg Tyr Cys Ser Ser Met Ser Asn Lys
 1               5                  10                  15

Lys Gly Leu Val Leu Gly Ile Tyr Asp Asn Glu Phe Asp Lys Lys Ile
            20                  25                  30

Arg Leu Thr Pro Thr Ala Glu Gln Phe Asn Arg Arg Leu Gln Gly Arg
        35                  40                  45

Leu Leu Asp Leu Ile His Leu Ser Gly Pro Ile Lys Leu Gly Lys Ser
    50                  55                  60

Arg Ile Phe Trp Asp Leu Asp Glu Phe Gly Ala Val Ala Val Ala Gly
65                  70                  75                  80

Leu Gly Asn His Ser Pro Cys Glu Leu Leu Glu Glu Leu Asp Val Leu
                85                  90                  95

Arg Glu Asn Ala Arg Ile Ala Ala Gly Ala Gly Cys Gln Ala Leu Ala
            100                 105                 110

Ala Asp Gly Ile Thr Thr Ile Ser Val Glu Val Trp Ser Thr Arg Arg
        115                 120                 125

Arg Pro Cys Glu Gly Ala Ile Leu Ser Thr Phe Lys Phe Arg Ser Thr
    130                 135                 140

Glu Glu Glu Ser Lys Cys Lys Pro Ile Pro Thr Ile Thr Pro Tyr Cys
145                 150                 155                 160

Leu Gln Asp Lys Asp Ala Pro Leu Trp Glu Leu Gly Gln Val Ser Ala
                165                 170                 175
```

-continued

```
Ala Ala Gln Asn Trp Ala Arg Thr Leu Met Asp Thr Pro Ala Asn Gln
            180                 185                 190

Met Thr Pro Phe Leu Phe Ala Glu Ala Ala Lys Glu Asn Leu Val Pro
        195                 200                 205

Leu Gly Val Lys Val Glu Ala Arg Asp Arg Lys Trp Ala Val Ser Met
    210                 215                 220

Lys Met Gly Ser Phe Leu Ser Val Ala Arg Gly Ser Asn Glu Pro Pro
225                 230                 235                 240

Val Phe Leu Glu Ile Ser Tyr Cys Gly Gly Pro Lys Asp Glu Ala Pro
                245                 250                 255

Phe Ala Leu Val Gly Lys Gly Val Thr Phe Asp Thr Gly Ile Ser
            260                 265                 270

Ile Lys Pro Ser Ala Ser Met Asp Glu Met Arg Gly Asp Met Gly Gly
        275                 280                 285

Ala Ala Cys Val Val Ser Thr Leu Ala Gln Leu Lys Ala Pro Val Asn
        290                 295                 300

Val Val Gly Leu Ile Pro Leu Thr Glu Asn Met Pro Gly Gly Lys Ala
305                 310                 315                 320

Thr Lys Pro Gly Asp Val Val Ala Met Asn Gly Lys Ser Ile Cys
                325                 330                 335

Val Asp Asn Thr Asp Ala Glu Gly Arg Leu Ile Leu Ala Asp Ala Leu
            340                 345                 350

Cys Tyr Ser Ala His Phe Lys Pro Lys Trp Val Leu Asp Ile Ala Thr
            355                 360                 365

Leu Thr Gly Ala Met Arg Val Ala Leu Gly Asp Cys Ala Thr Gly Val
        370                 375                 380

Phe Ser Ser Cys Asp Asn Leu Trp Asn Thr Leu His Glu Ala Gly Arg
385                 390                 395                 400

Val Thr Gly Asp Arg Met Trp Arg Phe Pro Leu Phe Lys His Tyr Ala
                405                 410                 415

Asn Arg Val Thr Glu Tyr Ser Gly Tyr Asp Val Asn Asn Ile Gly Lys
            420                 425                 430

Gly Lys Gly Gly Gly Ser Cys Leu Ala Ala Ala Phe Leu Asn Gln Phe
        435                 440                 445

Arg Pro Glu Asp Val Pro Trp Met His Leu Asp Ile Ala Gly Val Met
        450                 455                 460

Ser Asp Cys Ser Asp Gln Ser Tyr Leu Pro Lys Gly Met Thr Gly Arg
465                 470                 475                 480

Pro Thr Arg Thr Leu Val Gln Phe Ile Gln Ser Gln Lys Arg His Ser
                485                 490                 495
```

(2) INFORMATION FOR SEQ ID NO: 114:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 114:

GAGCTCTCGA GAGTTGTTGG AGGACTGGAA GC        32

```
(2) INFORMATION FOR SEQ ID NO: 115:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 115:

GGACCTCGAG AATTAGTTAT TTTCCATGGT C                                  31

(2) INFORMATION FOR SEQ ID NO: 116:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 116:

GAGCTCTCGA GCATCGTCGG CGGCACCAGT G                                  31

(2) INFORMATION FOR SEQ ID NO: 117:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 117:

GGACGAATTC TTAAAGACCA GTTTTTTTGC G                                  31

(2) INFORMATION FOR SEQ ID NO: 118:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 118:

GAGCTCTCGA GTATCATCGG AGGTGAAGTT GC                                 32

(2) INFORMATION FOR SEQ ID NO: 119:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 119:

GGACCTCGAG AATTATGCGC CGTCATTTGC                                    30
```

(2) INFORMATION FOR SEQ ID NO: 120:

(i) SEQUENCE CHARACTERISTICS:
        (A) LENGTH: 806 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..736
        (D) OTHER INFORMATION: /note= "At pos. bp 656, change G to
            S. At pos. aa 219, substitute Xaa."

(xi) SEQUENCE DESCRIPTION: SEQ ID NO: 120:

```
C TCG CAG TCT GCA CCC TTG GTG CTA GGC GTT CCT GAC TTT TGG AAC         46
  Ser Gln Ser Ala Pro Leu Val Leu Gly Val Pro Asp Phe Trp Asn
   1               5                  10                  15

AGG TTA GAT GGC AGA ATC GTT GGA GGA CAC GAT ACT AGC ATT GAC AAA       94
Arg Leu Asp Gly Arg Ile Val Gly Gly His Asp Thr Ser Ile Asp Lys
                 20                  25                  30

CAT CCT CAT CAA GTA TCT TTG ATT TAC ACA AAC CAC AAT TGT GGT GGT      142
His Pro His Gln Val Ser Leu Ile Tyr Thr Asn His Asn Cys Gly Gly
             35                  40                  45

TCT TTA ATT GCC AAA AAC TGG GTT TTA ACA GCA GCT CAT TGC ATC AGC      190
Ser Leu Ile Ala Lys Asn Trp Val Leu Thr Ala Ala His Cys Ile Ser
         50                  55                  60

TCA ACC TAC TAC AGA GTC CGG GTA GGA AGT TCA ATC AAG AAC AGT GGT      238
Ser Thr Tyr Tyr Arg Val Arg Val Gly Ser Ser Ile Lys Asn Ser Gly
     65                  70                  75

GGT GTT GTT CAC AGC GTT AAA AAC CAA ATC AAG CAT CCA AAA TTC GGT      286
Gly Val Val His Ser Val Lys Asn Gln Ile Lys His Pro Lys Phe Gly
 80                  85                  90                  95

GAT TCG GCG ACA CTC GAC TTC GAT TTT GCA CTT CTG GAA TTG GAT GAA      334
Asp Ser Ala Thr Leu Asp Phe Asp Phe Ala Leu Leu Glu Leu Asp Glu
                100                 105                 110

CCA GTT ACA GTA ACA AAA GAC GTC AAC ATC ATC AAA CTA GTA GAC CAA      382
Pro Val Thr Val Thr Lys Asp Val Asn Ile Ile Lys Leu Val Asp Gln
            115                 120                 125

GAT GTA GAA TTA ACA CCT GGA ACT ATG TGC ACT GTT ACT GGA TGG GGA      430
Asp Val Glu Leu Thr Pro Gly Thr Met Cys Thr Val Thr Gly Trp Gly
        130                 135                 140

TCA ACT GGA TCT GGT GGT CCA ATT ACA AAT GTT CTA CAA GAA GTC GAA      478
Ser Thr Gly Ser Gly Gly Pro Ile Thr Asn Val Leu Gln Glu Val Glu
    145                 150                 155

GTT CCA TTT ATC GAC TTC AAC ACC TGC CGA AAA TCC TAC TCA ACC AGC      526
Val Pro Phe Ile Asp Phe Asn Thr Cys Arg Lys Ser Tyr Ser Thr Ser
160                 165                 170                 175

TTA ACC GAC CGT ATG TTC TGC GCT GGA TTT TTG GGA ATT GGT GGT AAG      574
Leu Thr Asp Arg Met Phe Cys Ala Gly Phe Leu Gly Ile Gly Gly Lys
                180                 185                 190

GAC GCT TGT CAA GGT GAC TCT GGT GGC CCA GTT GTT GTC GAT GGT GTT      622
Asp Ala Cys Gln Gly Asp Ser Gly Gly Pro Val Val Val Asp Gly Val
            195                 200                 205

CTT CAC GGA ATC GTA TCA TGG GGA CGT GGT TGC SCC CTT CCT GAC TAC      670
Leu His Gly Ile Val Ser Trp Gly Arg Gly Cys Xaa Leu Pro Asp Tyr
        210                 215                 220

CCC GGA GTC TAC TCT AAG ATC TCA TAT GCC CGT GAC TGG ATT AAG GAA      718
Pro Gly Val Tyr Ser Lys Ile Ser Tyr Ala Arg Asp Trp Ile Lys Glu
    225                 230                 235
```

```
AAT CAC TGG TGT TTA ATT TAATATTTAT TATACCAAAT AATTATATAT        766
Asn His Trp Cys Leu Ile
240                 245

AAATATATAC TATTTTAAAT ACAAAAAAAA AAAAAAAAA                      806
```

(2) INFORMATION FOR SEQ ID NO: 121:

(i) SEQUENCE CHARACTERISTICS:
        (A) LENGTH: 245 amino acids
        (B) TYPE: amino acid
        (D) TOPOLOGY: linear (ii) MOLECULE TYPE: protein (xi) SEQUENCE DESCRIPTION: SEQ ID NO: 121:

```
Ser Gln Ser Ala Pro Leu Val Leu Gly Val Pro Asp Phe Trp Asn Arg
1               5                   10                  15

Leu Asp Gly Arg Ile Val Gly Gly His Asp Thr Ser Ile Asp Lys His
                20                  25                  30

Pro His Gln Val Ser Leu Ile Tyr Thr Asn His Asn Cys Gly Gly Ser
            35                  40                  45

Leu Ile Ala Lys Asn Trp Val Leu Thr Ala Ala His Cys Ile Ser Ser
    50                  55                  60

Thr Tyr Tyr Arg Val Arg Val Gly Ser Ser Ile Lys Asn Ser Gly Gly
65                  70                  75                  80

Val Val His Ser Val Lys Asn Gln Ile Lys His Pro Lys Phe Gly Asp
                85                  90                  95

Ser Ala Thr Leu Asp Phe Asp Phe Ala Leu Leu Glu Leu Asp Glu Pro
            100                 105                 110

Val Thr Val Thr Lys Asp Val Asn Ile Ile Lys Leu Val Asp Gln Asp
        115                 120                 125

Val Glu Leu Thr Pro Gly Thr Met Cys Thr Val Thr Gly Trp Gly Ser
    130                 135                 140

Thr Gly Ser Gly Gly Pro Ile Thr Asn Val Leu Gln Glu Val Glu Val
145                 150                 155                 160

Pro Phe Ile Asp Phe Asn Thr Cys Arg Lys Ser Tyr Ser Thr Ser Leu
                165                 170                 175

Thr Asp Arg Met Phe Cys Ala Gly Phe Leu Gly Ile Gly Gly Lys Asp
            180                 185                 190

Ala Cys Gln Gly Asp Ser Gly Gly Pro Val Val Val Asp Gly Val Leu
        195                 200                 205

His Gly Ile Val Ser Trp Gly Arg Gly Cys Xaa Leu Pro Asp Tyr Pro
    210                 215                 220

Gly Val Tyr Ser Lys Ile Ser Tyr Ala Arg Asp Trp Ile Lys Glu Asn
225                 230                 235                 240

His Trp Cys Leu Ile
                245
```

(2) INFORMATION FOR SEQ ID NO: 122:

(i) SEQUENCE CHARACTERISTICS:
        (A) LENGTH: 436 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..436
        (D) OTHER INFORMATION: /note= "At pos. bp 301, change A to
            W; at pos. bp 342, change C to Y; at pos. bp 397, change
            C to Y; at pos. bp 431, change G to S. At pos. aa 100,
            114 and 144, substitute Xaa."

(xi) SEQUENCE DESCRIPTION: SEQ ID NO: 122:

| | | | | | | | | | | | | | | | |
|---|---|---|---|---|---|---|---|---|---|---|---|---|---|---|---|
| A | GTT | AGT | CTT | TCC | AAT | TCG | ATC | AGA | CCT | TCT | TGT | TTA | TGG | GCC | AAT | 46 |
| | Val | Ser | Leu | Ser | Asn | Ser | Ile | Arg | Pro | Ser | Cys | Leu | Trp | Ala | Asn | |
| | 1 | | | 5 | | | | | 10 | | | | | 15 | | |

GAC GAG TTC GAC ACA GAT AGT TCA ATT GCT ACT GGT TGG GGA AAG ATA    94
Asp Glu Phe Asp Thr Asp Ser Ser Ile Ala Thr Gly Trp Gly Lys Ile
                20                  25                  30

GAC TAT GCT GAG AGC AGA AGT GAT GAC CTA CTG AAA GTA GTA CTG AAA    142
Asp Tyr Ala Glu Ser Arg Ser Asp Asp Leu Leu Lys Val Val Leu Lys
            35                  40                  45

ATT ATT GAT AAT AGG CAA TGC GCT CCC TTA TAC GTT GAT CAG ATT AAT    190
Ile Ile Asp Asn Arg Gln Cys Ala Pro Leu Tyr Val Asp Gln Ile Asn
        50                  55                  60

AGA AGA AGA TTG AGA AAT GGA ATT GTA GAT ACA CAG ATG TGT GCA GGA    238
Arg Arg Arg Leu Arg Asn Gly Ile Val Asp Thr Gln Met Cys Ala Gly
    65                  70                  75

GAA TTG GAT GGT GGC AAA GAC ACT TGC CAG GGA GAT TCA GGT GGG CCA    286
Glu Leu Asp Gly Gly Lys Asp Thr Cys Gln Gly Asp Ser Gly Gly Pro
80                  85                  90                  95

TTG CAA ATA ACA AAW CAA AGC AAC AAA TGT ATC TTC TAC ATA GTG GGA    334
Leu Gln Ile Thr Xaa Gln Ser Asn Lys Cys Ile Phe Tyr Ile Val Gly
                100                 105                 110

ATA ACA TYA TTC GGA AGG GGA TGT GGT GCT CCT AAT AGC CCC GGT GTT    382
Ile Thr Xaa Phe Gly Arg Gly Cys Gly Ala Pro Asn Ser Pro Gly Val
            115                 120                 125

TAT ACT AGA GTC AGY AAG TAT GTT GAC TGG ATT GAA AGT GTT GTT TGG    430
Tyr Thr Arg Val Ser Lys Tyr Val Asp Trp Ile Glu Ser Val Val Trp
        130                 135                 140

SCA AAT                                                            436
Xaa Asn
    145

(2) INFORMATION FOR SEQ ID NO: 123:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO: 123:

Val Ser Leu Ser Asn Ser Ile Arg Pro Ser Cys Leu Trp Ala Asn Asp
1               5                   10                  15

Glu Phe Asp Thr Asp Ser Ser Ile Ala Thr Gly Trp Gly Lys Ile Asp
            20                  25                  30

Tyr Ala Glu Ser Arg Ser Asp Asp Leu Leu Lys Val Val Leu Lys Ile
        35                  40                  45

Ile Asp Asn Arg Gln Cys Ala Pro Leu Tyr Val Asp Gln Ile Asn Arg
    50                  55                  60

Arg Arg Leu Arg Asn Gly Ile Val Asp Thr Gln Met Cys Ala Gly Glu
65                  70                  75                  80

Leu Asp Gly Gly Lys Asp Thr Cys Gln Gly Asp Ser Gly Gly Pro Leu
                85                  90                  95

```
Gln Ile Thr Xaa Gln Ser Asn Lys Cys Ile Phe Tyr Ile Val Gly Ile
            100                 105                 110

Thr Xaa Phe Gly Arg Gly Cys Gly Ala Pro Asn Ser Pro Gly Val Tyr
        115                 120                 125

Thr Arg Val Ser Lys Tyr Val Asp Trp Ile Glu Ser Val Val Trp Xaa
    130                 135                 140

Asn
145

(2) INFORMATION FOR SEQ ID NO: 124:

(i) SEQUENCE CHARACTERISTICS:
        (A) LENGTH: 307 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..306

(xi) SEQUENCE DESCRIPTION: SEQ ID NO: 124:

CAA ATA TTT AAG CAT GAA CCT GTG AAC GTG GTA TTA TTT CTT GTA GAA        48
Gln Ile Phe Lys His Glu Pro Val Asn Val Val Leu Phe Leu Val Glu
  1               5                  10                  15

GAT CGC TTC AAT TTT GAA ATT ACT AAC GCG CGC CCT GTT GCC CTA CCA        96
Asp Arg Phe Asn Phe Glu Ile Thr Asn Ala Arg Pro Val Ala Leu Pro
                 20                  25                  30

GCA GAG AAC GAG GAA ACC GAA ACA GGG TCA CCA CTC ACG GTG ACG GGT       144
Ala Glu Asn Glu Glu Thr Glu Thr Gly Ser Pro Leu Thr Val Thr Gly
             35                  40                  45

TGG GGA ACT ACA GAG AGT ACT GAA TCA TCA CAC CAC CTG AAA GAA GTT       192
Trp Gly Thr Thr Glu Ser Thr Glu Ser Ser His His Leu Lys Glu Val
     50                  55                  60

GAA GTG AAC GCT GTA TCT AAT AGT GAA TGT CAA AAG GCC TAT GAA GAT       240
Glu Val Asn Ala Val Ser Asn Ser Glu Cys Gln Lys Ala Tyr Glu Asp
 65                  70                  75                  80

CTT GCT ACT ATA TCA TCA CAT GAG ATA TGT GCA AGC GTT CCT GGT GGC       288
Leu Ala Thr Ile Ser Ser His Glu Ile Cys Ala Ser Val Pro Gly Gly
                 85                  90                  95

GGC AAA GAT TCT TGT CAA G                                             307
Gly Lys Asp Ser Cys Gln
            100

(2) INFORMATION FOR SEQ ID NO: 125:

(i) SEQUENCE CHARACTERISTICS:
        (A) LENGTH: 102 amino acids
        (B) TYPE: amino acid
        (D) TOPOLOGY: linear (ii) MOLECULE TYPE: protein (xi) SEQUENCE DESCRIPTION: SEQ ID NO: 125:

Gln Ile Phe Lys His Glu Pro Val Asn Val Val Leu Phe Leu Val Glu
  1               5                  10                  15

Asp Arg Phe Asn Phe Glu Ile Thr Asn Ala Arg Pro Val Ala Leu Pro
                 20                  25                  30

Ala Glu Asn Glu Glu Thr Glu Thr Gly Ser Pro Leu Thr Val Thr Gly
             35                  40                  45
```

```
Trp Gly Thr Thr Glu Ser Thr Glu Ser Ser His His Leu Lys Glu Val
        50                  55                  60

Glu Val Asn Ala Val Ser Asn Ser Glu Cys Gln Lys Ala Tyr Glu Asp
65                      70                  75                  80

Leu Ala Thr Ile Ser Ser His Glu Ile Cys Ala Ser Val Pro Gly Gly
                85                  90                  95

Gly Lys Asp Ser Cys Gln
            100
```

(2) INFORMATION FOR SEQ ID NO: 126:

(i) SEQUENCE CHARACTERISTICS:
        (A) LENGTH: 758 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..738
        (D) OTHER INFORMATION: /note= "At pos. aa 241, substitute
            Xaa."

(xi) SEQUENCE DESCRIPTION: SEQ ID NO: 126:

```
AAG GTA CTG ATC GTT TTA GCA GTC ATT GAA TTC GCA TCA GCG TCT TCA        48
Lys Val Leu Ile Val Leu Ala Val Ile Glu Phe Ala Ser Ala Ser Ser
 1               5                  10                  15

ATC GGC TGG AGA ATC GTG GGT GGT GAA AAT GCT AAA GAA AAA TCG GTG        96
Ile Gly Trp Arg Ile Val Gly Gly Glu Asn Ala Lys Glu Lys Ser Val
                20                  25                  30

CCC TAT CAA GTT TCA CTT CGA AAT GCT GAA AAC AAA CAT TTC TGT GGA       144
Pro Tyr Gln Val Ser Leu Arg Asn Ala Glu Asn Lys His Phe Cys Gly
            35                  40                  45

GGA GCA ATT ATT GAC GAT TAT TGG GTT TTG ACT GCT GCT CAT TGC ATG       192
Gly Ala Ile Ile Asp Asp Tyr Trp Val Leu Thr Ala Ala His Cys Met
        50                  55                  60

GGA CAA CGT TTT GAA GTC GTT GCC GGC GTG AAT AAA CTG GAT GAA GTA       240
Gly Gln Arg Phe Glu Val Val Ala Gly Val Asn Lys Leu Asp Glu Val
65                  70                  75                  80

GGT GAA CGA TAT AGA ATA GAA AAA ACT ATT ACT GAC AAG TTT GAT GAA       288
Gly Glu Arg Tyr Arg Ile Glu Lys Thr Ile Thr Asp Lys Phe Asp Glu
                85                  90                  95

CAA ACT GCC GCA AAT GAT TTG GCA CTT GTA AAA CTT CGG AAT AAA ATA       336
Gln Thr Ala Ala Asn Asp Leu Ala Leu Val Lys Leu Arg Asn Lys Ile
            100                 105                 110

AAA TTC AGC GAT AAA GTG CAA AAA ATT CAA TTT GAA GAT AAA TAT ATC       384
Lys Phe Ser Asp Lys Val Gln Lys Ile Gln Phe Glu Asp Lys Tyr Ile
        115                 120                 125

GGA GGC GGA GAG GAT GCT CGT TTG ACT GGA TGG GGA CGA TTG GGA AAA       432
Gly Gly Gly Glu Asp Ala Arg Leu Thr Gly Trp Gly Arg Leu Gly Lys
    130                 135                 140

GAT TCA CCG CCA CCT AAT GAT TTA CAG GAA TTA AAT ACA TTT ACC ATC       480
Asp Ser Pro Pro Pro Asn Asp Leu Gln Glu Leu Asn Thr Phe Thr Ile
145                 150                 155                 160

CCC CAA AGT GTT TGC AGA AGA ATG TTT AAT GAG GAT AAG ATT CCA ATC       528
Pro Gln Ser Val Cys Arg Arg Met Phe Asn Glu Asp Lys Ile Pro Ile
                165                 170                 175

CAC GAT AGC CAA ATA TGC ACT TTT GCA GAT ATG GGC AAG GGT GCA TGT       576
His Asp Ser Gln Ile Cys Thr Phe Ala Asp Met Gly Lys Gly Ala Cys
            180                 185                 190
```

```
AAG GGT GAT TCC GGT GGC CCC TTA GTC ATC AAT GGA CAA CTT CAT GGA      624
Lys Gly Asp Ser Gly Gly Pro Leu Val Ile Asn Gly Gln Leu His Gly
        195                 200                 205

ATT GTT TCC TGG GGC ATT CCT TGC GCT GTC GGC AAG CCT GAT GTA TTC      672
Ile Val Ser Trp Gly Ile Pro Cys Ala Val Gly Lys Pro Asp Val Phe
    210                 215                 220

ACA AGA GTT TCT CAT TAT GTC GAT TGG ATT AAA TCC AAA ATT GCC AAA      720
Thr Arg Val Ser His Tyr Val Asp Trp Ile Lys Ser Lys Ile Ala Lys
225                 230                 235                 240

TAA AAT TGT TTA GTG TAT TAAAAAAAAA AAAAAAAAA                         758
Xaa Asn Cys Leu Val Tyr
            245
```

(2) INFORMATION FOR SEQ ID NO: 127:

(i) SEQUENCE CHARACTERISTICS:
        (A) LENGTH: 246 amino acids
        (B) TYPE: amino acid
        (D) TOPOLOGY: linear (ii) MOLECULE TYPE: protein (xi) SEQUENCE DESCRIPTION: SEQ ID NO: 127:

```
Lys Val Leu Ile Val Leu Ala Val Ile Glu Phe Ala Ser Ala Ser Ser
 1               5                  10                  15

Ile Gly Trp Arg Ile Val Gly Gly Glu Asn Ala Lys Glu Lys Ser Val
            20                  25                  30

Pro Tyr Gln Val Ser Leu Arg Asn Ala Glu Asn Lys His Phe Cys Gly
        35                  40                  45

Gly Ala Ile Ile Asp Asp Tyr Trp Val Leu Thr Ala Ala His Cys Met
    50                  55                  60

Gly Gln Arg Phe Glu Val Val Ala Gly Val Asn Lys Leu Asp Glu Val
65                  70                  75                  80

Gly Glu Arg Tyr Arg Ile Glu Lys Thr Ile Thr Asp Lys Phe Asp Glu
                85                  90                  95

Gln Thr Ala Ala Asn Asp Leu Ala Leu Val Lys Leu Arg Asn Lys Ile
            100                 105                 110

Lys Phe Ser Asp Lys Val Gln Lys Ile Gln Phe Glu Asp Lys Tyr Ile
        115                 120                 125

Gly Gly Gly Glu Asp Ala Arg Leu Thr Gly Trp Gly Arg Leu Gly Lys
    130                 135                 140

Asp Ser Pro Pro Asn Asp Leu Gln Glu Leu Asn Thr Phe Thr Ile
145                 150                 155                 160

Pro Gln Ser Val Cys Arg Arg Met Phe Asn Glu Asp Lys Ile Pro Ile
                165                 170                 175

His Asp Ser Gln Ile Cys Thr Phe Ala Asp Met Gly Lys Gly Ala Cys
            180                 185                 190

Lys Gly Asp Ser Gly Gly Pro Leu Val Ile Asn Gly Gln Leu His Gly
        195                 200                 205

Ile Val Ser Trp Gly Ile Pro Cys Ala Val Gly Lys Pro Asp Val Phe
    210                 215                 220

Thr Arg Val Ser His Tyr Val Asp Trp Ile Lys Ser Lys Ile Ala Lys
225                 230                 235                 240

Xaa Asn Cys Leu Val Tyr
            245
```

(2) INFORMATION FOR SEQ ID NO: 128:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..762
        (D) OTHER INFORMATION: /note= "At pos. bp 453, change A to
            M; at 454, change G to V; at 456, G to V; at 457, A to M;
            at 460, A to R; at 470, G to S; at 493, A to R. At pos.
            aa 120, 136, 152, 153, 154, 157 and 165, substitute Xaa."

(xi) SEQUENCE DESCRIPTION: SEQ ID NO: 128:

```
ATT TTA TTA AGC GCA TTA TTT GCA AGT GTA ATT TGC TCC TTT AAC GCG        48
Ile Leu Leu Ser Ala Leu Phe Ala Ser Val Ile Cys Ser Phe Asn Ala
  1               5                  10                  15

GAA GTA CAA AAT CGA ATC GTT GGT GGC AAT GAT GTA AGT ATT TCA AAA        96
Glu Val Gln Asn Arg Ile Val Gly Gly Asn Asp Val Ser Ile Ser Lys
             20                  25                  30

ATT GGG TGG CAA GTA TCT ATT CAA AGT AAT AAC CAA CAT TTC TGT GGT       144
Ile Gly Trp Gln Val Ser Ile Gln Ser Asn Asn Gln His Phe Cys Gly
         35                  40                  45

GGT TCA ATC ATT GCT AAA GAT TGG GTA CTG ACT TCT TCT CAA TGC GTC       192
Gly Ser Ile Ile Ala Lys Asp Trp Val Leu Thr Ser Ser Gln Cys Val
     50                  55                  60

GTG GAC AAA CAA AGT CCA CCG AAG GAT TTA ACT GTT CGT GTT GGA ACT       240
Val Asp Lys Gln Ser Pro Pro Lys Asp Leu Thr Val Arg Val Gly Thr
 65                  70                  75                  80

AGC ACT CAC AAT GAT GGA GGA AAA GTG TAT GAT GTT ATT GAA ATT ATA       288
Ser Thr His Asn Asp Gly Gly Lys Val Tyr Asp Val Ile Glu Ile Ile
                 85                  90                  95

AAA CAT CCG AAA TAT AAT AAA GCA GTG CCA GAT GAT TTT GAT GTT GCA       336
Lys His Pro Lys Tyr Asn Lys Ala Val Pro Asp Asp Phe Asp Val Ala
            100                 105                 110

CTT TTA CGG ATC AAA GAG CCA ATC ATT TAC TCC ATG CAC AGT AAC TCC       384
Leu Leu Arg Ile Lys Glu Pro Xaa Ile Tyr Ser Met His Ser Asn Ser
        115                 120                 125

TGT AAA ATT AAT ACA ATC GGG AAA GAA GTA CCG AAG GGA ACA ACT TTG       432
Cys Lys Ile Asn Thr Ile Gly Xaa Glu Val Pro Lys Gly Thr Thr Leu
    130                 135                 140

AGT GTA ACT GGA TGG GGC GCM VCV MAG RAA TGG GGG CSC AAT TTC GCC       480
Ser Val Thr Gly Trp Gly Ala Xaa Xaa Xaa Trp Gly Xaa Asn Phe Ala
145                 150                 155                 160

AAA GTT ACA AGA RAG TTA AAG TTA AAG CTA CTC AAG TCA AGA ATG CAA       528
Lys Val Thr Arg Xaa Leu Lys Leu Lys Leu Leu Lys Ser Arg Met Gln
                165                 170                 175

GAA CAG TCT GCT ATT AAC AGT GAC ATC ATT TCT GAC AGT ATG ATG TGC       576
Glu Gln Ser Ala Ile Asn Ser Asp Ile Ile Ser Asp Ser Met Met Cys
            180                 185                 190

GCT GGT TTT CCT CAA GGA CAA AAA GAT ACT TGT CAT GGG GAT AGC GGT       624
Ala Gly Phe Pro Gln Gly Gln Lys Asp Thr Cys His Gly Asp Ser Gly
        195                 200                 205

GGC ACT GTA GAT AAA AAA CAG GTT CAA GTA GGA GTT ATA TCC TGG AGG       672
Gly Thr Val Asp Lys Lys Gln Val Gln Val Gly Val Ile Ser Trp Arg
    210                 215                 220

CGA GGA TGC GCG CGA CCT GGA TAT CCT GGC GTA TAT ACA AAA TTG AGC       720
Arg Gly Cys Ala Arg Pro Gly Tyr Pro Gly Val Tyr Thr Lys Leu Ser
225                 230                 235                 240
```

```
CAC CCG GAA ATC CAA CAG TTT ATT AAA AAC AAT GTA AAA CTT         762
His Pro Glu Ile Gln Gln Phe Ile Lys Asn Asn Val Lys Leu
            245                 250

TAAATCATAA AACTGTATGA AATAACAAT AACAATTACG GGAAAAAAAA AAA       815
```

(2) INFORMATION FOR SEQ ID NO: 129:

(i) SEQUENCE CHARACTERISTICS:
        (A) LENGTH: 254 amino acids
        (B) TYPE: amino acid
        (D) TOPOLOGY: linear (ii) MOLECULE TYPE: protein (xi) SEQUENCE DESCRIPTION: SEQ ID NO: 129:

```
Ile Leu Leu Ser Ala Leu Phe Ala Ser Val Ile Cys Ser Phe Asn Ala
 1               5                  10                  15

Glu Val Gln Asn Arg Ile Val Gly Gly Asn Asp Val Ser Ile Ser Lys
                20                  25                  30

Ile Gly Trp Gln Val Ser Ile Gln Ser Asn Asn Gln His Phe Cys Gly
            35                  40                  45

Gly Ser Ile Ile Ala Lys Asp Trp Val Leu Thr Ser Ser Gln Cys Val
        50                  55                  60

Val Asp Lys Gln Ser Pro Pro Lys Asp Leu Thr Val Arg Val Gly Thr
65                  70                  75                  80

Ser Thr His Asn Asp Gly Gly Lys Val Tyr Asp Val Ile Glu Ile Ile
                85                  90                  95

Lys His Pro Lys Tyr Asn Lys Ala Val Pro Asp Phe Asp Val Ala
                    100                 105                 110

Leu Leu Arg Ile Lys Glu Pro Xaa Ile Tyr Ser Met His Ser Asn Ser
            115                 120                 125

Cys Lys Ile Asn Thr Ile Gly Xaa Glu Val Pro Lys Gly Thr Thr Leu
        130                 135                 140

Ser Val Thr Gly Trp Gly Ala Xaa Xaa Xaa Trp Gly Xaa Asn Phe Ala
145                 150                 155                 160

Lys Val Thr Arg Xaa Leu Lys Leu Lys Leu Leu Lys Ser Arg Met Gln
                165                 170                 175

Glu Gln Ser Ala Ile Asn Ser Asp Ile Ile Ser Asp Ser Met Met Cys
            180                 185                 190

Ala Gly Phe Pro Gln Gly Gln Lys Asp Thr Cys His Gly Asp Ser Gly
        195                 200                 205

Gly Thr Val Asp Lys Lys Gln Val Gln Val Gly Val Ile Ser Trp Arg
    210                 215                 220

Arg Gly Cys Ala Arg Pro Gly Tyr Pro Gly Val Tyr Thr Lys Leu Ser
225                 230                 235                 240

His Pro Glu Ile Gln Gln Phe Ile Lys Asn Asn Val Lys Leu
                245                 250
```

(2) INFORMATION FOR SEQ ID NO: 130:

(i) SEQUENCE CHARACTERISTICS:
        (A) LENGTH: 855 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..759
    (D) OTHER INFORMATION: /note= "At pos. bp 693, change C to N. At pos. aa 231, substitute Xaa."

(xi) SEQUENCE DESCRIPTION: SEQ ID NO: 130:

```
ATG GCT TAT ATT ATA TTA GTT ACT TTA ATT AGT TTG GGA TCG TTG GTT      48
Met Ala Tyr Ile Ile Leu Val Thr Leu Ile Ser Leu Gly Ser Leu Val
 1               5                  10                  15

TCT TCC GAA TAC CTT TCG TTT TCT ACT GAT CCT CGG ATA ATT GGT GGT      96
Ser Ser Glu Tyr Leu Ser Phe Ser Thr Asp Pro Arg Ile Ile Gly Gly
             20                  25                  30

GAA GAT GCT CCC GAG GGT TCT GCA CCA TAT CAG GTT TCA TTA AGA AAT     144
Glu Asp Ala Pro Glu Gly Ser Ala Pro Tyr Gln Val Ser Leu Arg Asn
         35                  40                  45

TCT GAC TTG CAG CAT TTT TGT GGT GGT TCC ATC CTA AAC AAA CGA TGG     192
Ser Asp Leu Gln His Phe Cys Gly Gly Ser Ile Leu Asn Lys Arg Trp
     50                  55                  60

ATT TTA ACA GCA GCA CAT TGT CTC GAA CCT GGT TTT TTA AAT TCT GTA     240
Ile Leu Thr Ala Ala His Cys Leu Glu Pro Gly Phe Leu Asn Ser Val
 65                  70                  75                  80

TAC ATG GGT TCG AAT TTG TTG GAT CGA AAA GGC AGA TAT TAC GAT GTA     288
Tyr Met Gly Ser Asn Leu Leu Asp Arg Lys Gly Arg Tyr Tyr Asp Val
                 85                  90                  95

GAA AGA TTT GTG ATG CAC CAT AAT TAT ACT GGA AAG ATA GTT GCC AAT     336
Glu Arg Phe Val Met His His Asn Tyr Thr Gly Lys Ile Val Ala Asn
            100                 105                 110

GTC GCT GAT ATA GGT CTA ATA AAA CTA GCA GAA GAT ATA AAA TTC AGT     384
Val Ala Asp Ile Gly Leu Ile Lys Leu Ala Glu Asp Ile Lys Phe Ser
        115                 120                 125

GAC AAG GTA CAA CCT GTA AAA ATT CAT CAA ACT CAA ATC AAG GGC GGA     432
Asp Lys Val Gln Pro Val Lys Ile His Gln Thr Gln Ile Lys Gly Gly
    130                 135                 140

GAG ATT TGC AAA GCT ACT GGA TGG GGC AGG TTG GGT GCT GAT CAG CCT     480
Glu Ile Cys Lys Ala Thr Gly Trp Gly Arg Leu Gly Ala Asp Gln Pro
145                 150                 155                 160

GTA CCA AAT AAA TTA CAA CAA TTG GAG ACA ATT GCT ATT AGT GAT GAG     528
Val Pro Asn Lys Leu Gln Gln Leu Glu Thr Ile Ala Ile Ser Asp Glu
                165                 170                 175

AAA TGT TAT GCA GAT ACA GGG TTT TTA GAA CCT ACA TCT CAA ATA TGT     576
Lys Cys Tyr Ala Asp Thr Gly Phe Leu Glu Pro Thr Ser Gln Ile Cys
            180                 185                 190

GTA TTC AGT GCA TTT GGA AAA GGA GTT TGT TTT GGA GAT TCT GGT GGT     624
Val Phe Ser Ala Phe Gly Lys Gly Val Cys Phe Gly Asp Ser Gly Gly
        195                 200                 205

CCA TTA GTT TAC AAA GGT GAA CAA GTA GGA GTT GCA TCA TTC ATC ATG     672
Pro Leu Val Tyr Lys Gly Glu Gln Val Gly Val Ala Ser Phe Ile Met
    210                 215                 220

ATC ACT TGT GGT GGT GGC AGN CCA GAT GTA TTT GTT AGA GTA CTC GAT     720
Ile Thr Cys Gly Gly Gly Xaa Pro Asp Val Phe Val Arg Val Leu Asp
225                 230                 235                 240

TAT CAG GAT TGG ATA AAT TCA TTT ATT TCT GGA GAT AAC TAGTCTTTAA      769
Tyr Gln Asp Trp Ile Asn Ser Phe Ile Ser Gly Asp Asn
                245                 250

TGTAAAATGA ACTATTATAA TATATATTTT TTATTCTTAT AAAATATATA CATTTTATT    829

CGCACAAAAA AAAAAAAAAA AAAAA                                         855
```

(2) INFORMATION FOR SEQ ID NO: 131:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO: 131:

```
Met Ala Tyr Ile Ile Leu Val Thr Leu Ile Ser Leu Gly Ser Leu Val
 1               5                  10                  15

Ser Ser Glu Tyr Leu Ser Phe Ser Thr Asp Pro Arg Ile Ile Gly Gly
             20                  25                  30

Glu Asp Ala Pro Glu Gly Ser Ala Pro Tyr Gln Val Ser Leu Arg Asn
         35                  40                  45

Ser Asp Leu Gln His Phe Cys Gly Gly Ser Ile Leu Asn Lys Arg Trp
     50                  55                  60

Ile Leu Thr Ala Ala His Cys Leu Glu Pro Gly Phe Leu Asn Ser Val
 65                  70                  75                  80

Tyr Met Gly Ser Asn Leu Leu Asp Arg Lys Gly Arg Tyr Tyr Asp Val
                 85                  90                  95

Glu Arg Phe Val Met His His Asn Tyr Thr Gly Lys Ile Val Ala Asn
            100                 105                 110

Val Ala Asp Ile Gly Leu Ile Lys Leu Ala Glu Asp Ile Lys Phe Ser
        115                 120                 125

Asp Lys Val Gln Pro Val Lys Ile His Gln Thr Gln Ile Lys Gly Gly
    130                 135                 140

Glu Ile Cys Lys Ala Thr Gly Trp Gly Arg Leu Gly Ala Asp Gln Pro
145                 150                 155                 160

Val Pro Asn Lys Leu Gln Gln Leu Glu Thr Ile Ala Ile Ser Asp Glu
                165                 170                 175

Lys Cys Tyr Ala Asp Thr Gly Phe Leu Glu Pro Thr Ser Gln Ile Cys
            180                 185                 190

Val Phe Ser Ala Phe Gly Lys Gly Val Cys Phe Gly Asp Ser Gly Gly
        195                 200                 205

Pro Leu Val Tyr Lys Gly Glu Gln Val Gly Val Ala Ser Phe Ile Met
    210                 215                 220

Ile Thr Cys Gly Gly Gly Xaa Pro Asp Val Phe Val Arg Val Leu Asp
225                 230                 235                 240

Tyr Gln Asp Trp Ile Asn Ser Phe Ile Ser Gly Asp Asn
                245                 250
```

(2) INFORMATION FOR SEQ ID NO: 132:

(i) SEQUENCE CHARACTERISTICS:
        (A) LENGTH: 595 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..595
        (D) OTHER INFORMATION: /note= "At pos. bp 509, change C to Y; at pos. 556, change C to Y; at pos. 557, change C to Y; at 561, change C to Y; at 573, change C to Y. At pos. aa. 170, 186, 187, 190 and 191, substitute Xaa."

(xi) SEQUENCE DESCRIPTION: SEQ ID NO: 132:

```
T GGT TCC ATC TTG AAC AAA CGT TGG ATT GTA ACA GCT GCA CAT TGC       46
  Gly Ser Ile Leu Asn Lys Arg Trp Ile Val Thr Ala Ala His Cys
   1               5                  10                  15

CTA AAC GCT GGC ATT TTA AAA TCC GTC TAT TTG GGA TCA AAC TCA TTA     94
Leu Asn Ala Gly Ile Leu Lys Ser Val Tyr Leu Gly Ser Asn Ser Leu
                    20                  25                  30

GAT GGC GAT GGT ACA TAC TAC GAC GTC GAA CGT TTT GTG ATG CAT GAT    142
Asp Gly Asp Gly Thr Tyr Tyr Asp Val Glu Arg Phe Val Met His Asp
                35                  40                  45

AAA TAT ACA CCA AGA ATC ACT GTC AAC TAT GCT GAT ATT GGT CTA ATA    190
Lys Tyr Thr Pro Arg Ile Thr Val Asn Tyr Ala Asp Ile Gly Leu Ile
            50                  55                  60

AAA GTG GCA AAA GAC ATT GTA TTC GGT GAC AAA GTC CAA CCG ATC AAA    238
Lys Val Ala Lys Asp Ile Val Phe Gly Asp Lys Val Gln Pro Ile Lys
     65                  70                  75

ATT AGC AAG AGA AAC ATC AAG GGT GGT GAA ATT TGC AAG GCA ACT GGT    286
Ile Ser Lys Arg Asn Ile Lys Gly Gly Glu Ile Cys Lys Ala Thr Gly
 80                  85                  90                  95

TGG GGT CTA TTA GGT TCT GTG GAC TCA GTA CCA AAC GAA TTA CAA CAA    334
Trp Gly Leu Leu Gly Ser Val Asp Ser Val Pro Asn Glu Leu Gln Gln
                    100                 105                 110

GTA GAA ACC ACT GCA ATA ACA GAC GAA AAG TGC TTT GAA TTG ACT CAA    382
Val Glu Thr Thr Ala Ile Thr Asp Glu Lys Cys Phe Glu Leu Thr Gln
                115                 120                 125

TTC ATT GAC CCA ACT TCG CAA ATA TGT ACA TTC AGG GAA TTT GGT AGA    430
Phe Ile Asp Pro Thr Ser Gln Ile Cys Thr Phe Arg Glu Phe Gly Arg
            130                 135                 140

GGC ATT TGC TTT GGT GAT TCT GGT GGA CCA CTA GTT TAC AAA AAT GAA    478
Gly Ile Cys Phe Gly Asp Ser Gly Gly Pro Leu Val Tyr Lys Asn Glu
        145                 150                 155

CTT GTT GGC ATT ACA TCG ATG CAC TTA TAC YCC TGC AGA GGT GGC AGG    526
Leu Val Gly Ile Thr Ser Met His Leu Tyr Xaa Cys Arg Gly Gly Arg
160                 165                 170                 175

CCA GAT ATT TTT TGT GAA AGT GCG AGA TTY YCA AYC CTG GAT TAA AYT    574
Pro Asp Ile Phe Cys Glu Ser Ala Arg Phe Xaa Xaa Leu Asp Xaa Xaa
                    180                 185                 190

CTG AAA TTG AAA AAA ATT AAA                                        595
Leu Lys Leu Lys Lys Ile Lys
                195
```

(2) INFORMATION FOR SEQ ID NO: 133:

(i) SEQUENCE CHARACTERISTICS:
        (A) LENGTH: 198 amino acids
        (B) TYPE: amino acid
        (D) TOPOLOGY: linear (ii) MOLECULE TYPE: protein (xi) SEQUENCE DESCRIPTION: SEQ ID NO: 133:

```
Gly Ser Ile Leu Asn Lys Arg Trp Ile Val Thr Ala Ala His Cys Leu
 1               5                  10                  15

Asn Ala Gly Ile Leu Lys Ser Val Tyr Leu Gly Ser Asn Ser Leu Asp
                20                  25                  30

Gly Asp Gly Thr Tyr Tyr Asp Val Glu Arg Phe Val Met His Asp Lys
            35                  40                  45

Tyr Thr Pro Arg Ile Thr Val Asn Tyr Ala Asp Ile Gly Leu Ile Lys
     50                  55                  60
```

```
Val Ala Lys Asp Ile Val Phe Gly Asp Lys Val Gln Pro Ile Lys Ile
 65                  70                  75                  80

Ser Lys Arg Asn Ile Lys Gly Glu Ile Cys Lys Ala Thr Gly Trp
                 85                  90                  95

Gly Leu Leu Gly Ser Val Asp Ser Val Pro Asn Glu Leu Gln Gln Val
            100                 105                 110

Glu Thr Thr Ala Ile Thr Asp Glu Lys Cys Phe Glu Leu Thr Gln Phe
        115                 120                 125

Ile Asp Pro Thr Ser Gln Ile Cys Thr Phe Arg Glu Phe Gly Arg Gly
130                 135                 140

Ile Cys Phe Gly Asp Ser Gly Gly Pro Leu Val Tyr Lys Asn Glu Leu
145                 150                 155                 160

Val Gly Ile Thr Ser Met His Leu Tyr Xaa Cys Arg Gly Gly Arg Pro
                165                 170                 175

Asp Ile Phe Cys Glu Ser Ala Arg Phe Xaa Xaa Leu Asp Xaa Xaa Leu
            180                 185                 190

Lys Leu Lys Lys Ile Lys
            195
```

(2) INFORMATION FOR SEQ ID NO: 134:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..423

(xi) SEQUENCE DESCRIPTION: SEQ ID NO: 134:

```
GTA GTT ACA GCT GCA CAT TGT GTC ACC GTT GGA GGA CAT AAC CAA GTC      48
Val Val Thr Ala Ala His Cys Val Thr Val Gly Gly His Asn Gln Val
 1               5                  10                  15

GTA GCT GTT GTA GGA ACC AAC AAA TTG AGC TCC GGA GGC ACC ACA TAC      96
Val Ala Val Val Gly Thr Asn Lys Leu Ser Ser Gly Gly Thr Thr Tyr
             20                  25                  30

AAA GCT GAA CGT GTT GTT GTA CAC GAA CGT TAT GGC AAT GCT GAT ATT     144
Lys Ala Glu Arg Val Val Val His Glu Arg Tyr Gly Asn Ala Asp Ile
         35                  40                  45

GAC AAC GAT CTT GCC TTG ATC AAG TTG ACC CAA GAT GTC GTA TTC ACT     192
Asp Asn Asp Leu Ala Leu Ile Lys Leu Thr Gln Asp Val Val Phe Thr
 50                  55                  60

GAC CGC GTA CAG CCC GTC ACC GTA TCC AGA ACT ACA GTC AAA GGA GGA     240
Asp Arg Val Gln Pro Val Thr Val Ser Arg Thr Thr Val Lys Gly Gly
 65                  70                  75                  80

GAA ACC TTG AGA ATC ACT GGA TGG GGT TAC ACC AAC CAC GGT GGC CCA     288
Glu Thr Leu Arg Ile Thr Gly Trp Gly Tyr Thr Asn His Gly Gly Pro
                 85                  90                  95

GTT CTG CCC GAC AGT TTG CAA GAA CTT CAT GTA ACC GCC CAG ACC CCA     336
Val Leu Pro Asp Ser Leu Gln Glu Leu His Val Thr Ala Gln Thr Pro
            100                 105                 110

AGC ACA TGC CAA AAA TAC ACA CCA GCC GCC ACA CAA TTG TGC ACT TTC     384
Ser Thr Cys Gln Lys Tyr Thr Pro Ala Ala Thr Gln Leu Cys Thr Phe
        115                 120                 125

TTG AAG ACT GGA CAA GGA GTT TGC AAC GGT GAT TCT GGA                 423
Leu Lys Thr Gly Gln Gly Val Cys Asn Gly Asp Ser Gly
130                 135                 140
```

(2) INFORMATION FOR SEQ ID NO: 135:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO: 135:

```
Val Val Thr Ala Ala His Cys Val Thr Val Gly Gly His Asn Gln Val
 1               5                  10                  15

Val Ala Val Val Gly Thr Asn Lys Leu Ser Ser Gly Gly Thr Thr Tyr
                20                  25                  30

Lys Ala Glu Arg Val Val His Glu Arg Tyr Gly Asn Ala Asp Ile
            35                  40                  45

Asp Asn Asp Leu Ala Leu Ile Lys Leu Thr Gln Asp Val Val Phe Thr
         50                  55                  60

Asp Arg Val Gln Pro Val Thr Val Ser Arg Thr Thr Val Lys Gly Gly
 65                  70                  75                  80

Glu Thr Leu Arg Ile Thr Gly Trp Gly Tyr Thr Asn His Gly Gly Pro
                 85                  90                  95

Val Leu Pro Asp Ser Leu Gln Glu Leu His Val Thr Ala Gln Thr Pro
                100                 105                 110

Ser Thr Cys Gln Lys Tyr Thr Pro Ala Ala Thr Gln Leu Cys Thr Phe
            115                 120                 125

Leu Lys Thr Gly Gln Gly Val Cys Asn Gly Asp Ser Gly
            130                 135                 140
```

(2) INFORMATION FOR SEQ ID NO: 136:

(i) SEQUENCE CHARACTERISTICS:
        (A) LENGTH: 410 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..408

(xi) SEQUENCE DESCRIPTION: SEQ ID NO: 136:

```
TGG GTT GTT ACT GCT GCT CAT TGT TTG AGA GGC AAA GAC CAC CTC CTG      48
Trp Val Val Thr Ala Ala His Cys Leu Arg Gly Lys Asp His Leu Leu
 1               5                  10                  15

GAC AAA CTG TTC ATT GCA GTC GGC CTG ACA AAT TTA GGT GAA GGA GGC      96
Asp Lys Leu Phe Ile Ala Val Gly Leu Thr Asn Leu Gly Glu Gly Gly
                20                  25                  30

ACC GTG TAT CCT GTA GAA AAA GGC ATC ATG CAC GAA GAA TAT GAA CAT     144
Thr Val Tyr Pro Val Glu Lys Gly Ile Met His Glu Glu Tyr Glu His
            35                  40                  45

TAT GAC ATA GTC AAC GAT ATT GCA CTA ATC AAA GTC AAA TCT CCG ATA     192
Tyr Asp Ile Val Asn Asp Ile Ala Leu Ile Lys Val Lys Ser Pro Ile
         50                  55                  60

GAA TTC AAT GAA AAA GTA ACG ACT GTA AAA TTA GGT GAG GAT TAT GTT     240
Glu Phe Asn Glu Lys Val Thr Thr Val Lys Leu Gly Glu Asp Tyr Val
 65                  70                  75                  80

GGC GGA GAC GTC CAA CTT CGA TTG ACA GGA TGG GGA GTT ACA ACA AAT     288
Gly Gly Asp Val Gln Leu Arg Leu Thr Gly Trp Gly Val Thr Thr Asn
                 85                  90                  95
```

```
GAG GGA ATC GGA AGC CCG AGT CAA AAA TTA CAG GTC ATG ACA GCC AAA       336
Glu Gly Ile Gly Ser Pro Ser Gln Lys Leu Gln Val Met Thr Ala Lys
            100                 105                 110

TCA CTA ACT TAT GAG GAT TGC AAA AAC GCA ATT TAT AAA AAA GAC TTT       384
Ser Leu Thr Tyr Glu Asp Cys Lys Asn Ala Ile Tyr Lys Lys Asp Phe
        115                 120                 125

CGA AAG CCA AAT TTG TGC ACA GGC TA                                    410
Arg Lys Pro Asn Leu Cys Thr Gly
130                 135
```

(2) INFORMATION FOR SEQ ID NO: 137:

(i) SEQUENCE CHARACTERISTICS:
        (A) LENGTH: 136 amino acids
        (B) TYPE: amino acid
        (D) TOPOLOGY: linear (ii) MOLECULE TYPE: protein (xi) SEQUENCE DESCRIPTION: SEQ ID NO: 137:

```
Trp Val Val Thr Ala Ala His Cys Leu Arg Gly Lys Asp His Leu Leu
 1               5                  10                  15

Asp Lys Leu Phe Ile Ala Val Gly Leu Thr Asn Leu Gly Glu Gly Gly
            20                  25                  30

Thr Val Tyr Pro Val Glu Lys Gly Ile Met His Glu Glu Tyr Glu His
        35                  40                  45

Tyr Asp Ile Val Asn Asp Ile Ala Leu Ile Lys Val Lys Ser Pro Ile
    50                  55                  60

Glu Phe Asn Glu Lys Val Thr Val Lys Leu Gly Glu Asp Tyr Val
65                  70                  75                  80

Gly Gly Asp Val Gln Leu Arg Leu Thr Gly Trp Gly Val Thr Thr Asn
                85                  90                  95

Glu Gly Ile Gly Ser Pro Ser Gln Lys Leu Gln Val Met Thr Ala Lys
            100                 105                 110

Ser Leu Thr Tyr Glu Asp Cys Lys Asn Ala Ile Tyr Lys Lys Asp Phe
        115                 120                 125

Arg Lys Pro Asn Leu Cys Thr Gly
130                 135
```

(2) INFORMATION FOR SEQ ID NO: 138:

(i) SEQUENCE CHARACTERISTICS:
        (A) LENGTH: 864 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..781
        (D) OTHER INFORMATION: /note= "At pos. bp 456, change G to
            K; at pos. bp 504, change A to R. At pos. aa 152 and
            168, substitute Xaa."

(xi) SEQUENCE DESCRIPTION: SEQ ID NO: 138:

```
T ACA AAA CCT ATT ACA ATT CAA AAG TTG TTC CAA ATG ATG GCA AAT         46
  Thr Lys Pro Ile Thr Ile Gln Lys Leu Phe Gln Met Met Ala Asn
   1               5                  10                  15

TTT GTG CTA TTC ACC TTA CTA GCC TTA GTA TCA GTA GCA TGT TCC AAA       94
Phe Val Leu Phe Thr Leu Leu Ala Leu Val Ser Val Ala Cys Ser Lys
                20                  25                  30
```

```
TAT ATT GAT CCA AGA ATC ATT GGA GGC GAA GAT GCT CCT GAA GGC TCG      142
Tyr Ile Asp Pro Arg Ile Ile Gly Gly Glu Asp Ala Pro Glu Gly Ser
             35                  40                  45

GCT CCG TAT CAA GTT TCA CTG AGA AAT CGG GAC CTA GAG CAT TTC TGT      190
Ala Pro Tyr Gln Val Ser Leu Arg Asn Arg Asp Leu Glu His Phe Cys
         50                  55                  60

GGT GGC TCC ATC TTA AAC AAA CGT TGG ATT GTG ACG GCT GCA CAT TGC      238
Gly Gly Ser Ile Leu Asn Lys Arg Trp Ile Val Thr Ala Ala His Cys
     65                  70                  75

CTA AAA CCT GGC ATT TTA AAA TCC GTC TAT ATG GGA TCA AAC TCA TTA      286
Leu Lys Pro Gly Ile Leu Lys Ser Val Tyr Met Gly Ser Asn Ser Leu
 80                  85                  90                  95

GAT GGC AAT GGT ACA TAC TAC GAC GTC GAA CGT TTT GTG ATG CAT CAT      334
Asp Gly Asn Gly Thr Tyr Tyr Asp Val Glu Arg Phe Val Met His His
                100                 105                 110

AAA TAT ACA CCA AAA ATT ACT GTC AAC TAT GCT GAT ATT GGT CTA ATA      382
Lys Tyr Thr Pro Lys Ile Thr Val Asn Tyr Ala Asp Ile Gly Leu Ile
             115                 120                 125

AAA GTG ACA AAA GAC ATT ATA TTC AGT GAC AAA GTT CAA CCA ATC AAA      430
Lys Val Thr Lys Asp Ile Ile Phe Ser Asp Lys Val Gln Pro Ile Lys
         130                 135                 140

ATA GCA AAA AAA ATA TCA AGG GTG GKG AAT CTG CAA GGC CAC TGG TTG      478
Ile Ala Lys Lys Ile Ser Arg Val Xaa Asn Leu Gln Gly His Trp Leu
     145                 150                 155

GGG TCG ATT GGC GGA TGG GGC CCC CRG TAC CAA ACG AAT TGC AAC AAG      526
Gly Ser Ile Gly Gly Trp Gly Pro Xaa Tyr Gln Thr Asn Cys Asn Lys
160                 165                 170                 175

GTG GAA ACC ACT GCA ATA ACA AAT GAA AAG TGC TAC GAA TTG TCT CAA      574
Val Glu Thr Thr Ala Ile Thr Asn Glu Lys Cys Tyr Glu Leu Ser Gln
                180                 185                 190

TTC GTT GAG CCA ACT TCG CAA ATA TGT ACA TTA AGG GAA TTT TTA AGA      622
Phe Val Glu Pro Thr Ser Gln Ile Cys Thr Leu Arg Glu Phe Leu Arg
             195                 200                 205

GGC ATT TGC TTT GGT GAT TCT GGT GGA CCA CTG GTT TAC AAA GGT GAA      670
Gly Ile Cys Phe Gly Asp Ser Gly Gly Pro Leu Val Tyr Lys Gly Glu
         210                 215                 220

CTG GTT GGC GTT TCT TCG TTT GTC TTG TAC ACT TGC GGA GCT GGA CGC      718
Leu Val Gly Val Ser Ser Phe Val Leu Tyr Thr Cys Gly Ala Gly Arg
     225                 230                 235

CCA GAT GTT TTT GTT AAA GTG CGT GAT TTC CAA TCT TGG ATC AAT TCT      766
Pro Asp Val Phe Val Lys Val Arg Asp Phe Gln Ser Trp Ile Asn Ser
240                 245                 250                 255

GAA ATT AGA AAA AAA TAAATAGATT TCAATCATGA TTTGTTGTAA TAAAAAATGG      821
Glu Ile Arg Lys Lys
                260

TTAAATAAAG GCAGCATAAT TTAAAAAAAA AAAAAAAAAA AAA                      864
```

(2) INFORMATION FOR SEQ ID NO: 139:

(i) SEQUENCE CHARACTERISTICS:
        (A) LENGTH: 260 amino acids
        (B) TYPE: amino acid
        (D) TOPOLOGY: linear (ii) MOLECULE TYPE: protein (xi) SEQUENCE DESCRIPTION: SEQ ID NO: 139:

```
Thr Lys Pro Ile Thr Ile Gln Lys Leu Phe Gln Met Met Ala Asn Phe
 1               5                  10                  15

Val Leu Phe Thr Leu Leu Ala Leu Val Ser Val Ala Cys Ser Lys Tyr
             20                  25                  30
```

-continued

```
Ile Asp Pro Arg Ile Ile Gly Gly Glu Asp Ala Pro Glu Gly Ser Ala
        35                  40                  45

Pro Tyr Gln Val Ser Leu Arg Asn Arg Asp Leu Glu His Phe Cys Gly
    50                  55                  60

Gly Ser Ile Leu Asn Lys Arg Trp Ile Val Thr Ala Ala His Cys Leu
65                  70                  75                  80

Lys Pro Gly Ile Leu Lys Ser Val Tyr Met Gly Ser Asn Ser Leu Asp
                85                  90                  95

Gly Asn Gly Thr Tyr Tyr Asp Val Glu Arg Phe Val Met His His Lys
            100                 105                 110

Tyr Thr Pro Lys Ile Thr Val Asn Tyr Ala Asp Ile Gly Leu Ile Lys
        115                 120                 125

Val Thr Lys Asp Ile Ile Phe Ser Asp Lys Val Gln Pro Ile Lys Ile
    130                 135                 140

Ala Lys Lys Ile Ser Arg Val Xaa Asn Leu Gln Gly His Trp Leu Gly
145                 150                 155                 160

Ser Ile Gly Gly Trp Gly Pro Xaa Tyr Gln Thr Asn Cys Asn Lys Val
                165                 170                 175

Glu Thr Thr Ala Ile Thr Asn Glu Lys Cys Tyr Glu Leu Ser Gln Phe
            180                 185                 190

Val Glu Pro Thr Ser Gln Ile Cys Thr Leu Arg Glu Phe Leu Arg Gly
        195                 200                 205

Ile Cys Phe Gly Asp Ser Gly Gly Pro Leu Val Tyr Lys Gly Glu Leu
    210                 215                 220

Val Gly Val Ser Ser Phe Val Leu Tyr Thr Cys Gly Ala Gly Arg Pro
225                 230                 235                 240

Asp Val Phe Val Lys Val Arg Asp Phe Gln Ser Trp Ile Asn Ser Glu
                245                 250                 255

Ile Arg Lys Lys
        260
```

(2) INFORMATION FOR SEQ ID NO: 140:

(i) SEQUENCE CHARACTERISTICS:
        (A) LENGTH: 610 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..555
        (D) OTHER INFORMATION: /note= "At pos. bp 133, change A to
           H; at pos. bp 168, change A to W. At pos. aa 45,
           substitute Xaa."

(xi) SEQUENCE DESCRIPTION: SEQ ID NO: 140:

```
GTT TTG ACA GCT GCT CAT TGT GTA GAA AAG TAT AAA TTG ACT GTT AGA      48
Val Leu Thr Ala Ala His Cys Val Glu Lys Tyr Lys Leu Thr Val Arg
 1               5                  10                  15

GTT GGC AGC AGC GAT TTG GAA TCA GGA GGC AAA ATA CAT ACC ATT AAA      96
Val Gly Ser Ser Asp Leu Glu Ser Gly Gly Lys Ile His Thr Ile Lys
                20                  25                  30

AAA ATC CAT GTT CAT CCA TAT TAC GAA CCG GTT GAC HAC GAT TTT GCC     144
Lys Ile His Val His Pro Tyr Tyr Glu Pro Val Asp Xaa Asp Phe Ala
        35                  40                  45
```

```
TTG CTG GGA CTT GAT GAA CCA GTW TTC TTG AGC AAC AAA GTT CAA CTT        192
Leu Leu Gly Leu Asp Glu Pro Val Phe Leu Ser Asn Lys Val Gln Leu
 50                  55                  60

GTG AAA CTT GTA GAA CAA GGT GTA GAT CTG GAT GAA GGA ACC TTT CTT        240
Val Lys Leu Val Glu Gln Gly Val Asp Leu Asp Glu Gly Thr Phe Leu
 65                  70                  75                  80

AAT GCC ACT GGA TGG GGT ACA ACA GCG ACC GAA GAT TTG GCT CCA GTT        288
Asn Ala Thr Gly Trp Gly Thr Thr Ala Thr Glu Asp Leu Ala Pro Val
                 85                  90                  95

CTT CAA TTA GTA ACA GTT CCA GTA GTC AAC ACA TAT ACT TGC AGC AAA        336
Leu Gln Leu Val Thr Val Pro Val Val Asn Thr Tyr Thr Cys Ser Lys
            100                 105                 110

ATT TAC GAC TTT GGT ATC ACA CAA AGA ATG TTT TGC GCT GGT TAT ATG        384
Ile Tyr Asp Phe Gly Ile Thr Gln Arg Met Phe Cys Ala Gly Tyr Met
            115                 120                 125

GAT GGA ACT CTT AAG GAC ATC TGC TCT GGA GAT TCA GGT AGT CCT GTG        432
Asp Gly Thr Leu Lys Asp Ile Cys Ser Gly Asp Ser Gly Ser Pro Val
130                 135                 140

GTG AAG GAT GGT ATC CAA TAT GGT GTG GTG TCT TGG GGA AAA GCT TGT        480
Val Lys Asp Gly Ile Gln Tyr Gly Val Val Ser Trp Gly Lys Ala Cys
145                 150                 155                 160

GCC GAT CCA AGA TAT CCA AAT GTT TAT TCC AAA GTT AGC TAC GAA CGT        528
Ala Asp Pro Arg Tyr Pro Asn Val Tyr Ser Lys Val Ser Tyr Glu Arg
                165                 170                 175

ATA TGG ATT AAA GAA GTG TCT GGA GTT TAAGTAGATG CATTCTTTAT             575
Ile Trp Ile Lys Glu Val Ser Gly Val
            180                 185

TATAATAAAA TTGTTTAATT AAAAAAAAAA AAAAA                                 610

(2) INFORMATION FOR SEQ ID NO: 141:

(i) SEQUENCE CHARACTERISTICS:
        (A) LENGTH: 185 amino acids
        (B) TYPE: amino acid
        (D) TOPOLOGY: linear (ii) MOLECULE TYPE: protein (xi) SEQUENCE DESCRIPTION: SEQ ID NO: 141:

Val Leu Thr Ala Ala His Cys Val Glu Lys Tyr Lys Leu Thr Val Arg
  1               5                  10                  15

Val Gly Ser Ser Asp Leu Glu Ser Gly Gly Lys Ile His Thr Ile Lys
                 20                  25                  30

Lys Ile His Val His Pro Tyr Tyr Glu Pro Val Asp Xaa Asp Phe Ala
             35                  40                  45

Leu Leu Gly Leu Asp Glu Pro Val Phe Leu Ser Asn Lys Val Gln Leu
 50                  55                  60

Val Lys Leu Val Glu Gln Gly Val Asp Leu Asp Glu Gly Thr Phe Leu
 65                  70                  75                  80

Asn Ala Thr Gly Trp Gly Thr Thr Ala Thr Glu Asp Leu Ala Pro Val
                 85                  90                  95

Leu Gln Leu Val Thr Val Pro Val Val Asn Thr Tyr Thr Cys Ser Lys
            100                 105                 110

Ile Tyr Asp Phe Gly Ile Thr Gln Arg Met Phe Cys Ala Gly Tyr Met
            115                 120                 125

Asp Gly Thr Leu Lys Asp Ile Cys Ser Gly Asp Ser Gly Ser Pro Val
130                 135                 140

Val Lys Asp Gly Ile Gln Tyr Gly Val Val Ser Trp Gly Lys Ala Cys
145                 150                 155                 160
```

```
Ala Asp Pro Arg Tyr Pro Asn Val Tyr Ser Lys Val Ser Tyr Glu Arg
            165                 170                 175

Ile Trp Ile Lys Glu Val Ser Gly Val
            180                 185
```

(2) INFORMATION FOR SEQ ID NO: 142:

(i) SEQUENCE CHARACTERISTICS:
        (A) LENGTH: 386 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..384
        (D) OTHER INFORMATION: /note= "At pos. bp 3, change A to R."

(xi) SEQUENCE DESCRIPTION: SEQ ID NO: 142:

```
AAR ATT GGT ACT AGC CAT AGG ATA CTT TAT GGT AGA GTG ATA GAC ATA      48
Lys Ile Gly Thr Ser His Arg Ile Leu Tyr Gly Arg Val Ile Asp Ile
 1               5                  10                  15

AAA GAA ATT ATA ATG CAT CCA GAC TAT ACG TCT GTA TCA GGA AGT GGA      96
Lys Glu Ile Ile Met His Pro Asp Tyr Thr Ser Val Ser Gly Ser Gly
                20                  25                  30

TAC GAT GTA GCA CTA TTG AAA CCG TCT ACA AAA ATT GTT TTT AAC TCA     144
Tyr Asp Val Ala Leu Leu Lys Pro Ser Thr Lys Ile Val Phe Asn Ser
            35                  40                  45

AAA TCT ATC AAA CCT GTA AAG CTA ATT GAT GAA GGA ATC GAA ACG GCT     192
Lys Ser Ile Lys Pro Val Lys Leu Ile Asp Glu Gly Ile Glu Thr Ala
         50                  55                  60

AAT GGT TCA ATA GCA ACC GTG GCA GGT TGG GGT AAA GTA GTG GAT GGT     240
Asn Gly Ser Ile Ala Thr Val Ala Gly Trp Gly Lys Val Val Asp Gly
 65                  70                  75                  80

TTT CCG TAC ATA CCT AAT TAT TTA TTG GCT GTA AAT GTA CCG ATT ATT     288
Phe Pro Tyr Ile Pro Asn Tyr Leu Leu Ala Val Asn Val Pro Ile Ile
                85                  90                  95

GAT AGC GAT ACA TGC AAG TCG ATG AAT ATT GAA TAT CAA AAA TAT TTG     336
Asp Ser Asp Thr Cys Lys Ser Met Asn Ile Glu Tyr Gln Lys Tyr Leu
            100                 105                 110

AAA CCA AAT ATG ATA TGC GCC GGA TAT GCA AAA GGT GGT AAA GAT TCT     384
Lys Pro Asn Met Ile Cys Ala Gly Tyr Ala Lys Gly Gly Lys Asp Ser
        115                 120                 125

TG                                                                   386
```

(2) INFORMATION FOR SEQ ID NO: 143:

(i) SEQUENCE CHARACTERISTICS:
        (A) LENGTH: 128 amino acids
        (B) TYPE: amino acid
        (D) TOPOLOGY: linear (ii) MOLECULE TYPE: protein (xi) SEQUENCE DESCRIPTION: SEQ ID NO: 143:

```
Lys Ile Gly Thr Ser His Arg Ile Leu Tyr Gly Arg Val Ile Asp Ile
 1               5                  10                  15

Lys Glu Ile Ile Met His Pro Asp Tyr Thr Ser Val Ser Gly Ser Gly
                20                  25                  30

Tyr Asp Val Ala Leu Leu Lys Pro Ser Thr Lys Ile Val Phe Asn Ser
            35                  40                  45
```

```
Lys Ser Ile Lys Pro Val Lys Leu Ile Asp Glu Gly Ile Glu Thr Ala
         50                  55                  60

Asn Gly Ser Ile Ala Thr Val Ala Gly Trp Gly Lys Val Val Asp Gly
 65                  70                  75                  80

Phe Pro Tyr Ile Pro Asn Tyr Leu Leu Ala Val Asn Val Pro Ile Ile
                 85                  90                  95

Asp Ser Asp Thr Cys Lys Ser Met Asn Ile Glu Tyr Gln Lys Tyr Leu
            100                 105                 110

Lys Pro Asn Met Ile Cys Ala Gly Tyr Ala Lys Gly Gly Lys Asp Ser
            115                 120                 125
```

(2) INFORMATION FOR SEQ ID NO: 144:

(i) SEQUENCE CHARACTERISTICS:
        (A) LENGTH: 923 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..802
        (D) OTHER INFORMATION: /note= "At pos. bp 896, change G to
            B; at pos. bp 899, change A to W."

(xi) SEQUENCE DESCRIPTION: SEQ ID NO: 144:

```
A TTA ACA ATG ATG AAA CTT TTG GTA GTT TTT GCG ATT TTC GCT CAA        46
  Leu Thr Met Met Lys Leu Leu Val Val Phe Ala Ile Phe Ala Gln
   1               5                  10                  15

ATC AGT TTT GTT TTT GGA AAT AAT GTA ACA GAA TTC GAT GAC CGA ATC      94
Ile Ser Phe Val Phe Gly Asn Asn Val Thr Glu Phe Asp Asp Arg Ile
                20                  25                  30

GTT GGA GGT GAA GAT GTT GAT ATA TCA ACT TGT GGT TGG CAA ATT TCA     142
Val Gly Gly Glu Asp Val Asp Ile Ser Thr Cys Gly Trp Gln Ile Ser
            35                  40                  45

TTT CAA AGT GAA AAC CTT CAT TTT TGT GGA GGA TCA ATT ATT GCA CCA     190
Phe Gln Ser Glu Asn Leu His Phe Cys Gly Gly Ser Ile Ile Ala Pro
        50                  55                  60

AAA TGG ATT CTA ACT GCT GCA CAC TGT GTT GAA TGG TTG AAA AAG CCG     238
Lys Trp Ile Leu Thr Ala Ala His Cys Val Glu Trp Leu Lys Lys Pro
 65                  70                  75

CTC AAA GAC ATA ACC GTA CGT ATA GGA AGC AGT ATA CGT AAC AAA GGT     286
Leu Lys Asp Ile Thr Val Arg Ile Gly Ser Ser Ile Arg Asn Lys Gly
 80                  85                  90                  95

GGT CGA GTT CAT AAA GTA ATA GAT TTC CAC ATG CAT CCC TCG TAC AAT     334
Gly Arg Val His Lys Val Ile Asp Phe His Met His Pro Ser Tyr Asn
                100                 105                 110

AAG AGG GCG GAT TAT GAT TTT GAC GTT GCT GTA CTA GAA CTT GAA AAA     382
Lys Arg Ala Asp Tyr Asp Phe Asp Val Ala Val Leu Glu Leu Glu Lys
            115                 120                 125

CCA GTC TCA TAT ACG GTT TGT ACA GTA GTA TCA GTA GAT TTA GCC GAA     430
Pro Val Ser Tyr Thr Val Cys Thr Val Val Ser Val Asp Leu Ala Glu
        130                 135                 140

AGT GGA ACT GAA GTT AAA CCT GGA GCA ATA CTT AGT GTC ACT GGA TGG     478
Ser Gly Thr Glu Val Lys Pro Gly Ala Ile Leu Ser Val Thr Gly Trp
145                 150                 155

GGT GCA ACT AAG GAA GGT GGT GGC GGA ACT TTG CAA CTA CAA GGT GTG     526
Gly Ala Thr Lys Glu Gly Gly Gly Gly Thr Leu Gln Leu Gln Gly Val
160                 165                 170                 175
```

```
AAA GTT CCA GCT ATC TCT CCC AAA GAT TGT GCT AAG GGA TAT CCA CCT        574
Lys Val Pro Ala Ile Ser Pro Lys Asp Cys Ala Lys Gly Tyr Pro Pro
                180                 185                 190

TCT GGA GGT AAA GAC AAA ATT ACA GAC AGC ATG TTA TGT GCT GGT CTT        622
Ser Gly Gly Lys Asp Lys Ile Thr Asp Ser Met Leu Cys Ala Gly Leu
            195                 200                 205

CCT GAA GGA GGT AAA GAT TCC TGC CAA GGC GAC AGT GGC GGT CCA CTG        670
Pro Glu Gly Gly Lys Asp Ser Cys Gln Gly Asp Ser Gly Gly Pro Leu
        210                 215                 220

GTA GAT GAA AAT AGA AAG CAA GTA GGA GTG GTT TCT TGG GGT CAA GGA        718
Val Asp Glu Asn Arg Lys Gln Val Gly Val Val Ser Trp Gly Gln Gly
    225                 230                 235

TGT GCC AGA CCA GGA AAA CCA GGA ATT TAT GCT AAA GTG TCA CAC CCC        766
Cys Ala Arg Pro Gly Lys Pro Gly Ile Tyr Ala Lys Val Ser His Pro
240                 245                 250                 255

GAA ATC AGA AAA TTT ATT GAA AAA TAT GCT AAT GTT TAAGTGGATT             812
Glu Ile Arg Lys Phe Ile Glu Lys Tyr Ala Asn Val
                260                 265

TCATTTTCAA TATAATGTGA TTTAAGATAC TCTTTAATGT TATGATATGA ATTGTGATA       872

ATTAAATAAT AAAGATTGAA GAABTGWTAA AAAAAAAAAA AAAAAAAAA A                923

(2) INFORMATION FOR SEQ ID NO: 145:

(i) SEQUENCE CHARACTERISTICS:
        (A) LENGTH: 267 amino acids
        (B) TYPE: amino acid
        (D) TOPOLOGY: linear (ii) MOLECULE TYPE: protein (xi) SEQUENCE DESCRIPTION: SEQ ID NO: 145:

Leu Thr Met Met Lys Leu Leu Val Val Phe Ala Ile Phe Ala Gln Ile
  1               5                  10                  15

Ser Phe Val Phe Gly Asn Asn Val Thr Glu Phe Asp Asp Arg Ile Val
                 20                  25                  30

Gly Gly Glu Asp Val Asp Ile Ser Thr Cys Gly Trp Gln Ile Ser Phe
             35                  40                  45

Gln Ser Glu Asn Leu His Phe Cys Gly Gly Ser Ile Ile Ala Pro Lys
         50                  55                  60

Trp Ile Leu Thr Ala Ala His Cys Val Glu Trp Leu Lys Lys Pro Leu
 65                  70                  75                  80

Lys Asp Ile Thr Val Arg Ile Gly Ser Ser Ile Arg Asn Lys Gly Gly
                 85                  90                  95

Arg Val His Lys Val Ile Asp Phe His Met His Pro Ser Tyr Asn Lys
                100                 105                 110

Arg Ala Asp Tyr Asp Phe Asp Val Ala Val Leu Glu Leu Glu Lys Pro
            115                 120                 125

Val Ser Tyr Thr Val Cys Thr Val Ser Val Asp Leu Ala Glu Ser
        130                 135                 140

Gly Thr Glu Val Lys Pro Gly Ala Ile Leu Ser Val Thr Gly Trp Gly
145                 150                 155                 160

Ala Thr Lys Glu Gly Gly Gly Thr Leu Gln Leu Gln Gly Val Lys
                165                 170                 175

Val Pro Ala Ile Ser Pro Lys Asp Cys Ala Lys Gly Tyr Pro Pro Ser
            180                 185                 190

Gly Gly Lys Asp Lys Ile Thr Asp Ser Met Leu Cys Ala Gly Leu Pro
        195                 200                 205
```

```
Glu Gly Gly Lys Asp Ser Cys Gln Gly Asp Ser Gly Pro Leu Val
    210                 215                 220

Asp Glu Asn Arg Lys Gln Val Gly Val Val Ser Trp Gly Gln Gly Cys
225                 230                 235                 240

Ala Arg Pro Gly Lys Pro Gly Ile Tyr Ala Lys Val Ser His Pro Glu
                245                 250                 255

Ile Arg Lys Phe Ile Glu Lys Tyr Ala Asn Val
                260                 265
```

(2) INFORMATION FOR SEQ ID NO: 146:

(i) SEQUENCE CHARACTERISTICS:
        (A) LENGTH: 612 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..612

(xi) SEQUENCE DESCRIPTION: SEQ ID NO: 146:

```
GTT TGC AAG ATG GCA ACA ACT CTG TTT TCT CTT GCC ATA GTT TTG TTT      48
Val Cys Lys Met Ala Thr Thr Leu Phe Ser Leu Ala Ile Val Leu Phe
  1               5                  10                  15

ATC TCT ACT TCA GAA GAA TCA GCA CAT ATT TCG CAA GGA TCT CGA ATA      96
Ile Ser Thr Ser Glu Glu Ser Ala His Ile Ser Gln Gly Ser Arg Ile
             20                  25                  30

TTA GGA GGT AGA AAT GCA AAA CTC GGA GAT GCT CCT TAT CAA GTA TCA     144
Leu Gly Gly Arg Asn Ala Lys Leu Gly Asp Ala Pro Tyr Gln Val Ser
         35                  40                  45

CTA AGA GAT AAT TTT GGA CAT TTT TGT GGA GGT TCT ATC ATT AGT GAA     192
Leu Arg Asp Asn Phe Gly His Phe Cys Gly Gly Ser Ile Ile Ser Glu
     50                  55                  60

AAT TTT GTG ATT ACA GCA GCT CAT TGC CTT GAT GGA TAC ACA GTG AGC     240
Asn Phe Val Ile Thr Ala Ala His Cys Leu Asp Gly Tyr Thr Val Ser
 65                  70                  75                  80

AAA TTT AAA GTA GCA ACT GGT ACA ATC GAG TAT GGT AAA GGA GGT GAC     288
Lys Phe Lys Val Ala Thr Gly Thr Ile Glu Tyr Gly Lys Gly Gly Asp
                 85                  90                  95

GAA TAT AAA GTC ATC AAC TTT GTT GTC CGG GAT GAC TTT CAA TAT GTC     336
Glu Tyr Lys Val Ile Asn Phe Val Val Arg Asp Asp Phe Gln Tyr Val
            100                 105                 110

AAA TTA GAA AAT GAT ATT GCT ATA GTA CAA ATA GAT GGA TCT TTT AAA     384
Lys Leu Glu Asn Asp Ile Ala Ile Val Gln Ile Asp Gly Ser Phe Lys
        115                 120                 125

TTT AAT GAC TAT GTA AAG CCT ATA AAA TTG CCA AAT CAA GAT ACT AAA     432
Phe Asn Asp Tyr Val Lys Pro Ile Lys Leu Pro Asn Gln Asp Thr Lys
    130                 135                 140

GTT GGC GCG GAT GTT GTC CTA ACA GGA TGG GGA AAA ATG GAA GGT GGT     480
Val Gly Ala Asp Val Val Leu Thr Gly Trp Gly Lys Met Glu Gly Gly
145                 150                 155                 160

AAA AAT CCA GAA ACT CTA CAA ATC TTG AAC TTA AAA ACA ATT GAT CAA     528
Lys Asn Pro Glu Thr Leu Gln Ile Leu Asn Leu Lys Thr Ile Asp Gln
                165                 170                 175

GGA GAA TGC AAA CAA GCT TTG GCA GAA GTA AAC ACA GTT CTT CCA AGT     576
Gly Glu Cys Lys Gln Ala Leu Ala Glu Val Asn Thr Val Leu Pro Ser
            180                 185                 190
```

```
CAA ATT TGT ACC TAT GTT GGT GTT GGC AAA GGA GCT                      612
Gln Ile Cys Thr Tyr Val Gly Val Gly Lys Gly Ala
        195                 200
```

(2) INFORMATION FOR SEQ ID NO: 147:

(i) SEQUENCE CHARACTERISTICS:
        (A) LENGTH: 204 amino acids
        (B) TYPE: amino acid
        (D) TOPOLOGY: linear (ii) MOLECULE TYPE: protein (xi) SEQUENCE DESCRIPTION: SEQ ID NO: 147:

```
Val Cys Lys Met Ala Thr Thr Leu Phe Ser Leu Ala Ile Val Leu Phe
 1               5                  10                  15

Ile Ser Thr Ser Glu Glu Ser Ala His Ile Ser Gln Gly Ser Arg Ile
                20                  25                  30

Leu Gly Gly Arg Asn Ala Lys Leu Gly Asp Ala Pro Tyr Gln Val Ser
            35                  40                  45

Leu Arg Asp Asn Phe Gly His Phe Cys Gly Ser Ile Ile Ser Glu
        50                  55                  60

Asn Phe Val Ile Thr Ala Ala His Cys Leu Asp Gly Tyr Thr Val Ser
 65                 70                  75                  80

Lys Phe Lys Val Ala Thr Gly Thr Ile Glu Tyr Gly Lys Gly Gly Asp
                85                  90                  95

Glu Tyr Lys Val Ile Asn Phe Val Val Arg Asp Asp Phe Gln Tyr Val
                100                 105                 110

Lys Leu Glu Asn Asp Ile Ala Ile Val Gln Ile Asp Gly Ser Phe Lys
            115                 120                 125

Phe Asn Asp Tyr Val Lys Pro Ile Lys Leu Pro Asn Gln Asp Thr Lys
130                 135                 140

Val Gly Ala Asp Val Val Leu Thr Gly Trp Gly Lys Met Glu Gly Gly
145                 150                 155                 160

Lys Asn Pro Glu Thr Leu Gln Ile Leu Asn Leu Lys Thr Ile Asp Gln
                165                 170                 175

Gly Glu Cys Lys Gln Ala Leu Ala Glu Val Asn Thr Val Leu Pro Ser
            180                 185                 190

Gln Ile Cys Thr Tyr Val Gly Val Gly Lys Gly Ala
        195                 200
```

(2) INFORMATION FOR SEQ ID NO: 148:

(i) SEQUENCE CHARACTERISTICS:
        (A) LENGTH: 641 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..641
        (D) OTHER INFORMATION: /note= "At pos. bp 91, change G to
        N; at pos. bp 385, change A to M; at bp 404, change A to
        W. At pos. aa 30, 128 and 134, substitute Xaa."

(xi) SEQUENCE DESCRIPTION: SEQ ID NO: 148:

```
CA AAC ATG AAA CTT TAT GTT TTT ACA TTG ATC ATC GCA GCC GCT GTT        47
   Asn Met Lys Leu Tyr Val Phe Thr Leu Ile Ile Ala Ala Ala Val
    1               5                  10                  15
```

```
GCT GCA CCA ACA AAC GAA ATC GAT TGG ATA GGC TTT CCC GAA GNT TTT        95
Ala Ala Pro Thr Asn Glu Ile Asp Trp Ile Gly Phe Pro Glu Xaa Phe
            20                  25                  30

CCT CGT GTA GTT GGT GGC CAG ACT GCC AAA CCT CAC CAG TTC CCC TGG       143
Pro Arg Val Val Gly Gly Gln Thr Ala Lys Pro His Gln Phe Pro Trp
                35                  40                  45

CAG GTT TCC CTG CAA AGG TCC GGA AAG CAT TTG TGC GGC GGT TCC ATC       191
Gln Val Ser Leu Gln Arg Ser Gly Lys His Leu Cys Gly Gly Ser Ile
                    50                  55                  60

TTG AAC GAC AGG TGG GTC TTG ACA GCC GCG CAC TGC ATC AGC GGA ACT       239
Leu Asn Asp Arg Trp Val Leu Thr Ala Ala His Cys Ile Ser Gly Thr
                65                  70                  75

GAA AAT TAC GAG GCT GTA GTC GGA AAA CAC GAT TTG TCG AAA AGC GAA       287
Glu Asn Tyr Glu Ala Val Val Gly Lys His Asp Leu Ser Lys Ser Glu
 80                  85                  90                  95

TCA TCT GAG CAA CGT TGC GCC TAC AAG AGG ACC ATC GTC CAC TCG TCC       335
Ser Ser Glu Gln Arg Cys Ala Tyr Lys Arg Thr Ile Val His Ser Ser
                    100                 105                 110

TTC ACT GGA AGG GTG GGT CCT TAC GAT GTC GCT TTG ATT GAA TTA GAA       383
Phe Thr Gly Arg Val Gly Pro Tyr Asp Val Ala Leu Ile Glu Leu Glu
                115                 120                 125

AMA CCT TTC AAA TTG AAC GAW AAA TGT AAG CCA ATC AGA CTT CCA TTG       431
Xaa Pro Phe Lys Leu Asn Xaa Lys Cys Lys Pro Ile Arg Leu Pro Leu
            130                 135                 140

AAA GAT GAA GCA CAT TCT GGA CAA GTG ACG CTT TCT GGT TGG GGA TCT       479
Lys Asp Glu Ala His Ser Gly Gln Val Thr Leu Ser Gly Trp Gly Ser
145                 150                 155

ACT TCA ACT ACC ATC TTC CCC ACT TAC CCA AAT GAA CTA CAG TAT GTT       527
Thr Ser Thr Thr Ile Phe Pro Thr Tyr Pro Asn Glu Leu Gln Tyr Val
160                 165                 170                 175

GAC AAA CCG ATT GTT CCA TAT ACT GAT TGC GAA AAT GCT ATG GGC GGA       575
Asp Lys Pro Ile Val Pro Tyr Thr Asp Cys Glu Asn Ala Met Gly Gly
                180                 185                 190

CCA GGA GCA TCT CCT CTT GAT CCT TTG AAC ATC TGC ACT GGT CCC TTG       623
Pro Gly Ala Ser Pro Leu Asp Pro Leu Asn Ile Cys Thr Gly Pro Leu
                195                 200                 205

ACT GGT GGC ATC AGT GCT                                               641
Thr Gly Gly Ile Ser Ala
            210
```

(2) INFORMATION FOR SEQ ID NO: 149:

(i) SEQUENCE CHARACTERISTICS:
        (A) LENGTH: 213 amino acids
        (B) TYPE: amino acid
        (D) TOPOLOGY: linear (ii) MOLECULE TYPE: protein (xi) SEQUENCE DESCRIPTION: SEQ ID NO: 149:

```
Asn Met Lys Leu Tyr Val Phe Thr Leu Ile Ile Ala Ala Val Ala
 1               5                  10                  15

Ala Pro Thr Asn Glu Ile Asp Trp Ile Gly Phe Pro Glu Xaa Phe Pro
            20                  25                  30

Arg Val Val Gly Gly Gln Thr Ala Lys Pro His Gln Phe Pro Trp Gln
                35                  40                  45

Val Ser Leu Gln Arg Ser Gly Lys His Leu Cys Gly Gly Ser Ile Leu
        50                  55                  60

Asn Asp Arg Trp Val Leu Thr Ala Ala His Cys Ile Ser Gly Thr Glu
65                  70                  75                  80
```

```
Asn Tyr Glu Ala Val Val Gly Lys His Asp Leu Ser Lys Ser Glu Ser
                85                  90                  95

Ser Glu Gln Arg Cys Ala Tyr Lys Arg Thr Ile Val His Ser Ser Phe
            100                 105                 110

Thr Gly Arg Val Gly Pro Tyr Asp Val Ala Leu Ile Glu Leu Glu Xaa
        115                 120                 125

Pro Phe Lys Leu Asn Xaa Lys Cys Lys Pro Ile Arg Leu Pro Leu Lys
    130                 135                 140

Asp Glu Ala His Ser Gly Gln Val Thr Leu Ser Gly Trp Gly Ser Thr
145                 150                 155                 160

Ser Thr Thr Ile Phe Pro Thr Tyr Pro Asn Glu Leu Gln Tyr Val Asp
                165                 170                 175

Lys Pro Ile Val Pro Tyr Thr Asp Cys Glu Asn Ala Met Gly Gly Pro
            180                 185                 190

Gly Ala Ser Pro Leu Asp Pro Leu Asn Ile Cys Thr Gly Pro Leu Thr
        195                 200                 205

Gly Gly Ile Ser Ala
    210
```

(2) INFORMATION FOR SEQ ID NO: 150:

(i) SEQUENCE CHARACTERISTICS:
        (A) LENGTH: 626 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..626

(xi) SEQUENCE DESCRIPTION: SEQ ID NO: 150:

```
TG ACT ATG AAC TTT GCA TTG TGG TTT GTG ACT CTT GTG TCC ATC ACC        47
   Thr Met Asn Phe Ala Leu Trp Phe Val Thr Leu Val Ser Ile Thr
    1               5                  10                  15

AGC GCT GAT CCA ATT CGT GTT TCC TCA ATT GGA AAT GCT AAT ATG AAA       95
Ser Ala Asp Pro Ile Arg Val Ser Ser Ile Gly Asn Ala Asn Met Glu
            20                  25                  30

TCT CGC GTT GTT GGT GGC GAA AAC GCA GAA GTA GGA GCT GCT CCT TAC      143
Ser Arg Val Val Gly Gly Glu Asn Ala Glu Val Gly Ala Ala Pro Tyr
        35                  40                  45

CAA GTT TCT TTG AAA TAC AAT AAT GGA GCT CAT TTT TGC GGA GGT GTC      191
Gln Val Ser Leu Lys Tyr Asn Asn Gly Ala His Phe Cys Gly Gly Val
    50                  55                  60

GTG ATA ACC AAA ACT TGG GTG CTA ACT GCT GCA CGT TGT ATT CAC GAG      239
Val Ile Thr Lys Thr Trp Val Leu Thr Ala Ala Arg Cys Ile His Glu
65                  70                  75

GAG GAA CCC GAC AGA TTC ACA GTG GTT GTT GGT ACC AAC ACT TTA AAT      287
Glu Glu Pro Asp Arg Phe Thr Val Val Val Gly Thr Asn Thr Leu Asn
80                  85                  90                  95

GCT GGA GGA GAA GGT TAC AAC GTT AAA CAG ATA GTT ATT CAT ATG CAA      335
Ala Gly Gly Glu Gly Tyr Asn Val Lys Gln Ile Val Ile His Met Gln
            100                 105                 110

TTC AAC CAA GTT TAT CTT CTG AAC GAT ATT GGT TTG ATC GAA ACC GAA      383
Phe Asn Gln Val Tyr Leu Leu Asn Asp Ile Gly Leu Ile Glu Thr Glu
        115                 120                 125

TCA CCA ATA CAA TTT CAT GAT CTG GTT AAG CCA ATC TCA GTC CCC AAT      431
Ser Pro Ile Gln Phe His Asp Leu Val Lys Pro Ile Ser Val Pro Asn
    130                 135                 140
```

```
ATG CAT GTT GAA GAT GGC ACG AGA GTT ACT CTT TTT GGA TGG GGA AAT    479
Met His Val Glu Asp Gly Thr Arg Val Thr Leu Phe Gly Trp Gly Asn
    145                 150                 155

TTA ACG GCT GAA GGA CAT ATG CCA AAC CAT TTA CAA ACA ATT GAT TTG    527
Leu Thr Ala Glu Gly His Met Pro Asn His Leu Gln Thr Ile Asp Leu
160                 165                 170                 175

TTA ACA ATA AAT CTG AGT GAA TGC TCC CGA TTA TTA CCT GAA CCA AGT    575
Leu Thr Ile Asn Leu Ser Glu Cys Ser Arg Leu Leu Pro Glu Pro Ser
                180                 185                 190

ATG ATC AGT ACA AAA CAC ATT TGC ACC TTT GTT TCA TAT GGA AAA GGA    623
Met Ile Ser Thr Lys His Ile Cys Thr Phe Val Ser Tyr Gly Lys Gly
            195                 200                 205

CTT                                                                626
Leu
```

(2) INFORMATION FOR SEQ ID NO: 151:

(i) SEQUENCE CHARACTERISTICS:
        (A) LENGTH: 208 amino acids
        (B) TYPE: amino acid
        (D) TOPOLOGY: linear (ii) MOLECULE TYPE: protein (xi) SEQUENCE DESCRIPTION: SEQ ID NO: 151:

```
Thr Met Asn Phe Ala Leu Trp Phe Val Thr Leu Val Ser Ile Thr Ser
 1               5                  10                  15

Ala Asp Pro Ile Arg Val Ser Ser Ile Gly Asn Ala Asn Met Glu Ser
            20                  25                  30

Arg Val Val Gly Gly Glu Asn Ala Glu Val Gly Ala Ala Pro Tyr Gln
        35                  40                  45

Val Ser Leu Lys Tyr Asn Asn Gly Ala His Phe Cys Gly Gly Val Val
    50                  55                  60

Ile Thr Lys Thr Trp Val Leu Thr Ala Ala Arg Cys Ile His Glu Glu
65                  70                  75                  80

Glu Pro Asp Arg Phe Thr Val Val Val Gly Thr Asn Thr Leu Asn Ala
                85                  90                  95

Gly Gly Glu Gly Tyr Asn Val Lys Gln Ile Val Ile His Met Gln Phe
            100                 105                 110

Asn Gln Val Tyr Leu Leu Asn Asp Ile Gly Leu Ile Glu Thr Glu Ser
        115                 120                 125

Pro Ile Gln Phe His Asp Leu Val Lys Pro Ile Ser Val Pro Asn Met
    130                 135                 140

His Val Glu Asp Gly Thr Arg Val Thr Leu Phe Gly Trp Gly Asn Leu
145                 150                 155                 160

Thr Ala Glu Gly His Met Pro Asn His Leu Gln Thr Ile Asp Leu Leu
                165                 170                 175

Thr Ile Asn Leu Ser Glu Cys Ser Arg Leu Leu Pro Glu Pro Ser Met
            180                 185                 190

Ile Ser Thr Lys His Ile Cys Thr Phe Val Ser Tyr Gly Lys Gly Leu
        195                 200                 205
```

(2) INFORMATION FOR SEQ ID NO: 152:

(i) SEQUENCE CHARACTERISTICS:
        (A) LENGTH: 433 base pairs
        (B) TYPE: nucleic acid
        (C) STRANDEDNESS: single
        (D) TOPOLOGY: linear (ii) MOLECULE TYPE: cDNA (ix) FEATURE:
    (A) NAME/KEY: CDS
    (B) LOCATION: 1..432

(xi) SEQUENCE DESCRIPTION: SEQ ID NO: 152:

```
GTA ACT GCT GCA CAT TGC TTT TAT GGA ACG TTA TTT CCG ATT GGA TTC      48
Val Thr Ala Ala His Cys Phe Tyr Gly Thr Leu Phe Pro Ile Gly Phe
 1               5                  10                  15

TCT GCG AGA GCC GGC AGC AGT ACT GTG AAT TCA GGA GGA ACT GTG CAT      96
Ser Ala Arg Ala Gly Ser Ser Thr Val Asn Ser Gly Gly Thr Val His
             20                  25                  30

ACA ATT TTG TAT TGG TAT ATT CAT CCA AAT TAT GAT TCA CAA AGT ACA     144
Thr Ile Leu Tyr Trp Tyr Ile His Pro Asn Tyr Asp Ser Gln Ser Thr
         35                  40                  45

GAC TTT GAT GTT TCT GTA GTT CGA CTA TTA TCT TCT TTA AAT TTG AAT     192
Asp Phe Asp Val Ser Val Val Arg Leu Leu Ser Ser Leu Asn Leu Asn
     50                  55                  60

GGA GGT TCT ATT CGA CCG GCT AGG TTA GTG GAT TCT GGA ACT GAT TTG     240
Gly Gly Ser Ile Arg Pro Ala Arg Leu Val Asp Ser Gly Thr Asp Leu
 65                  70                  75                  80

CCA GCC GGT GAG ATG GTT ACA GTA ACT GGA TGG GGA CGA CTT TCG GAA     288
Pro Ala Gly Glu Met Val Thr Val Thr Gly Trp Gly Arg Leu Ser Glu
                 85                  90                  95

AAT ACT TCT GTT CCC TCG CCA TCA ACT CTT CAA GGA GTT ACA GTA CCA     336
Asn Thr Ser Val Pro Ser Pro Ser Thr Leu Gln Gly Val Thr Val Pro
            100                 105                 110

GTT GTA AGT AAT TCG GAA TGT CAA CAA CAA TTG CAA AAT CAG ACA ATC     384
Val Val Ser Asn Ser Glu Cys Gln Gln Gln Leu Gln Asn Gln Thr Ile
        115                 120                 125

ACT GAC AAT ATG TTT TGT GCT GGT GAA TTA GAA GGA GGA AAG GAC TCT     432
Thr Asp Asn Met Phe Cys Ala Gly Glu Leu Glu Gly Gly Lys Asp Ser
    130                 135                 140

T                                                                    433
```

(2) INFORMATION FOR SEQ ID NO: 153:

(i) SEQUENCE CHARACTERISTICS:
        (A) LENGTH: 144 amino acids
        (B) TYPE: amino acid
        (D) TOPOLOGY: linear (ii) MOLECULE TYPE: protein (xi) SEQUENCE DESCRIPTION: SEQ ID NO: 153:

```
Val Thr Ala Ala His Cys Phe Tyr Gly Thr Leu Phe Pro Ile Gly Phe
 1               5                  10                  15

Ser Ala Arg Ala Gly Ser Ser Thr Val Asn Ser Gly Gly Thr Val His
             20                  25                  30

Thr Ile Leu Tyr Trp Tyr Ile His Pro Asn Tyr Asp Ser Gln Ser Thr
         35                  40                  45

Asp Phe Asp Val Ser Val Val Arg Leu Leu Ser Ser Leu Asn Leu Asn
     50                  55                  60

Gly Gly Ser Ile Arg Pro Ala Arg Leu Val Asp Ser Gly Thr Asp Leu
 65                  70                  75                  80

Pro Ala Gly Glu Met Val Thr Val Thr Gly Trp Gly Arg Leu Ser Glu
                 85                  90                  95

Asn Thr Ser Val Pro Ser Pro Ser Thr Leu Gln Gly Val Thr Val Pro
            100                 105                 110
```

```
Val Val Ser Asn Ser Glu Cys Gln Gln Gln Leu Gln Asn Gln Thr Ile
        115                 120                 125

Thr Asp Asn Met Phe Cys Ala Gly Glu Leu Glu Gly Gly Lys Asp Ser
130                 135                 140
```

(2) INFORMATION FOR SEQ ID NO: 154:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..426

(xi) SEQUENCE DESCRIPTION: SEQ ID NO: 154:

```
GCC ACG ACA CCA AAT TCG AAC CTG AAG GTG CGT TTG GGC GAA TGG GAC       48
Ala Thr Thr Pro Asn Ser Asn Leu Lys Val Arg Leu Gly Glu Trp Asp
 1               5                  10                  15

GTT CGC GAC CAC GAT GAG CGA CTG AAC CAC GAG GAA TAC GCA ATC GAA       96
Val Arg Asp His Asp Glu Arg Leu Asn His Glu Glu Tyr Ala Ile Glu
                20                  25                  30

CGC AAA GAA GTT CAT CCT TCA TAT TCA CCA ACC GAT TTC CGG AAT GAT      144
Arg Lys Glu Val His Pro Ser Tyr Ser Pro Thr Asp Phe Arg Asn Asp
            35                  40                  45

GTA GCC TTA GTG AAA CTC GAT AGA ACT GTT ATT TTC AAA CAA CAT ATT      192
Val Ala Leu Val Lys Leu Asp Arg Thr Val Ile Phe Lys Gln His Ile
         50                  55                  60

TTA CCT GTC TGC TTA CCT CAT AAG CAA ATG AAA CTG GCT GGA AAA ATG      240
Leu Pro Val Cys Leu Pro His Lys Gln Met Lys Leu Ala Gly Lys Met
 65                  70                  75                  80

GCA ACA GTC GCC GGA TGG GGA CGG ACG AGG CAC GGG CAG AGC ACT GTG      288
Ala Thr Val Ala Gly Trp Gly Arg Thr Arg His Gly Gln Ser Thr Val
                 85                  90                  95

CCG GCT GTC TTA CAA GAA GTC GAT GTC GAG GTG ATT CCG AAT GAA AGA      336
Pro Ala Val Leu Gln Glu Val Asp Val Glu Val Ile Pro Asn Glu Arg
            100                 105                 110

TGC CAG AGG TGG TTC CGT GCT GCG GGT CGA CGA GAA ACC ATT CAC GAT      384
Cys Gln Arg Trp Phe Arg Ala Ala Gly Arg Arg Glu Thr Ile His Asp
        115                 120                 125

GTC TTT CTC TGC GCC GGA TAT AAA GAG GGT GGT CGT GAT TCA              426
Val Phe Leu Cys Ala Gly Tyr Lys Glu Gly Gly Arg Asp Ser
130                 135                 140
```

(2) INFORMATION FOR SEQ ID NO: 155:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO: 155:

```
Ala Thr Thr Pro Asn Ser Asn Leu Lys Val Arg Leu Gly Glu Trp Asp
 1               5                  10                  15

Val Arg Asp His Asp Glu Arg Leu Asn His Glu Glu Tyr Ala Ile Glu
                20                  25                  30
```

```
Arg Lys Glu Val His Pro Ser Tyr Ser Pro Thr Asp Phe Arg Asn Asp
         35                  40                  45

Val Ala Leu Val Lys Leu Asp Arg Thr Val Ile Phe Lys Gln His Ile
 50                  55                  60

Leu Pro Val Cys Leu Pro His Lys Gln Met Lys Leu Ala Gly Lys Met
 65                  70                  75                  80

Ala Thr Val Ala Gly Trp Gly Arg Thr Arg His Gly Gln Ser Thr Val
                 85                  90                  95

Pro Ala Val Leu Gln Glu Val Asp Val Glu Val Ile Pro Asn Glu Arg
                100                 105                 110

Cys Gln Arg Trp Phe Arg Ala Ala Gly Arg Arg Glu Thr Ile His Asp
        115                 120                 125

Val Phe Leu Cys Ala Gly Tyr Lys Glu Gly Gly Arg Asp Ser
130                 135                 140

(2) INFORMATION FOR SEQ ID NO: 156:

(i) SEQUENCE CHARACTERISTICS:
        (A) LENGTH: 390 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..390

(xi) SEQUENCE DESCRIPTION: SEQ ID NO: 156:

GTA TAT GGC AGA GCA ACT CCA TCA CTG TTC ACC GTT GTA TCA GGC GCA         48
Val Tyr Gly Arg Ala Thr Pro Ser Leu Phe Thr Val Val Ser Gly Ala
 1               5                  10                  15

CTT TAC TTA ACT GAA GGT GGA GAA CAT CAT GCT GTT GCT TCC ATC AAA         96
Leu Tyr Leu Thr Glu Gly Gly Glu His His Ala Val Ala Ser Ile Lys
                 20                  25                  30

TAT CAC GAA AAG TAC AGC CCA AAC ACT TTG GAC AAT GAT GTG GCA GTT        144
Tyr His Glu Lys Tyr Ser Pro Asn Thr Leu Asp Asn Asp Val Ala Val
         35                  40                  45

TTG AAG TTG AAA CAG CCA TTG ACT TTC AAT GCT AAC CAG AAA CCT GTC        192
Leu Lys Leu Lys Gln Pro Leu Thr Phe Asn Ala Asn Gln Lys Pro Val
 50                  55                  60

GCC TTG GCC TCA AAG GAT ACA CCT GGA GAC CTC AAA TGC AAA TTC TCT        240
Ala Leu Ala Ser Lys Asp Thr Pro Gly Asp Leu Lys Cys Lys Phe Ser
 65                  70                  75                  80

GGT TGG GGA TTA GAC GCA TAT CCA AGT GAT GTT TTA CCA AAT CAC TTA        288
Gly Trp Gly Leu Asp Ala Tyr Pro Ser Asp Val Leu Pro Asn His Leu
                 85                  90                  95

CAA AAA ATG GAT GTT CTG ACC TAC AAT AAC GCT GAC TGC CAA AAG TTC        336
Gln Lys Met Asp Val Leu Thr Tyr Asn Asn Ala Asp Cys Gln Lys Phe
                100                 105                 110

CAT AAT GCT GGA CCT AAA TCT AAC ACA ATC TAC CCA GGA ATG TTG TGC        384
His Asn Ala Gly Pro Lys Ser Asn Thr Ile Tyr Pro Gly Met Leu Cys
        115                 120                 125

GGA TTC                                                                390
Gly Phe
130
```

(2) INFORMATION FOR SEQ ID NO: 157:

(i) SEQUENCE CHARACTERISTICS:
        (A) LENGTH: 130 amino acids
        (B) TYPE: amino acid
        (D) TOPOLOGY: linear (ii) MOLECULE TYPE: protein (xi) SEQUENCE DESCRIPTION: SEQ ID NO: 157:

```
Val Tyr Gly Arg Ala Thr Pro Ser Leu Phe Thr Val Val Ser Gly Ala
 1               5                  10                  15

Leu Tyr Leu Thr Glu Gly Gly Glu His His Ala Val Ala Ser Ile Lys
             20                  25                  30

Tyr His Glu Lys Tyr Ser Pro Asn Thr Leu Asp Asn Asp Val Ala Val
         35                  40                  45

Leu Lys Leu Lys Gln Pro Leu Thr Phe Asn Ala Asn Gln Lys Pro Val
 50                  55                  60

Ala Leu Ala Ser Lys Asp Thr Pro Gly Asp Leu Lys Cys Lys Phe Ser
 65                  70                  75                  80

Gly Trp Gly Leu Asp Ala Tyr Pro Ser Asp Val Leu Pro Asn His Leu
                 85                  90                  95

Gln Lys Met Asp Val Leu Thr Tyr Asn Asn Ala Asp Cys Gln Lys Phe
                100                 105                 110

His Asn Ala Gly Pro Lys Ser Asn Thr Ile Tyr Pro Gly Met Leu Cys
                115                 120                 125

Gly Phe
130
```

(2) INFORMATION FOR SEQ ID NO: 158:

(i) SEQUENCE CHARACTERISTICS:
        (A) LENGTH: 197 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..197

(xi) SEQUENCE DESCRIPTION: SEQ ID NO: 158:

```
GT GGT GGG CTG CCT TCT TCA ATA ACA TTA GCG CGA GTC AGA CTC GGC      47
   Gly Gly Leu Pro Ser Ser Ile Thr Leu Ala Arg Val Arg Leu Gly
    1               5                  10                  15

GAA CAT AAT GAT CAA TCG GGT ATA GAT TGC GAG GAC GAT GTT TGC GCA     95
Glu His Asn Asp Gln Ser Gly Ile Asp Cys Glu Asp Asp Val Cys Ala
                 20                  25                  30

GAA CCT GTC CAA GAT TTC GAT CCT GTG AAA ATA ATT CCA CAT CCA GAA    143
Glu Pro Val Gln Asp Phe Asp Pro Val Lys Ile Ile Pro His Pro Glu
             35                  40                  45

TAC AAA GAC GAA CTA TTT AAA CAT GAT ATA GCT CTG ATA AAA TTG GTA    191
Tyr Lys Asp Glu Leu Phe Lys His Asp Ile Ala Leu Ile Lys Leu Val
 50                  55                  60

GAA AAT                                                            197
Glu Asn
65
```

(2) INFORMATION FOR SEQ ID NO: 159:

(i) SEQUENCE CHARACTERISTICS:
        (A) LENGTH: 65 amino acids
        (B) TYPE: amino acid
        (D) TOPOLOGY: linear (ii) MOLECULE TYPE: protein (xi) SEQUENCE DESCRIPTION: SEQ ID NO: 159:

```
Gly Gly Leu Pro Ser Ser Ile Thr Leu Ala Arg Val Arg Leu Gly Glu
 1               5                  10                  15

His Asn Asp Gln Ser Gly Ile Asp Cys Glu Asp Val Cys Ala Glu
             20                  25                  30

Pro Val Gln Asp Phe Asp Pro Val Lys Ile Ile Pro His Pro Glu Tyr
             35                  40                  45

Lys Asp Glu Leu Phe Lys His Asp Ile Ala Leu Ile Lys Leu Val Glu
         50                  55                  60

Asn
65
```

(2) INFORMATION FOR SEQ ID NO: 160:

(i) SEQUENCE CHARACTERISTICS:
        (A) LENGTH: 261 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..261

(xi) SEQUENCE DESCRIPTION: SEQ ID NO: 160:

```
CCG ACT ACC TTA GGC GGA TCT ACT GGT CAC AGC AAT GAT ATT GCC CTA      48
Pro Thr Thr Leu Gly Gly Ser Thr Gly His Ser Asn Asp Ile Ala Leu
 1               5                  10                  15

ATC AAA GTC GAT AGA GAT ATC AAA TTC AGC AAA ACT GTC CAA CCT ATC      96
Ile Lys Val Asp Arg Asp Ile Lys Phe Ser Lys Thr Val Gln Pro Ile
             20                  25                  30

AAA TTG CAC AAA AGT TTA ATA AAT GGA GGT GAA AAA TTG AAA ATT ACT     144
Lys Leu His Lys Ser Leu Ile Asn Gly Gly Glu Lys Leu Lys Ile Thr
         35                  40                  45

GGA TGG GGA TTG ACG AAT CAA AGT CAT AGT GAT GAA CCA GAT GTT CTT     192
Gly Trp Gly Leu Thr Asn Gln Ser His Ser Asp Glu Pro Asp Val Leu
     50                  55                  60

CAA GAG TTG CAT GTA AAA GCA CTT ACT GAT TCT GAG TGC GAG AAA GCT     240
Gln Glu Leu His Val Lys Ala Leu Thr Asp Ser Glu Cys Glu Lys Ala
65                   70                  75                  80

ACA GGT GAA GAC CAT CCT ACA                                          261
Thr Gly Glu Asp His Pro Thr
                 85
```

(2) INFORMATION FOR SEQ ID NO: 161:

(i) SEQUENCE CHARACTERISTICS:
        (A) LENGTH: 87 amino acids
        (B) TYPE: amino acid
        (D) TOPOLOGY: linear (ii) MOLECULE TYPE: protein (xi) SEQUENCE DESCRIPTION: SEQ ID NO: 161:

```
Pro Thr Thr Leu Gly Gly Ser Thr Gly His Ser Asn Asp Ile Ala Leu
 1               5                  10                  15

Ile Lys Val Asp Arg Asp Ile Lys Phe Ser Lys Thr Val Gln Pro Ile
            20                  25                  30

Lys Leu His Lys Ser Leu Ile Asn Gly Glu Lys Leu Lys Ile Thr
            35                  40                  45

Gly Trp Gly Leu Thr Asn Gln Ser His Ser Asp Glu Pro Asp Val Leu
 50                  55                  60

Gln Glu Leu His Val Lys Ala Leu Thr Asp Ser Glu Cys Glu Lys Ala
 65                  70                  75                  80

Thr Gly Glu Asp His Pro Thr
                85
```

(2) INFORMATION FOR SEQ ID NO: 162:

(i) SEQUENCE CHARACTERISTICS:
        (A) LENGTH: 341 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 3..341

(xi) SEQUENCE DESCRIPTION: SEQ ID NO: 162:

```
GA AAA TCT CGA ATT GGG CGA CAG CTT AAA ATT CAC TAT GGA AAT AAC      47
   Lys Ser Arg Ile Gly Arg Gln Leu Lys Ile His Tyr Gly Asn Asn
    1               5                  10                  15

GAC TGG CAC TTT GGC TTC GTT AGT ATT GTA AAA AAG GCT ATT ATT CAT     95
Asp Trp His Phe Gly Phe Val Ser Ile Val Lys Lys Ala Ile Ile His
                20                  25                  30

CCA AAT TAC AAC CCA GTG ACA TTT GAT AGT GAT GTG GCC CTT CTG AAG    143
Pro Asn Tyr Asn Pro Val Thr Phe Asp Ser Asp Val Ala Leu Leu Lys
             35                  40                  45

CTG CAC TCT CCA ATT ACC TTC ACA AAT GGC GTT CAT AAA GTG TCG CTG    191
Leu His Ser Pro Ile Thr Phe Thr Asn Gly Val His Lys Val Ser Leu
             50                  55                  60

GTC GAA AAA GGT CAA GAT CCT GTA CCT TAT TCA CCT GCG ATG ATC ACT    239
Val Glu Lys Gly Gln Asp Pro Val Pro Tyr Ser Pro Ala Met Ile Thr
 65                  70                  75

GGC TGG GGC CAT ACA ATG GAA GGT GAT ACT AGT ATT TCG CAA ATT TTA    287
Gly Trp Gly His Thr Met Glu Gly Asp Thr Ser Ile Ser Gln Ile Leu
 80                  85                  90                  95

CAA GGA GCT GTG GTC CCA ATC GTA AAC AGA AAT GAT TGT CCG AAT TAT    335
Gln Gly Ala Val Val Pro Ile Val Asn Arg Asn Asp Cys Pro Asn Tyr
                 100                 105                 110

GGA CTC                                                             341
Gly Leu
```

(2) INFORMATION FOR SEQ ID NO: 163:

(i) SEQUENCE CHARACTERISTICS:
        (A) LENGTH: 113 amino acids
        (B) TYPE: amino acid
        (D) TOPOLOGY: linear (ii) MOLECULE TYPE: protein (xi) SEQUENCE DESCRIPTION: SEQ ID NO: 163:

Lys Ser Arg Ile Gly Arg Gln Leu Lys Ile His Tyr Gly Asn Asn Asp
1               5                   10                  15

Trp His Phe Gly Phe Val Ser Ile Val Lys Lys Ala Ile Ile His Pro
            20                  25                  30

Asn Tyr Asn Pro Val Thr Phe Asp Ser Asp Val Ala Leu Leu Lys Leu
        35                  40                  45

His Ser Pro Ile Thr Phe Thr Asn Gly Val His Lys Val Ser Leu Val
    50                  55                  60

Glu Lys Gly Gln Asp Pro Val Pro Tyr Ser Pro Ala Met Ile Thr Gly
65                  70                  75                  80

Trp Gly His Thr Met Glu Gly Asp Thr Ser Ile Ser Gln Ile Leu Gln
                85                  90                  95

Gly Ala Val Val Pro Ile Val Asn Arg Asn Asp Cys Pro Asn Tyr Gly
                100                 105                 110

Leu (2) INFORMATION FOR SEQ ID NO: 164:

(i) SEQUENCE CHARACTERISTICS:
        (A) LENGTH: 267 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..267

(xi) SEQUENCE DESCRIPTION: SEQ ID NO: 164:

```
CCG ACT ACC TTA GGC GGA TCT ACT GGT CAC AGC AAT GAT ATT GCC CTA        48
Pro Thr Thr Leu Gly Gly Ser Thr Gly His Ser Asn Asp Ile Ala Leu
1               5                   10                  15

ATC AAA GTC GAT AGA GAT ATC AAA TTC AGC AAA ACT GTC CAA CCT ATC        96
Ile Lys Val Asp Arg Asp Ile Lys Phe Ser Lys Thr Val Gln Pro Ile
            20                  25                  30

AAA TTG CAC AAA AGT TTA ATA AAT GGA GGT GAA AAA TTG AAA ATT ACT       144
Lys Leu His Lys Ser Leu Ile Asn Gly Gly Glu Lys Leu Lys Ile Thr
        35                  40                  45

GGA TGG GGA TTG ACG AAT CAA AGT CAT AGT GAT GAA CCA GAT GTT CTT       192
Gly Trp Gly Leu Thr Asn Gln Ser His Ser Asp Glu Pro Asp Val Leu
50                  55                  60

CAA GAG TTG CAT GTA AAA GCA CTT ACT GAT TCT GAG TGC GAG AAA GCT       240
Gln Glu Leu His Val Lys Ala Leu Thr Asp Ser Glu Cys Glu Lys Ala
65                  70                  75                  80

ACA GGT GAA GAC CAT CCT ACA CAC CTT                                   267
Thr Gly Glu Asp His Pro Thr His Leu
                85
```

(2) INFORMATION FOR SEQ ID NO: 165:

(i) SEQUENCE CHARACTERISTICS:
        (A) LENGTH: 89 amino acids
        (B) TYPE: amino acid
        (D) TOPOLOGY: linear (ii) MOLECULE TYPE: protein (xi) SEQUENCE DESCRIPTION: SEQ ID NO: 165:

Pro Thr Thr Leu Gly Gly Ser Thr Gly His Ser Asn Asp Ile Ala Leu
1               5                   10                  15

Ile Lys Val Asp Arg Asp Ile Lys Phe Ser Lys Thr Val Gln Pro Ile
            20                  25                  30

Lys Leu His Lys Ser Leu Ile Asn Gly Gly Glu Lys Leu Lys Ile Thr
        35                  40                  45

Gly Trp Gly Leu Thr Asn Gln Ser His Ser Asp Glu Pro Asp Val Leu
    50                  55                  60

Gln Glu Leu His Val Lys Ala Leu Thr Asp Ser Glu Cys Glu Lys Ala
65              70                  75                  80

Thr Gly Glu Asp His Pro Thr His Leu
                85

(2) INFORMATION FOR SEQ ID NO: 166:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 166:

CCCAAATTTT CCATWGCNCC NGC                                       23

(2) INFORMATION FOR SEQ ID NO: 167:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 167:

Leu Ala Thr Thr Gln Phe Gln Ala Thr His Ala Arg Ser Ala Phe Pr
1               5                   10                  15

Cys Phe Asp Glu Pro Ala Met
            20

(2) INFORMATION FOR SEQ ID NO: 168:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..20
        (D) OTHER INFORMATION: /label= primer (xi) SEQUENCE DESCRIPTION: SEQ ID NO: 168:

CAATTYCAAG CTACYCATGC                                           20

(2) INFORMATION FOR SEQ ID NO: 169:

(i) SEQUENCE CHARACTERISTICS:
        (A) LENGTH: 383 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..382

(xi) SEQUENCE DESCRIPTION: SEQ ID NO: 169:

```
C CGT AGT GCT TTC CCT TGT TTC GAT GAA CCA GCA ATG AAG GCC CAT      46
  Arg Ser Ala Phe Pro Cys Phe Asp Glu Pro Ala Met Lys Ala His
   1               5                  10                  15

TTC GAA ATC AGC CTT ATA CAC CAT GAA AAA TTG AAA GCA ATT TCC AAT    94
Phe Glu Ile Ser Leu Ile His His Glu Lys Leu Lys Ala Ile Ser Asn
             20                  25                  30

ATG GGT GTA GCA AAG GAA GAA AAC TTA GAT AAC AAC CGA AAA AGA ACA   142
Met Gly Val Ala Lys Glu Glu Asn Leu Asp Asn Asn Arg Lys Arg Thr
         35                  40                  45

ACA TTC GAA CAA TCA GTT CTC ATG TCT CCA TAC CTG GTG GCG TTT ATT   190
Thr Phe Glu Gln Ser Val Leu Met Ser Pro Tyr Leu Val Ala Phe Ile
     50                  55                  60

ATC TCA GAT TTC GAA TAT GTA GAA AAA ATT TCA GGA CCA GTG AAA TAC   238
Ile Ser Asp Phe Glu Tyr Val Glu Lys Ile Ser Gly Pro Val Lys Tyr
 65                  70                  75

AGA ATA TAT ACT GAT CCT TTC TCG ATT GAT CAA GCT GAC TAT GCA TTG   286
Arg Ile Tyr Thr Asp Pro Phe Ser Ile Asp Gln Ala Asp Tyr Ala Leu
 80                  85                  90                  95

ACT ATG AGC CCC AAA AAT TTT AAC GGC TTT GGA ACA ACT CAC AGG TGT   334
Thr Met Ser Pro Lys Asn Phe Asn Gly Phe Gly Thr Thr His Arg Cys
                100                 105                 110

AAA ATA TGT TTT GAA CAA GTT GGA CCA AGC AGC CAT TCC AGA TTT TGC   382
Lys Ile Cys Phe Glu Gln Val Gly Pro Ser Ser His Ser Arg Phe Cys
             115                 120                 125

T                                                                 383
```

(2) INFORMATION FOR SEQ ID NO: 170:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO: 170:

```
Arg Ser Ala Phe Pro Cys Phe Asp Glu Pro Ala Met Lys Ala His Phe
 1               5                  10                  15

Glu Ile Ser Leu Ile His His Glu Lys Leu Lys Ala Ile Ser Asn Met
             20                  25                  30

Gly Val Ala Lys Glu Glu Asn Leu Asp Asn Asn Arg Lys Arg Thr Thr
         35                  40                  45

Phe Glu Gln Ser Val Leu Met Ser Pro Tyr Leu Val Ala Phe Ile Ile
     50                  55                  60

Ser Asp Phe Glu Tyr Val Glu Lys Ile Ser Gly Pro Val Lys Tyr Arg
 65                  70                  75                  80

Ile Tyr Thr Asp Pro Phe Ser Ile Asp Gln Ala Asp Tyr Ala Leu Thr
             85                  90                  95
```

```
Met Ser Pro Lys Asn Phe Asn Gly Phe Gly Thr Thr His Arg Cys Lys
            100                 105                 110
Ile Cys Phe Glu Gln Val Gly Pro Ser Ser His Ser Arg Phe Cys
        115                 120                 125
```

(2) INFORMATION FOR SEQ ID NO: 171:

(i) SEQUENCE CHARACTERISTICS:
        (A) LENGTH: 537 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..535

(xi) SEQUENCE DESCRIPTION: SEQ ID NO: 171:

```
A TAT ATT TTG GAA ATA AAA GGC TTC AAA TCT ACT TTG AGA GAT GAC        46
  Tyr Ile Leu Glu Ile Lys Gly Phe Lys Ser Thr Leu Arg Asp Asp
  1               5                   10                  15

ATG GCT GGC TTC TAC AAA AGT TCA TAC AAA ACG CCA AAA GGA GAA ACA      94
Met Ala Gly Phe Tyr Lys Ser Ser Tyr Lys Thr Pro Lys Gly Glu Thr
                    20                  25                  30

AGA TGG TTG GCT ACA ACC CAG TTT CAG GCA ACT CAT GCC CGT AGT GCT     142
Arg Trp Leu Ala Thr Thr Gln Phe Gln Ala Thr His Ala Arg Ser Ala
                35                  40                  45

TTC CCT TGT TTC GAT GAA CCA GCA ATG AAG GCC CAT TTC GAA ATC AGC     190
Phe Pro Cys Phe Asp Glu Pro Ala Met Lys Ala His Phe Glu Ile Ser
            50                  55                  60

CTT ATA CAC CAT GAA AAA TTG AAA GCA ATT TCC AAT ATG GGT GTA GCA     238
Leu Ile His His Glu Lys Leu Lys Ala Ile Ser Asn Met Gly Val Ala
        65                  70                  75

AAG GAA GAA AAC TTA GAT AAC AAC CGA AAA AGA ACA ACA TTC GAA CAA     286
Lys Glu Glu Asn Leu Asp Asn Asn Arg Lys Arg Thr Thr Phe Glu Gln
80                  85                  90                  95

TCA GTT CTC ATG TCT CCA TAC CTG GTG GCG TTT ATT ATC TCA GAT TTC     334
Ser Val Leu Met Ser Pro Tyr Leu Val Ala Phe Ile Ile Ser Asp Phe
                    100                 105                 110

GAA TAT GTA GAA AAA ATT TCA GGA CCA GTG AAA TAC AGA ATA TAT ACT     382
Glu Tyr Val Glu Lys Ile Ser Gly Pro Val Lys Tyr Arg Ile Tyr Thr
                115                 120                 125

GAT CCT TTC TCG ATT GAT CAA GCT GAC TAT GCA TTG ACT ATG AGC CCC     430
Asp Pro Phe Ser Ile Asp Gln Ala Asp Tyr Ala Leu Thr Met Ser Pro
            130                 135                 140

AAA AAT TTT AAC GGC TTT GGA ACA ACT CAC AGG TGT AAA ATA TGT TTT     478
Lys Asn Phe Asn Gly Phe Gly Thr Thr His Arg Cys Lys Ile Cys Phe
        145                 150                 155

GAA CAA GTT GGA CCA AGC AGC CAT TCC AGA TTT TGC TGC CGG CGC AAT     526
Glu Gln Val Gly Pro Ser Ser His Ser Arg Phe Cys Cys Arg Arg Asn
160                 165                 170                 175

GGA AAA TTT GG                                                       537
Gly Lys Phe
```

(2) INFORMATION FOR SEQ ID NO: 172:

(i) SEQUENCE CHARACTERISTICS:
        (A) LENGTH: 178 amino acids
        (B) TYPE: amino acid
        (D) TOPOLOGY: linear (ii) MOLECULE TYPE: protein (xi) SEQUENCE DESCRIPTION: SEQ ID NO: 172:

| Tyr | Ile | Leu | Glu | Ile | Lys | Gly | Phe | Lys | Ser | Thr | Leu | Arg | Asp | Asp | Met |
|---|---|---|---|---|---|---|---|---|---|---|---|---|---|---|---|
| 1 | | | | 5 | | | | | 10 | | | | | 15 | |

| Ala | Gly | Phe | Tyr | Lys | Ser | Ser | Tyr | Lys | Thr | Pro | Lys | Gly | Glu | Thr | Arg |
|---|---|---|---|---|---|---|---|---|---|---|---|---|---|---|---|
| | | | 20 | | | | | 25 | | | | | 30 | | |

| Trp | Leu | Ala | Thr | Thr | Gln | Phe | Gln | Ala | Thr | His | Ala | Arg | Ser | Ala | Phe |
|---|---|---|---|---|---|---|---|---|---|---|---|---|---|---|---|
| | | | 35 | | | | | 40 | | | | | 45 | | |

| Pro | Cys | Phe | Asp | Glu | Pro | Ala | Met | Lys | Ala | His | Phe | Glu | Ile | Ser | Leu |
|---|---|---|---|---|---|---|---|---|---|---|---|---|---|---|---|
| | 50 | | | | | 55 | | | | | 60 | | | | |

| Ile | His | His | Glu | Lys | Leu | Lys | Ala | Ile | Ser | Asn | Met | Gly | Val | Ala | Lys |
|---|---|---|---|---|---|---|---|---|---|---|---|---|---|---|---|
| 65 | | | | | 70 | | | | | 75 | | | | | 80 |

| Glu | Glu | Asn | Leu | Asp | Asn | Asn | Arg | Lys | Arg | Thr | Thr | Phe | Glu | Gln | Ser |
|---|---|---|---|---|---|---|---|---|---|---|---|---|---|---|---|
| | | | | 85 | | | | | 90 | | | | | 95 | |

| Val | Leu | Met | Ser | Pro | Tyr | Leu | Val | Ala | Phe | Ile | Ile | Ser | Asp | Phe | Glu |
|---|---|---|---|---|---|---|---|---|---|---|---|---|---|---|---|
| | | | | 100 | | | | | 105 | | | | | 110 | |

| Tyr | Val | Glu | Lys | Ile | Ser | Gly | Pro | Val | Lys | Tyr | Arg | Ile | Tyr | Thr | Asp |
|---|---|---|---|---|---|---|---|---|---|---|---|---|---|---|---|
| | | | 115 | | | | | 120 | | | | | 125 | | |

| Pro | Phe | Ser | Ile | Asp | Gln | Ala | Asp | Tyr | Ala | Leu | Thr | Met | Ser | Pro | Lys |
|---|---|---|---|---|---|---|---|---|---|---|---|---|---|---|---|
| | 130 | | | | | 135 | | | | | 140 | | | | |

| Asn | Phe | Asn | Gly | Phe | Gly | Thr | Thr | His | Arg | Cys | Lys | Ile | Cys | Phe | Glu |
|---|---|---|---|---|---|---|---|---|---|---|---|---|---|---|---|
| 145 | | | | | 150 | | | | | 155 | | | | | 160 |

| Gln | Val | Gly | Pro | Ser | Ser | His | Ser | Arg | Phe | Cys | Cys | Arg | Arg | Asn | Gly |
|---|---|---|---|---|---|---|---|---|---|---|---|---|---|---|---|
| | | | | 165 | | | | | 170 | | | | | 175 | |

Lys Phe (2) INFORMATION FOR SEQ ID NO: 173:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 173:

TTGGGATACA CTTTGACTGT TAACC                                      25

(2) INFORMATION FOR SEQ ID NO: 174:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 174:

GTGAGCAACC ATTATTTCCA TATC                                       24

(2) INFORMATION FOR SEQ ID NO: 175:

(i) SEQUENCE CHARACTERISTICS:
        (A) LENGTH: 23 base pairs
        (B) TYPE: nucleic acid
        (C) STRANDEDNESS: single
        (D) TOPOLOGY: linear

```
    (ii) MOLECULE TYPE: other nucleic acid
        (A) DESCRIPTION: /desc = "primer"

(ix) FEATURE:
        (A) NAME/KEY: misc_feature
        (B) LOCATION: 1..23
        (D) OTHER INFORMATION: /label= primer (xi) SEQUENCE DESCRIPTION: SEQ ID NO: 175:

CTTGTACGAT TGTCTCAACA GGC                                         23

(2) INFORMATION FOR SEQ ID NO: 176:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..27
        (D) OTHER INFORMATION: /label= primer (xi) SEQUENCE DESCRIPTION: SEQ ID NO: 176:

CTTTCCTCAC AATACCACCA AGGAAGC                                     27

(2) INFORMATION FOR SEQ ID NO: 177:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..573

(xi) SEQUENCE DESCRIPTION: SEQ ID NO: 177:

CGA TCT TTT AGA CAA GCG AAA TTG ATA ACG AAG TTT TCG AAG TCG GAT      48
Arg Ser Phe Arg Gln Ala Lys Leu Ile Thr Lys Phe Ser Lys Ser Asp
 1               5                  10                  15

GAA GTA AAA ACC TTG CGT TGG TTT CCC CGG TCC CAG GAT CAG GAA CAG      96
Glu Val Lys Thr Leu Arg Trp Phe Pro Arg Ser Gln Asp Gln Glu Gln
                20                  25                  30

TTG CAC TTT ACC CCA ATG AGG GAA TTC GTG CAT CCC CAT TTT ACC GAA     144
Leu His Phe Thr Pro Met Arg Glu Phe Val His Pro His Phe Thr Glu
            35                  40                  45

CAT ATT GAT GAA GAA TTC CAC CGA TTC ATC AAT AAA CAC GGA AAA ATT     192
His Ile Asp Glu Glu Phe His Arg Phe Ile Asn Lys His Gly Lys Ile
    50                  55                  60

TAT AAT AAA AAT GAA GAA CAT CAT TTC CGC AAA GAA ATT TTC AGA CTA     240
Tyr Asn Lys Asn Glu Glu His His Phe Arg Lys Glu Ile Phe Arg Leu
65                  70                  75                  80

AAC TTG AGG TAC ATT TTT TCT AAG AAT CGT GCA AAT TTG GGA TAC ACT     288
Asn Leu Arg Tyr Ile Phe Ser Lys Asn Arg Ala Asn Leu Gly Tyr Thr
                85                  90                  95

TTG ACT GTT AAC CAT TTG GCT GAT CGT ACT GAA GCT GAA CTT AAG GCT     336
Leu Thr Val Asn His Leu Ala Asp Arg Thr Glu Ala Glu Leu Lys Ala
           100                 105                 110
```

```
TTG AGA GGA CAC AGA CCT TCC TCC GGT TAT AAT GGC GGT TTA CCC TTT       384
Leu Arg Gly His Arg Pro Ser Ser Gly Tyr Asn Gly Gly Leu Pro Phe
    115                 120                 125

CCT CAC AAT ACC ACC AAG GAA GCA AGA AAT TTA CCA GAT TCT TTC GAC       432
Pro His Asn Thr Thr Lys Glu Ala Arg Asn Leu Pro Asp Ser Phe Asp
130                 135                 140

TGG CGA ATT TAT GGA GCT GTT ACT CCA GTT AAA GAT CAA TCT GTT TGT       480
Trp Arg Ile Tyr Gly Ala Val Thr Pro Val Lys Asp Gln Ser Val Cys
145                 150                 155                 160

GGT TCC TGC TGG TCT TTC GGA ACA ATT GGA GCA ATC GAA GGT GCA TAT       528
Gly Ser Cys Trp Ser Phe Gly Thr Ile Gly Ala Ile Glu Gly Ala Tyr
                165                 170                 175

TTC TTG AAA ACG GCG GTA ATC TGT ACG ATG TCT CAC AGC TTG ATG           573
Phe Leu Lys Thr Ala Val Ile Cys Thr Met Ser His Ser Leu Met
            180                 185                 190
```

(2) INFORMATION FOR SEQ ID NO: 178:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 178:

```
Arg Ser Phe Arg Gln Ala Lys Leu Ile Thr Lys Phe Ser Lys Ser Asp
1               5                   10                  15

Glu Val Lys Thr Leu Arg Trp Phe Pro Arg Ser Gln Asp Gln Glu Gln
                20                  25                  30

Leu His Phe Thr Pro Met Arg Glu Phe Val His Pro His Phe Thr Glu
            35                  40                  45

His Ile Asp Glu Glu Phe His Arg Phe Ile Asn Lys His Gly Lys Ile
        50                  55                  60

Tyr Asn Lys Asn Glu Glu His His Phe Arg Lys Glu Ile Phe Arg Leu
65                  70                  75                  80

Asn Leu Arg Tyr Ile Phe Ser Lys Asn Arg Ala Asn Leu Gly Tyr Thr
                85                  90                  95

Leu Thr Val Asn His Leu Ala Asp Arg Thr Glu Ala Glu Leu Lys Ala
            100                 105                 110

Leu Arg Gly His Arg Pro Ser Ser Gly Tyr Asn Gly Gly Leu Pro Phe
        115                 120                 125

Pro His Asn Thr Thr Lys Glu Ala Arg Asn Leu Pro Asp Ser Phe Asp
130                 135                 140

Trp Arg Ile Tyr Gly Ala Val Thr Pro Val Lys Asp Gln Ser Val Cys
145                 150                 155                 160

Gly Ser Cys Trp Ser Phe Gly Thr Ile Gly Ala Ile Glu Gly Ala Tyr
                165                 170                 175

Phe Leu Lys Thr Ala Val Ile Cys Thr Met Ser His Ser Leu Met
            180                 185                 190
```

(2) INFORMATION FOR SEQ ID NO: 179:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 179:

Ile Val Gly Gly Glu Asp Val Asp Ile Ser Thr Cys Gly Trp Cys
1               5                   10                  15

(2) INFORMATION FOR SEQ ID NO: 180:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 180:

Ile Val Gly Gly His Asp Thr Ser Ile Lys Gln His Pro Tyr Gln Va
1               5                   10                  15
Ser (2) INFORMATION FOR SEQ ID NO: 181:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 181:

Ile Val Gly Gly Val Ser Val Asn Ile Asn Asp Tyr Gly Tyr Gln Le
1               5                   10                  15
Ser Leu Gln Ser Asn Gly Arg
            20

(2) INFORMATION FOR SEQ ID NO: 182:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..32
        (D) OTHER INFORMATION: /label= primer (xi) SEQUENCE DESCRIPTION: SEQ ID NO: 182:

GGACGAATTC TTAAACACCA GACACTTCCT TG                                      32

(2) INFORMATION FOR SEQ ID NO: 183:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..32
        (D) OTHER INFORMATION: /label= primer (xi) SEQUENCE DESCRIPTION: SEQ ID NO: 183:

GAGCTCTCGA GAATCGTAGG AGGACACGAT AC                               32

(2) INFORMATION FOR SEQ ID NO: 184:

(i) SEQUENCE CHARACTERISTICS:
        (A) LENGTH: 34 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 184:

Ile Val Gly Gly Glu Asp Val Asp Ile Ser Thr Cys Gly Trp Gln Il
1               5                   10                  15

Ser Phe Gln Ser Glu Asn Leu His Phe Cys Gly Gly Ser Ile Ile Al
                20                  25                  30

Pro Lys (2) INFORMATION FOR SEQ ID NO: 185:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..26
        (D) OTHER INFORMATION: /label= primer (xi) SEQUENCE DESCRIPTION: SEQ ID NO: 185:

GAAGATGTWG ATATTTCWAC ATGTGG                                      26

(2) INFORMATION FOR SEQ ID NO: 186:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(ix) FEATURE:
        (A) NAME/KEY: misc_feature
        (B) LOCATION: 1..27
        (D) OTHER INFORMATION: /label= primer (xi) SEQUENCE DESCRIPTION: SEQ ID NO: 186:

GAAAATGAAA TCCACTTAAA CATTACG                                     27

(2) INFORMATION FOR SEQ ID NO: 187:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 187:

CTCTTATTGT ACGAGGGATG C    21

(2) INFORMATION FOR SEQ ID NO: 188:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO: 188:

ATTCCTCGTG GTTCAGTCGC TC    22

(2) INFORMATION FOR SEQ ID NO: 189:

(i) SEQUENCE CHARACTERISTICS:
        (A) LENGTH: 778 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..778
        (D) OTHER INFORMATION: /note= "At pos. bp 13, change A to
            N. At pos. aa 4, substitute Xaa."

(xi) SEQUENCE DESCRIPTION: SEQ ID NO: 189:

```
T GAT ACC TCA GAN TTG CCG GTA CAA AGG CGA ACG GTT TCG AGT GCG        46
  Asp Thr Ser Xaa Leu Pro Val Gln Arg Arg Thr Val Ser Ser Ala
  1               5                   10                  15

GTT TGT CAA TTT TCG TGC GTC CTG GGC GGC GGA AAA CCT CTT GAC CTG      94
Val Cys Gln Phe Ser Cys Val Leu Gly Gly Gly Lys Pro Leu Asp Leu
                20                  25                  30

TGC AGC GGC GGA ATG ATC TGG TCG TGC TGC GTC GAC AGG GAC ATT CGG     142
Cys Ser Gly Gly Met Ile Trp Ser Cys Cys Val Asp Arg Asp Ile Arg
            35                  40                  45

CCT GAG CCG CAG CAC CAG GGC GCT CTG CAG AAC GCA ACT TGT GGA GAA     190
Pro Glu Pro Gln His Gln Gly Ala Leu Gln Asn Ala Thr Cys Gly Glu
        50                  55                  60

TTG TAC ACG AGG TCT AAT AGA ATC GTA GGA GGT CAT TCA ACA GGA TTC     238
Leu Tyr Thr Arg Ser Asn Arg Ile Val Gly Gly His Ser Thr Gly Phe
    65                  70                  75

GGG TCT CAT CCT TGG CAG GCG GCT TTG ATC AAA TCA GGA TTT TTG AGT     286
Gly Ser His Pro Trp Gln Ala Ala Leu Ile Lys Ser Gly Phe Leu Ser
80                  85                  90                  95

AAA AAA TTA TCT TGC GGT GGC GCT TTA GTT AGC GAT CGA TGG GTT ATA     334
Lys Lys Leu Ser Cys Gly Gly Ala Leu Val Ser Asp Arg Trp Val Ile
                100                 105                 110

ACT GCT GCA CAT TGC GTT GCC ACG ACA CCA AAT TCG AAC CTG AAG GTG     382
Thr Ala Ala His Cys Val Ala Thr Thr Pro Asn Ser Asn Leu Lys Val
            115                 120                 125

CGA TTG GGC GAA TGG GAC GTC CGC GAC CAC GAT GAG CGA CTG AAC CAC     430
Arg Leu Gly Glu Trp Asp Val Arg Asp His Asp Glu Arg Leu Asn His
        130                 135                 140

GAG GAA TAC GCA ATC GAA CGC AAA GAA GTT CAT CCT TCA TAT TCA CCA     478
Glu Glu Tyr Ala Ile Glu Arg Lys Glu Val His Pro Ser Tyr Ser Pro
    145                 150                 155
```

```
ACC GAT TTC CGG AAT GAT GTA GCC TTA GTG AAA CTC GAT AGA ACT GTT    526
Thr Asp Phe Arg Asn Asp Val Ala Leu Val Lys Leu Asp Arg Thr Val
160                 165                 170                 175

ATT TTC AAA CAA CAT ATT TTA CCT GTC TGC TTA CCT CAT AAG CAA ATG    574
Ile Phe Lys Gln His Ile Leu Pro Val Cys Leu Pro His Lys Gln Met
                180                 185                 190

AAA CTG GCT GGA AAA ATG GCA ACA GTC GCC GGA TGG GGA CGG ACG AGG    622
Lys Leu Ala Gly Lys Met Ala Thr Val Ala Gly Trp Gly Arg Thr Arg
            195                 200                 205

CAC GGG CAG AGC ACT GTG CCG GCT GTC TTA CAA GAA GTC GAT GTC GAG    670
His Gly Gln Ser Thr Val Pro Ala Val Leu Gln Glu Val Asp Val Glu
        210                 215                 220

GTG ATT CCG AAT GAA AGA TGC CAG AGG TGG TTC CGT GCT GCG GGT CGA    718
Val Ile Pro Asn Glu Arg Cys Gln Arg Trp Phe Arg Ala Ala Gly Arg
    225                 230                 235

CGA GAA ACC ATT CAC GAT GTC TTT CTC TGC GCC GGA TAT AAA GAG GGT    766
Arg Glu Thr Ile His Asp Val Phe Leu Cys Ala Gly Tyr Lys Glu Gly
240                 245                 250                 255

GGT CGT GAT TCA                                                    778
Gly Arg Asp Ser
```

(2) INFORMATION FOR SEQ ID NO: 190:

(i) SEQUENCE CHARACTERISTICS:
        (A) LENGTH: 259 amino acids
        (B) TYPE: amino acid
        (D) TOPOLOGY: linear (ii) MOLECULE TYPE: protein (xi) SEQUENCE DESCRIPTION: SEQ ID NO: 190:

```
Asp Thr Ser Xaa Leu Pro Val Gln Arg Arg Thr Val Ser Ser Ala Val
1               5                   10                  15

Cys Gln Phe Ser Cys Val Leu Gly Gly Gly Lys Pro Leu Asp Leu Cys
                20                  25                  30

Ser Gly Gly Met Ile Trp Ser Cys Cys Val Asp Arg Asp Ile Arg Pro
            35                  40                  45

Glu Pro Gln His Gln Gly Ala Leu Gln Asn Ala Thr Cys Gly Glu Leu
        50                  55                  60

Tyr Thr Arg Ser Asn Arg Ile Val Gly Gly His Ser Thr Gly Phe Gly
65                  70                  75                  80

Ser His Pro Trp Gln Ala Ala Leu Ile Lys Ser Gly Phe Leu Ser Lys
                85                  90                  95

Lys Leu Ser Cys Gly Gly Ala Leu Val Ser Asp Arg Trp Val Ile Thr
                100                 105                 110

Ala Ala His Cys Val Ala Thr Thr Pro Asn Ser Asn Leu Lys Val Arg
            115                 120                 125

Leu Gly Glu Trp Asp Val Arg Asp His Asp Glu Arg Leu Asn His Glu
        130                 135                 140

Glu Tyr Ala Ile Glu Arg Lys Glu Val His Pro Ser Tyr Ser Pro Thr
145                 150                 155                 160

Asp Phe Arg Asn Asp Val Ala Leu Val Lys Leu Asp Arg Thr Val Ile
                165                 170                 175

Phe Lys Gln His Ile Leu Pro Val Cys Leu Pro His Lys Gln Met Lys
                180                 185                 190

Leu Ala Gly Lys Met Ala Thr Val Ala Gly Trp Gly Arg Thr Arg His
            195                 200                 205
```

-continued

```
Gly Gln Ser Thr Val Pro Ala Val Leu Gln Glu Val Asp Val Glu Val
    210                 215                 220

Ile Pro Asn Glu Arg Cys Gln Arg Trp Phe Arg Ala Ala Gly Arg Arg
225                 230                 235                 240

Glu Thr Ile His Asp Val Phe Leu Cys Ala Gly Tyr Lys Glu Gly Gly
                245                 250                 255

Arg Asp Ser
```

US 6,180,383 B1

FLEA LEUCINE AMINOPEPTIDASE PROTEINS AND USES THEREOF

CROSS-REFERENCE TO RELATED APPLICATIONS

The present invention is a continuation of U.S. application Ser. No. 08/639,075, filed Apr. 24, 1996, which is a continuation-in-part of U.S. patent application Ser. No. 08/484,211 now U.S. Pat. No. 5,972,645, 08/482,130 (issued as U.S. Pat. No. 5,962,257 on Oct. 5, 1999), 08/485,443, and 08/485,455 (issued as U.S. Pat. No. 5,712,143 on Jan. 27, 1998), each of which was filed on Jun. 7, 1995 and each of which is a continuation-in-part of U.S. patent application Ser. No. 08/326,773, filed Oct. 18, 1994, which issued as U.S. Pat. No. 5,766,609 on Jun. 16, 1998, which is a continuation-in-part of U.S. patent application Ser. No. 07/806,482, filed Dec. 13, 1991, which issued as U.S. Pat. No. 5,356,622 on Oct. 18, 1994. The present application is also a continuation-in-part of pending U.S. patent application Ser. No. 08/326,773, ibid., as well as of PCT/US95/14442, the international filing date of which is Oct. 18, 1995. PCT/US95/14442 claims priority to U.S. patent application Ser. Nos. 08/326,773, 08/484,211, 08/482,130, 08/485,443 and 08/485,455, ibid. Each of the applications referred to in this section is incorporated herein by reference in its entirety.

FIELD OF THE INVENTION

The present invention relates to novel flea protease proteins and their use to reduce flea infestation of animals. The present invention also relates to the use of anti-flea protease antibodies and other compounds that reduce flea protease activity to reduce flea infestation of animals.

BACKGROUND OF THE INVENTION

Fleas, which belong to the insect order Siphonaptera, are obligate ectoparasites for a wide variety of animals, including birds and mammals. Flea infestation of animals is of health and economic concern because fleas are known to cause and/or transmit a variety of diseases. Fleas cause and/or carry infectious agents that cause, for example, flea allergy dermatitis, anemia, murine typhus, plague and tapeworm. In addition, fleas are a problem for animals maintained as pets because the infestation becomes a source of annoyance for the pet owner who may find his or her home generally contaminated with fleas which feed on the pets. As such, fleas are a problem not only when they are on an animal but also when they are in the general environment of the animal.

The medical and veterinary importance of flea infestation has prompted the development of reagents capable of controlling flea infestation. Commonly encountered methods to control flea infestation are generally focussed on use of insecticides in formulations such as sprays, shampoos, dusts, dips, or foams, or in pet collars. While some of these products are efficacious, most, at best, offer protection of a very limited duration. Furthermore, many of the methods are often not successful in reducing flea populations on the pet for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide. Additional anti-flea products include non-toxic reagents such as insect growth regulators (IGRs), including methoprene, which mimics flea hormones and affect flea larval development.

An alternative method for controlling flea infestation is the use of flea vaccines to be administered to animals prior to or during flea infestation. However, despite considerable interest in developing anti-flea reagents, no flea vaccine presently exists.

SUMMARY OF THE INVENTION

The present invention relates to flea serine protease proteins, to flea aminopeptidase proteins, and to flea cysteine protease proteins; to flea serine protease, aminopeptidase and/or cysteine protease nucleic acid molecules, including those that encode such proteins; to antibodies raised against such proteins; and to compounds that inhibit flea serine protease, aminopeptidase and/or cysteine protease activities. The present invention also includes methods to obtain such proteins, nucleic acid molecules, antibodies, and inhibitors. Also included in the present invention are therapeutic compositions comprising such proteins, nucleic acid molecules, antibodies, and/or inhibitors as well as the use of such therapeutic compositions to protect a host animal from flea infestation.

One embodiment of the present invention is an isolated flea serine protease nucleic acid molecule that hybridizes under stringent hybridization conditions with a flea serine protease gene. Particularly preferred flea serine protease nucleic acid molecules include nucleic acid sequences SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, and SEQ ID NO:38, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78, SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, the nucleic acid sequences disclosed in Table 2, SEQ ID NO:120, SEQ. ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 and/or SEQ ID NO:189 and/or nucleic acid sequences encoding proteins having amino acid sequences SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO: 25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79, SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:179, SEQ ID NO:180, SEQ ID NO:181, SEQ ID NO:184 and/or SEQ ID NO:190, and/or the amino acid sequences disclosed in Table 2; as well as allelic variants of any of the listed nucleic acid sequences or complements of any of the listed nucleic acid sequences.

Another embodiment of the present invention is an isolated flea aminopeptidase nucleic acid molecule that hybridizes under stringent hybridization conditions with a flea aminopeptidase gene. A particularly preferred flea aminopeptidase nucleic acid molecule includes nucleic acid sequence SEQ ID NO:50, SEQ ID NO:112, SEQ ID NO:169 and/or SEQ ID NO:171, and/or nucleic acid sequences encoding proteins having amino acid sequences SEQ ID NO:51, SEQ ID NO:113, SEQ ID NO:167, SEQ ID NO:170, SEQ ID NO:172, as well as allelic variants of any of those nucleic acid sequences or complements of any of the listed nucleic acid sequences.

Another embodiment of the present invention is an isolated flea cysteine protease nucleic acid molecule that hybridizes under stringent hybridization conditions with a flea cysteine protease gene. A particularly preferred flea cysteine protease nucleic acid molecule includes nucleic acid sequence SEQ ID NO:177, and/or nucleic acid sequences encoding proteins having amino acid sequence SEQ ID NO:178, as well as allelic variants of any of those nucleic acid sequences or complements of any of the listed nucleic acid sequences.

The present invention also includes a nucleic acid molecule comprising a nucleic acid sequence that encodes a flea protease protein, including a larval serine protease protein, an adult serine protease protein, a larval aminopeptidase protein, an adult aminopeptidase protein, a larval cysteine protease protein and/or an adult cysteine protease protein The present invention also relates to recombinant molecules, recombinant viruses and recombinant cells that include flea serine protease, aminopeptidase and/or cysteine protease nucleic acid molecules of the present invention. Also included are methods to produce such nucleic acid molecules, recombinant molecules, recombinant viruses and recombinant cells.

Another embodiment of the present invention includes an isolated flea serine protease protein, including a protein that includes a flea serine protease protein. A preferred flea serine protease protein is capable of eliciting an immune response against a natural flea protease when administered to an animal and/or of having serine protease activity. Particularly preferred flea serine protease proteins are those encoded by preferred flea serine protease nucleic acid molecules of the present invention.

Yet another embodiment of the present invention includes an isolated flea aminopeptidase protein, including a protein that includes a flea aminopeptidase protein. A preferred flea aminopeptidase protein is capable of eliciting an immune response against a natural flea protease when administered to an animal and/or of having aminopeptidase activity.

Yet another embodiment of the present invention includes an isolated flea cysteine protease protein, including a protein that includes a flea cysteine protease protein. A preferred flea cysteine protease protein is capable of eliciting an immune response against a natural flea protease when administered to an animal and/or of having cysteine protease activity.

The present invention also relates to mimetopes of flea serine protease, aminopeptidase and/or cysteine protease proteins as well as to isolated antibodies that selectively bind to flea serine protease proteins or mimetopes thereof, to flea aminopeptidase proteins or mimetopes thereof, or to flea cysteine protease proteins or mimetopes thereof. Also included are methods, including recombinant methods, to produce proteins, mimetopes and antibodies of the present invention.

Yet another embodiment of the present invention is a therapeutic composition that is capable of reducing flea infestation. Such a therapeutic composition includes one or more of the following protective compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein; an inhibitor of flea serine protease activity identified by its ability to inhibit flea serine protease activity; an isolated flea aminopeptidase protein or a mimetope thereof; an isolated flea aminopeptidase nucleic acid molecule that hybridizes under stringent hybridization conditions with a flea aminopeptidase gene; an isolated antibody that selectively binds to a flea aminopeptidase protein; an inhibitor of flea aminopeptidase activity identified by its ability to inhibit flea aminopeptidase activity; an isolated flea cysteine protease protein or a mimetope thereof; an isolated flea cysteine protease nucleic acid molecule that hybridizes under stringent hybridization conditions with a flea cysteine protease gene; an isolated antibody that selectively binds to a flea cysteine protease protein; an inhibitor of flea cysteine protease activity identified by its ability to inhibit flea cysteine protease activity. A preferred therapeutic composition of the present invention also includes an excipient, an adjuvant and/or a carrier. Also included in the present invention is a method to reduce flea infestation. The method includes the step of administering to the animal a therapeutic composition of the present invention.

Another embodiment of the present invention is a method to identify a compound capable of inhibiting flea serine protease, flea aminopeptidase or flea cysteine protease activity. The method includes the steps of: (a) contacting an isolated flea serine protease protein, a flea aminopeptidase protein or a flea cysteine protease protein, with a putative inhibitory compound under conditions in which, in the absence of the compound, the protein has, respectively, serine protease, aminopeptidase or cysteine protease activity; and (b) determining if the putative inhibitory compound inhibits the respective activity. Also included in the present invention is a test kit to identify a compound capable of inhibiting flea serine protease, flea aminopeptidase or cysteine protease activity. Such a kit includes an isolated flea serine protease protein having serine protease activity, an isolated flea aminopeptidase protein having aminopeptidase activity or an isolated flea cysteine protease protein having cysteine protease activity and a means for determining the extent of inhibition of the respective activity in the presence of a putative inhibitory compound.

DETAILED DESCRIPTION OF THE INVENTION

Figure 1:
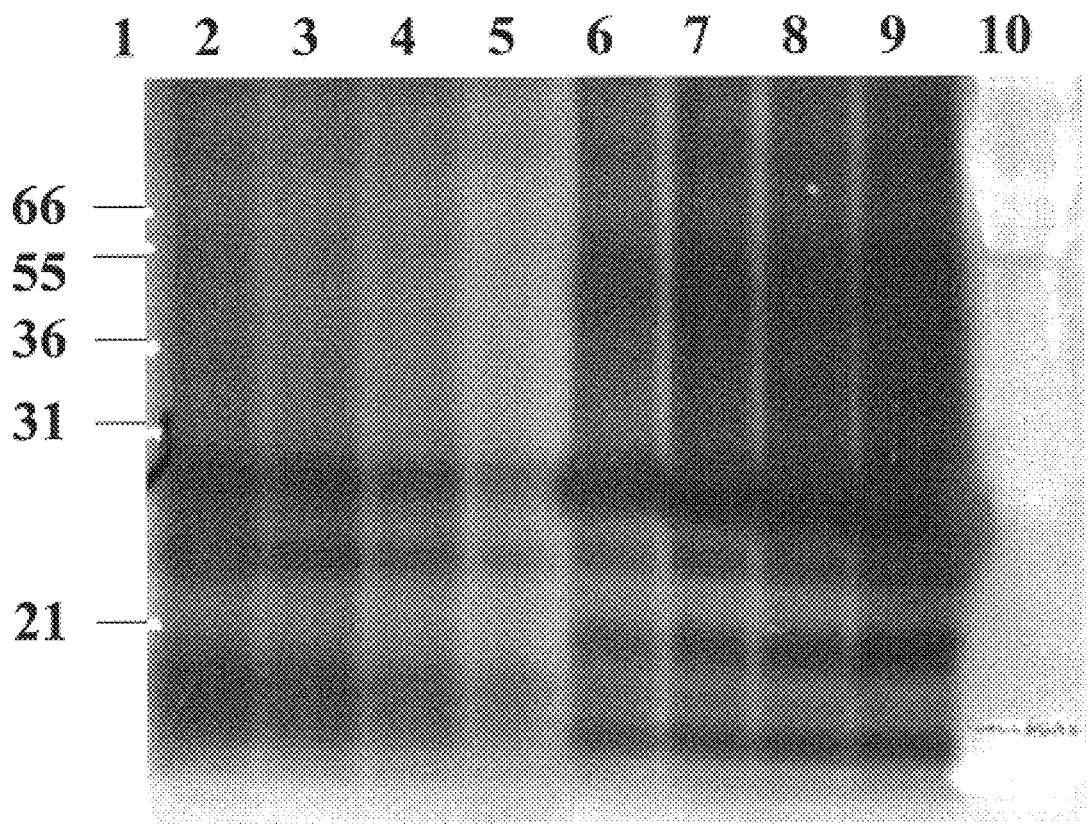
FIG. 1 depicts a protease substrate gel analysis of the relative proteolytic activity in 1, 2, 5 or 10 midguts from either fed or unfed female fleas.

The present invention includes the use of compounds that inhibit flea protease activity to protect a host animal from flea infestation. The inventors have discovered that proteases are significant components of the flea midgut and are good targets for immunotherapeutic and/or chemotherapeutic intervention to reduce flea burden both on the host animal and in the immediate (i.e., surrounding) environment of the animal. The inventors have shown, for example, that the viability and/or fecundity of fleas consuming a blood meal is reduced when the blood meal contains compounds that reduce flea protease activity, probably because the compounds interfere with flea digestion and other functions. Compounds that reduce the amount and/or activity of flea proteases without substantially harming the host animal are included in the present invention. Such compounds include flea protease vaccines, anti-flea protease antibodies, flea protease inhibitors, and/or compounds that suppress protease synthesis; such compounds are discussed in more detail below.

One embodiment of the present invention is a method to protect a host animal from flea infestation by treating the animal with a composition that includes a compound that reduces the protease activity of fleas feeding (includes fleas in the process of feeding as well as fleas having fed) from the treated animal thereby reducing the flea burden on the animal and in the environment of the animal. It is to be noted that the term "a" or "an" entity refers to one or more of that entity; for example, a compound refers to one or more compounds. As such, the terms "a" (or "an"), "one or more" and "at least one" can be used interchangeably herein. Thus, a composition of the present invention can include one or more compounds that target (reduced the activity of) one or more proteases in the flea.

As used herein, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment surrounding the animal (i.e., in the environment of the animal). Such an environment can include not only adult fleas, but also flea eggs and/or flea larvae. The environment can be of any size such that fleas in the environment are able to jump onto and off of a host animal. As such, it is desirable not only to reduce the flea burden on an animal per se, but also to reduce the flea burden in the environment surrounding the animal.

In accordance with the present invention, a host animal is treated by administering to the animal a compound of the present invention in such a manner that the compound itself (e.g., a protease inhibitor, protease synthesis suppressor or anti-flea protease antibody) or a product generated by the animal in response to administration of the compound (e.g., antibodies produced in response to a flea protease vaccine, or conversion of an inactive inhibitor "prodrug" to an active protease inhibitor) ultimately enters the flea midgut. An animal is preferably treated in such a way that the compound or product thereof enters the blood stream of the animal. Fleas are then exposed to the compound when they feed from the animal. For example, flea protease inhibitors administered to an animal are administered in such a way that the inhibitors enter the blood stream of the animal, where they can be taken up by feeding fleas. In another embodiment, when a host animal is administered a flea protease vaccine, the treated animal mounts an immune response resulting in the production of antibodies against the protease (anti-flea protease antibodies) which circulate in the animal's blood stream and are taken up by fleas upon feeding. Blood taken up by fleas enters the flea midgut where compounds of the present invention, or products thereof, such as anti-flea protease antibodies, flea protease inhibitors, and/or protease synthesis suppressors, interact with, and reduce proteolytic activity in the flea midgut. The present invention also includes the ability to reduce larval flea infestation in that when fleas feed from a host animal that has been administered a therapeutic composition of the present invention, at least a portion of compounds of the present invention, or products thereof, in the blood taken up by the flea are excreted by the flea in feces, which is subsequently ingested by flea larvae. It is of note that flea larvae obtain most, if not all, of their nutrition from flea feces.

In accordance with the present invention, reducing proteolytic activity in flea midguts can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal and/or (g) altering the development of flea larvae (e.g., by decreasing feeding behavior, inhibiting growth, inhibiting (e.g., slowing or blocking) molting, and/or otherwise inhibiting maturation to adults). One embodiment of the present invention is a composition that includes one or more compounds that reduce the activity of one or more flea proteases directly (e.g., an anti-flea protease antibody or a flea protease inhibitor) and/or indirectly (e.g., a flea protease vaccine). Suitable flea proteases to target include flea aminopeptidases, flea carboxypeptidases and/or flea endopeptidases. Such proteases can include cytosolic and/or membrane-bound forms of a protease. Preferred flea proteases to target include, but are not limited to, serine proteases, metalloproteases, aspartic acid proteases and/or cysteine proteases. It is to be noted that these preferred groups of proteases include aminopeptidases, carboxypeptidases and/or endopeptidases. Preferred flea proteases to target include, but are not limited to, proteases that degrade hemoglobin, proteases involved in blood coagulation and/or lytic (anti-coagulation) pathways, proteases involved in the maturation of peptide hormones, proteases that inhibit complement or other host immune response elements (e.g., antibodies) and/or proteases involved in vitellogenesis. A number of proteases are known to those skilled in the art, including, but not limited to, aminopeptidases, such as leucine aminopeptidase and aminopeptidases B and M; astacin-like metalloproteases; calpains; carboxypeptidases, such as carboxypeptidases A, P and Y; cathepsins, such as cathepsins B, D, E, G, H, and L, chymotrypsins; cruzipains; meprins; papains; pepsins; renins; thermolysins and trypsins. A particularly preferred protease to target is a protease having a proteolytic activity that, when targeted with a composition of the present invention, reduces flea burden without substantially harming the host animal. Such a protease can be identified using, for example, methods as disclosed herein.

One aspect of the present invention is the discovery that a substantial amount of the proteolytic activity found in flea midguts is serine protease activity. Both in vitro and in vivo studies using a number of protease inhibitors substantiate this discovery, details of which are disclosed in the Examples. As such a particularly preferred protease to target is a serine protease. Examples of serine proteases, include, but are not limited to, acrosins, bromelains, cathepsin G, chymotrypsins, collagenases, elastases, factor Xa, ficins, kallikreins, papains, plasmins, Staphylococcal V8 proteases, thrombins and trypsins. In one embodiment, a preferred flea serine protease to target includes a protease having trypsin-like or chymotrypsin-like activity. It is appreciated by those skilled in the art that an enzyme having "like" proteolytic activity has similar activity to the referenced protease, although the exact structure of the preferred substrate cleaved may differ. "Like" proteases usually have similar tertiary structures as their referenced counterparts.

Protease inhibitor studies disclosed in the Examples section also indicate that additional preferred proteases to target include aminopeptidases and/or metalloproteases. Examples of such proteases include exo- and endo-metalloproteases, digestive enzymes, and enzymes involved in peptide hormone maturation. One example of an aminopeptidase that is also a metalloprotease is leucine aminopeptidase.

Suitable compounds to include in compositions of the present invention include, but are not limited to, a vaccine comprising a flea protease (a flea protease vaccine), an antibody that selectively binds to a flea protease (an anti-flea protease antibody), a flea protease inhibitor (a compound other than a vaccine or an antibody that inhibits a flea protease), and a mixture of such compounds. As used herein, a mixture thereof refers to a combination of one or more of the cited entities. Compositions of the present invention can also include compounds to suppress protease synthesis or maturation, such as, but not limited to, protease modulating peptides.

A preferred embodiment of the present invention is a flea protease vaccine and its use to reduce the flea population on and around an animal. A flea protease vaccine can include one or more proteins capable of eliciting an immune response against a flea protease and can also include other components. Preferred flea protease vaccines include a flea serine protease, a flea metalloprotease, a flea aspartic acid protease and/or a flea cysteine protease, with flea serine protease, flea metalloprotease and/or flea aminopeptidase vaccines being more preferred. Examples of flea protease vaccines include soluble flea midgut preparations of the present invention as well as one or more isolated proteins of the present invention.

One embodiment of the present invention is a soluble flea midgut preparation. Such a preparation includes primarily components naturally present in the lumen of a flea midgut and, depending on the method of preparation, can also include one or more peripheral midgut membrane proteins. Methods to preferentially include, or exclude, membrane proteins from such a preparation are known to those skilled in the art. The present invention includes the discovery that such a preparation has proteolytic activity, of which a substantial portion is serine protease activity. Preferably at least about 70 percent of the proteolytic activity in a soluble flea midgut soluble preparation is serine protease activity, as can be indicated by the ability to inhibit at least about 70 percent of the proteolytic activity with 4-2-aminoethyl-benzenesulfonylfluoride-hydrochloride (AEBSF). Serine protease activity can also be identified using other known inhibitors or substrates. Other preferred inhibitors that can inhibit at least about 70 percent of the proteolytic activity of a soluble flea midgut preparation of the present invention include soybean trypsin inhibitor, 1,3-diisopropylfluorophosphate or leupeptin.

A soluble flea midgut preparation of the present invention includes proteases that range in molecular weight from about 5 kilodaltons (kD or kDa) to about 200 kD, as determined by SDS-PAGE (sodium dodecyl sulfate polyacrylamide gel electrophoresis), with at least a substantial portion of the serine proteases ranging in molecular weight from about 5 kD to about 60 kD, as determined by SDS-PAGE. A substantial portion of protease activity in a soluble flea midgut preparation of the present invention has a pH activity optimum ranging from about pH 5 to about pH 10, preferably an activity optimum ranging from about pH 7 to about pH 9, and even more preferably an activity optimum of about pH 8. While not being bound by theory, such a pH optimum suggests that a large proportion of proteases in soluble flea midgut preparations of the present invention are serine proteases. It is also interesting to note that the pH of the flea midgut is also about pH 8. The findings that proteases in soluble flea midgut preparations of the present invention exhibit a varied pattern of inhibition by protease inhibitors of a given type (e.g., serine protease inhibitors), as well as variances seen in molecular weights and pH optima of the proteases, suggest that there are a number of protease isoforms in such preparations.

A soluble flea midgut preparation of the present invention is preferably prepared by a method that includes the steps of (a) disrupting a flea midgut to produce a mixture including a liquid portion and a solid portion and (b) recovering the liquid portion to obtain a soluble flea midgut preparation. Such a method is a simplified version of methods disclosed in U.S. Pat. No. 5,356,622, ibid. It is to be noted that in accordance with the present invention, methods disclosed in U.S. Pat. No. 5,356,622, ibid. can also be used to prepare soluble flea midgut preparations having similar proteolytic activities.

Flea midguts can be obtained (e.g., dissected from) from unfed fleas or from fleas that recently consumed a blood meal (i.e., blood-fed fleas) Such midguts are referred to herein as, respectively, unfed flea midguts and fed flea midguts. Flea midguts can be obtained from either male or female fleas. As demonstrated in the Examples section, female flea midguts exhibit somewhat more proteolytic activity than do male flea midguts. Furthermore, fed flea midguts have significantly more proteolytic activity than do unfed flea midguts. While not being bound by theory, it is believed that blood feeding induces in flea midguts the synthesis and/or activation of proteases as well as other factors (e.g., enzymes, other proteins, co-factors, etc.) important in digesting the blood meal, as well as in neutralizing host molecules potentially damaging to the flea (e.g., complement, immunoglobulins, blood coagulation factors). It is also to be appreciated that unfed flea midguts may contain significant targets not found in fed flea midguts and vice versa. Furthermore, although the present application focusses primarily on flea midgut proteases, it is to be noted that the present invention also includes other components of soluble flea midgut preparations of the present invention that provide suitable targets to reduce flea burden on an animal and in the environment of that animal; see also U.S. Pat. No. 5,356,622, ibid.

Methods to disrupt flea midguts in order to obtain a soluble flea midgut preparation are known to those skilled in the art and can be selected according to, for example, the volume being processed and the buffers being used. Such methods include any technique that promotes cell lysis, such as, but are not limited to, chemical disruption techniques (e.g., exposure of midguts to a detergent) as well as mechanical disruption techniques (e.g., homogenization, sonication, use of a tissue blender or glass beads, and freeze/thaw techniques).

Methods to recover a soluble flea midgut preparation are also known to those skilled in the art and can include any method by which the liquid portion of disrupted flea midguts is separated from the solid portion (e.g., filtration or centrifugation). In a preferred embodiment, disrupted flea midguts are subjected to centrifugation, preferably at an acceleration ranging from about 10,000×g to about 15,000×g for several minutes (e.g., from about 1 min. to about 15 min.). The supernatant from such a centrifugation comprises a soluble flea midgut preparation of the present invention.

The present invention also includes an isolated protein that includes an amino acid sequence encoded by a nucleic acid molecule capable of hybridizing under stringent conditions (i.e., that hybridize under stringent hybridization conditions) with a nucleic acid molecule that encodes a protease present (i.e., the nucleic acid molecules hybridize with the nucleic acid strand that is complementary to the coding strand) in (i.e., can be found in) a flea midgut, such as a midgut from a blood-fed female flea, a midgut from a blood-fed male flea, a midgut from an unfed female flea or a midgut from an unfed male flea. A preferred midgut protease is present in the lumen of the midgut.

An isolated protein of the present invention, also referred to herein as an isolated protease protein, preferably is capable of eliciting an immune response against a flea midgut protease and/or has proteolytic activity. According to the present invention, an isolated, or biologically pure, protein, is a protein that has been removed from its natural milieu. As such, "isolated" and "biologically pure" do not necessarily reflect the extent to which the protein has been purified. An isolated protease protein can be obtained from its natural source. Such an isolated protein can also be produced using recombinant DNA technology or chemical synthesis.

As used herein, an isolated protein of the present invention can be a full-length protein or any homologue of such a protein, such as a protein in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue comprises a protein having an amino acid sequence that is sufficiently similar to a natural flea midgut protease that a nucleic acid sequence encoding the homologue is capable of hybridizing under stringent conditions to (i.e., with) the complement of a nucleic acid sequence encoding the corresponding natural flea midgut protease amino acid sequence. As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., ibid., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protease protein homologue of the present invention is from about 12 to about 18 nucleotides in length. There is no limit, other than a practical limit, on the maximal size of such a nucleic acid molecule in that the nucleic acid molecule can include a portion of a gene, an entire gene, or multiple genes, or portions thereof. Similarly, the minimal size of a protease protein homologue of the present invention is from about 4 to about 6 amino acids in length, with preferred sizes depending on whether a full-length, multivalent (i.e., fusion protein having more than one domain each of which has a function), or functional portions of such proteins are desired. Protease protein homologues of the present invention preferably have protease activity and/or are capable of eliciting an immune response against a flea midgut protease.

A protease protein homologue of the present invention can be the result of allelic variation of a natural gene encoding a flea protease. A natural gene refers to the form of the gene found most often in nature. Protease protein homologues can be produced using techniques known in the art including, but not limited to, direct modifications to a gene encoding a protein using, for example, classic or recombinant DNA techniques to effect random or targeted mutagenesis. Isolated protease proteins of the present invention, including homologues, can be identified in a straightforward manner by the proteins' ability to effect proteolytic activity and/or to elicit an immune response against a flea midgut protease. Such techniques are known to those skilled in the art.

A preferred protease protein of the present invention is a flea serine protease, a flea metalloprotease, a flea aspartic acid protease, a flea cysteine protease, or a homologue of any of these proteases. A more preferred protease protein is a flea serine protease, a flea metalloprotease or a homologue of either. Also preferred is a flea aminopeptidase or a homologue thereof. Also preferred is a flea cysteine protease or a homologue thereof. Particularly preferred is a flea serine protease or a homologue thereof.

Preferred protease proteins of the present invention are flea protease proteins having molecular weights ranging from about 5 kD to about 200 kD, as determined by SDS-PAGE, and homologues of such proteins. More preferred are flea protease proteins having molecular weights ranging from about 5 kD to about 60 kD, as determined by SDS-PAGE, and homologues of such proteins. Even more preferred are flea serine protease proteins, particularly those having molecular weights of about 26 kD (denoted PfSP26, now denoted PafSP-26K to distinguish from flea PfSP26 as described in Example 26), about 24 kD (denoted PfSP24, now denoted PafSP-24K to distinguish from flea PfSP24 as described in Example 27), about 19 kD (denoted PfSP19, now denoted PafSP-19K to distinguish from flea PfSP19 as described in Example 32), about 6 kD (denoted PfSP6, now denoted PafSP-6K to distinguish from flea PfSP6 as described in Example 11), about 31 kD (denoted PfSP28), about 25 kD (denoted PlfSP-25K1) from 1st instar larvae, about 25 kD (denoted PlfSP-25K3) from 3rd instar larvae, about 28 kD (denoted PlfSP-28K3) and about 31 kD (denoted PlfSP-31K3), and flea aminopeptidase proteins, particularly those having molecular weights of about 95 kD (denoted PfAP-95K) as determined by SDS-PAGE, and homologues of such proteins.

One preferred embodiment of the present invention is an isolated flea protease protein that includes an amino acid sequence encoded by a nucleic acid molecule that hybridizes under stringent hybridization conditions with a flea serine protease gene, with a flea aminopeptidase gene or with a flea cysteine protease gene. As used herein, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself.

The inventors have discovered an extensive family of serine proteases, encoded by a family of serine protease genes. Such a gene family may be due to allelic variants (i.e., genes having similar, but different, sequences at a given locus in a population of fleas) and/or to, the existence of serine protease genes at more than one locus in the flea genome. As such, the present invention includes flea serine protease genes comprising not only the nucleic acid sequences disclosed herein (e.g., genes including nucleic acid sequences SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38 and/or the nucleic acid sequences disclosed in Table 2 (i.e., SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78), SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 and/or SEQ ID NO:189, and/or nucleic acid sequences encoding proteins having amino acid sequences as disclosed herein (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, the amino acid sequences disclosed in Table 2 (i.e., SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, SEQ ID NO:79), SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:179, SEQ ID NO:180, SEQ ID NO:181, SEQ ID NO:184 and/or SEQ ID NO:190), but also allelic variants of any of those nucleic acid sequences. (It should be noted that since nucleic acid sequencing technology is not entirely error-free, all sequences represented herein are at best apparent (i.e., deduced) nucleic acid or amino acid sequences.)

A preferred flea aminopeptidase gene includes nucleic acid sequence SEQ ID NO:50, which encodes an aminopeptidase protein including SEQ ID NO:51. Another preferred flea aminopeptidase gene includes nucleic acid sequence SEQ ID NO:112, which encodes an aminopeptidase protein including SEQ ID NO:113. Another preferred flea aminopeptidase gene includes nucleic acid sequences SEQ ID NO:169 and/or SEQ ID NO:171; the gene encodes a putative membrane-bound form of an aminopeptidase protein that includes SEQ ID NO:167, SEQ ID NO:170 and/or SEQ ID NO:172. Additional preferred aminopeptidase genes include allelic variants of SEQ ID NO:50, of SEQ ID NO:112 SEQ ID NO:169 or SEQ ID NO:171.

A preferred flea cysteine protease gene includes nucleic acid sequence SEQ ID NO:SEQ ID NO:177, which encodes a cysteine protease protein including SEQ ID NO:178. Additional preferred cysteine protease genes include allelic variants of SEQ ID NO:177.

A preferred flea serine protease protein of the present invention is encoded by a nucleic acid molecule that hybridizes under stringent hybridization conditions with at least one of the following nucleic acid molecules: nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16, nfSP17, nfSP18, nfSP19, nfSP20, nfSP21, nfSP23, nfSP24, nfSP25, nfSP26, nfSP27, nfSP28, nfSP29, nfSP30, nfSP31, nfSP32, nfSP33, nfSP34, nfSP36, nfSP37, nfSP38 and nfSP39. As used herein, each of these nucleic acid molecules represent the entire coding region of a flea serine protease gene of the present invention (at least portions of which are also referred to by flea clone numbers, as described in the Examples). Nucleic acid molecules that contain partial coding regions or other parts of the corresponding gene are denoted by names that include the size of those nucleic acid molecules (e.g., nfSP4$_{156}$). Nucleic acid molecules containing apparent full length coding regions for which the size is known also are denoted by names that include the size of those nucleic acid molecules (e.g., nfSP4$_{672}$). The production, and at least partial nucleic acid sequence, of such nucleic acid molecules is disclosed in the Examples.

Particularly preferred serine protease proteins are encoded by a nucleic acid molecule that hybridizes under stringent hybridization conditions with at least one of the following nucleic acid molecules: nfSP4$_{672}$, nfSP1$_{156}$, nfSP2$_{168}$, nfSP3$_{177}$, nfSP4$_{156}$, nfSP5$_{159}$, nfSP6$_{168}$, nfSP7$_{159}$, nfSP8$_{186}$, nfSP9$_{168}$, nfSP10$_{120}$, and nfSP11$_{162}$ as well as other specific nucleic acid molecules disclosed in the Examples section, such as, but not limited to, nfSP1$_{779}$, nfSP2$_{944}$, nfSP3$_{177}$, nfSP4$_{672}$, nfSP5$_{157}$, nfSP5$_{218}$, nfSP6$_{932}$, nfSP7$_{894}$, nfSP8$_{299}$, nfSP9$_{266}$, nfSP10$_{378}$, nfSP11$_{252}$, nfSP12$_{144}$, nfSP12$_{225}$, nfSP13$_{850}$, nfSP14$_{213}$, nfSP15$_{252}$, nfSP16$_{168}$, nfSP18$_{534}$, nfSP19$_{359}$, nfSP20$_{841}$, nfSP5$_{806}$, nfSP11$_{307}$, nfSP8$_{515}$, nfSP12$_{758}$, nfSP26$_{610}$, nfSP27$_{386}$, nfSP23$_{423}$, nfSP24$_{410}$, nfSP33$_{426}$, nfSP34$_{390}$, nfSP36$_{197}$, nfSP38$_{341}$, nfSP37$_{261}$, nfSP39$_{267}$ nfSP29$_{612}$, nfSP30$_{641}$, nfSP31$_{626}$, nfSP32$_{433}$, nfSP15$_{815}$, nfSP19$_{855}$, nfSP25$_{864}$, nfSP21$_{595}$, nfSP28$_{923}$ and/or nfSP33$_{778}$. Even more preferred serine protease proteins include the following amino acid sequences: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, and/or the amino acid sequences presented in Table 2 (i.e., SEQ ID NO:53, SEQ ID NO:55, SEQ ID NO:57, SEQ ID NO:59, SEQ ID NO:61, SEQ ID NO:63, SEQ ID NO:65, SEQ ID NO:67, SEQ ID NO:69, SEQ ID NO:71, SEQ ID NO:73, SEQ ID NO:75, SEQ ID NO:77, and/or SEQ ID NO:79), as well as SEQ ID NO:81, SEQ ID NO:83, SEQ ID NO:85, SEQ ID NO:87, SEQ ID NO:89, SEQ ID NO:91, SEQ ID NO:93, SEQ ID NO:95, SEQ ID NO:97, SEQ ID NO:99, SEQ ID NO:101, SEQ ID NO:103, SEQ ID NO:105, SEQ ID NO:107, SEQ ID NO:109, SEQ ID NO:111, SEQ ID NO:113, SEQ ID NO:121, SEQ ID NO:123, SEQ ID NO:125, SEQ ID NO:127, SEQ ID NO:129, SEQ ID NO:131, SEQ ID NO:133, SEQ ID NO:135, SEQ ID NO:137, SEQ ID NO:139, SEQ ID NO:141, SEQ ID NO:143, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:179, SEQ ID NO:180, SEQ ID NO:181, SEQ ID NO:184 and/or SEQ ID NO:190. Additional particularly preferred serine protease proteins are encoded by allelic variants of nucleic acid molecules encoding proteins that include the cited amino acid sequences. Also preferred are flea serine protease proteins including regions that have at least about 50%, preferably at least about 75%, and more preferably at least about 90% identity with flea serine protease proteins having amino acid sequences as cited herein.

One embodiment of the present invention is a flea serine protease that degrades IgG antibodies circulating in a host animal (i.e., flea IgGase). An example of a flea IgGase is presented in the Examples section.

A preferred flea aminopeptidase proteins of the present invention is encoded by a nucleic acid molecule that hybridizes under stringent hybridization conditions with nfAP and/or nfAP2. Particularly preferred flea aminopeptidase proteins of the present invention are encoded by a nucleic acid molecule that hybridizes under stringent hybridization conditions with nucleic acid molecule nfAP$_{453}$, nfAP$_{1580}$ and/or nfAP2$_{537}$, the production of which are described in the Examples. Even more preferred is an aminopeptidase that includes amino acid sequence SEQ ID NO:51, SEQ ID NO:113, SEQ ID NO:167, SEQ ID NO:170 and/or SEQ ID NO:172 or an aminopeptidase encoded by an allelic variant of a nucleic acid molecule that includes SEQ ID NO:50, SEQ ID NO:112, SEQ ID NO:169 and/or SEQ ID NO:171. Also preferred are flea aminopeptidase proteins including regions that have at least about 50%, preferably at least about 75%, and more preferably at least about 90% identity with SEQ ID NO:51, SEQ ID NO:113, SEQ ID NO:167, SEQ ID NO:170 and/or SEQ ID NO:172.

A preferred flea cysteine protease protein of the present invention is encoded by a nucleic acid molecule that hybridizes under stringent hybridization conditions with nucleic acid molecule nfCP1 (a flea cysteine protease full-length coding region that includes nfCP1$_{573}$, the production of which is described in the Examples). Even more preferred is a cysteine protease that includes amino acid sequence SEQ ID NO:178 or a cysteine protease encoded by an allelic variant of a nucleic acid molecule that includes SEQ ID NO:177. Also preferred is a flea cysteine protease protein including regions that have at least about 50%, preferably at least about 75%, and more preferably at least about 90% identity with SEQ ID NO:178.

One embodiment of the present invention is an isolated protein having proteolytic activity that is substantially inhibited by a serine protease inhibitor, an aminopeptidase inhibitor and/or a cysteine protease inhibitor. Such inhibition can be measured by techniques known to those skilled in the art. To be substantially inhibited means, for example, for a serine protease, that at least half of the proteolytic activity of the protease protein is inhibited by a serine protease inhibitor. Preferably at least about 70 percent, and even more preferably at least about 90 percent of the proteolytic activity of the protease protein is inhibited by a serine protease inhibitor.

An isolated protein of the present invention can be produced in a variety of ways, including recovering such a protein from a flea midgut and producing such a protein recombinantly. In one embodiment, a flea midgut protease can be recovered by methods heretofore disclosed for obtaining a soluble flea midgut preparation. A flea midgut protease protein can be further purified from a disrupted flea midgut by a number of techniques known to those skilled in the art, including, but not limited to, affinity chromatography, ion exchange chromatography, filtration, electrophoresis (e.g., standard, capillary and flow-through electrophoresis), hydrophobic interaction chromatography, gel filtration chromatography, reverse phase chromatography, concanavalin A chromatography, chromatofocusing and differential solubilization. In one embodiment, a flea midgut protease is purified using protease inhibitor affinity chromatography, an example of which is disclosed in the Examples section.

Another embodiment of the present invention is a method to produce an isolated protein of the present invention using recombinant DNA technology. Such a method includes the steps of (a) culturing a recombinant cell comprising a nucleic acid molecule encoding a protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques, as heretofore disclosed.

Isolated proteins of the present invention are preferably retrieved in "substantially pure" form. As used herein, "substantially pure" refers to a purity that allows for the effective use of the protein as a vaccine. A vaccine for animals, for example, should exhibit no substantial toxicity and should be capable of stimulating the production of antibodies in a vaccinated animal.

Another embodiment of the present invention is an isolated nucleic acid molecule capable of hybridizing under stringent conditions with a gene encoding a flea protease present in a flea midgut. Such a nucleic acid molecule is also referred to herein as a flea protease nucleic acid molecule. Particularly preferred is an isolated nucleic acid molecule that hybridizes under stringent conditions with a flea serine protease gene, with a flea aminopeptidase gene or with a flea cysteine protease gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a flea protease gene includes all nucleic acid sequences related to a natural flea protease gene such as regulatory regions that control production of a flea protease protein encoded by that gene (such as, but not limited to, transcription, translation or post-translation control regions) as well as the coding region itself. A nucleic acid molecule of the present invention can be an isolated natural flea protease nucleic acid molecule or a homologue thereof. A nucleic acid molecule of the present invention can include one or more regulatory regions, full-length or partial coding regions, or combinations thereof. The minimal size of a flea protease nucleic acid molecule of the present invention is the minimal size capable of forming a stable hybrid under stringent hybridization conditions with a corresponding natural gene. Flea protease nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning) or chemical synthesis. Isolated flea protease nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the nucleic acid molecule's ability to encode a flea protease protein of the present invention or to form stable hybrids under stringent conditions with natural nucleic acid molecule isolates.

A flea protease nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against a flea protease and/or to have proteolytic activity) and/or by hybridization with isolated flea protease nucleic acids under stringent conditions.

An isolated flea protease nucleic acid molecule of the present invention can include a nucleic acid sequence that encodes at least one flea protease protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an flea protease protein.

One embodiment of the present invention is a flea protease nucleic acid molecule of the present invention that is capable of hybridizing under stringent conditions to a nucleic acid strand that encodes at least a portion of a flea protease or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Preferred is a flea protease nucleic acid molecule that includes a nucleic acid sequence having at least about 65 percent, preferably at least about 75 percent, more preferably at least about 85 percent, and even more preferably at least about 95 percent homology with the corresponding region(s) of the nucleic acid sequence encoding at least a portion of a flea protease protein. Particularly preferred is a flea protease nucleic acid molecule capable of encoding at least a portion of a flea protease that naturally is present in flea midguts and preferably is included in a soluble flea midgut preparation of the present invention. Examples of nucleic acid molecules of the present invention are disclosed in the Examples section.

A preferred flea serine protease nucleic acid molecule of the present invention is a nucleic acid molecule that hybridizes under stringent hybridization conditions with at least one of the following nucleic acid molecules: nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16, nfSP17, nfSP18, nfSP19, nfSP20, nfSP21, nfSP23, nfSP24, nfSP25, nfSP26, nfSP27, nfSP28, nfSP29, nfSP30, nfSP31, nfSP32, nfSP33, nfSP34, nfSP36, nfSP37, nfSP38 and/or nfSP39. More preferred is a nucleic acid molecule that hybridizes under stringent hybridization conditions with at least one of the following nucleic acid molecules: $nfSP4_{672}$, $nfSP1_{156}$, $nfSP2_{168}$, $nfSP3_{177}$, $nfSP4_{156}$, $nfSP5_{159}$, $nfSP6_{168}$, $nfSP7_{159}$, $nfSP8_{186}$, $nfSP9_{168}$, $nfSP10_{120}$, $nfSP11_{162}$, $nfSP5_{806}$, $nfSP11_{307}$, $nfSP8_{515}$, $nfSP12_{758}$, $nfSP26_{610}$, $nfSP27_{386}$, $nfSP23_{423}$, $nfSP24_{410}$, $nfSP33_{426}$, $nfSP34_{390}$, $nfSP36_{197}$, $nfSP38_{341}$, $nfSP37_{261}$, $nfSP39_{267}$ $nfSP29_{612}$, $nfSP30_{641}$, $nfSP31_{626}$, $nfSP32_{433}$, $nfSP15_{815}$, $nfSP19_{855}$, $nfSP25_{864}$, $nfSP21_{595}$, $nfSP28_{923}$ and/or $nfSP33_{778}$, as well as other specific nucleic acid molecules disclosed in the Examples section. Even more preferred are nucleic acid molecules that include nfSP1, nfSP2, nfSP3, nfSP4, nfSP5, nfSP6, nfSP7, nfSP8, nfSP9, nfSP10, nfSP11, nfSP12, nfSP13, nfSP14, nfSP15, nfSP16, nfSP17, nfSP18, nfSP19, nfSP20, nfSP21, nfSP23, nfSP24, nfSP25, nfSP26, nfSP27, nfSP28, nfSP29, nfSP30, nfSP31, nfSP32, nfSP33, nfSP34, nfSP36, nfSP37, nfSP38 and/or nfSP39 and even more particularly, $nfSP4_{672}$, $nfSP1_{156}$, $nfSP2_{168}$, $nfSP3_{177}$, $nfSP4_{156}$, $nfSP5_{159}$, $nfSP6_{168}$, $nfSP7_{159}$, $nfSP8_{186}$, $nfSP9_{168}$, $nfSP10_{120}$, $nfSP11_{162}$, $nfSP5_{806}$, $nfSP11_{307}$, $nfSP8_{515}$, $nfSP12_{758}$, $nfSP26_{610}$, $nfSP27_{386}$, $nfSP23_{423}$, $nfSP24_{410}$, $nfSP33_{426}$, $nfSP34_{390}$, $nfSP36_{197}$, $nfSP38_{341}$, $nfSP37_{261}$, $nfSP39_{267}$ $nfSP29_{612}$, $nfSP30_{641}$, $nfSP31_{626}$, $nfSP32_{433}$, $nfSP15_{815}$, $nfSP19_{855}$, $nfSP25_{864}$, $nfSP21_{595}$, $nfSP28_{923}$, $nfSP33_{778}$, as well as other specific nucleic acid molecules disclosed in the Examples section.

Particularly preferred flea serine protease nucleic acid molecules include at least one of the following sequences: SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, and/or nucleic acid sequences disclosed in Table 2 (i.e., SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, SEQ ID NO:70, SEQ ID NO:72, SEQ ID NO:74, SEQ ID NO:76, SEQ ID NO:78), as well as SEQ ID NO:80, SEQ ID NO:82, SEQ ID NO:84, SEQ ID NO:86, SEQ ID NO:88, SEQ ID NO:90, SEQ ID NO:92, SEQ ID NO:94, SEQ ID NO:96, SEQ ID NO:98, SEQ ID NO:100, SEQ ID NO:102, SEQ ID NO:104, SEQ ID NO:106, SEQ ID NO:108, SEQ ID NO:110, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:136, SEQ ID NO:138, SEQ ID NO:140, SEQ ID NO:142, SEQ ID NO:144, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164 and/or SEQ ID NO:189, and complements thereof. Also preferred are allelic variants of such nucleic acid molecules.

A preferred flea aminopeptidase nucleic acid molecule of the present invention is a nucleic acid molecule that hybridizes under stringent hybridization conditions with nfAP and/or nfAP2. A more preferred flea aminopeptidase nucleic acid molecule of the present invention is a nucleic acid molecule that hybridizes under stringent hybridization conditions with $nfAP_{453}$, $nfAP_{900}$, $nfAP_{732}$, $nfAP_{1580}$, $nfAP2_{383}$ and/or $nfAP2_{537}$. More preferred is an aminopeptidase nucleic acid molecule that includes $nfAP_{453}$, $nfAP_{900}$, $nfAP_{732}$, $nfAP_{1580}$, $nfAP2_{383}$ and/or $nfAP2_{537}$. Particularly preferred is a nucleic acid molecule that includes nucleic acid sequence SEQ ID NO:50, SEQ ID NO:112, SEQ ID NO:169 and/or SEQ ID NO:171, a complement of any of such sequences, or allelic variants thereof.

A preferred flea cysteine protease nucleic acid molecule of the present invention is a nucleic acid molecule that hybridizes under stringent hybridization conditions with $nfCP1_5$ More preferred is a cysteine protease nucleic acid molecule that includes $nfCP1_{573}$. Particularly preferred is a nucleic acid molecule that includes nucleic acid sequence SEQ ID NO:177, a complement of SEQ ID NO:177, or allelic variants of such nucleic acid molecule.

Knowing a nucleic acid molecule of a flea protease protein of the present invention allows one skilled in the art to make copies of that nucleic acid molecule as well as to obtain a nucleic acid molecule including additional portions of flea protease protein-encoding genes (e.g., nucleic acid molecules that include the translation start site and/or transcription and/or translation control regions), and/or flea protease nucleic acid molecule homologues. Knowing a portion of an amino acid sequence of a flea protease protein of the present invention allows one skilled in the art to clone nucleic acid sequences encoding such a flea protease protein. In addition, a desired flea protease nucleic acid molecule can be obtained in a variety of ways including screening appropriate expression libraries with antibodies which bind to flea protease proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used). To isolate flea protease nucleic acid molecules, preferred cDNA libraries include cDNA libraries made from unfed whole fleas, fed whole fleas, fed flea midguts, unfed flea midguts, and flea salivary glands. Techniques to clone and amplify genes are disclosed, for example, in Sambrook et al., ibid. The Examples section includes examples of the isolation of cDNA sequences encoding flea protease proteins of the present invention.

The present invention also includes nucleic acid molecules that are oligonucleotides capable of hybridizing, under stringent conditions, with complementary regions of other, preferably longer, nucleic acid molecules of the present invention that encode at least a portion of a flea protease protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to inhibit flea protease production. Such therapeutic applications include the use of such oligonucleotides in, for example, antisense-, triplex formation-, ribozyme- and/or RNA drug-based technologies. The present invention, therefore, includes such oligonucleotides and methods to interfere with the production of flea protease proteins by use of one or more of such technologies.

The present invention also includes a recombinant vector, which includes a flea protease nucleic acid molecule of the present invention inserted into any vector capable of delivering the nucleic acid molecule into a host cell. Such a vector contains heterologous nucleic acid sequences, that is nucleic acid sequences that are not naturally found adjacent to flea protease nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of flea protease nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a flea protease protein of the present invention by culturing a cell capable of expressing the protein under conditions effective to produce the protein, and recovering the protein. A preferred cell to culture is a recombinant cell that is capable of expressing the flea protease protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced flea protease protein. Such cells are, therefore, capable of producing flea protease proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal and plant cells. Preferred host cells include bacterial, yeast, insect and mammalian cells, with bacterial (e.g., $E.$ $coli$) and insect (e.g., Spodoptera) cells being particularly preferred.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence which is capable of controlling the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth, insect and mammalian cells, such as, but not limited to, tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T71ac, bacteriophage T3, bacteriophage SP6, bacteriophage SP01, metallothionein, alpha mating factor, Pichia alcohol oxidase, alphavirus subgenomic promoters (such as Sindbis virus subgenomic promoters), baculovirus, $Heliothis$ $zea$ insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding a flea protease protein.

Expression vectors of the present invention may also contain secretory signals (i.e., signal segment nucleic acid sequences) to enable an expressed flea protease protein to be secreted from the cell that produces the protein. Suitable signal segments include a flea protease protein signal segment or any heterologous signal segment capable of directing the secretion of a flea protease protein, including fusion proteins, of the present invention. Preferred signal segments include, but are not limited to, flea protease, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a flea protease nucleic acid molecule of the present invention can enhance the stability during production, storage and/or use of the protein encoded by the nucleic acid molecule. Furthermore, a fusion segment can function as a tool to simplify purification of a flea protease protein, such as to enable purification of the resultant fusion protein using affinity chromatography. A suitable fusion segment can be a domain of any size that has the desired function (e.g., increased stability and/or purification tool). It is within the scope of the present invention to use one or more fusion segments. Fusion segments can be joined to amino and/or carboxyl termini of a flea protease protein. Linkages between fusion segments and flea protease proteins can be constructed to be susceptible to cleavage to enable straightforward recovery of the flea protease proteins. Fusion proteins are preferably produced by culturing a recombinant cell transformed with a fusion nucleic acid sequence that encodes a protein including the fusion segment attached to either the carboxyl and/or amino terminal end of a flea protease protein.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed. A preferred recombinant molecule includes one or more nucleic acid molecules of the present invention, with those that encode one or more flea protease proteins, and particularly one or more flea serine protease, aminopeptidase and/or cysteine protease proteins, being more preferred. Similarly, a preferred recombinant cell includes one or more nucleic acid molecules of the present invention, with those that encode one or more flea protease proteins, and particularly one or more flea serine protease, aminopeptidase, and/or cysteine protease proteins, being more preferred.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce flea protease proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing a flea protease protein. Such a medium is typically an aqueous medium comprising assimilable carbohydrate, nitrogen and phosphate sources, as well as appropriate salts, minerals, metals and other nutrients, such as vitamins. The medium may comprise complex nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant flea protease proteins may either remain within the recombinant cell; be secreted into the fermentation medium; be secreted into a space between two cellular membranes, such as the periplasmic space in E. coli; or be retained on the outer surface of a cell or viral membrane. Methods to purify such proteins are heretofore disclosed.

The present invention also includes isolated anti-flea protease antibodies and their use to reduce flea infestation on a host animal as well as in the environment of the animal. An anti-flea protease antibody is an antibody capable of selectively binding to a protease present in a flea midgut, including female and male fed midguts as well as female and male unfed midguts. An anti-flea protease antibody preferably binds to the protease in such a way as to reduce the proteolytic activity of that protease.

Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protease against which the antibody was raised (i.e., to be able to distinguish that protease from unrelated components in a mixture.). Binding affinities typically range from about $10^3$ M$^{-1}$ to about $10^{12}$ M$^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immunoelectron microscopy; see, for example, Sambrook et al., ibid.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a flea protease nucleic acid molecule of the present invention.

Anti-flea antibodies of the present invention include antibodies raised in an animal administered a flea protease vaccine of the present invention that exert their effect when fleas feed from the vaccinated animal's blood containing such antibodies. Anti-flea antibodies of the present invention also include antibodies raised in an animal against one or more flea protease proteins, or soluble flea midgut preparations, of the present invention that are then recovered from the animal using techniques known to those skilled in the art. Yet additional antibodies of the present invention are produced recombinantly using techniques as heretofore disclosed for flea protease proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-flea protease antibodies of the present invention have a variety of uses that are within the scope of the present invention. For example, such antibodies can be used in a composition of the present invention to passively immunize an animal in order to protect the animal from flea infestation. Anti-flea antibodies can also be used as tools to screen expression libraries and/or to recover desired proteins of the present invention from a mixture of proteins and other contaminants. Furthermore, antibodies of the present invention can be used to target cytotoxic agents to fleas in order to kill fleas. Targeting can be accomplished by conjugating (i.e., stably joining) such antibodies to the cytotoxic agents using techniques known to those skilled in the art.

A preferred anti-flea protease antibody of the present invention can selectively bind to, and preferentially reduce the proteolytic activity of, a flea serine protease, a flea metalloprotease, a flea aspartic acid protease and/or a flea cysteine protease. More preferred anti-flea protease antibodies include anti-flea serine protease antibodies, anti-flea metalloprotease antibodies, anti-flea aminopeptidase antibodies, and anti-flea cysteine protease antibodies. Particularly preferred are anti-flea serine protease antibodies, anti-flea aminopeptidase antibodies, and anti-flea cysteine protease antibodies, including those raised against flea serine protease proteins, flea aminopeptidase proteins or cysteine protease proteins of the present invention.

The present invention also includes the use of protease inhibitors that reduce proteolytic activity of flea proteases to reduce flea infestation of animals and the surrounding environment. As used herein, protease inhibitors are compounds that interact directly with a protease thereby inhibiting that protease's activity, usually by binding to or otherwise interacting with the protease's active site. Protease inhibitors are usually relatively small compounds and as such differ from anti-protease antibodies that interact with the active site of a protease.

Protease inhibitors can be used directly as compounds in compositions of the present invention to treat animals as long as such compounds are not harmful to the animals being treated. Protease inhibitors can also be used to identify preferred types of flea proteases to target using compositions of the present invention. For example, the inventors have shown herein the predominance of serine proteases in flea midguts, particularly in soluble flea midgut preparations, using protease inhibitors. Such knowledge suggests that effective reduction of flea infestation of an animal can be achieved using serine protease vaccines, anti-flea serine protease antibodies and other inhibitors of serine protease synthesis and activity that can be tolerated by the animal. For example, flea IgGase activity disclosed herein can be targeted to reduce flea infestation. That other proteases are also present in flea midguts according to the present invention also suggests targeting such proteases. Methods to use protease inhibitors are known to those skilled in the art; examples of such methods are disclosed herein.

In one embodiment, a protease inhibitor that can be used in a composition of the present invention to treat an animal is identified by a method including the following steps: (a) identifying candidate (i.e., putative, possible) inhibitor compounds by testing the efficacy of one or more protease inhibitors (i) in vitro for their ability to inhibit flea protease activity and/or (ii) in a flea feeding assay for their ability to reduce the survival and/or fecundity of fleas by adding the inhibitors to the blood meal of a flea being maintained, for example, in a feeding system, such as that described by Wade et al., 1988, *J.Med Entomol.* 25, 186–190; and (b) testing the efficacy of the candidate inhibitor compounds in animals infested with fleas. Although one does not need both in vitro assay data and flea feeding assay data to determine which candidate compounds to administer to animals, evaluation of both sets of data is preferred since data from neither of the assays necessarily predicts data to be obtained from the other assay. For example, candidate compounds identified using the in vitro assay may work "in the test tube" but may not work in vivo for a number of reasons, including the presence of interfering components in the blood meal that inhibit the activity of such compounds; e.g., although aprotinin can inhibit at least some flea serine proteases in vitro, aprotinin does not work well in the presence of serum proteins, such as are found in the blood. Furthermore, candidate inhibitor compounds identified by the flea feeding assays can include not only desired compounds but also compounds that reduce the viability and/or fecundity of fleas due to general toxicity (e.g., affecting the mitochondria of fleas).

In another embodiment, protease inhibitors are used in the purification of corresponding proteases by, for example, affinity chromatography, in which, a protease inhibitor is incubated with a mixture containing a desired protease under conditions that the inhibitor forms a complex with the protease. The protease can then be recovered from the complex. The protease inhibitor can be attached to a solid support and/or be labelled with, for example, a radioactive, fluorescent, or enzymatic tag that can be used to detect and/or recover the complex.

Suitable protease inhibitors to use in accordance with the present invention include serine protease inhibitors (including IgGase inhibitors), metalloprotease inhibitors, aspartic acid protease inhibitors, cysteine protease inhibitors and aminopeptidase inhibitors. Preferred protease inhibitors include serine protease inhibitors, metalloprotease inhibitors, aminopeptidase inhibitors and cysteine protease inhibitors, particularly those that are broad spectrum inhibitors. More preferred are broad spectrum serine protease inhibitors.

There is a wide variety of protease inhibitors, as is known to one skilled in the art. Examples include, but are not limited to, AEBSF, aprotinin, bestatin, chloromethyl ketones TLCK (Nα-p-tosyl-L-lysine chloromethyl ketone) and TPCK (N-tosyl-L-phenylalanine chloromethyl ketone), chymostatin, cystatin, 3'4-dichloroisocoumarin, E-64 (trans-epoxysuccinyl-L-leucylamido-(4-guanidino)butane), EDTA (ethylenediaminetetraacetic acid), leupeptin, methyl ketones having a variety of leaving groups, oxidized L-leucinethiol, pepstatin, 1,10-orthophenanthroline, phosphoramidon, soybean trypsin/chymotrypsin inhibitor and soybean trypsin inhibitor. Preferred protease inhibitors for use in the present invention include AEBSF, bestatin, E-64 leupeptin, pepstatin, 1,10-orthophenanthroline, phosphoramidon, TLCK and TPCK, with AEBSF (a broad spectrum serine protease inhibitor), bestatin (an inhibitor of leucine aminopeptidase) and 1,10-orthophenanthroline (a broad spectrum metalloprotease inhibitor) being particularly preferred.

Protease inhibitors can be produced using methods known to those skilled in the art. Protein- or peptide-based protease inhibitors, such as cystatin or small peptides comprising a protease substrate, can be produced recombinantly and modified as necessary.

The present invention also includes the use of proteolytically active flea protease proteins of the present invention to identify additional protease inhibitors, and preferably protease inhibitor compounds that can be included in a composition of the present invention to be administered to animals. A method to identify a flea protease inhibitor includes the steps of (a) contacting (e.g., combining, mixing) an isolated flea protease protein with a putative (i.e., candidate) inhibitory compound under conditions in which, in the absence of the compound, the protein has proteolytic activity, and (b) determining if the putative inhibitory compound inhibits the proteolytic activity of the protein. Putative inhibitory compounds to screen include organic molecules, antibodies (including functional equivalents thereof) and substrate analogs. Methods to determine protease activity are known to those skilled in the art, as heretofore disclosed. Particularly preferred for use in identifying inhibitors are flea serine protease proteins, flea aminopeptidase proteins and flea cysteine protease proteins of the present invention.

The present invention also includes a test kit to identify a compound capable of inhibiting flea protease activity. Such a test kit includes an isolated flea protease protein having proteolytic activity and a means for determining the extent of inhibition of proteolytic activity in the presence of (i.e., effected by) a putative inhibitory compound.

The present invention also includes inhibitors isolated by such a method, and/or test kit, and their use to inhibit any flea protease that is susceptible to such an inhibitor.

It is to be appreciated that the present invention also includes mimetopes of compounds of the present invention that can be used in accordance with methods as disclosed for compounds of the present invention. As used herein, a mimetope of a proteinaceous compound of the present invention (e.g., a flea protease protein, an anti-flea protease antibody, a proteinaceous inhibitor of protease activity or synthesis) refers to any compound that is able to mimic the activity of that proteinaceous compound, often because the mimetope has a structure that mimics the proteinaceous compound. For example, a mimetope of a flea protease protein is a compound that has an activity similar to that of an isolated flea protease protein of the present invention. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

The present invention includes therapeutic compositions, also referred to herein as compositions, that include a (i.e., at least one) compound of the present invention. Preferred compounds to include in a composition of the present invention include flea protease vaccines, anti-flea protease antibodies and/or protease inhibitors as disclosed herein. Such a therapeutic composition can protect an animal from flea infestation by reducing flea protease activity, thereby reducing flea burden on the animal and in the environment of the animal.

Particularly preferred therapeutic compositions of the present invention include at least one of the following compounds: an isolated flea serine protease protein or a mimetope thereof; an isolated flea serine protease nucleic acid molecule that hybridizes under stringent hybridization conditions with a flea serine protease gene; an isolated antibody that selectively binds to a flea serine protease protein; an inhibitor of flea serine protease activity identified by its ability to inhibit flea serine protease activity; an isolated flea aminopeptidase protein or a mimetope thereof; an isolated flea aminopeptidase nucleic acid molecule that hybridizes under stringent hybridization conditions with a flea aminopeptidase gene; an isolated antibody that selectively binds to a flea aminopeptidase protein; an inhibitor of flea aminopeptidase activity identified by its ability to inhibit flea aminopeptidase activity; an isolated flea cysteine protease protein or a mimetope thereof; an isolated flea cysteine protease nucleic acid molecule that hybridizes under stringent hybridization conditions with a flea cysteine protease gene; an isolated antibody that selectively binds to a flea cysteine protease protein; and an inhibitor of flea cysteine protease activity identified by its ability to inhibit flea cysteine protease activity.

Another embodiment of the present invention is a therapeutic composition that includes a first compound that reduces flea protease activity and a second compound that reduces flea burden by a method other than by reducing flea protease activity. The present invention also includes a method to protect an animal from flea infestation by administering to the animal such a composition. The first compound of such a composition by effectively reducing flea protease activity in the midgut, enhances the activity of the second compound. While not being bound by theory, it is believed that a number of anti-flea treatments, particularly those that are proteinaceous, are not very effective because they are degraded in the flea midgut. The present invention permits the effective use of such anti-flea treatments by reducing proteolytic degradation of such treatments by the flea midgut.

Preferred first compounds to include in such a composition include flea protease vaccines, anti-flea protease antibodies and/or protease inhibitors as disclosed herein, such compounds that target flea IgGase activity.

Suitable second compounds include any anti-flea agent(s), including, but not limited to, proteinaceous compounds, insecticides and flea collars. Preferred second compounds are proteinaceous compounds that effect active immunization (e.g., antigen vaccines), passive immunization (e.g., antibodies), or that otherwise inhibit a flea activity that when inhibited can reduce flea burden on and around an animal. Examples of second compounds include a compound that inhibits binding between a flea membrane protein and its ligand (e.g., a compound that inhibits flea ATPase activity or a compound that inhibits binding of a peptide or steroid hormone to its receptor), a compound that inhibits hormone (including peptide or steroid hormones) synthesis, a compound that inhibits vitellogenesis (including production of vitellin and transport and maturation thereof into a major egg yolk protein), a compound that inhibits fat body function, a compound that inhibits flea muscle action, a compound that inhibits the flea nervous system, a compound that inhibits the flea immune system and/or a compound that inhibits flea feeding.

Compositions of the present invention can also include other components such as a pharmaceutically acceptable excipient, an adjuvant, and/or a carrier. For example, compositions of the present invention can be formulated in an excipient that the animal to be treated can tolerate.

Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the composition can also include an immunopotentiator, such as an adjuvant or a carrier. Adjuvants are typically substances that generally enhance the immune response of an animal to a specific antigen. Suitable adjuvants include, but are not limited to, Freund's adjuvant; other bacterial cell wall components; aluminum-based salts; calcium-based salts; silica; polynucleotides; toxoids; serum proteins; viral coat proteins; other bacterial-derived preparations; gamma interferon; block copolymer adjuvants, such as Hunter's Titermax adjuvant (Vaxcel™, Inc. Norcross, Ga.); Ribi adjuvants (available from Ribi ImmunoChem Research, Inc., Hamilton, Mont.); and saponins and their derivatives, such as Quil A (available from Superfos Biosector A/S, Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

One embodiment of the present invention is a controlled release formulation that is capable of slowly releasing a composition of the present invention into an animal. As used herein a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to reduce protease activity in fleas feeding from the animal over a period of time ranging from about 1 to about 12 months. A controlled release formulation of the present invention is capable of effecting a treatment for preferably at least about 1 month, more preferably at least about 3 months and even more preferably for at least about 6 months, even more preferably for at least about 9 months, and even more preferably for at least about 12 months.

In order to protect an animal from flea infestation, a therapeutic composition of the present invention is administered to the animal in an effective manner such that the protease activity of fleas feeding from the blood stream of animals treated with the composition is reduced. As such, a treated animal is an animal that is competent to reduce the flea burden by reducing flea protease activity, or by reducing flea protease activity and at least one other flea activity. Preferably, the protease activity is reduced by at least about 50 percent, more preferably by at least about 70 percent and even more preferably by at least about 90 percent. Methods to administer compositions to the animal in order to render the animal competent depend on the nature of the composition and administration regime. Animals administered a protease vaccine with at least one booster shot usually become competent at about the same time as would be expected for any vaccine treatment. For example, animals administered a booster dose about 4 to 6 weeks after a primary dose usually become competent within another about 3 to 4 weeks. Animals administered a composition including an anti-flea protease antibody or protease inhibitor become competent as soon as appropriate serum levels of the compound are achieved, usually with one to three days.

In a preferred embodiment, a composition of the present invention when administered to a host animal is able to reduce flea viability by at least about 50 percent within at least about 21 days after the fleas begin feeding from the treated animal. (Note that fleas usually live about 40 days to about 50 days on one or more animals.) A more preferred composition when administered to a host animal is able to reduce flea viability by at least about 65 percent within at least about 14 days after the fleas begin feeding from the treated animal. An even more preferred composition when administered to an animal is able to reduce flea viability by at least about 90 percent within at least about 7 days after the fleas begin feeding from the treated animal.

In another preferred embodiment, a composition of the present invention when administered to a host animal is able to reduce flea fecundity (i.e., egg laying ability) by at least about 50 percent, more preferably by at least about 70 percent, and even more preferably by at least about 90 percent, within at least about 30 days after the fleas begin feeding from the treated animal. (Note that fleas usually do not begin laying eggs until about 7 days after taking a blood meal.)

In accordance with the present invention, compositions are administered to an animal in a manner such that the animal becomes competent to reduce flea protease activity in a flea that feeds from the competent; i.e., the animal becomes a treated animal. For example, a flea protease vaccine of the present invention, when administered to an animal in an effective manner, is able to elicit (i.e., stimulate) an immune response that produces an antibody titer in the blood stream of the animal sufficient to reduce flea protease activity. Similarly, an anti-flea protease antibody of the present invention, when administered to an animal in an effective manner, is administered in an amount so as to be present in the animal's blood stream at a titer that is sufficient to reduce flea protease activity. A protease inhibitor compound of the present invention, when administered to an animal in an effective manner, is administered in a manner so as to be present in the animal's blood stream at a concentration that is sufficient to reduce flea protease activity. Oligonucleotide nucleic acid molecules of the present invention can also be administered in an effective manner, thereby reducing expression of flea proteases.

Compositions of the present invention can be administered to animals prior to or during flea infestation. It is to be noted that when vaccines of the present invention are administered to an animal, a time period is required for the animal to elicit an immune response before the animal is competent to inhibit protease activity of fleas feeding from that animal. Methods to obtain an immune response in an animal are known to those skilled in the art.

Acceptable protocols to administer compositions in an effective manner include individual dose size, number of doses, frequency of dose administration, and mode of administration. Determination of such protocols can be accomplished by those skilled in the art. A suitable single dose is a dose that is capable of protecting an animal from flea infestation when administered one or more times over a suitable time period. For example, a preferred single dose of a protease vaccine or a mimetope thereof ranges from about 1 microgram ($\mu$g, also denoted ug) to about 10 milligrams (mg) of the composition per kilogram body weight of the animal. Booster vaccinations can be administered from about 2 weeks to several years after the original administration. Booster vaccinations preferably are administered when the immune response of the animal becomes insufficient to protect the animal from flea infestation. A preferred administration schedule is one in which from about 10 $\mu$g to about 1 mg of the vaccine per kg body weight of the animal is administered from about one to about two times over a time period of from about 2 weeks to about 12 months. In one embodiment, a booster dose of a composition of the present invention is administered about 4 to 6 weeks after the primary dose, and additional boosters are administered about once or twice a year. Modes of administration can include, but are not limited to, oral, nasal, topical, transdermal, rectal, and parenteral routes. Parenteral routes can include, but are not limited to subcutaneous, intradermal, intravenous, and intramuscular routes.

In another embodiment, a preferred single dose of an anti-flea protease antibody composition or a mimetope thereof ranges from about 1 $\mu$g to about 10 mg of the composition per kilogram body weight of the animal. Anti-flea antibodies can be re-administered from about 1 hour to about biweekly for several weeks following the original administration. Booster treatments preferably are administered when the titer of antibodies of the animal becomes insufficient to protect the animal from flea infestation. A preferred administration schedule is one in which from about 10 $\mu$g to about 1 mg of an anti-flea protease antibody composition per kg body weight of the animal is administered about every 2 to every 4 weeks. Suitable modes of administration are as disclosed herein and are known to those skilled in the art.

According to one embodiment, a nucleic acid molecule of the present invention can be administered to an animal in a fashion to enable expression of that nucleic acid molecule into a protective protein (e.g., flea protease vaccine, anti-flea protease antibody, or proteinaceous protease inhibitor) or protective RNA (e.g., antisense RNA, ribozyme or RNA drug) in the animal to be protected from disease. Nucleic acid molecules can be delivered to an animal in a variety of methods including, but not limited to, (a) direct injection (e.g., as "naked" DNA or RNA molecules, such as is taught, for example in Wolff et al., 1990, *Science* 247, 1465–1468) or (b) packaged as a recombinant virus particle vaccine or as a recombinant cell vaccine (i.e., delivered to a cell by a vehicle selected from the group consisting of a recombinant virus particle vaccine and a recombinant cell vaccine).

A recombinant virus particle vaccine of the present invention includes a recombinant molecule of the present invention that is packaged in a viral coat and that can be expressed in an animal after administration. Preferably, the recombinant molecule is packaging-deficient. A number of recombinant virus particles can be used, including, but not limited to, those based on alphaviruses, poxviruses, adenoviruses, herpesviruses, and retroviruses.

When administered to an animal, a recombinant virus particle vaccine of the present invention infects cells within the immunized animal and directs the production of a protective protein or RNA nucleic acid molecule that is capable of protecting the animal from disease caused by a parasite of the present invention. A preferred single dose of a recombinant virus particle vaccine of the present invention is from about $1\times10^4$ to about $1\times10^7$ virus plaque forming units (pfu) per kilogram body weight of the animal. Administration protocols are similar to those described herein for protein-based vaccines.

A recombinant cell vaccine of the present invention includes recombinant cells of the present invention that express at least one protein of the present invention. Preferred recombinant cells include Salmonella, *E. coli,* Mycobacterium, *S. frugiperda,* baby hamster kidney, myoblast G8, COS, MDCK and CRFK recombinant cells, with Salmonella recombinant cells being more preferred. Such recombinant cells can be administered in a variety of ways but have the advantage that they can be administered orally, preferably at doses ranging from about $10^8$ to about $10^{12}$ bacteria per kilogram body weight. Administration protocols are similar to those described herein for protein-based vaccines. Recombinant cell vaccines can comprise whole cells or cell lysates.

Compositions of the present invention can be administered to any animal susceptible to flea infestation, including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets and/or economic food animals, being more preferred. Particularly preferred animals to protect are cats and dogs.

The present invention includes compositions to treat flea infestation by any flea. As such, compositions of the present invention can be derived from any flea species. Preferred fleas to target include fleas of the following genera: Ctenocephalides, Cyopsyllus, Diamanus (Oropsylla), Echidnophaga, Nosopsyllus, Pulex, Tunga, and Xenopsylla, with those of the species *Ctenocephalides canis, Ctenocephalides felis, Diamanus montanus, Echidnophaga gallinacea, Nosopsyllus faciatus, Pulex irritans, Pulex simulans, Tunga penetrans* and *Xenopsylla cheopis* being more preferred. Particularly preferred fleas from which to protect animals include fleas of the species *Ctenocephalides felis, Ctenocephalides canis,* and Pulex species (e.g., *Pulex irritans* and *Pulex simulans*). It is also within the scope of the present invention to administer compositions of the present invention directly to fleas.

The present invention also includes the use of compositions of the present invention to reduce infestation by other ectoparasites as well as the use of compositions including protease vaccines, anti-protease antibodies and compounds that inhibit protease synthesis and/or activity derived from any ectoparasite to reduce ectoparasite infestation, particularly controlled release formulations containing such compositions. Preferred ectoparasites to target include arachnids, insects and leeches. More preferred ectoparasites to target include fleas; ticks, including both hard ticks of the family Ixodidae (e.g., Ixodes and Amblyomma) and soft ticks of the family Argasidae (e.g., Ornithodoros, such as *O. parkeri* and *O. turicata*); flies, such as midges (e.g., Culicoides), mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs, including those carrying Chagas disease. Even more preferred ectoparasites to target include fleas, mosquitos, midges, sandflies, blackflies, ticks and Rhodnius.

The following examples are provided for the purposes of illustration and are not intended to limit the scope of the present invention.

EXAMPLES

EXAMPLE 1

This Example demonstrates that soluble flea midgut preparations contain serine protease activity as well as leucine aminopeptidase activity.

Using a homogenization/sonication protocol as described in U.S. Pat. No. 5,356,622, ibid., followed by an about 2 minute centrifugation step at about 10,000×g, soluble flea midgut preparations were obtained from fed and unfed fleas. Pellets from the centrifugation step were also collected and resuspended for analysis. Also prepared were whole flea lysates. Peptide substrate screening studies using the synthetic chromogenic trypsin substrate BAPNA (Nα-benzoyl-DL-arginine-p-nitroanilide; available from Sigma Chemical Co., St. Louis Mo.) demonstrated significant proteolytic activity in both soluble flea midgut preparations as well as some proteolytic activity in resuspended midgut pellets. Soluble unfed flea midgut preparations exhibited about 10 times as much activity as did controls (samples to which no flea midgut fractions were added), whereas soluble fed flea midgut preparations exhibited about 20 times as much activity as did controls. Whole flea preparations exhibited about 2 to 3 times as much activity as did controls.

The ability of soluble fed and unfed flea midgut preparations to cleave BAPNA was almost completely inhibited (i.e., nearly 100%) by aprotinin (available from Sigma), whereas PMSF (phenylmethane-7-sulfonyl fluoride; available from Sigma) inhibited such proteolytic activity by about 50%. EDTA inhibited proteolytic activity of the preparations by about 10%, whereas addition of calcium ions stimulated proteolytic activity by about 25%. These results indicate the presence of serine protease activity, and more particularly of trypsin-like activity, in these soluble flea midgut preparations. These results also suggest the presence of serine protease isoforms in the preparations. It is also of interest to note that flea trypsin-like activity appears to be distinctive from that of mosquitos in that mosquito trypsins are not affected by EDTA or calcium ions.

Using a methyl-hemoglobin substrate, the pH optimum of the proteolytic activity in the soluble flea midgut preparations was found to be between pH 7 and pH 9, with a pH of about pH 8 giving the best activity. Such pH optima suggest the presence of serine proteases in soluble flea midgut preparations.

Soluble preparations of both unfed and fed flea midgut soluble preparations also were able to cleave the leucine aminopeptidase specific substrate LPNA (L-leucine-p-nitroanilide; available from Sigma) using standard conditions, indicating the presence of leucine aminopeptidase (LAP) activity in such preparations.

EXAMPLE 2

The following example evaluated the number of proteases in flea midguts that could be assessed by protease substrate gel analysis.

Protease substrate gels (available from Novex, San Diego, Calif., as Novex Zymogels) were 10% polyacrylamide-SDS gels with 0.1% gelatin. Samples and gels were processed according to Novex instructions. Briefly, samples were diluted in SDS-PAGE sample buffer without reducing agents. Tris-glycine SDS-PAGE was carried out by standard procedures. After electrophoresis, gels were incubated in 0.25% Triton X-100 at room temperature for 30 minutes (min), then in developing buffer (50 mM (millimolar) Tris-HCl pH 7.0, 5 mM $CaCl_2$, 0.02% Brij 35, 0.2 M (molar) NaCl) at room temperature for 30 min, and then incubated with fresh developing buffer at 37° C., usually overnight. Gels were then stained 30 min in 0.5% coomassie R-250, 40% methanol, 10% acetic acid and destained in 40% methanol, 10% acetic acid.

The following flea midguts were dissected directly into sample buffer: 100 midguts from unfed males; 100 midguts from unfed females; 100 midguts from fed males; and 100 midguts from fed females. Samples containing 10 or 20 midguts each were evaluated using protease substrate gel analysis and numerous negative staining bands were observed. The general pattern was the same for female and male midguts, although there appeared to be more activity in gel lanes containing female midguts. There were distinct differences noted between gel lanes containing fed and unfed midguts. There was a definite increase in overall activity in the fed midgut lanes, and, in addition, there were differences in the band patterns.

Fed and unfed female midguts were further evaluated using protease substrate gel analysis and the results are shown in FIG. 1. The protease substrate gel shown in FIG. 1 demonstrates the relative proteolytic activity in 1, 2, 5 or 10 midguts from either fed or unfed female fleas. Specifically, lane 1 contains a set of molecular weight markers. Lanes 2 through 5 contain, respectively, 10, 5, 2 and 1 unfed midguts. Lanes 6 through 9 contain, respectively, 1, 2, 5 and 10 fed midguts. Lane 10 contains 100 μg of dried bovine blood.

Proteolytic activity could easily be detected in one fed or one unfed female midgut, although there was considerably more activity in the fed midgut. Lane 10 evaluated 100 μg of dried bovine blood to assess if the increase in activity seen in the fed midgut lane was due to proteases in the blood meal. No activity was seen in the blood lane.

EXAMPLE 3

This example evaluated the protease classes present in flea midguts.

Three unfed female midguts and 0.75 fed female midguts were evaluated in duplicate in several protease substrate gels. Each gel was cut in half. Half was processed as described in Example 2, while the other half contained protease inhibitors in all incubation buffers. The following inhibitors were evaluated:

(a) the serine protease inhibitor AEBSF (available from Boehringer Mannheim, Indianapolis, Ind.) was used at a final concentration of 1 mM;

(b) the serine protease inhibitor soybean trypsin inhibitor (available from Sigma) was used at a final concentration of 100 μg/ml (milliliter);

(c) the cysteine and serine protease inhibitor leupeptin (available from Sigma) was used at a final concentration of 10 μg/ml;

(d) the aminopeptidase inhibitor bestatin (available from Sigma) was used at a final concentration of 0.25 mM;

(e) the metalloprotease inhibitor EDTA (available from Sigma) was used at a final concentration of 2 mM; and (f) the cysteine protease E-64 (available from Sigma) was used at a final concentration of 10 μg/ml.

Figure 2:
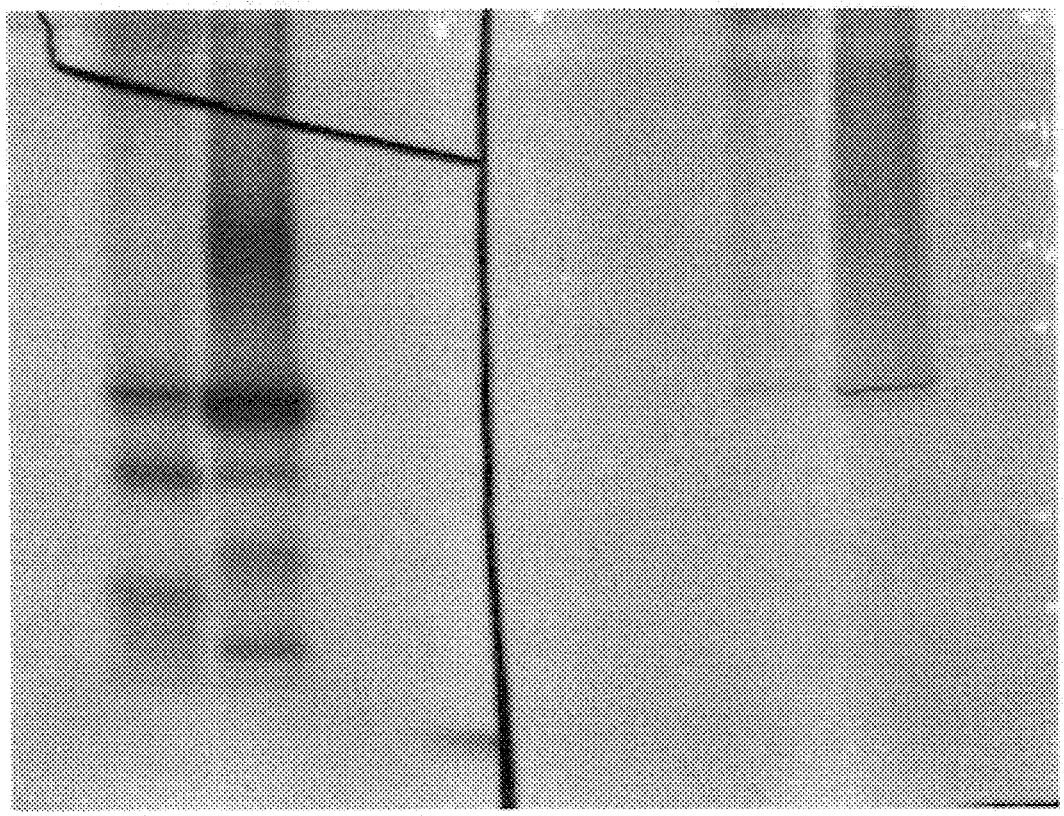
FIG. 2 depicts a protease substrate gel analysis of fed and unfed midgut preparations incubated in the presence or absence of a serine protease inhibitor.

AEBSF, soybean trypsin inhibitor and leupeptin were the only inhibitors to have any effect at the sensitivity of this assay. It was determined that serine proteases were the predominant, if not only, proteases present in the midgut preparations evaluated. FIG. 2 shows a protease substrate gel with fed (lanes 2 and 4) and unfed (lanes 1 and 3) midgut preparations with (lanes 3 and 4) and without (lanes 1 and 2) AEBSF. Residual activity in the inhibitor lanes could have been due to proteolysis that occurred during electrophoresis and prior to saturation of the gel with inhibitor in the incubation buffers.

EXAMPLE 4

This Example evaluates protease activity contained in a soluble fed midgut preparation of the present invention.

Figure 3:
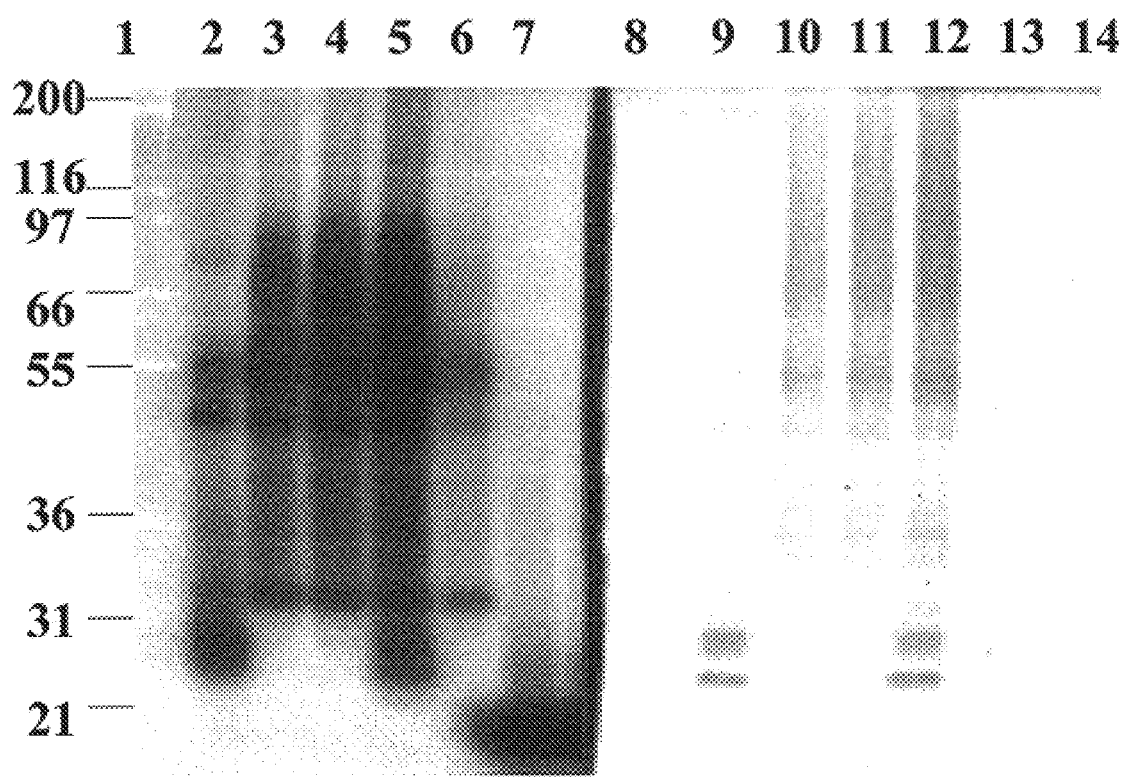
FIG. 3 depicts a protease substrate gel analysis of various fractions obtained in the preparation of a soluble flea midgut preparation incubated in the presence or absence of a serine protease inhibitor.

Mixed-sex fed flea midguts were processed as described in U.S. Pat. No. 5,356,622, ibid. Aliquots of several steps of the procedure were evaluated by loading an equivalent of 0.4 midguts per lane of a protease substrate gel as described in Example 2. The results are shown in FIG. 3. Samples were from the low speed supernatant (lanes 2 and 9), sonicated midguts (lanes 3 and 10), high speed supernatant (lanes 4 and 11), combined low and high speed supernatants (FGS) (lanes 5 and 12) and the high speed pellet (lanes 6 and 13). Lanes 7 and 8 contained 50 nanograms (ng) of trypsin as a control. Duplicate lanes were evaluated. The gel was cut in half, and lanes 1–7 were processed as described in Example 2, and lanes 8–14 were processed with 100 μg/ml soybean trypsin inhibitor in all the incubation buffers.

Protease activity was seen in all preparations, the most being observed in the FGS lane (lane 5). It was also evident that the majority of the activity was inhibited by soybean trypsin inhibitor, a serine protease inhibitor.

EXAMPLE 5

This Example demonstrates the increase in flea midgut protease activity after blood feeding by fleas.

Figure 4:
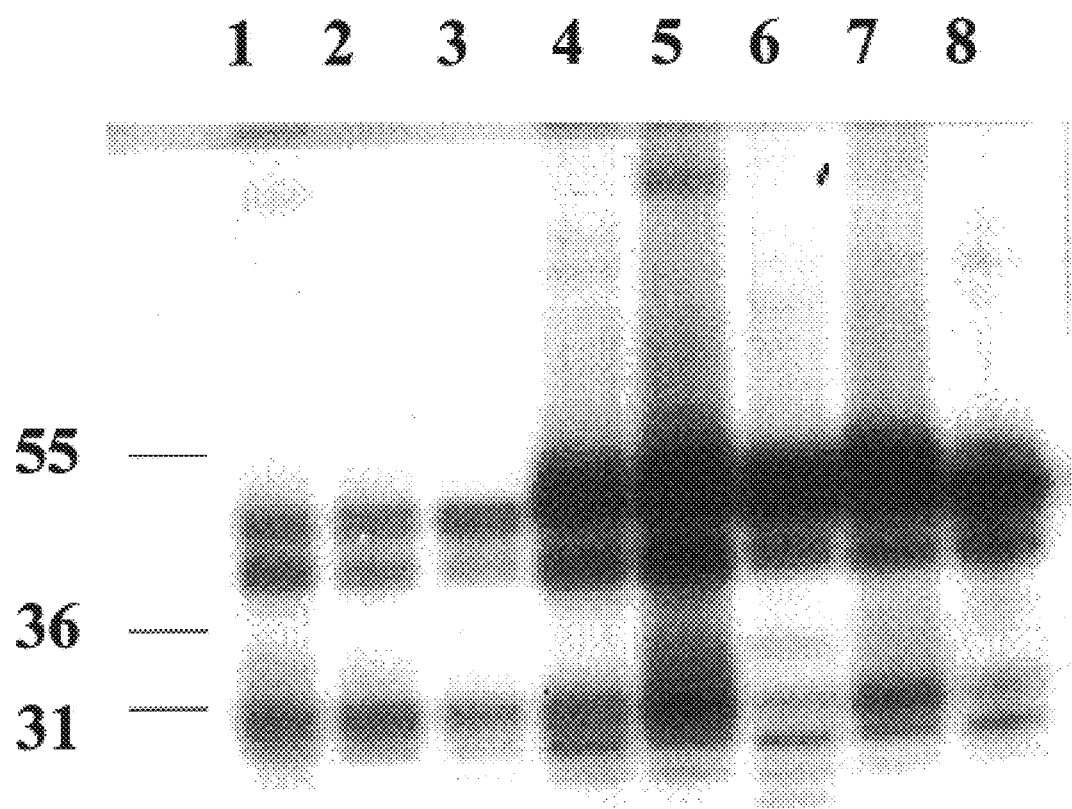
FIG. 4 depicts a protease substrate gel showing midgut protease activity as a function of time after flea blood feeding.

Fleas were fed on a dog for 15 minutes. At timed intervals after feeding, two midguts were dissected directly into sample buffer and proteases evaluated by protease substrate gel analysis as described in Example 2. FIG. 4 depicts a gel showing midgut protease activity at 30 min (lane 1), 1 hr (lane 2), 2 hr (lane 3), 4 hr (lane 4), 6 hr (lane 5), 8 hr (lane 6), 24 hr (lane 7) and 56 hr (lane 8) after blood feeding ended.

Increases in proteolytic activity were first observed 2 hr (lane 3) after feeding, although at 4 hr (lane 4) there was a much greater increase in activity noted. This increase in activity was still noticed 56 hr after feeding (lane 8).

EXAMPLE 6

This Example evaluates the effect of a number of protease inhibitors on flea viability and fecundity in a flea feeding system as described by Wade et al. ibid.

The following protease inhibitors were tested at the indicated final concentrations in blood meals:

(a) Aminopeptidase inhibitor bestatin at 1.3 mM and 13 mM;

(b) Aspartic acid protease inhibitor pepstatin A at 1 μg/ml and 10 μg/ml;

(c) Cysteine protease inhibitor E-64 at 1 μg/ml and 10 μg/ml.

(d) Metalloprotease inhibitor phosphoramidon at 10 μg/ml and 100 μg/ml; and (e) the following serine protease inhibitors:
AEBSF at 0.3 mM, 0.5 mM, 5.0 mM and 6.0 mM;
Aprotinin at 2 μg/ml and 20 μg/ml;
Leupeptin at 5 μg/ml and 50 μg/ml;
Soybean trypsin inhibitor at 10 μg/ml and 100 μg/ml;
Soybean trypsin/chymotrypsin inhibitor at 10 μg/ml and 100 μg/ml;

AEBSF is available from Boehringer Mannheim; all other listed inhibitors are available from Sigma.

Protease inhibitor compounds were tested in groups of 3 to 6 including appropriate control groups. Inhibitors were not tested in groups of common inhibition types. Rather, they were tested in groups based on the diluent needed to dissolve them. (AEBSF, aprotinin, bestatin, leupeptin, phosphoramidon, soybean trypsin inhibitor and soybean trypsin/chymotrypsin inhibitor were dissolved in water; E-64 and pepstatin were dissolved in ethanol). This reduced the number of control (diluent only) groups needed within a particular assay. Inhibitor concentrations were chosen such that the lower concentration used was within the range recommended by the supplier for that inhibitor. The higher concentration was typically 10 times above the lower concentration and was used to look for dose response.

The general protocol for all of the assays was as follows: Approximately 2000 newly emerged adult fleas were placed in feeding chambers to feed on normal blood for about 24 to 48 hr. The fleas were prefed for two reasons: The first was to be certain that only fleas that would feed in the feeding system were used in the comparative study. The second was to prime female fleas for egg laying, since female fleas typically do not begin laying maximal numbers of eggs per day until the third day of feeding.

The prefed fleas were placed in "minifeeder" feeding chambers at a ratio of about 80 female fleas to about 20 male fleas for a total of about 100 fleas per chamber. Actual total number of fleas per chamber varied from about 90 to 125 fleas. Previous experiments have not demonstrated any differences in adult survival or fecundity based on such variance in numbers of fleas in a chamber. Three chambers were prepared for each experimental and control group. A fresh blood meal containing the appropriate inhibitor in 3 ml total volume was placed on each chamber daily through the 7 day extent of an assay.

On days 3, 5, and 7 of the assay, surviving adult fleas were transferred to clean chambers. The contents of the original chambers were dissolved in about 40 ml of PBS (phosphate-buffered saline) in a 50 ml Falcon tube. The contents of a given tube were then filtered through a pre-weighed #1 Whatman filter disk inserted into a vacuum filter. The 50 ml tube and the filter funnel were rinsed with distilled water which was then passed through the filter. Once the chamber contents had been filtered, dead adult fleas were removed from the filter paper and placed in a labelled tube so that they could be counted and sexed. The filter paper was then placed into a preweighed 12×75 polypropylene tube and dried in the SpeedVac for 2.5 hr with the heater on. After drying the filter paper was weighed. The weight of the filter paper and tube was subtracted to obtain the dry weight of the eggs and this value was converted to an estimated number of eggs using the formula $y=41384.361x+162.37$, where $x$=dry weight of eggs.

On day 7, adult fleas that had survived the study were frozen, counted and sexed. The numbers were added to the number of male and female fleas that had died during the assay to verify the number of male and female fleas in each chamber at the start of the study.

Female, male and total adult flea survival were calculated for all experimental and control groups on days 3, 5, and 7 of each assay. Additionally, the number of eggs per surviving female was calculated on days 3, 5 and 7. Female fleas found dead on a given collection date were included in the total number of egg-laying females for the days between that date and the previous collection date, providing a conservative estimate of fecundity. Fecundity values were averaged for the three collection dates to obtain an average for each group over 7 days.

Results of these studies are presented below in Table 1 and FIG. 6 through FIG. 9. All survival and fecundity values are presented below as a percent of control value.

TABLE 1

Effect of Protease Inhibitors on Flea Viability and Fecundity

| Compound | Conc. | Fecundity[1] Days 1–7 | Adult Survival[1] Female | Male | Total |
|---|---|---|---|---|---|
| AEBSF | | | | | |
| | 6.0 mM | 17.2% | 4.1% | 0.0 | 3.4% |
| | 5.0 mM | 1.4% | 6.8% | 0.0% | 5.6% |
| | 0.5 mM | 95.0% | 103.9% | 104.2% | 103.6% |
| | 0.3 mM | 82.4% | 116.2% | 103.0% | 111.9% |
| Aprotinin | | | | | |
| | 20 ug/ml | 84.2% | 100.0% | 101.7% | 99.9% |
| | 2 ug/ml | 83.2% | 103.2% | 104.9% | 103.3% |
| Leupeptin | | | | | |
| | 50 ug/ml | 77.6% | 101.5% | 111.7% | 104.6% |
| | 5 ug/ml | 85.0% | 71.0% | 61.4% | 68.4% |
| Soybean Trypsin Inhibitor | | | | | |
| | 100 ug/ml | 79.1% | 76.5% | 76.0% | 76.3% |
| | 10 ug/ml | 96.1% | 80.1% | 101.7% | 83.9% |
| Trypsin/ Chymotrypsin Inhibitor | | | | | |
| | 100 ug/ml | 81.1% | 88.0% | 95.4% | 89.9% |
| | 10 ug/ml | 100.7% | 115.1% | 143.5% | 120.7% |
| E-64 | | | | | |
| | 10 ug/ml | 177.4% | 110.2% | 139.0% | 114.2% |
| | 1 ug/ml | 109.4% | 99.9% | 102.9% | 100.1% |
| | 10 ug/ml | 84.1% | 90.2% | 91.1% | 90.6% |
| | 1 ug/ml | 95.2% | 77.3% | 80.0% | 77.5% |
| Phosphoramidon | | | | | |
| | 100 ug/ml | 84.9% | 70.2% | 64.6% | 69.7% |
| | 10 ug/ml | 89.0% | 98.8% | 95.2% | 97.8% |
| Pepstatin A | | | | | |
| | 10 ug/ml | 83.9% | 113.6% | 133.4% | 116.2% |
| | 1 ug/ml | 67.7% | 77.6% | 96.6% | 80.5% |
| Bestatin | | | | | |
| | 13.0 mM | 23.3% | 121.0% | 103.4% | 117.0% |
| | 1.3 mM | 60.4% | 119.5% | 116.3% | 116.8% |

[1]All experimental values are expressed as a percent of the corresponding control group.

The aminopeptidase inhibitor bestatin caused a significant ($p<0.05$) reduction in fecundity at 13 mM (77% reduction) and at 1.3 mM (40% reduction) indicating the presence of an aminopeptidase or other exopeptidase in flea midguts. Bestatin at the concentrations tested, however, had no significant effect on adult viability at either concentration. These results suggest that aminopeptidases may play a role in ovarian function, or a related process, such as vitellogenesis.

The aspartic acid protease inhibitor pepstatin A caused a significant reduction ($p<0.05$) in fecundity at 1 µg/ml (32% reduction), but not at 10 µg/ml. Pepstatin A had no significant effect on adult viability at either concentration.

The cysteine protease inhibitor E-64 showed no statistically significant reduction in fecundity in this assay. There was a small, but significant ($p<0.05$), reduction in total adult flea survival when E-64 was dissolved in grain alcohol and added to blood at 1 µg/ml. However, this reduction was not evident in the group that was fed blood containing 10 µg/ml E-64 in grain alcohol.

The metalloprotease inhibitor phosphoramidon caused a reduction in adult viability of about 30%, which, however was not statistically significant. There was no significant reduction in fecundity.

Results using serine protease inhibitors were particularly interesting and suggest the significance of serine proteases in flea midguts. AEBSF administered at concentrations ranging from about 5 mM to about 6 mM reduced flea fecundity by more than 80%. In addition, adult survival was reduced to near zero ($p<0.05$).

Aprotinin, however, had no significant effect on either fecundity or viability, likely due to the ability of serum proteins, such as albumin, to interfere with aprotinin's inhibitory activity.

Leupeptin had no effect on fecundity at both concentrations, but reduced adult viability by 30% at 5 µg/ml. However, adult viability was not affected by 50 µg/ml leupeptin and none of the observed reductions were statistically significant.

Soybean trypsin inhibitor caused a small (20%) statistically insignificant reduction in fecundity at 100 µg/ml. The lower concentration had no effect. Soybean trypsin inhibitor, on the other hand, is very effective in in vitro studies as disclosed in several of the examples and was used to purify serine proteases as disclosed in Example 7. Soybean trypsin/chymotrypsin inhibitor had no effect on adult viability or fecundity.

EXAMPLE 7

This Example describes the production of a preferred soluble flea midgut preparation of the present invention and purification of flea serine proteases therefrom. Also included is amino acid sequence analysis of a flea serine protease of the present invention.

The soluble flea midgut preparation was prepared as follows. Flea midguts (3,735) from a mix of female and male fed fleas were homogenized in a homogenization buffer comprising 1.5 ml 50 mM Tris-HCl, 0.5 M NaCl, pH 8.5. The homogenate was centrifuged at 14,000×g for 10 min. The resultant pellet was processed again in another 1.5 ml of the homogenization. The two supernatant solutions were combined to form the soluble flea midgut preparation.

The preparation was added to 3 ml of p-aminobenzamidine-sepharose 6 B (affinity matrix for trypsin-like proteases, available from Sigma) and incubated at 5° C. overnight on a rocker. The sepharose beads were drained and washed with 7.5 ml of the homogenization buffer. The adsorbed proteins were eluted with 5 ml 0.1 M p-aminobenzamidine in the same buffer. This eluate was concentrated and the buffer exchanged to 50 mM Tris-HCl pH 8.5, 0.1 mM $CaCl_2$ by ultrafiltration through a membrane with a 3 kD cutoff, the final volume being 140 µl (microliters).

Figure 5A:
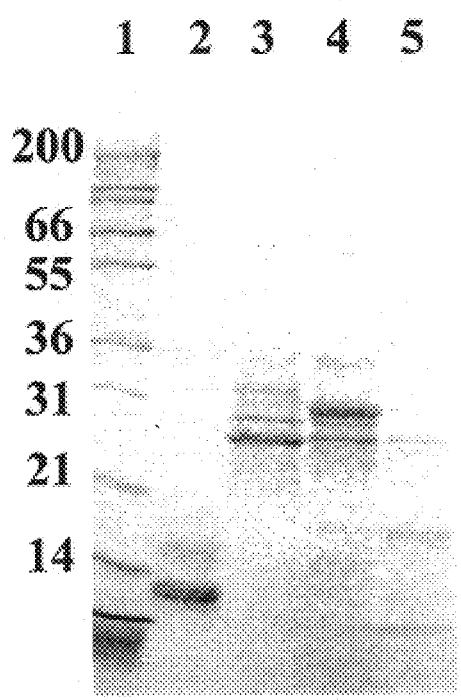
FIG. 5A depicts a Coomassie stained SDS-PAGE of partially purified (1,3-$^3$H)-diisopropylfluoro-phosphate (DFP)-labeled fed flea midgut serine proteases.
Figure 5B:
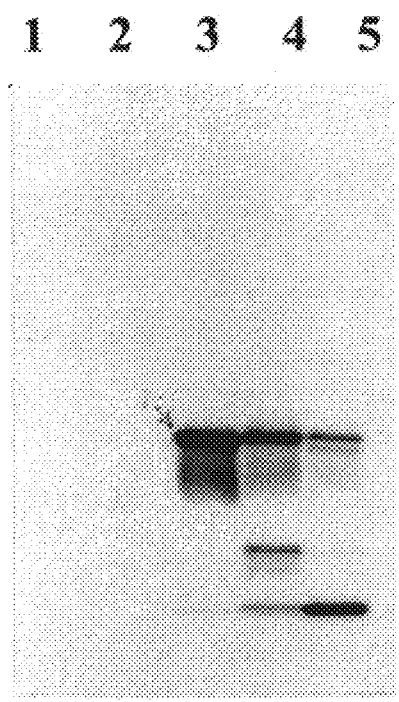
FIG. 5B depicts an autoradiogram of the SDS-PAGE gel of FIG. 5A of partially purified DFP-labeled fed flea midgut serine proteases.
Figure 6:
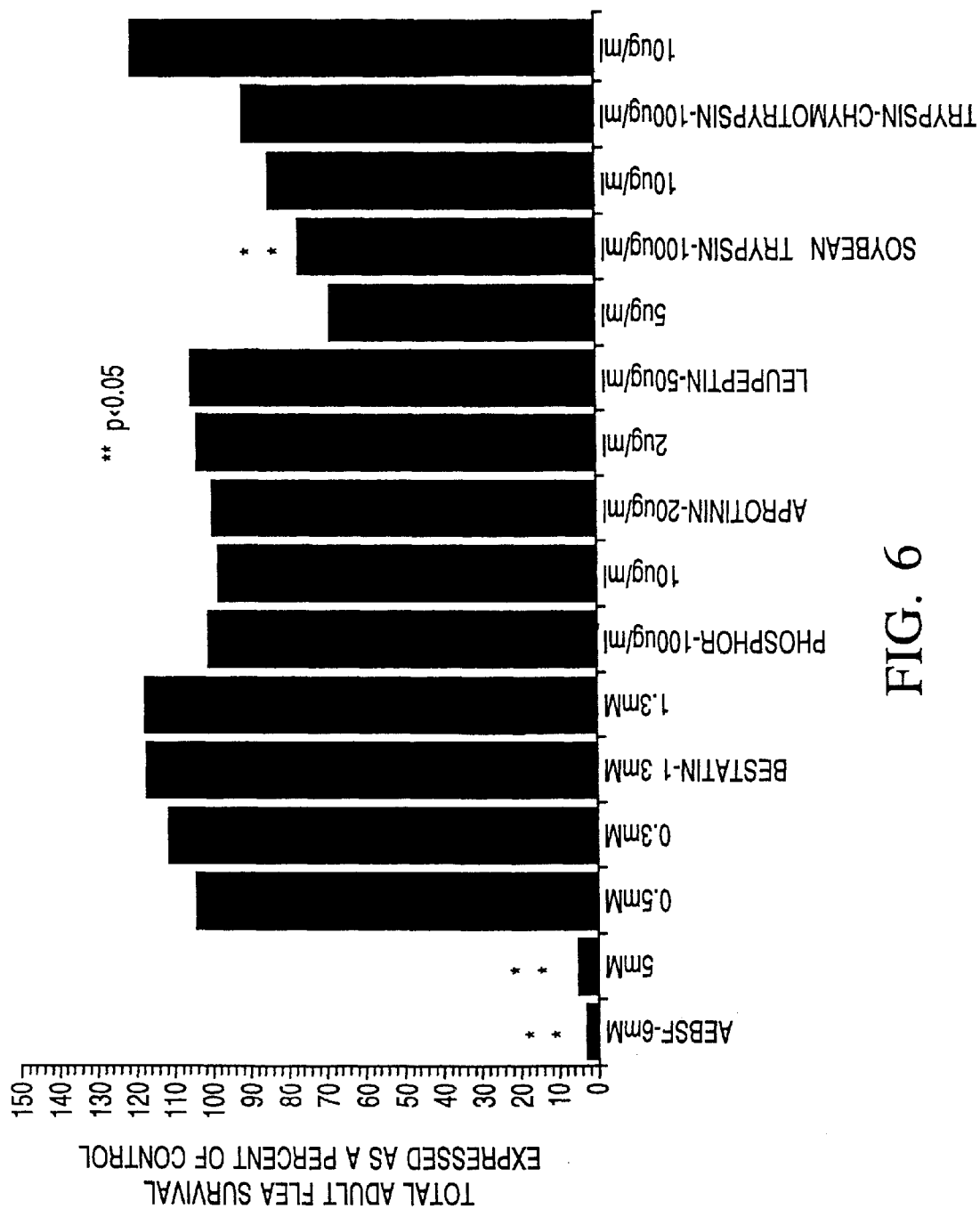
FIG. 6 depicts the mean viability of adult (both male and female) fleas fed blood containing certain protease inhibitors.
Figure 7:
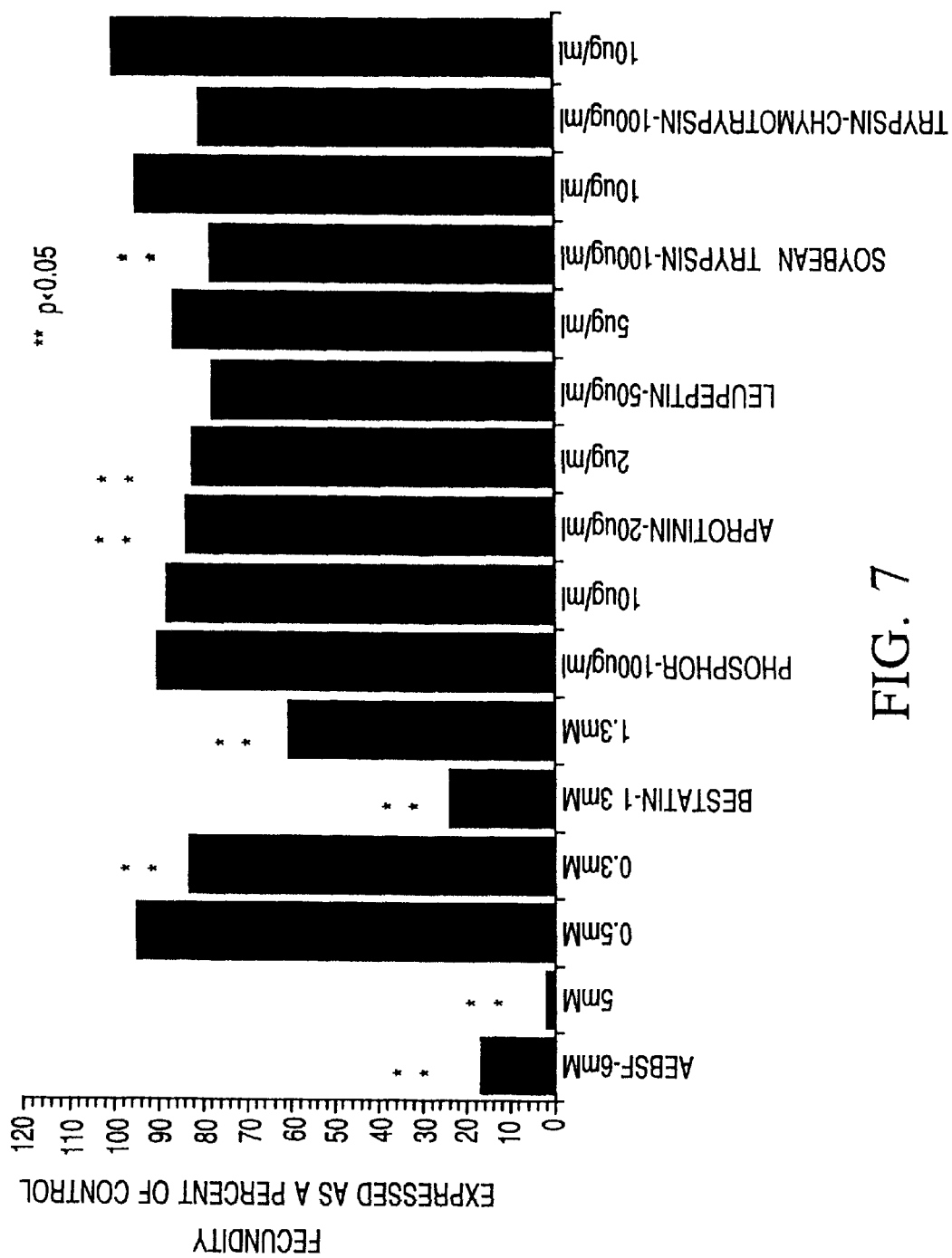
FIG. 7 depicts the mean fecundity of adult female fleas fed blood containing certain protease inhibitors.
Figure 8:
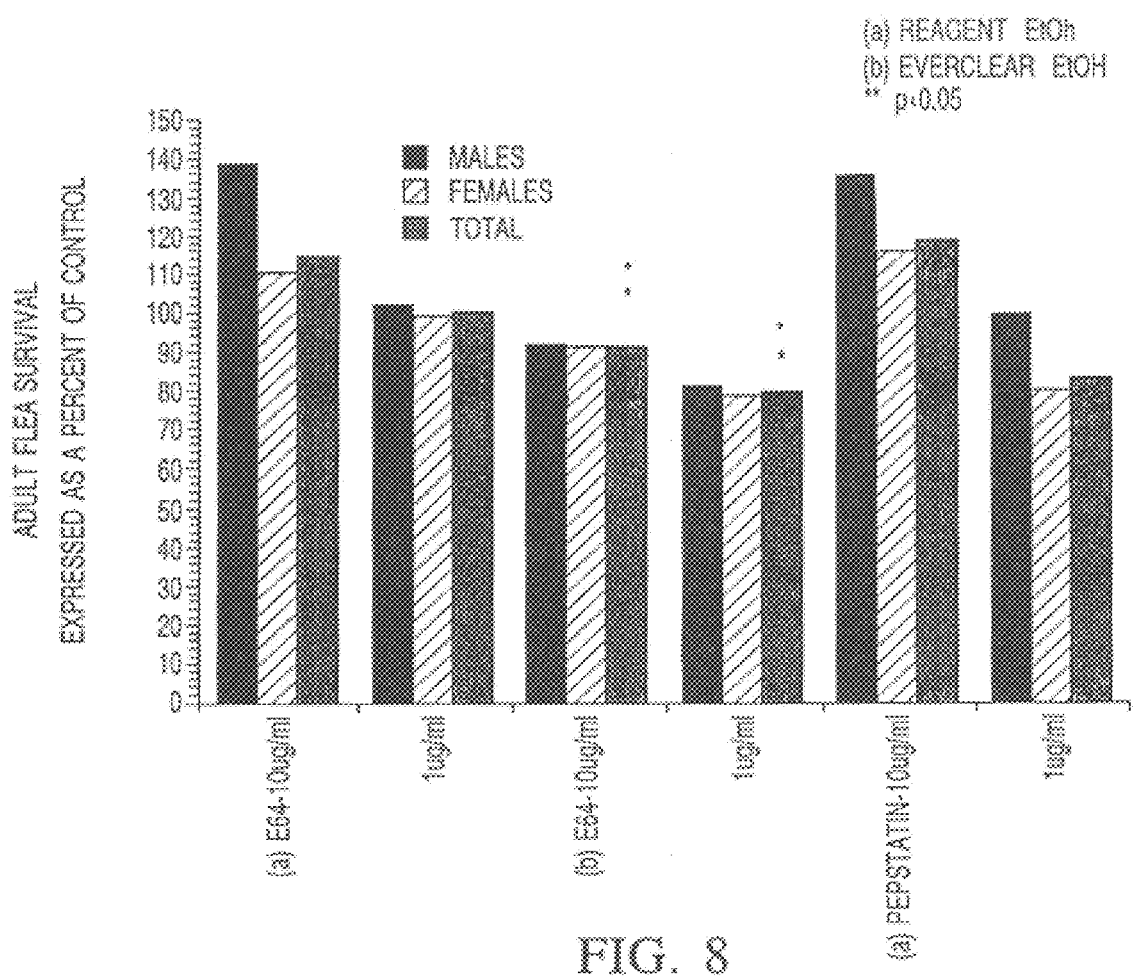
FIG. 8 depicts the mean viability of adult (both male and female) fleas fed blood containing certain protease inhibitors.
Figure 9:
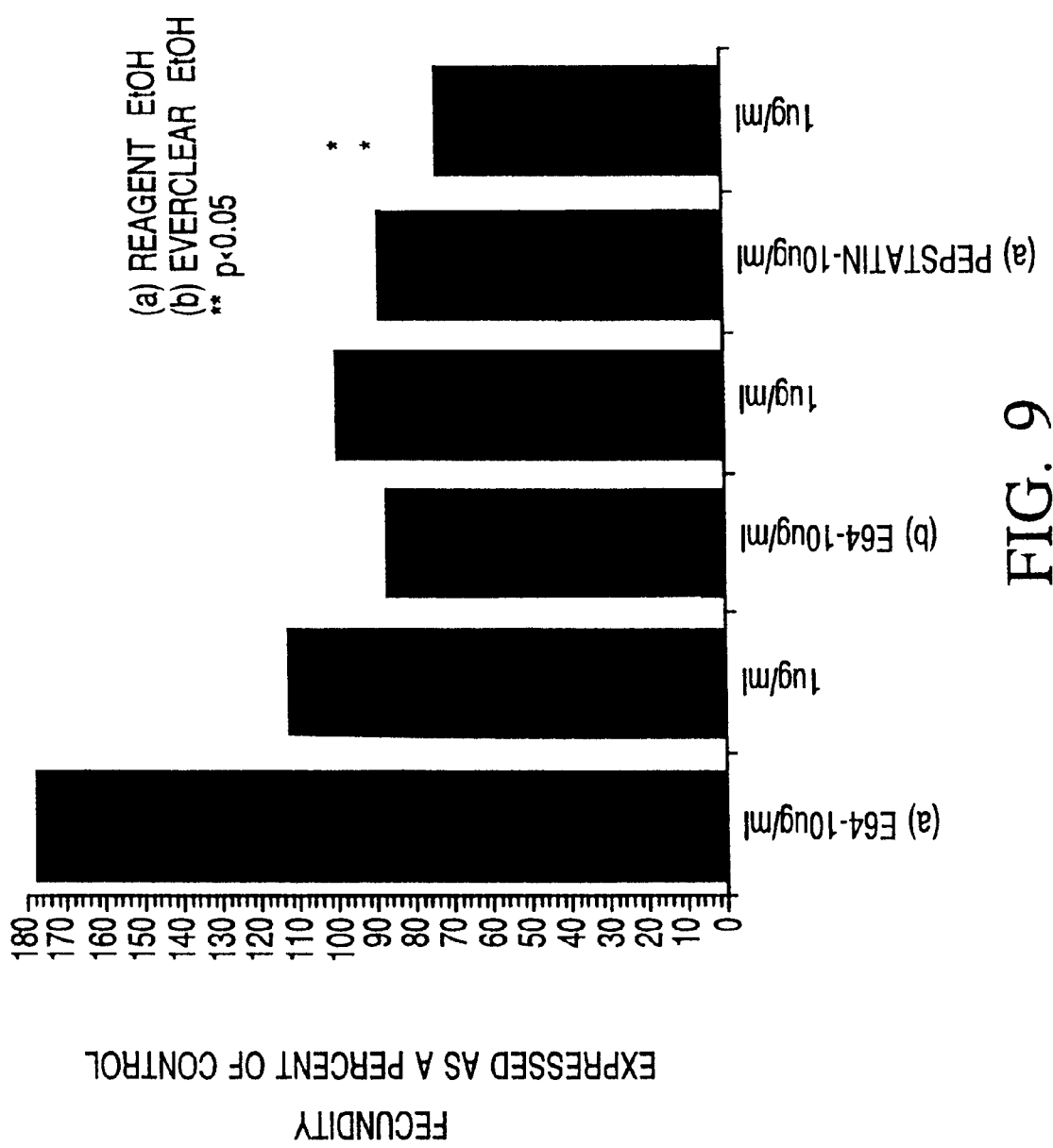
FIG. 9 depicts the mean fecundity of adult female fleas fed blood containing certain protease inhibitors.

Labeling of proteins was performed by adding 10 µl of (1,3-$^3$H)-diisopropylfluorophosphate (available from New England Nuclear, Beverly, Mass., at 6.0 Ci (Curies)/mmole, 1.0 mCi/ml) to 90 µl of the affinity purified proteins and incubating at 5° C. for 18 hours. The reaction was divided in half, each half then being separated by C4 reverse phase chromatography according to the following protocol:

Buffer A: 0.1% TFA in water
Buffer B: 0.085% TFA, 90% Acetonitrile
0.8 ml/min, 220 nm, 1 min fractions
5.6% B 15 min
5.6% to 100% B over 60 min Ten microliters of each fraction was added to scintillation fluid and counted. Most protein-associated counts were found in fractions 44–47. FIG. 5A shows electrophoresis of fractions 40 (lane 2), 44 (lane 3), 46 (lane 4) and 47 (lane 5) from one chromatography run through a 14% Tris-glycine polyacrylamide-SDS gel, followed by coomassie staining. This gel was then processed with Entensigy (NEN) and exposed to film for 18 hours, as shown in FIG. 5B. Each fraction contained several proteins as shown in FIG. 5A, but only 4 bands were labeled, the most prominent being 26 kd (seen in lanes 3, 4 and 5), and denoted herein as PfSP26 (now denoted PafSP-26K). A faint band of 24 kd, denoted herein as PfSP24 (now denoted PafSP-24K), was also noticed in lane 5. A band of 19 kD, denoted herein as PfSP19 (now denoted PafSP-19K), was labeled in lane 4 that was associated with a very faintly staining protein band. Some labeled proteins were seen at the dye front of lanes 4 and 5, indicating a molecular weight less than 6 kd, denoted herein as PfSP6 (now denoted PafSP-6K), and could be degradation products.

Fraction 44 (analogous to lane 3) from a second C4 chromatography separation experiment was electrophoresed, blotted onto PVDF, stained with Coomassie R-250 and destained via standard procedures. The 26 kd band, corresponding to PfSP26 (also referred to herein as PfSP44-E, indicating the fraction in which the protein eluted and the gel/filter band from which the protein was excised), was excised and subjected to N-terminal amino acid sequencing using techniques known to those skilled in the art. A partial N-terminal amino acid sequence of about 32 amino acids was deduced and is represented herein as SEQ ID NO:1:

I I G G E V A G E G S A P Y Q V S L R T K E G N H F S G G S I L,

It should be noted that since amino acid sequencing technology is not entirely error-free, SEQ ID NO:1 represents, at best, an apparent partial N-terminal amino acid sequence of PfSP26. This caution is particularly relevant in light of the sequencing of this protein having been done at a low picomolar concentration.

A homology search of the non-redundant protein sequence database was performed through the National Center for Biotechnology Information using the BLAST network. This database includes +SwissProt+PIR+SPUpdate+GenPept+GPUpdate.ole level. Results of the search indicate that the N-terminus of PfSP26 shares significant amino sequence homology with a number of serine proteases, including a variety of trypsins, chymotrypsins and plasmins. The 32-amino acid N-terminal amino acid sequence of PfSP26 shared the highest degree of homology with a hornet chymotrypsin II.

EXAMPLE 8

This example describes the cloning of certain flea protease nucleic acid molecules of the present invention. This example also describes the production of certain recombinant molecules, recombinant cells and flea protease proteins of the present invention.

Several flea serine protease nucleic acid molecules, ranging in size from about 250 to about 500 nucleotides, and representing one or more partial flea serine protease genes, were PCR amplified from a fed flea midgut cDNA library that was prepared from RNA isolated from fed flea midguts using standard protocols as described in Sambrook et al., ibid. Several pairs of primers were used in PCR amplification reactions that represented degenerate oligonucleotides designed from published sequences of serine protease genes isolated from biting insects (e.g., mosquitos and black flies). Each primer pair was designed so that a properly amplified fragment of a flea serine protease gene would include a domain corresponding to the most conserved domain of trypsin protease genes (thought to be the active site) given that such a domain is contained in flea serine protease gene(s).

The amplified PCR fragments were of predicted size, ranging from about 250 nucleotides to about 500 nucleotides, depending on which primer pairs were used. PCR fragments that hybridized to a probe designed from the domain most conserved among all known trypsin genes were gel purified and cloned, for example, into the pCRII cloning vector (available from InVitrogen, Corp., San Diego, Calif.), following manufacturer's instructions. Nucleic acid sequences of the fragments are being determined using standard techniques.

The amplified PCR fragments are also being used as probes to identify full-length flea protease genes in unfed and fed flea midgut cDNA libraries and in flea salivary gland cDNA libraries, as well as in flea genomic DNA libraries, using standard procedures.

Recombinant molecules and recombinant cells including the amplified PCR fragments as well as full-length flea protease genes are being produced using standard procedures. Culturing of such recombinant cells leads to the production of flea protease proteins of the present invention.

EXAMPLE 9

This Example describes the testing of a flea protease protein as a flea protease vaccine of the present invention, that is for the ability of such a protein, upon administration to an animal, to elicit the production of antibodies that reduce flea protease activity and, as such, reduce flea viability and/or fecundity. This Example also demonstrates the use of such a flea protease protein as a vaccine on a dog subsequently infested with fleas.

A flea protease protein produced as described in Example 7 is administered to rabbits according to a standard immunization protocol known to those skilled in the art, including appropriate booster shots. Such a protein is also administered to guinea pigs and to dogs following a similar protocol.

Sera is collected from the treated rabbits and is verified to contain anti-flea protease antibodies. Such sera is then fed to fleas in a feeding system as reported by Wade et al. ibid. Fleas feeding on such a sera show reduced viability compared to fleas feeding on sera collected from rabbits not administered the flea protease protein. Sera from treated guinea pigs and dogs are verified in a similar manner.

Dogs treated with a flea protease protein are then infested with fleas as are dogs not treated with a flea protease protein. Dogs treated with a flea protease protein show a significant reduction in flea burden compared to untreated dogs.

EXAMPLE 10

This Example describes the determination of the partial N-terminal amino acid sequence of additional flea serine protease proteins of the present invention.

An additional eight flea serine proteases were purified and consensus partial N-terminal amino acid sequences were determined as described in Example 7. The results are as follows, the proteins being named by the fraction in which they were eluted and the SDS-PAGE gel band from which they were excised. Each of the proteases bore at least some sequence homology to known proteases, the highest percent identity estimated to be no more than about 30–40%.

Flea protease PfSP45-C had a partial N-terminal amino acid sequence of X V G G H D T S I D X H P H Q V T, also represented herein as SEQ ID NO:2. PfSP45-C was most similar in amino acid sequence to a fruit fly trypsin epsilon.

Flea protease PfSP46-C had a partial N-terminal amino acid sequence of I V G G A D A A P G N A P F Q V S L R D K G, also represented herein as SEQ ID NO:3. PfSP46-C was most similar in amino acid sequence to a collagenolytic 36 kD protease from a Kamchatda crab.

Flea protease PfSP46-A had a partial N-terminal amino acid sequence of I V G G Q D A D I A K Y G Y Q A S L Q V F N E H F X G A X I L N N Y, also represented herein as SEQ ID NO:4. PfSP46-A was most similar in amino acid sequence to a hornet chymotrypsin II.

Flea protease PfSP46-B had a partial N-terminal amino acid sequence of I V G G T D V N I E N F G W Q V S L F D R N G H F, also represented herein as SEQ ID NO:5. PfSP46-B was most similar in amino acid sequence to a fruit fly trypsin beta.

Flea protease PfSP48-A had a partial N-terminal amino acid sequence of I V G G H D T S I D K H P F Q V S L I D K N, also represented herein as SEQ ID NO:6. PfSP48-A was most similar in amino acid sequence to a fruit fly trypsin epsilon.

Flea protease PfSP48-B had a partial N-terminal amino acid sequence of V V G G L E A A E G S A P Y Q V X L Q W G N F, also represented herein as SEQ ID NO:7. PfSP48-B was most similar in amino acid sequence to a human Factor 12.

Flea protease PfSP48-D had a partial N-terminal amino acid sequence of I V G G E D A E L G E X P T Q, also represented herein as SEQ ID NO:8. PfSP48-D was most similar in amino acid sequence to a bovine Factor 9.

Flea protease PfSP40-B had a partial N-terminal amino acid sequence of D E D G K D D S A P G E I, also represented herein as SEQ ID NO:9. PfSP40-B was most similar in amino acid sequence to a fruit fly furin-like protease I.

EXAMPLE 11

This Example describes the isolation of nucleic acid molecules encoding flea serine protease proteins of the present invention.

Several midgut proteinase cDNA genes have been isolated in a manner similar to that described in Example 8, using two degenerate primers, the design of which was based on a highly conserved serine proteinase amino acid sequence (C Q/N G D S G G P L, denoted SEQ ID NO:10) located about 195 amino acid residues (based on an average protease size of about 240 residues) from the mature amino terminus in a number of known serine proteases. Complementing primers for use in the PCR amplification reaction were primers corresponding to the vectors in which nucleic acid molecules of the present invention had been ligated. The actual primers used in PCR amplification of serine protease nucleic acid molecules from whole fed flea cDNA expression libraries (produced as described in Example 8) included the following serine protease specific primers: cat-try #1 having nucleic acid sequence 5' TAA WGG WCC WCC YGA ATC TCC CTG GCA 3' (Y indicating C or T; W indicating A or T), represented herein as SEQ ID NO:11; and cat-try #2 having nucleic acid sequence 5' TAA WGG WCC AGA RTC TCC TTG ACA 3' (R indicating A or G), represented herein as SEQ ID NO:12. Vector specific primers included: M13 Reverse having nucleic acid sequence 5' GGAAACAGCTATGACCATG 3', represented herein as SEQ ID NO:13; and T3 Primer having nucleic acid sequence 5' ATTAACCCTCACTAAAG 3', represented herein as SEQ ID NO:14. The resultant PCR products, obtained using standard PCR conditions (e.g., Sambrook et al., ibid.), were about 600 to about 700 nucleotides in length.

The PCR products were hybridized under standard hybridization conditions (e.g., Sambrook et al., ibid.) with (i.e., to) an internal synthetic oligonucleotide probe named H57, the sequence of which corresponds to a region including a conserved histidine residue in known serine proteases. The nucleic acid sequence of H57 is 5' TGG GTW GTW ACW GCW GCW CAT TG 3', represented herein as SEQ ID NO:15. PCR products which hybridized strongly to the probe were gel purified and cloned into the TA Vector™ (available from InVitrogen, Corp.). Approximately 80 recombinant TA vector clones were isolated.

To prevent repetitive sequencing of the same serine proteinase clones, a number of the clones were characterized to identify those having unique restriction endonuclease patterns using the enzymes HaeII and HaeIII. About 11 plasmids apparently containing unique flea serine proteinase nucleic acid molecules of about 600 to about 700 nucleotides in length were isolated using this procedure. These nucleic acid molecules were subjected to nucleic acid sequencing using the Sanger dideoxy chain termination method, as described in Sambrook et al., ibid.

The complete nucleic acid sequence of one of the flea serine protease nucleic molecules, namely $nfSP4_{672}$ is represented herein as SEQ ID NO:16. Translation of SEQ ID NO:16 yields a protein of about 223 amino acids, denoted $PfSP4_{223}$, having amino acid sequence SEQ ID NO:17. Although the entire amino acid sequence of $PfSP4_{223}$ is not highly conserved to that of known serine proteases, there are several conserved regions of note (as numbered for SEQ ID NO:17), including: (a) the sequence IVGG spanning from about amino acid 5 through about amino acid 9; (b) the active-site histidine at about amino acid 46 and surrounding sequences spanning from about amino acid 41 through about amino acid 47; (c) the conserved aspartic acid residue at about amino acid 90; (d) the GWG sequence spanning from about amino acid 124 through about amino acid 126; the conserved cysteines at about amino acid 152 and about amino acid 165; and the conserved sequence around the active site serine, spanning from about amino acid 174 through about amino acid 182.

Nucleic acid and amino acid sequences of all 11 flea serine protease nucleic acid molecules were determined for the regions corresponding to the region in known serine proteases to span from the conserved GWG sequence to the conserved CXGDSGGP sequence (denoted SEQ ID NO:10). Flea nucleic acid molecule $nfSP1_{156}$ has the nucleic acid sequence represented herein as SEQ ID NO:18, which encodes a protein $PfSP1_{52}$ having an amino acid sequence represented herein as SEQ ID NO:19. Flea nucleic acid molecule $nfSP2_{168}$ has the nucleic acid sequence represented herein as SEQ ID NO:20, which encodes a protein $PfSP2_{56}$ having an amino acid sequence represented herein as SEQ ID NO:21. Flea nucleic acid molecule $nfSP3_{177}$ has the nucleic acid sequence represented herein as SEQ ID NO:22, which encodes a protein $PfSP3_{59}$ having an amino acid sequence represented herein as SEQ ID NO:23. Flea nucleic acid molecule $nfSP4_{156}$ has the nucleic acid sequence represented herein as SEQ ID NO:24, which encodes a protein $PfSP4_{52}$ having an amino acid sequence represented herein as SEQ ID NO:25. Flea nucleic acid molecule $nfSP5_{159}$ has the nucleic acid sequence represented herein as SEQ ID NO:26, which encodes a protein $PfSP5_{53}$ having an amino acid sequence represented herein as SEQ ID NO:27. Flea nucleic acid molecule $nfSP6_{168}$ has the nucleic acid sequence represented herein as SEQ ID NO:28, which encodes a protein $PfSP6_{56}$ having an amino acid sequence represented herein as SEQ ID NO:29. Flea nucleic acid molecule $nfSP7_{159}$ has the nucleic acid sequence represented herein as SEQ ID NO:30, which encodes a protein $PfSP7_{53}$ having an amino acid sequence represented herein as SEQ ID NO:31. Flea nucleic acid molecule $nfSP8_{186}$ has the nucleic acid sequence represented herein as SEQ ID NO:32, which encodes a protein $PfSP8_{62}$ having an amino acid sequence represented herein as SEQ ID NO:33. Flea nucleic acid molecule $nfSP9_{168}$ has the nucleic acid sequence represented herein as SEQ ID NO:34, which encodes a protein $PfSP9_{56}$ having an amino acid sequence represented herein as SEQ ID NO:35. Flea nucleic acid molecule $nfSP10_{120}$ has the nucleic acid sequence represented herein as SEQ ID NO:36, which encodes a protein $PfSP10_{40}$ having an amino acid sequence represented herein as SEQ ID NO:37. Flea nucleic acid molecule $nfSP11_{162}$ has the nucleic acid sequence represented herein as SEQ ID NO:38, which encodes a protein $PfSP11_{54}$ having an amino acid sequence represented herein as SEQ ID NO:39.

Comparison of the nucleic acid sequences of the flea serine proteases with that of a mosquito (*A. aegypti*) trypsin indicates that SEQ ID NO:18 is about 33% identical, SEQ ID NO:20 is about 33% identical, SEQ ID NO:22 is about 24% identical, SEQ ID NO:24 is about 25% identical, SEQ ID NO:26 is about 32% identical, SEQ ID NO:28 is about 38% identical, SEQ ID NO:30 is about 33% identical, SEQ ID NO:32 is about 33% identical, SEQ ID NO:34 is about 40% identical, SEQ ID NO:36 is about 33% identical, and SEQ ID NO:38 is about 29% identical, to the corresponding region of the mosquito trypsin. Comparison of the nucleic acid sequences of the flea serine proteases with that of a black fly (*S. vittatum*) trypsin indicates that SEQ ID NO:18 is about 34% identical, SEQ ID NO:20 is about 34% identical, SEQ ID NO:22 is about 25% identical, SEQ ID NO:24 is about 28% identical, SEQ ID NO:26 is about 36% identical, SEQ ID NO:28 is about 45% identical, SEQ ID NO:30 is about 29% identical, SEQ ID NO:32 is about 36% identical SEQ ID NO:34 is about 42% identical, SEQ ID NO:36 is about 34% identical, and SEQ ID NO:38 is about 30% identical, to the corresponding region of the black fly trypsin. It is to be noted that the mosquito and black fly trypsins are about 50% identical in the same regions.

Comparison of the amino acid sequences of the flea serine proteases with that of a mosquito (*A. aegypti*) trypsin indicates that SEQ ID NO:19 is about 11% identical, SEQ ID NO:21 is about 30% identical, SEQ ID NO:23 is about 19% identical, SEQ ID NO:25 is about 19% identical, SEQ ID NO:27 is about 28% identical, SEQ ID NO.:29 is about 21% identical, SEQ ID NO:31 is about 14% identical, SEQ ID NO:33 is about 22% identical, SEQ ID NO:35 is about 30% identical, SEQ ID NO:37 is about 22% identical, and SEQ ID NO:39 is about 29% identical, to the corresponding region of the mosquito trypsin. Comparison of the amino acid sequences of the flea serine proteases with that of a black fly (*S. vittatum*) trypsin indicates that SEQ ID NO:19 is about 14% identical, SEQ ID NO:21 is about 28% identical, SEQ ID NO:23 is about 16% identical, SEQ ID NO:25 is about 17% identical, SEQ ID NO:27 is about 35% identical, SEQ ID NO:29 is about 33% identical, SEQ ID NO:31 is about 11% identical, SEQ ID NO:33 is about 22% identical, SEQ ID NO:35 is about 33% identical, SEQ ID NO:37 is about 21% identical, and SEQ ID NO:39 is about 25% identical, to the corresponding region of the black fly trypsin. It is to be noted that the mosquito and black fly trypsins are about 50% identical in the same regions.

Partial N-terminal amino acid sequences were deduced for each of the cloned flea serine protease nucleic acid molecules, four of which were identical to the following amino acid sequences derived from N-terminal sequencing of serine proteases as described in Example 10: SEQ ID NO:1, SEQ ID NO:4, SEQ ID NO:6 and SEQ ID NO:7. The remaining nucleic acid molecules had the following deduced N-terminal amino acid sequences: SEQ ID NO:40, namely I V G G E N A K E K S D V P Y Q V S L R N A E N K H F C G G A I I D D Y W V L T, which was most similar in amino acid sequence to mite fecal allergen Der pIII; SEQ ID NO:41, namely I V G G L E A K N G S A P F N V S L Q A E D Y F H, which was most similar in amino acid sequence to a chymotrypsin-like protein; SEQ ID NO:42, namely I I G G E V A G E G S A P Y Q V S L R T K E G N H F, which was most similar in amino acid sequence to a chymotrypsin-like protein; SEQ ID NO:43, namely I V G G T A V D I R G F P G R Y Q F K P K P S F L W W F Y, which did not substantially match any protein in the data base; SEQ ID NO:44, namely I V N G L E A G V G Q F P I Q V F L D L T N I R D E K S R C G G A L F, which was most similar in amino acid sequence to a trypsin precursor; SEQ ID NO:45, namely I V G G L E A K N G I T P F I G F F A S G R L F, which was most similar in amino acid sequence to a chymotrypsin-like protease; SEQ ID NO:46, namely I V G G N D V S X K I F W Q V S I Q S N X Q H F C G, which was most similar in amino acid sequence to a trypsin; and SEQ ID NO:47, namely I I G G E D A P E G S A P Y Q V S L R N Q N L E H F C G G S I, which was most similar in amino acid sequence to a chymotrypsin-like protein.

Additional amino terminal and carboxyl terminal sequences of flea serine protease nucleic acid molecules comprising sequences listed above as well as additional nucleic acid molecules identified using the techniques described herein are presented in Table 2.

TABLE 2

Additional Flea Serine Protease Sequences

A. The apparent N-terminal nucleic acid sequence (SEQ ID NO:52), as well as deduced amino acid sequence (SEQ ID NO:53) of nfSP1 is:
```
TCA GCA CTC GTT GCC TTG TCT GCA GCT ATT CCT CAC TCC AAC AGA GTC
 S   A   L   V   A   L   S   A   A   I   P   H   S   N   R   V GTT GGA GGA CTG GAA GCT GCA GAG GGT TCT GCA CCT TAT CAA GTA TCC
 V   G   G   L   E   A   A   E   G   S   A   P   Y   Q   V   S TTG CAA GTT GGC AAC TTC CAC TTC TGT GGT GGT TCA ATT CTG AAC GAA
 L   Q   V   G   N   F   H   F   C   G   G   S   I   L   N   E TAT TGG GTT TTG ACT GCT GCT CAC TGT TTG GGT TAT GAC TTC GAC GTG
 Y   W   V   L   T   A   A   H   C   L   G   Y   D   F   D   V GTA GTT GGA ACA AAC AAA CTT GAT CAA CCA GGT GAA AGA TAC CTC GTA
 V   V   G   T   N   K   L   D   Q   P   G   E   R   Y   L   V

GAA CAA ACT TTT GTT CAC
 E   Q   T   F   V   H
```

B. The apparent N-terminal nucleic acid sequence (SEQ ID NO:54), as well as deduced amino acid sequence (SEQ ID NO:55) of nfSP2 is:
```
TTA GAT GGG CGC ATT GTT GGA GGA CAA GAT GCT GAT ATT GCC AAA TAT
 L   D   G   R   I   V   G   G   Q   D   A   D   I   A   K   Y GGC TAT CAA GCT TCA CTC CAA GTA TTT AAC GAA CAT TTC TGT GGA GCT
 G   Y   Q   A   S   L   Q   V   F   N   E   H   F   C   G   A TCA ATA TTG AAT AAT TAT TGG ATT GTC ACA GCA GCT CAT TGC ATA TAT
 S   I   L   N   N   Y   W   I   V   T   A   A   H   C   I   Y GAT GAA TTC ACG TAT TCA GTT CGA GTC GGC ACC AGT TTC CAA GGA AGA
 D   E   F   T   Y   S   V   R   V   G   T   S   F   Q   G   R
```

TABLE 2-continued

Additional Flea Serine Protease Sequences

```
CGT GGT TCC GTT CAT CCT GTG GCA CAA ATT ATC AAG CAT CCT GCA
TAC
 R   G   S   V   H   P   V   A   Q   I   I   K   H   P   A
 Y
```

C. The apparent N-terminal nucleic acid sequence (SEQ ID NO:56), as well as deduced amino acid sequence (SEQ ID NO:57) of nfSP4 is:

```
AGG GAA CAA AAG CTG GAG CTC CAC CGC GGT GCG CCG GCT CTA GAA
CTA
 R   E   Q   K   L   E   L   H   R   G   A   P   A   L   E
 L

GTG GAT CCC CCG GGT CTG CAG GAA TTG GCA CGA GGA TGT TCT TGG
CTG
 V   D   P   P   G   L   Q   E   L   A   R   G   C   S   W
 L

TGT TTA GTA GCT ATT CTT TGT GCA GTG GCT GCT GGG CCT ACT AAT
CGC
 C   L   V   A   I   L   C   A   V   A   A   G   P   T   N
 R

ATT GTT GGA GGA TTG GAG GCG AAA AAT GGA ATC ACC CCA TTC ATC
GGT
 I   V   G   G   L   E   A   K   N   G   I   T   P   F   I
 G

TTC TTT GCA AGC GGA AGA CTA TTT CA
 F   F   A   S   G   R   L   F
```

D. The apparent N-terminal nucleic acid sequence (SEQ ID NO:58), as well as deduced amino acid sequence (SEQ ID NO:59) of nfSP5 is:

```
ACG AGG TTT CGC TTA GCA ATT GTA TGT GCT CTC GCT GTC TGC ACA
TTC
 T   R   F   R   L   A   I   V   C   A   L   A-
     V       C           T       F>

GGT GCC AGT GTT CCA GAA CCA TGG AAA AGA TTA GAT GGT AGA ATC
GTA
 G   A   S   V   P   E   P   W   K   R   L   D-
     G   R               I                   V>

GGA GGA CAC GAT ACC AGC ATC GAT AAA CAC CCT CAT CAA GTA TCT
TTA
 G   G   H   D   T   S   I   D   K   H   P   H   Q   V   S
 L>

TTG TAC TCC AGC GAC AAT TGT GGT GGT TCC TTG ATT GCC AAA AAC
TGG
 L   Y   S   S   H   N   C   G   G   S   L   I   A   K   N
 W>

GTT TTG ACT GCA GCT CAT TGC ATT GGA GTT AAC AAA TAC AAT GTC
CGT
 V   L   T   A   A   H   C   I   G   V   N   K   Y   N   V
 R>
```

E. The apparent N-terminal nucleic acid sequence (SEQ ID NO:60), as well as deduced amino acid sequence (SEQ ID NO:61) of nfSP6 is:

```
CCC TCA CTA AAG GGA ACA AAA GCT GGA GCT CCA CCG CGG TGC GCC
GCT
 P   S   L   K   G   T   K   A   G   A   P   P   R   C   A
 A

CTA GAA CTA GTG GAT CCC CCG GGC TGC AGG AAT TCG GCA CGA GCG
TTT
 L   E   L   V   D   P   P   G   C   R   N   S   A   R   A
 F

GGT TGG ATT GAG CGC GTC TCA TCT TAC AAG ATA AAG GAT AGA TTA
GAT
 G   W   I   E   R   V   S   S   Y   K   I   K   D   R   L
 D
```

TABLE 2-continued

Additional Flea Serine Protease Sequences

```
GGG CGC ATT GTT GGA GGA CAA GAT GCT GAT ATT GCC AAA TAT GGC
TAT
 G   R   I   V   G   G   Q   D   A   D   I   A   K   Y   G
Y

CAA GCT TCA CTC CAA GTA CTT AAC GAA CAT TTC TGT GGA GCT
 Q   A   S   L   Q   V   L   N   E   H   F   C   G   A
```

F. The apparent N-terminal nucleic acid sequence (SEQ ID NO:62), as well as deduced amino acid sequence (SEQ ID NO:63) of nfSP7 is:

```
GCG GTG ATT GTG TCA TTT GTT CTG GCT TGT GCA TTT TCT GTA CAG
GCT
 A   V   I   V   S   F   V   L   A   C   A   F   S   V   Q
A

CTT CCA TCA AGC AGA ATT GTC AAT GGA CTT GAA GCA GGA GTT GGA
CAA
 L   P   S   S   R   I   V   N   G   L   E   A   G   V   G
Q

TTT CCA ATT CAG GTT TTC TTA GAC TTG ACA AAT ATC AGA GAC GAA
AAA
 F   P   I   Q   V   F   L   D   L   T   N   I   R   D   E
K

TCC AGA TGT GGT GGT GCT TTG TTA TCA GAT TCA TGG GTT TTG ACT
GCT
 S   R   C   G   G   A   L   L   S   D   S   W   V   L   T
A

GCT CAT TGT TTT GAT GAT TTG AAG TCT ATG GTA GTG TCC GTT GGT
GCT
 A   H   C   F   D   D   L   K   S   M   V   V   S   V   G
A

CAT GAT GTC AGC AAA TCT GAA GAA CCT CAC AGG CAA ACC AGG AAA
CCT
 H   D   V   S   K   S   E   E   P   H   R   Q   T   R   K
P

GAA
 E
```

G. The apparent N-terminal nucleic acid sequence (SEQ ID NO:64), as well as deduced amino acid sequence (SEQ ID NO:65) of nfSP12 is:

```
GTA CTG ATC GTT TTA GCA GTC ATT GAA TTC GCA TCA GCG TCT TCA
ATC
 V   L   I   V   L   A   V   I   E   F   A   S   A   S   S
I

GGC TGG AGA ATC GTG GGT GGT GAA AAT GCT AAA GAA AAA TCG GTG
CCC
 G   W   R   I   V   G   G   E   N   A   K   E   K   S   V
P

TAT CAA GTT TCM CTT CGA AAT GCT GAA AAC AAA CAT TTY TGT GGR
GGR
 Y   Q   V   S   L   R   N   A   E   N   K   H   F   C   G
G
```

H. The apparent N-terminal nucleic acid sequence (SEQ ID NO:66), as well as deduced amino acid sequence (SEQ ID NO:67) of nfSP13 is:

```
TTC GGC TTC AAG CTA AGT CAT TTG GTA AGT AAG TAC GCT TGT GCA
 F   G   F   K   L   S   H   L   V   S   K   Y   A   C
A

TTA GCA TCG GCA CTG AAG TAC TCC ATC GAT CAT GGT CCT CGT ATC
 L   A   S   A   L   K   Y   S   I   D   H   G   P   R   I
I
```

TABLE 2-continued
Additional Flea Serine Protease Sequences

```
GGA GGT GAA GTT GCA GGT GAA GGA TCA GCA CCT TAC CAG GTG TCC
TTA
 G   G   E   V   A   G   E   G   S   A   P   Y   Q   V   S
L

AGA ACC AAG GAA GGA AAT CAT TTT TGC GGT GGA TCA ATA CTA AAT
AAG
 R   T   K   E   G   N   H   F   C   G   G   S   I   L   N
K

CGA TGG GTT GTA ACT GCA GCA CAT TGT CTT GAA CCG GAA ATA TTA
GTA
 R   W   V   V   T   A   A   H   C   L   E   P   E   I   L
D

TCG GTA TAC GTC GGA TCC AAT CAC TTA GAC CGA AAA GGC AGA TAT
TAC
 S   V   Y   V   G   S   N   H   L   D   R   K   G   R   Y
Y

GAC GTA GAA CGG TAT ATA ATT CAT GAA AAA TAT ATA GGA GAA CTA
AAT
 D   V   E   R   Y   I   I   H   E   K   Y   I   G   E   L
N

AAT TTT TAT GCT GAC ATC GGT CTA ATA AAA CTT GAT GGA AGA CTT
AGA
 N   F   Y   A   D   I   G   L   I   K   L   D   G   R   L
R

ATT CAA
 I   Q
```

I. The apparent N-terminal nucleic acid sequence (SEQ ID NO:68), as well as deduced amino acid sequence (SEQ ID NO:69 of nfSP14 is:

```
CGG GCT GCA GGA ATT CGG CAC GAG AAG AAA CTG CCA ATA TTA ATC
GCC
 R   A   A   G   I   R   H   E   K   K   L   P   I   L   I
A

TTG ATC GGA TGC GTT CTT TCT GAA GAA ATA GAG GAT CGC ATT GTC
GGC
 L   I   G   C   V   L   S   E   E   I   E   D   R   I   V
G

GGA ACG GCA GTT GAT ATA AGA GGT TTT CCC TGG CAG GTA TCA ATT
CAA
 G   T   A   V   D   I   R   G   F   P   W   Q   V   S   I
Q

ACC GAA AAC CGT CAT TTT TGT GGT GGT TCT ATT ATC GAT AAA AGC
TGG
 T   E   N   R   H   F   C   G   G   S   I   I   D   K   S
W

ATA TTA ACT GCC GCA CAT TGT GTA CMC GAT ATG AAG ATG TCG AAC
TGG
 I   L   T   A   A   H   C   V   X   D   M   K   M   S   N
W
```

J. The apparent N-terminal nucleic acid sequence (SEQ ID NO:70), as well as deduced amino acid sequence (SEQ ID NO:71) of nfSP15 is:

```
CAC GAG ATT TTA TTA AGC GCA TTA TTT GCA AGT GTA ATT TGC TCC
TTT
 H   E   I   L   L   S   A   L   F   A   S   V   I   C   S
F

AAC GCG GAA GTA CAA AAT CGA ATC GTT GGT GGC AAT GAT GTA AGT
ATT
 N   A   E   V   Q   N   R   I   V   G   G   N   D   V   S
I
```

TABLE 2-continued

Additional Flea Serine Protease Sequences

```
TCA AAA ATT GGG TGG CAA GTA TCT ATT CAA AGT AAT AAA CAA CAT
TTC
 S   K   I   G   W   Q   V   S   I   Q   S   N   K   Q   H
 F

TGT GGT GGT TCA ATC ATT GCT AAA GAT GGG TCC
 C   G   G   S   I   I   A   K   D   G   S
```

K. The apparent N-terminal nucleic acid sequence (SEQ ID NO:72), as well as deduced amino acid sequence (SEQ ID NO:73) of nfSP16 is:

```
ATC ATG GCA AAT TTT AGG CTA TTC ACC TTA CTA GCC TTG GTT TCA
GTA
 I   M   A   N   F   R   L   F   T   L   L   A   L   V   S
 V

GCA ACT TCC AAA TAT ATT GAT CCA AGA ATA ATT GGA GGC GAA GAT
GCT
 A   T   S   K   Y   I   D   P   R   I   I   G   G   E   D
 A

CCT GAA GGC TCG GCT CCG TAC CAA GTT TCA TTG AGA AAT CAG AAT
CTG
 P   E   G   S   A   P   Y   Q   V   S   L   R   N   Q   N
 L

GAG CAT TTC TGT GGT GGT TCC ATT
 E   H   F   C   G   G   S   I
```

L. The apparent N-terminal nucleic acid sequence (SEQ ID NO:74), as well a deduced aimino acid sequence (SEQ ID NO:75) of nfSP17 is:

```
GCA CGA GAT CGC ATT GTT GGA GGA TTG GAG GCG AAA AAT GGA TCA
GCC
 A   R   D   R   I   V   G   G   L   E   A   K   N   G   S
 A

CCA TTC ATG GTT TCT TTG CAA GCG GAA GAC TAT TTT CAT TTT TGT
GGA
 P   F   M   V   S   L   Q   A   E   D   Y   F   H   F   C
 G

TCC TCT ATT CTG AAT GAG AGA TGG GTT CTT ACT GCT GCT CAC TGT
ATC
 S   S   I   L   N   E   R   W   V   L   T   A   A   H   C
 I

CAA CCA AAT GTA CAC AAG TAC GTT TAC GTC GGT TCG AAC AAC GTA
GAA
 Q   P   N   V   H   K   Y   V   Y   V   G   S   N   N   V
 E
```

M. The apparent C-terminal nucleic acid sequence (SEQ ID NO:76), as well as deduced amino acid sequence (SEQ ID NO:77) of nfSP2 is:

```
CCA ATC CAC GAT AGC CAA TAT GCA CTT TTG CAG ATA TGG GTC AAG
GGT
 P   I   H   D   S   Q   Y   A   L   L   Q   I   W   V   K
 G>

GCA TGT AAG GGT GAT TCC GGT GGC CCC TTA GTC ATC AAT GGA CAA
CTT
 A   C   K   G   D   S   G   G   P   L   V   I   N   G   Q
 L>

CAT GGA ATT GTT TCC TGG GGC ATT CCT TGC GCT GTC GCA AGC CTG
ATG
 H   G   I   V   S   W   G   I   P   C   A   V   A   S   L
 M>

TAT TCA CAA GAG TTT CTC ATT ATG TCG ATT GGA TTA AAT CCA AAA
TTG
 Y   S   Q   E   F   L   I   M   S   I   G   L   N   P   K
 L>

AAT AAA ATT GTT TAG
 N   K   I   V   *
```

TABLE 2-continued

Additional Flea Serine Protease Sequences

N. The apparent C-terminal nucleic acid sequence (SEQ ID
NO:78), as well as deduced amino acid sequence (SEQ ID
NO:79) of nfSP13 is (the initial GGPL is next to the
conserved active-site serine):
GGA GGT CCT TTG GCA ATC AAT GGT GAA CTT GTT GGT GTT ACT TCA
TTC
 G   G   P   L   A   I   N   G   E   L   V   G   V   T   S
 F ATT ATG GGG ACA TGT GGA GGA GGA CAT CCT GAT GTC TTC GGT CGA
GTC
 I   M   G   T   C   G   G   G   H   P   D   V   F   G   R
 V CTT GAC TTC AAA CCA TGG ATT GAT TCT CAT ATG GCA AAT GAC GGC
GCT
 L   D   F   K   P   W   I   D   S   H   M   A   N   D   G
 A

AAT/TCT/TTT/ATT/TAA
/N///S///F///I///*

EXAMPLE 12

This Example describes the purification of a flea aminopeptidase of the present invention.

The starting material for the isolation of a flea aminopeptidase was a flea midgut lysate preparation that had been depleted of serine proteases by passage over a benzamidine-Sepharose affinity column. To assay for aminopeptidase activity, the synthetic substrate L-Leucine-AMC (Leu-AMC), which releases a fluorescent AMC leaving group upon proteolytic cleavage, was incubated with the serine protease-depleted flea midgut preparation. Aminopeptidase activity was easily detectable with as little as 1.2 μg of lysate, both confirming the presence of an aminopeptidase (as indicated in other Examples herein) and allowing for the detection of aminopeptidase activity in fractions collected throughout subsequent fractionation and purification procedures.

Serine protease-depleted flea midgut lysates (samples of about 1.2 μg and about 12 μg) were incubated with Leu-AMC in the presence of the following inhibitors: 1 mM pefabloc, 1 mg/ml trypsin/chymotrypsin inhibitor, 1 mg/ml trypsin inhibitor, 1 mM TPCK, 1 μg/ml pepstatin, 10 μg/ml E-64, 10 μg/ml of leupeptin, 10 mM EDTA, and 86 μg/ml of bestatin. Only bestatin inhibited the flea protease that cleaved Leu-AMC, whereas both EDTA and bestatin inhibited the control protease, a leucine aminopeptidase. These results indicated that the flea protease being characterized was an aminopeptidase, but apparently was not a metalloaminopeptidase like the "classic" leucine aminopeptidases.

A flea aminopeptidase was purified using the following protocol. Flea midgut lysates cleared of serine protease activity were fractionated by anion-exchange chromatography. Those fractions containing aminopeptidase activity were pooled and subjected to cation-exchange chromatography, and the resulting fractions were again assayed for activity with L-Leu-AMC in 96-well plates.

Fractions containing aminopeptidase activity were subjected to SDS-PAGE and silver-stained to identify the protein(s) exhibiting that activity. Aminopeptidase activity was found to be associated with proteins that migrated at a molecular weight of about 95 kD and about 56 kD when subjected to SDS-PAGE. The 95 kD and 56 kD proteins may each be aminopeptidases or they may be subunits of a larger enzyme. A number of known aminopeptidases are multi-subunit enzymes comprised of subunits ranging from about 45 kD to about 55 kD and from about 90 kD to about 95 kD.

Additional purification studies have indicated that the majority of aminopeptidase activity was found to be associated with the membrane pellet preparation and could be solubilized with detergent. Aminopeptidase activity in such preparations was also monitored during purification using L-Leu-AMC, and appeared to be associated with the 95 kD and 56 kD proteins when active fractions were analyzed by SDS-PAGE and silver staining. The 95 kD and 56 kD protein were co-purified to greater than 90% purity by cation exchange chromatography, affinity chromatography using w-aminohexyl agarose, and C-4 reverse phase chromatography. N-terminal amino acid sequence analysis indicated that both isolated aminopeptidases appeared to be blocked at the amino terminus.

EXAMPLE 13

This Example describes the isolation of a flea aminopeptidase nucleic acid molecule of the present invention A nucleic acid molecule encoding a flea aminopeptidase was isolated in the following manner. A DNA fragment was PCR amplified from a whole fed flea cDNA expression library (prepared as described in Example 8 using degenerate primers, the design of which was based on conserved regions of bovine lens leucine aminopeptidase (LAP). The specific LAP-based primers used included: degenerate LAP sense primer A, corresponding to bovine lens LAP amino acid sequence from about amino acid 247 through 257 and having nucleic acid sequence 5' GTW GGW AAA GGW WTW ACW TTY GAT TCW GGW GG 3', represented herein as SEQ ID NO:48; and degenerate LAP antisense primer C, corresponding to bovine lens LAP amino acid sequence from about amino acid 335 through 329 and having nucleic acid sequence 5' CG WCC TTC WGC ATC WGT ATT 3', represented herein as SEQ ID NO:49. Also used were vector primers having SEQ ID NO:13 and SEQ ID NO:14, described in Example 11.

In a first experiment, the LAP primer C having SEQ ID NO:49 and the M13 reverse vector primer having SEQ ID NO:13 were used to PCR amplify DNA fragments from the expression library. The resultant PCR products were screened by hybridization under standard hybridization conditions with LAP primer A having SEQ ID NO:48. A PCR product that hybridized with SEQ ID NO:48 was subjected to nested (actually semi-nested) PCR amplification using LAP primer C and the T3 vector primer having SEQ ID NO:14. The resulting PCR product, which was about 900 nucleotides in length (denoted nfAP$_{900}$) and hybridized under standard (i.e., stringent) hybridization conditions with LAP primer A, was cloned into the TA™ vector and analyzed by DNA sequence analysis as described in Example 11.

The nucleic acid sequence of a portion of nfAP$_{900}$, namely of nfAP$_{453}$, is represented herein as SEQ ID NO:50. Translation of SEQ ID NO:50 yields a protein of about 151 amino acids, denoted herein as PfAP$_{151}$, the amino acid sequence of which is represented herein as SEQ ID NO:51. Analysis of SEQ ID NO:51 suggests that the sequence includes a leader segment of about 15 amino acids followed by a mature protein that has about 32% identity with the bovine lens LAP. The corresponding bovine and flea nucleotide sequences are about 29% identical.

EXAMPLE 14

This Example describes the production of an anti-flea midgut protease antiserum and its use to inhibit flea protease activity thereby supporting the utility of protease-based vaccines as anti-flea agents.

Anti-flea protease antiserum was produced in the following manner. A rabbit was immunized 3 times with approximately 40–50 μg of a flea midgut protease preparation that had been affinity-purified using benzamidine sepharose as described in Example 7 and then combined with Freund's complete adjuvant for the first immunization and with incomplete adjuvant for the second and third immunizations according to standard procedures. After the second immunization, endpoint titers of around 1:3200 were obtained, while the third immunization boosted the antiprotease titers to about 1:6400. Western blot analysis of the immunoreactivity of the resultant anti-flea protease antiserum against the affinity-purified midgut protease preparation demonstrated the presence of at least 7–8 reactive protease bands. This was an important observation since there are numerous reports in the literature of difficulties associated with generating high-titered antisera against certain classes of proteases.

To assess the inhibitory activity of the rabbit anti-flea protease antiserum against flea midgut proteases, an in vitro assay which measures trypsin activity as a function of absorbance at OD$_{450}$ using a defined protein substrate (i.e., succinylated casein) was established using a commercially available kit (available from Pierce, Rockford, Ill.). In preliminary assays, the proteolytic activity of the affinity-purified flea midgut protease preparation was about 25–30% of the activity observed with the trypsin control. This lower activity is not unexpected since the flea proteases may require different reaction conditions than the trypsin control for optimal activity. Also, the primary amino acid sequences determined for the flea proteases as described in Examples 7, 10 and 11 are suggestive of highly specialized functions that may require specific substrates for determining optimal activity. Incubation of the affinity purified midgut protease preparation with the succinylated casein substrate in the presence of about 500 ng of the rabbit anti-flea protease antibody-containing serum collected after the second immunization reduced the proteolytic activity of the protease preparation by about 20%. This result, using a suboptimal assay, supports the feasibility of using immunological methods to inhibit flea midgut protease activity.

Using a similar immunization protocol, anti-flea protease antiserum has also been generated in cats that has exhibited immunoreactivity, as identified by Western blot analysis, against several proteases in the affinity-purified midgut protease preparation. The cat anti-flea protease antiserum also reduced proteolytic activity of an affinity purified midgut protease preparation by about 20%, using the same assay as described for analyzing the rabbit antiserum.

EXAMPLE 15

This Example demonstrates that flea larvae have predominantly serine-type proteases.

Newly hatched flea larvae were raised in colony rearing dishes and fed on larval rearing media containing dried bovine blood using standard techniques. About 300 to 500 larvae were collected at different developmental stages, homogenized by sonication in flea gut dissection buffer (50 mM Tris, 100 mM CaCl$_2$, pH 8.0) and centrifuged to pellet cell debris. About 25 larval equivalents were incubated with about 2.5 μCi [1,3-$^3$H]-diisopropylfluorophosphate (DFP) overnight at 4° C. After incubation, about 10 larval equivalents were spotted onto filter paper, precipitated with 10% trichloroacetic acid, and counted in a liquid scintillation counter. Reducing SDS-PAGE was performed on samples comprising about 2.5 larval equivalents, and autoradiography was performed using standard techniques. In addition, adult flea midgut proteases were extracted and $^3$H-labeled in the same manner and examined by SDS-PAGE and autoradiography. Analysis of the gel indicated that, based on their ability to be labeled with DFP, larval proteases appear to be predominantly serine-type proteases, the production of which appears to be induced by blood feeding as occurs in adults. Blood-fed 3rd instars appeared to have the highest amount of proteolytic activity.

EXAMPLE 16

The Example demonstrates that flea feces has proteolytic activity, that is predominantly due to serine proteases.

Flea feces were collected from fleas fed in flea cages placed on a live cat or in a flea feeding system as described in Example 6 in which the fleas were fed bovine blood. Fresh feces were collected every 9–17 hours, resuspended in water at 150 mg feces/ml, and centrifuged to pellet insoluble material. The soluble fractions were then assayed using two techniques. Western blot analysis was performed on samples subjected to reducing SDS-PAGE, each lane having about 40 μg of protein. Blotted proteins were incubated overnight at 4° C. with 1:500 rabbit anti-flea protease antiserum produced as described in Example 14. Goat anti-rabbit secondary antibody was used at 1:2000 to develop the Western blot. Analysis of the Western blot indicated the presence of serine-type proteases in flea feces. Appearance of such proteases migrating at about 25 to about 30 kD in such a system suggests the presence of full-length serine proteases.

Zymogram analysis was performed by loading approximately 56 μg protein into each lane of the electrophoresis gel in non-reducing sample buffer. After electrophoresis, the zymogram gel was soaked in 2.5% Triton-X-100 to renature the samples and developed at 37° C. in 50 mM Tris, pH 7.6, 200 mM NaCl, 5 mM CaCl$_2$, 0.02% Brij 35. Coomassie staining the gel revealed clear plaques where active proteases digested the gelatin in the gel matrix. Both of these techniques indicated the presence of serine-type proteases in flea feces.

EXAMPLE 17

This Example demonstrates that fleas that have fed on antibody-containing blood have antibodies in their feces, suggesting an immunological method to eradicate flea larvae, which feed from flea feces.

The ability of antibodies in a blood meal to be taken up by fleas, pass through the midgut and be excreted in the feces was demonstrated in the following manner. A commercially available rabbit antibody against ovalbumin was added at near physiological concentration (i.e., at about 2 mg/ml) to the blood meal of adult fleas in a flea feeding system as described in Example 6. Feces were collected at 24 hr and 48 hr after feeding and rehydrated in phosphate saline buffer. The rehydrated fecal samples were subjected to Western blot analysis and shown to contain rabbit anti-ovalbumin antibodies that were apparently full-length, using a rabbit-specific secondary antibody screen against the Fc region of rabbit antibodies. Supernatants of flea midguts collected at the same time periods showed residual amounts of rabbit anti-ovalbumin antibodies.

In a second experiment, fleas were fed in a similar manner a blood meal containing cat-specific antiserum generated against keyhole limpet hemocyanin (KLH) and feces were collected at 24, 48 and 72 hours post-feeding. The sample collected at 24 hours was divided into halves, with one half rehydrated immediately in PBS while the second half was rehydrated 7 days later. Fecal samples collected at 48 and 72 hours were held for 6 and 5 days, respectively, after collection in desiccated form prior to rehydration. Aliquots of the bloodmeal containing the KLH antiserum fed to the fleas were also sampled at 1 and 2 days. All of the recovered antibodies were reactive against KLH by Western blot analysis, with a pattern or reactivity indistinguishable from the cat anti-KLH serum alone.

These studies demonstrate that antibodies are able to pass through the flea midgut in intact form and are able to maintain their antigen-binding characteristics, thereby supporting the feasibility of an immunological method to target larval development, since flea larvae in their normal habitat feed from flea feces.

EXAMPLE 18

This Example provides additional nucleic acid and deduced amino acid sequences of nucleic acid molecules encoding flea serine protease proteins of the present invention, examples of the isolation of which were described in Example 11.

A. Flea serine protease clone 1 was determined to comprise flea serine protease nucleic acid molecule $nfSP1_{779}$, the nucleic acid sequence of which is denoted herein as SEQ ID NO:80. Translation of SEQ ID NO:80 yielded a predicted serine protease protein referred to herein as $PfSP1_{232}$, the amino acid sequence of which is denoted herein as SEQ ID NO:81, SEQ ID NO:80 including an apparent stop codon spanning about nucleotides 699 through 701. The N-terminus of the mature form of $PfSP1_{232}$ apparently occurs at about amino acid 17 of SEQ ID NO:81, and a conserved GWG sequence spans about amino acids 132 through 134 of SEQ ID NO:81. $PfSP1_{232}$ apparently also includes SEQ ID NO:7 (a partial amino terminal sequence of a purified serine protease protein, the production of which is described in Example 10). $nfSP1_{779}$ also apparently includes SEQ ID NO:52 and SEQ ID NO:18 and, as such, $PfSP1_{232}$ apparently includes SEQ ID NO:53 and SEQ ID NO:19. A BLAST homology search indicated that SEQ ID NO:81 was most similar in amino acid sequence to an *Anopheles gambiae* chymotrypsin II and to a kallikrein. As is the case for any of these molecules, variations between sequences may be due to a number of factors, such as but not limited to, sequencing errors or allelic variation.

B. Flea serine protease clone 2 was determined to comprise flea serine protease nucleic acid molecule $nfSP2_{944}$, the nucleic acid sequence of which is denoted herein as SEQ ID NO:82. Translation of SEQ ID NO:82 yielded a predicted serine protease protein referred to herein as $PfSP2_{255}$, the amino acid sequence of which is denoted herein as SEQ ID NO:83, SEQ ID NO:82 including an apparent stop codon spanning about nucleotides 768 through 770. The N-terminus of the mature form of $PfSP2_{255}$ apparently occurs at about amino acid 23 of SEQ ID NO:81, and a conserved GWG sequence spans about amino acids 148 through 150 of SEQ ID NO:83. $PfSP2_{255}$ apparently also includes SEQ ID NO:5 (a partial amino terminal sequence of a purified serine protease protein, the production of which is described in Example 10). $nfSP2_{944}$ also apparently includes SEQ ID NO:20, and, as such, $PfSP2_{255}$ apparently includes SEQ ID NO:21. A BLAST homology search indicated that SEQ ID NO:83 was most similar in amino acid sequence to a *Bombix mori* vitellin-degrading protease precursor.

C. Flea serine protease clone 3 was determined to comprise flea serine protease nucleic acid molecule $nfSP3_{177}$, the nucleic acid sequence of which is denoted herein as SEQ ID NO:22. Translation of SEQ ID NO:22 yielded a predicted serine protease protein referred to herein as $PfSP3_{59}$, the amino acid sequence of which is denoted herein as SEQ ID NO:23. Flea serine protease protein $PfSP3_{59}$ includes a conserved GWG sequence that spans about amino acids 1 through 3 of SEQ ID NO:23. A BLAST homology search indicated that SEQ ID NO:23 was most similar in amino acid sequence to a rat trypsinogen.

D. Flea serine protease clone 4 was determined to comprise flea serine protease nucleic acid molecule $nfSP4_{672}$ described in Example 11. Nucleic acid molecule $nfSP4_{672}$ has nucleic acid sequence SEQ ID NO:16, translation of which yielded a predicted serine protease protein referred to herein as $PfSP4_{223}$, the amino acid sequence of which is denoted herein as SEQ ID NO:17, SEQ ID NO:16 including an apparent stop codon spanning about nucleotides 670 through 672. As stated above, the N-terminus of the mature form of $PfSP4_{223}$ apparently occurs at about amino acid 5 of SEQ ID NO:17, and a conserved GWG sequence spans about amino acids 124 through 126 of SEQ ID NO:17. $PfSP4_{223}$ apparently includes SEQ ID NO:41 and a sequence that is very similar to SEQ ID NO:45. $nfSP4_{672}$ also apparently includes SEQ ID NO:24, SEQ ID NO:56 (following nucleotide 141 of SEQ ID NO:56) and SEQ ID NO:74. As such, $PfSP4_{223}$ apparently contains SEQ ID NO:25 and SEQ ID NO:75 as well as a sequence that is very similar to SEQ ID NO:57 (following amino acid 47 of SEQ ID NO:57). A BLAST homology search indicated that SEQ ID NO:17 was most similar in amino acid sequence to an *A. gambiae* chymotrypsin I precursor.

E. Flea serine protease clone 5 was determined to comprise flea serine protease nucleic acid molecules: $nfSP5_{157}$, the nucleic acid sequence of which is denoted herein as SEQ ID NO:84; and $nfSP5_{218}$, the nucleic acid sequence of which is denoted herein as SEQ ID NO:86. Translation of SEQ ID NO:84 yielded a predicted serine protease protein referred to herein as $PfSP5_{52}$, the amino acid sequence of which is denoted herein as SEQ ID NO:85. The N-terminus of the mature form of the serine protease protein encoded by flea clone 5 apparently occurs at about amino acid 29 of SEQ ID NO:85. SEQ ID NO:85 apparently includes the first 10 amino acids of SEQ ID NO:2 as well as the first 10 amino acids of SEQ ID NO:6. SEQ ID NO:2 and SEQ ID NO:6 are partial N-terminal sequences of purified serine protease proteins, the production of which are described in Example 10. Translation of SEQ ID NO:86 yielded a predicted serine protease protein referred to herein as PfSP5$_{72}$, the amino acid sequence of which is denoted herein as SEQ ID NO:87. PfSP5$_{72}$ includes a conserved GWG sequence spanning about amino acids 14 through 16 of SEQ ID NO:87. nfSP5$_{218}$ apparently includes SEQ ID NO:26, and, as such, PfSP5$_{72}$ apparently includes SEQ ID NO:27. A BLAST homology search indicated that the protein encoded by flea clone 5 was most similar in amino acid sequence to a Drosophila trypsin eta precursor.

F. Flea serine protease clone 6 was determined to comprise flea serine protease nucleic acid molecule nfSP6$_{932}$, the nucleic acid sequence of which is denoted herein as SEQ ID NO:88. Translation of SEQ ID NO:88 yielded a predicted serine protease protein referred to herein as PfSP6$_{256}$, the amino acid sequence of which is denoted herein as SEQ ID NO:89, SEQ ID NO:88 including an apparent stop codon spanning nucleotides 770 through 772. The N-terminus of the mature form of PfSP6$_{256}$ apparently occurs at about amino acid 26 of SEQ ID NO:89, and a conserved GWG sequence spans about amino acids 149 through 151 of SEQ ID NO:89. PfSP6$_{256}$ apparently also includes SEQ ID NO:4 (a partial amino terminal sequence of a purified serine protease protein, the production of which is described in Example 10). nfSP6$_{932}$ also apparently includes SEQ ID NO:28, SEQ ID NO:54 and SEQ ID NO:60 (following about nucleotide 111 of SEQ ID NO:60). As such, PfSP6$_{256}$ apparently includes SEQ ID NO:29, SEQ ID NO:55 and SEQ ID NO:61 (following about amino acid 37 of SEQ ID NO:61). A BLAST homology search indicated that SEQ ID NO:89 was most similar in amino acid sequence to a *B. mori* vitellin-degrading protease.

G. Flea serine protease clone 7 was determined to comprise flea serine protease nucleic acid molecule nfSP7$_{894}$, the nucleic acid sequence of which is denoted herein as SEQ ID NO:90. Translation of SEQ ID NO:90 yielded a predicted serine protease protein referred to herein as PfSP7$_{255}$, the amino acid sequence of which is denoted herein as SEQ ID NO:91, SEQ ID NO:90 including an apparent stop codon spanning about nucleotides 766 through 768. The N-terminus of the mature form of PfSP7$_{255}$ apparently occurs at about amino acid 23 of SEQ ID NO:91, and a conserved GWG (in this case GWA) sequence spans about amino acids 152 through 154 of SEQ ID NO:91. PfSP7$_{255}$ apparently also includes SEQ ID NO:44. nfSP7$_{894}$ also apparently includes SEQ ID NO:30 and SEQ ID NO:62. As such, PfSP7$_{255}$ apparently includes SEQ ID NO: 31 and SEQ ID NO: 63. A BLAST homology search indicated that SEQ ID NO:91 was most similar in amino acid sequence to a hornet chymotrypsin II and to collagenase.

H. Flea serine protease clone 8 was determined to comprise flea serine protease nucleic acid molecule nfSP8$_{299}$, the nucleic acid sequence of which is denoted herein as SEQ ID NO:92. Translation of SEQ ID NO:92 yielded a predicted serine protease protein referred to herein as PfSP8$_{99}$, the amino acid sequence of which is denoted herein as SEQ ID NO:93. PfSP8$_{99}$ includes a conserved GWG sequence that spans about amino acids 31 through 33 of SEQ ID NO:93. nfSP8$_{299}$ also apparently includes SEQ ID NO:32, and, as such, PfSP8$_{99}$ apparently includes SEQ ID NO:33. A BLAST homology search indicated that SEQ ID NO:93 was most similar in amino acid sequence to a *Tachypleus tridentatus* coagulation factor B.

I. Flea serine protease clone 9 was determined to comprise flea serine protease nucleic acid molecule nfSP9$_{266}$, the nucleic acid sequence of which is denoted herein as SEQ ID NO:94. Translation of SEQ ID NO:94 yielded a predicted serine protease protein referred to herein as PfSP9$_{88}$, the amino acid sequence of which is denoted herein as SEQ ID NO:95. PfSP9$_{88}$ includes a conserved GWG sequence that spans amino acids about 33 through 35 of SEQ ID NO:95. nfSP9$_{266}$ also apparently includes SEQ ID NO:34, and, as such, PfSP9$_{88}$ apparently includes SEQ ID NO:35. A BLAST homology search indicated that SEQ ID NO:95 was most similar in amino acid sequence to an *A. gambiae* trypsin 2 precursor.

J. Flea serine protease clone 10 was determined to comprise flea serine protease nucleic acid molecule nfSP10$_{378}$, the nucleic acid sequence of which is denoted herein as SEQ ID NO:96. Translation of SEQ ID NO:96 yielded a predicted serine protease protein referred to herein as PfSP10$_{126}$, the amino acid sequence of which is denoted herein as SEQ ID NO:97. PfSP10$_{126}$ includes a conserved GWG sequence that spans about amino acids 63 through 65 of SEQ ID NO:97. nfSP10$_{378}$ also apparently includes SEQ ID NO:36, and, as such, PfSP10$_{126}$ apparently includes SEQ ID NO:37. A BLAST homology search indicated that SEQ ID NO:97 was most similar in amino acid sequence to an *A. gambiae* trypsin 1 precursor.

K. Flea serine protease clone 11 was determined to comprise flea serine protease nucleic acid molecule nfSP11$_{252}$, the nucleic acid sequence of which is denoted herein as SEQ ID NO:98. Translation of SEQ ID NO:98 yielded a predicted serine protease protein referred to herein as PfSP11$_{84}$, the amino acid sequence of which is denoted herein as SEQ ID NO:99. PfSP11$_{84}$ includes a conserved GWG sequence that spans about amino acids 23 through 25 of SEQ ID NO:99. nfSP11$_{252}$ also apparently includes SEQ ID NO:38, and, as such, PfSP11$_{84}$ apparently includes SEQ ID NO:39. A BLAST homology search indicated that SEQ ID NO:99 was most similar in amino acid sequence to a *Mus musculus* plasminogen precursor.

L. Flea serine protease clone 12 was determined to comprise flea serine protease nucleic acid molecules: nfSP12$_{144}$, the nucleic acid sequence of which is denoted herein as SEQ ID NO:64; and nfSP12$_{225}$, the nucleic acid sequence of which is denoted herein as SEQ ID NO:100. Translation of SEQ ID NO:64 yielded a predicted serine protease protein referred to herein as PfSP12$_{52}$, the amino acid sequence of which is denoted herein as SEQ ID NO:65. The N-terminus of the mature form of the serine protease protein encoded by flea clone 12 apparently occurs at about amino acid 20 of SEQ ID NO:65. SEQ ID NO:65 apparently includes the first 30 amino acids of SEQ ID NO:40. Translation of SEQ ID NO:100 yielded a predicted serine protease protein referred to herein as PfSP12$_{69}$, the amino acid sequence of which is denoted herein as SEQ ID NO:101, SEQ ID NO:100 apparently containing a stop codon spanning from about nucleotides 208 through 210. nfSP12$_{225}$ apparently includes SEQ ID NO:76, and, as such, PfSP12$_{69}$ apparently includes SEQ ID NO:77. A BLAST homology search indicated that the protein encoded by flea clone 12 was most similar in amino acid sequence to an *A. gambiae* trypsin.

M. Flea serine protease clone 13 was determined to comprise flea serine protease nucleic acid molecule nfSP13$_{850}$, the nucleic acid sequence of which is denoted herein as SEQ ID NO:102. Translation of SEQ ID NO:102 yielded a predicted serine protease protein referred to herein as PfSP13$_{252}$, the amino acid sequence of which is denoted herein as SEQ ID NO:103, SEQ ID NO:102 including an apparent stop codon spanning about nucleotides 758 through 760. The N-terminus of the mature form of PfSP13$_{252}$ apparently occurs at about amino acid 28 of SEQ ID NO:103, and a conserved GWG sequence spans about amino acids 137 through 139 of SEQ ID NO:103. PfSP13$_{252}$ apparently also includes SEQ ID NO:1 (a partial amino terminal sequence of a purified serine protease protein, the production of which is described in Example 10) and SEQ ID NO:42. nfSP13$_{850}$ also apparently includes SEQ ID NO:66 and SEQ ID NO:78 and, as such, PfSP13$_{252}$ apparently includes SEQ ID NO:67 and SEQ ID NO:79. A BLAST homology search indicated that SEQ ID NO:103 was most similar in amino acid sequence to an *A. gambiae* chymotrypsin.

N. Flea serine protease clone 14 was determined to comprise flea serine protease nucleic acid molecule nfSP14$_{213}$, the nucleic acid sequence of which is denoted herein as SEQ ID NO:68. Translation of SEQ ID NO:68 yielded a predicted serine protease protein referred to herein as PfSP14$_{71}$, the amino acid sequence of which is denoted herein as SEQ ID NO:69. The N-terminus of the mature form of the serine protease protein encoded by flea clone 12 apparently occurs at about amino acid 29 of SEQ ID NO:69. SEQ ID NO:69 apparently includes the first 13 amino acids of SEQ ID NO:43. A BLAST homology search indicated that the protein encoded by SEQ ID NO:69 was most similar in amino acid sequence to an *A. gambiae* trypsin.

O. Flea serine protease clone 15 was determined to comprise flea serine protease nucleic acid molecule nfSP15$_{252}$, the nucleic acid sequence of which is denoted herein as SEQ ID NO:104. Translation of SEQ ID NO:104 yielded a predicted serine protease protein referred to herein as PfSP15$_{84}$, the amino acid sequence of which is denoted herein as SEQ ID NO:105. The N-terminus of the mature form of the serine protease protein encoded by flea clone 15 apparently occurs at about amino acid 28 of SEQ ID NO:105. SEQ ID NO:105 apparently includes SEQ ID NO:46. nfSP15$_{252}$ also apparently includes SEQ ID NO:70, and, as such, PfSP15$_{84}$ apparently includes SEQ ID NO:71. A BLAST homology search indicated that the protein encoded by SEQ ID NO:105 was most similar in amino acid sequence to an *A. gambiae* trypsin.

P. Flea serine protease clone 16 was determined to comprise flea serine protease nucleic acid molecule nfSP16$_{168}$, the nucleic acid sequence of which is denoted herein as SEQ ID NO:72. Translation of SEQ ID NO:72 yielded a predicted serine protease protein referred to herein as PfSP16$_{56}$, the amino acid sequence of which is denoted herein as SEQ ID NO:73. The N-terminus of the mature form of the serine protease protein encoded by flea clone 16 apparently occurs at about amino acid 26 of SEQ ID NO:73. SEQ ID NO:73 apparently includes SEQ ID NO:47. A BLAST homology search indicated that the protein encoded by SEQ ID NO:73 was most similar in amino acid sequence to an acrosin.

Q. Flea serine protease clone 18 was determined to comprise flea serine protease nucleic acid molecule nfSP18$_{534}$, the nucleic acid sequence of which is denoted herein as SEQ ID NO:106. Translation of SEQ ID NO:106 yielded a predicted serine protease protein referred to herein as PfSP18$_{178}$, the amino acid sequence of which is denoted herein as SEQ ID NO:107. The N-terminus of the mature form of PfSP18$_{178}$ apparently occurs at about amino acid 284 of SEQ ID NO:107, and a conserved GWG sequence spans about amino acids 126 through 128 of SEQ ID NO:107. A BLAST homology search indicated that SEQ ID NO:107 was most similar in amino acid sequence to a chymotrypsin.

R. Flea serine protease clone 19 was determined to comprise flea serine protease nucleic acid molecule nfSP19$_{359}$, the nucleic acid sequence of which is denoted herein as SEQ ID NO:108. Translation of SEQ ID NO:108 yielded a predicted serine protease protein referred to herein as PfSP19$_{119}$, the amino acid sequence of which is denoted herein as SEQ ID NO:109. A conserved GWG sequence spans about amino acids 69 through 71 of SEQ ID NO:109. A BLAST homology search indicated that SEQ ID NO:109 was most similar in amino acid sequence to bovine duodenase I.

S. Flea serine protease clone 20 was determined to comprise flea serine protease nucleic acid molecule nfSP20$_{841}$, the nucleic acid sequence of which is denoted herein as SEQ ID NO:110. Translation of SEQ ID NO:110 yielded a predicted serine protease protein referred to herein as PfSP20$_{248}$, the amino acid sequence of which is denoted herein as SEQ ID NO:111, SEQ ID NO:110 including an apparent stop codon spanning about nucleotides 746 through 748. The N-terminus of the mature form of PfSP20$_{248}$ apparently occurs at about amino acid 27 of SEQ ID NO:111, and a conserved GWG sequence spans about amino acids 147 through 149 of SEQ ID NO:111. PfSP20$_{248}$ apparently also includes SEQ ID NO:2 and SEQ ID NO:6 (partial amino terminal sequences of purified serine protease proteins, the production of which is described in Example 10). nfSP20$_{841}$ also apparently includes SEQ ID NO:58, and, as such, PfSP20$_{248}$ apparently includes SEQ ID NO:59. A BLAST homology search indicated that SEQ ID NO:111 was most similar in amino acid sequence to a trypsin.

EXAMPLE 19

This Example provides additional nucleic acid and deduced amino acid sequences of nucleic acid molecules encoding flea aminopeptidase proteins of the present invention.

The nucleic acid sequence of the remainder of flea aminopeptidase nucleic acid molecule nfAP$_{900}$ was determined and used to design primers to use in combination with a vector primer (i.e., M13 universal primer) to PCR amplify the 3' terminal fragment of the flea aminopeptidase coding region from a whole fed flea cDNA expression library using methods as described in Example 13. The PCR product was subjected to DNA sequencing analysis, and a composite sequence representing a close to full-length flea aminopeptidase coding region was deduced. The nucleic acid sequence of the composite nucleic acid molecule, referred to herein as nfAP$_{1580}$, is denoted herein as SEQ ID NO:112. The primer used to obtain the 3' terminal fragment spans from about nucleotide 849 through 877 of SEQ ID NO:112. A probe spanning from about nucleotide 918 through 938 of SEQ ID NO:112 was used to verify that the 3' terminal fragment was a flea aminopeptidase nucleic acid molecule. The flea aminopeptidase gene-containing sequence of the 3' terminal fragment, referred to herein as nfAP$_{732}$, spans from about nucleotide 849 through 1580 of SEQ ID NO:112.

Translation of SEQ ID NO:112 yielded a deduced flea aminopeptidase protein of about 496 amino acids, denoted herein as PfAP$_{496}$, having amino acid sequence SEQ ID NO:113. The deduced mature flea aminopeptidase is about 48% identical to mature bovine leucine aminopeptidase. The corresponding bovine and flea nucleic acid sequences are about 33% identical.

EXAMPLE 20

This Example demonstrates the production of certain flea serine protease proteins of the present invention.

A. Flea serine protease protein $PfSP1_{216}$ was produced in the following manner. An about 670-bp DNA fragment, referred to herein as $nfSP1_{670}$ and designed to encode an apparently mature serine protease protein, was PCR amplified from flea serine protease clone 1 using the XhoI-site containing primers F1 sense 5' GAGCTCTCGAGAGTTGT-TGGAGGACTGGAAGC 3' (SEQ ID NO:114) and F1 antisense 5' GGACCTCGAGAATTAGTTATTTTCCATG-GTC 3' (SEQ ID NO:115). The PCR product $nfSP1_{670}$ was digested with XhoI restriction endonuclease, gel purified and subcloned into expression vector pTrcHisB (available from InVitrogen) that had been digested with XhoI and dephosphorylated. The resultant recombinant molecule, referred to herein as $pHis-nfSP1_{670}$, was transformed into $E.$ $coli$ HB101 competent cells (available from Gibco BRL, Gaithersburg, Md.) to form recombinant cell $E.$ $coli$:pHis-$nfSP1_{670}$. The recombinant cell was cultured in enriched bacterial growth medium containing 0.1 mg/ml ampicillin and 0.1% glucose at about 32° C. When the cells reached an OD600 of about 0.4–0.5, expression of $nfSP1_{670}$ was induced by the addition of 0.5 mM isopropyl-B-D-thiogalactoside (IPTG), and the cells were cultured for about 2 hours at about 32° C. Immunoblot analysis of recombinant cell $E.$ $coli$:pHis-$nfSP1_{670}$ lysates using a T7 tag monoclonal antibody (available from Novagen, Inc., Madison, Wis.) directed against the fusion portion of the recombinant PHIS-$PfSP1_{216}$ fusion protein identified a protein of the appropriate size, namely an about 29 kD protein.

B. Flea serine protease protein $PfSP2_{233}$ was produced in the following manner. An about 715-bp DNA fragment, referred to herein as $nfSP2_{715}$ and designed to encode an apparently mature serine protease protein, was PCR amplified from flea serine protease clone 2 using the XhoI-site containing primers F2 sense 5' GAGCTCTCGAG-CATCGTCGGCGGCACCAGTG 3' (SEQ ID NO:116) and F2 antisense 5' GGACGAATTCTTAAAGAC-CAGTTTTTTTGCG 3' (SEQ ID NO:117). The PCR product $nfSP2_{715}$ was digested with XhoI restriction endonuclease, gel purified and subcloned into expression vector pTrcHisB (available from InVitrogen) that had been digested with XhoI and dephosphorylated. The resultant recombinant molecule, referred to herein as $pHis-nfSP2_{715}$, was transformed into $E.$ $coli$ HB101 competent cells (available from Gibco BRL) to form recombinant cell $E.$ $coli$:pHis-$nfSP2_{715}$. The recombinant cell was cultured as described in Example 20A. Immunoblot analysis of recombinant cell $E.$ $coli$:pHis-$nfSP2_{715}$ lysates using a T7 tag monoclonal antibody (available from Novagen, Inc.) directed against the fusion portion of the recombinant PHIS-$PfSP2_{233}$ fusion protein identified a protein of the appropriate size, namely an about 35-kD protein.

C. Flea serine protease protein $PfSP13_{225}$ was produced in the following manner. An about 700-bp DNA fragment, referred to herein as $nfSP13_{700}$ and designed to encode an apparently mature serine protease protein, was PCR amplified from flea serine protease clone 13 using the XhoI-site containing primers F13 sense 5' GAGCTCTCGAGTAT-CATCGGAGGTGAAGTTGC 3' (SEQ ID NO:118) and F13 antisense 5' GGACCTCGAGAATTATGCGCCGT-CATTTGC 3' (SEQ ID NO:119). The PCR product $nfSP13_{700}$ was digested with XhoI restriction endonuclease, gel purified and subcloned into expression vector pTrcHisB (available from InVitrogen) that had been digested with XhoI and dephosphorylated. The resultant recombinant molecule, referred to herein as $pHis-nfSP13_{700}$, was transformed into $E.$ $coli$ HB101 competent cells (available from Gibco BRL) to form recombinant cell $E.$ $coli$:pHis-$nfSP13_{700}$. The recombinant cell was cultured as described in Example 20A. Immunoblot analysis of recombinant cell $E.$ $coli$: pHis-$nfSP13_{700}$ lysates using a T7 tag monoclonal antibody (available from Novagen, Inc.) directed against the fusion portion of the recombinant PHIS-$PfSP13_{225}$ fusion protein identified a protein of the appropriate size, namely an about 33-kD protein.

EXAMPLE 21

This Example demonstrates the temporal induction of serine proteases in fleas feeding on cats.

Fleas contained in chambers similar to those used for in vitro feeding experiments were placed on cats and were allowed to feed for various periods of time. Upon removal from the cats, soluble extracts of flea midgut tissues were prepared as described herein. Proteases contained within the extracts were quantitated by labeling the extracts with [1,3-$^3$H]DFP using a method similar to that described in Borovsky et al, 1988, $Arch.$ $Insect$ $Biochem.$ $Physiol.$ 7, 187–210. The labeled samples either (a) were precipitated and the radioactivity in the precipitate quantitated or (b) were applied to SDS-PAGE and exposed by autoradiography.

Figure 10:
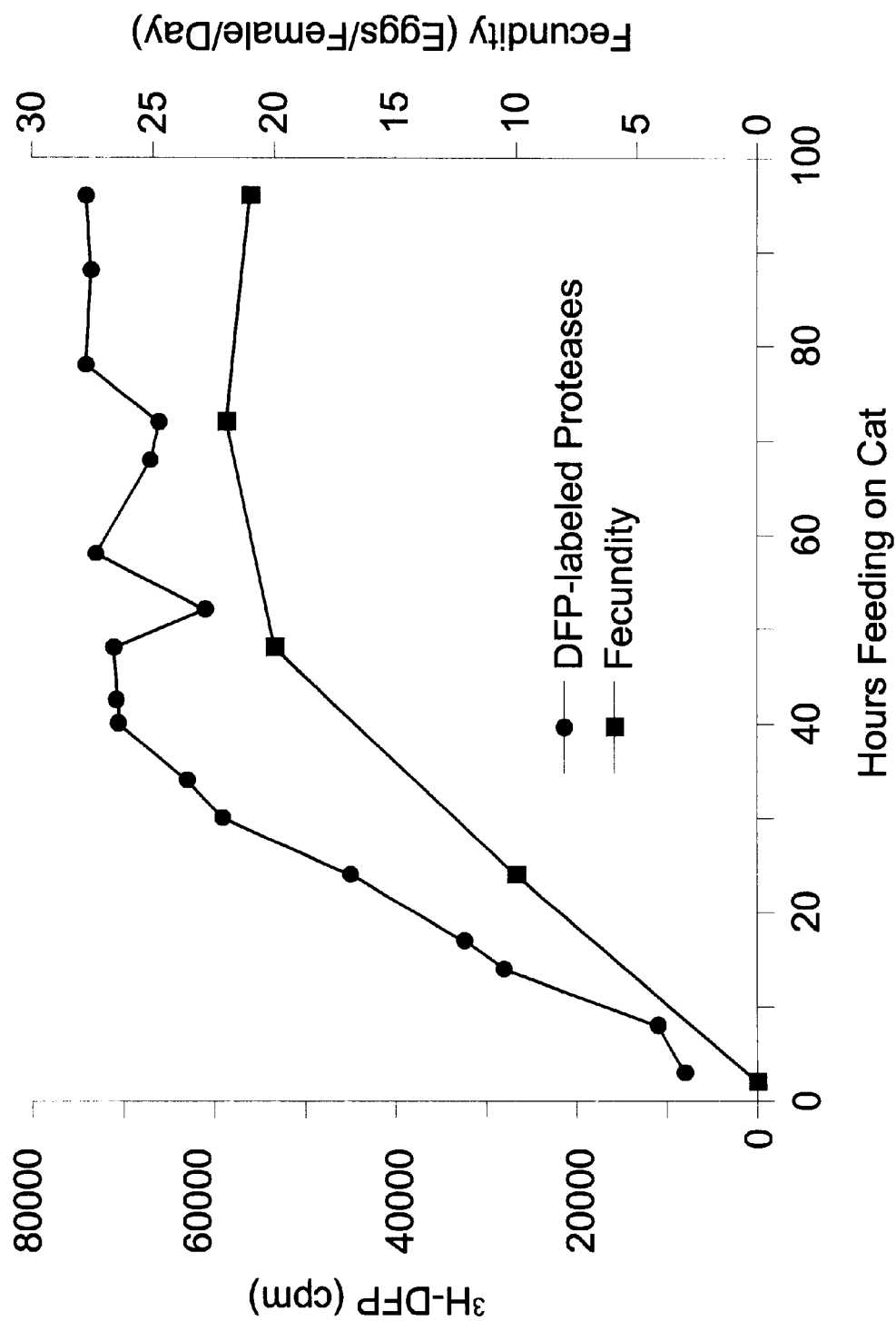
FIG. 10 depicts induction over time of DFP-labeled proteases in fleas feeding on a cat.

Data generated from counting samples are shown in FIG. 10, which plots [$^3$H]-DFP in counts per minute (cpm) per 10 flea midguts versus hours of flea feeding on cats. Also shown in FIG. 10 for comparison is a plot of the number of eggs laid per female flea per day for chamber-contained fleas feeding on cats for 1, 2, 3 and 4 days, respectively. These results suggest that DFP-labeled proteases (i.e., predominantly serine proteases) are induced in fleas in response to feeding. Induction is quite rapid once feeding begins and, unlike in mosquitos, is sustained over time. The results also suggest a positive correlation between flea protease activity and fecundity.

Figure 11:
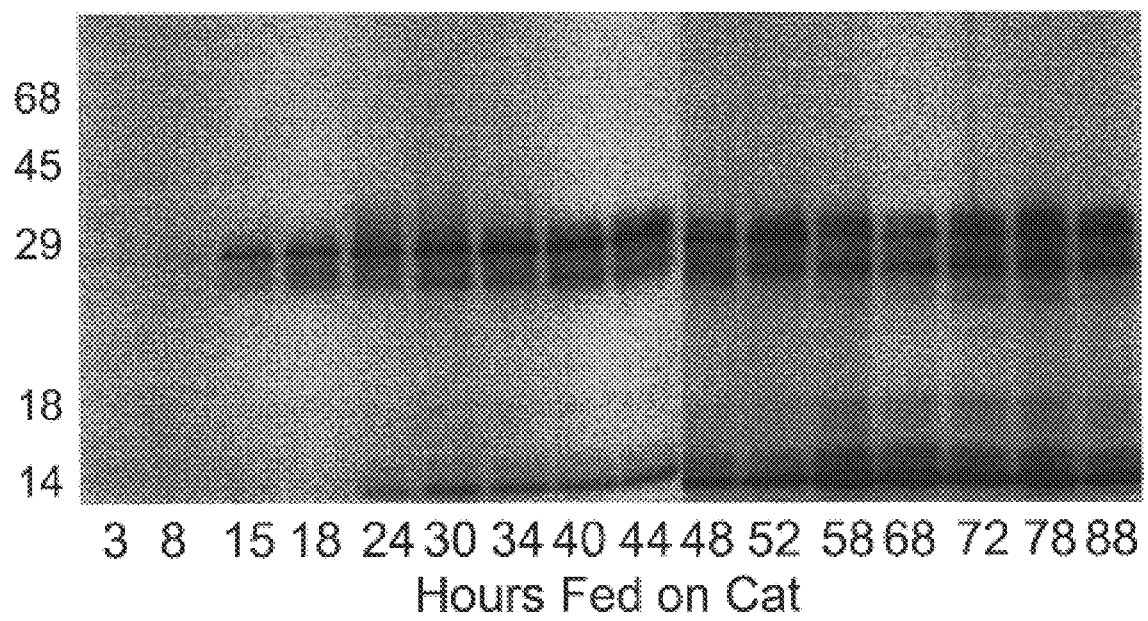
FIG. 11 depicts SDS-PAGE of induction over time of DFP-labeled proteases in fleas feeding on a cat.

In order to obtain a profile of the sizes of DFP-labeled proteases temporally induced in fleas during feeding, samples were applied to SDS-PAGE and autoradiographed. FIG. 11 indicates protein molecular weight standards and samples of soluble flea midgut extracts obtained from fleas having fed for various times on cats (i.e., at, respectively, 3, 8, 15, 18, 24, 30, 34, 40, 44, 48, 52, 58, 68, 72, 78 and 88 hours of feeding). Analysis of the results indicates that primarily proteases migrating with a molecular weight of about 25–35 kD are induced in a flea relatively soon after the flea has begun feeding (i.e., at least within about 3 to about 8 hours). The amount of such proteases increases over time for about the first 2 days. Over time, several intensely labeled bands of lower molecular weight (primarily in the range of about 12–15 kD) also appear that may be representative of proteases having undergone degradation.

EXAMPLE 22

This example describes the determination of internal amino acid sequence of a flea aminopeptidase.

About 10,200 cat blood-fed flea guts were dissected into 4 ml Gut Dissection Buffer (50 mM Tris-HCl, pH 8.0 and 100 mM $CaCl_2$). Flea gut extracts were prepared by sonicating the flea guts and centrifuging them at about 14,000 rpm for about 20 minutes. The resulting pellet was washed and briefly sonicated in 2 ml Gut Dissection Buffer and centrifuged again at about 14,000 rpm for about 20 minutes.

The resulting pellet was resuspended and sonicated in 4 ml buffer comprising 20 mM NaAc, pH 6.0, 0.1% Brij, complete protease inhibitor cocktail (available from Pierce) and 0.25 mM bestatin; the sonicate was centrifuged at about 14,000 rpm for about 20 minutes. Both the pellet and supernatant were recovered. The pellet was re-sonicated and centrifuged as above, and the resulting supernatant was combined with the original supernatant.

The pooled supernatant was applied to a polyCAT cation exchange HPLC column and protein was eluted with a NaCl gradient ranging from 0M to 1M NaCl in 20 mM NaAc, pH 6.0. Fractions collected from the column were assayed by H-Leu-AMC fluorescence, and active fractions were pooled and applied to a C-1 reverse phase HPLC column (TMS 250, Toso Hass). Proteins were eluted from the column using an acetonitrile gradient in 0.1% TFA in water, the gradient ranging between 20% and 100% acetonitrile. Proteins contained in fractions from the column were analyzed by SDS-PAGE gel electrophoresis and silver staining. The results of the gel electrophoresis indicated the presence of an about 95 kDa protein in some of the fractions. This protein correlates with the about 95 kDa protein described in Example 12 which was identified using membrane pellet from flea midgut lysates.

To determine internal amino acid sequence of the 95 kDa protein, those fractions containing the 95 kDa protein were pooled, dried and digested with BNPS-Skatole for about 72 hours at room temperature. The BNPS-Skatole digest was separated by 18% Tris-glycine PAGE gel electrophoresis and blotted onto PVDF membrane. A major band of about 28 kDa was cut out and N-terminally sequenced using techniques as described in Example 7. A partial N-terminal amino acid sequence of the internal peptide was obtained, namely LATTQFQATHARSAFPCFDEPAM (denoted herein SEQ ID NO:167).

EXAMPLE 23

This example describes the cloning and sequencing of another flea aminopeptidase nucleic acid molecule.

Primer APN3 corresponding to a conserved region in *Manduca sexta* and rat aminopeptidases, having nucleic acid sequence 5' CCC AAA TTT TCC ATW GCN CCN GC 3' (N indicating any nucleotide; represented herein as SEQ ID NO:166) was used in combination with primer M13 Reverse primer (SEQ ID NO:13) to PCR amplify a portion of a flea aminopeptidase gene from a bovine blood-fed whole flea cDNA expression library as described above in Example 8. The resulting product of the PCR amplification was diluted about 1:50 and used as a template in a second, semi-nested PCR amplification using a primer APN3 in combination with degenerate primer APN1C, designed using SEQ ID NO:167 (described in Example 22), having nucleic acid sequence 5' CAA TTY CAA GCT ACY CAT GC 3' (represented herein as SEQ ID NO:168). The resulting PCR product, named nfAP2$_{383}$, was approximately 383-bp when visualized on a 1% agarose gel. The PCR product nfAP2$_{383}$ was gel purified and cloned into the TA Vector® System, and subjected to standard DNA sequencing techniques. The nucleotide sequence of nfAP2$_{383}$ is denoted SEQ ID NO:169. Translation of SEQ ID NO:169 yielded a deduced flea aminopeptidase protein of about 127 amino acids, denoted herein as PfAP2$_{127}$, having amino acid sequence SEQ ID NO:170.

The PCR product nfAP2$_{383}$ was labelled with $^{32}$P and used as a probe to screen a bovine blood-fed whole flea phage expression library using standard hybridization techniques. A single plaque purified clone was isolated, which included a 2100-nucleotide insert, referred to herein as nfAP2$_{2100}$. Partial nucleic acid sequence was obtained using standard techniques from the 5' end of nfAP2$_{2100}$, to yield a flea aminopeptidase nucleic acid molecule named nfAP2$_{537}$ having nucleic acid sequence SEQ ID NO:171. Translation of SEQ ID NO:171 suggests that nucleic acid molecule nfAP2$_{537}$ encodes a non-full-length flea aminopeptidase protein of about 178 amino acids, referred to herein as PfAP$_{178}$, having amino acid sequence SEQ ID NO:172, assuming the first codon spans from about nucleotide 2 through about nucleotide 4 of SEQ ID NO:171. SEQ ID NO:172 contains SEQ ID NO:167.

Flea aminopeptidase nucleic acid sequence SEQ ID NO:171 was compared with additional nucleic acid sequences characterized from other organisms. The nucleic acid sequence is about 50% identical to *Manduca sexta* aminopeptidase N nucleotides between corresponding regions of the two nucleic acid molecules.

EXAMPLE 24

This example describes the cloning and sequencing of a flea cysteine protease nucleic acid molecule.

A flea cysteine protease nucleic acid molecule, referred to herein as nfCP1$_{573}$ was produced by PCR amplification using the following method. Primer Cal3F (designed to obtain a calreticulin gene), having nucleic acid sequence 5' TTG GGA TAC ACT TTG ACT GTT AAC C 3', represented herein as SEQ ID NO:173 was used in combination with the M13 universal primer, to PCR amplify, using standard techniques, a DNA fragment from a bovine blood-fed whole flea cDNA expression library as described above in Example 8. Surprisingly, the isolated DNA fragment correlated with a cysteine protease nucleic acid sequence. Sequence from this DNA fragment was used to design primer Cys1R, having the nucleic acid sequence 5' GTG AGC AAC CAT TAT TTC CAT ATC 3', represented herein as SEQ ID NO:174, which was used in a second PCR amplification in combination with the M13 reverse primer. A third PCR amplification was performed using primer Cys1F, having the nucleic acid sequence 5' CTT TCC TCA CAA TAC CAC CAA GGA AGC 3', represented herein as SEQ ID NO:176, in combination with the M13 universal primer. A fourth PCR amplification was performed using primer Cys2F, having the nucleic acid sequence 5' CTT GTA CGA TTG TCT CAA CAG GC 3', represented herein as SEQ ID NO:175, in combination with the M13 universal primer. The resulting PCR products were each gel purified and cloned into the TA Vector® System, and subjected to standard DNA sequencing techniques. A composite nucleic acid sequence representing a flea cysteine protease coding region was deduced, referred to herein as nfCP1$_{573}$, was deduced and is denoted herein as SEQ ID NO:177. Translation of SEQ ID NO:177 suggests that nucleic acid molecule nfCP1$_{573}$ encodes a non-full-length flea cysteine protease protein of about 191 amino acids, referred to herein as PfCP1$_{191}$, having amino acid sequence SEQ ID NO:178, assuming the first codon spans from about nucleotide 1 through about nucleotide 3 of SEQ ID NO:177.

The nucleic acid and amino acid sequences of the nfCP1$_{573}$ nucleic acid molecule and PfCP1$_{191}$ protein, respectively, were compared to known nucleic acid and amino acid sequences using a Genbank homology search. SEQ ID NO:178 was found to be similar to the amino acid sequence of *P. sativum* cysteine protease. The most highly conserved region of continuous similarity between SEQ ID NO:178 and *P. sativum* cysteine protease amino acid sequences spans from about amino acid 71 through about amino acid 165 of SEQ ID NO:178 and from about amino acid 17 through about amino acid 168 of the *P. sativum* cysteine protease, there being about 42% identity between the two regions. Comparison of the nucleic acid sequence encoding amino acids from about 205 through about 492 of nfCP1$_{573}$ indicate that those regions are about 54% identical.

EXAMPLE 25

This example describes the cloning and sequencing of certain flea serine protease nucleic acid molecules.

Additional serine protease cDNA nucleic acid molecules have been isolated in a manner similar to that described in Example 8. The actual primers used in PCR amplification of serine protease nucleic acid molecules from a bovine blood-fed flea cDNA expression library (produced as described in Example 8) included cat-try #2 (SEQ ID NO:12) in combination with either M13 reverse primer (SEQ ID NO:13) or H57 primer (SEQ ID NO:15). The resultant PCR products were gel purified and cloned into the TA Vector™. Two recombinant TA vector clones were isolated and found to correspond to previously cloned serine protease genes. These newly cloned nucleic acid molecules were subjected to nucleic acid sequencing using the Sanger dideoxy chain termination method, as described in Sambrook et al., ibid.

A. A nucleic acid sequence of the flea serine protease nucleic molecule corresponding to flea clone 5 (produced using primers cat try #2 and M13 reverse), namely nfSP5$_{806}$ is represented herein as SEQ ID NO:120. SEQ ID NO: 84 and SEQ ID NO:86 are both contained within the sequence of the nucleic acid molecule nfSP5$_{806}$. Translation of SEQ ID NO:120 suggests that nucleic acid molecule nfSP5$_{806}$ encodes a close to full-length flea serine protease protein of about 245 amino acids, referred to herein as PfSP5$_{245}$, having amino acid sequence SEQ ID NO:121, assuming an open reading frame in which the first codon spans from about nucleotide 2 through about nucleotide 4 of SEQ ID NO:120 and a stop codon spanning from about nucleotide 737 through about nucleotide 739 of SEQ ID NO:120. A Genbank homology search revealed most homology between SEQ ID NO:120 and a *Gallus gallus* trypsin gene, there being about 52% identity between corresponding regions of the two nucleic acid molecules.

B. A nucleic acid sequence of the flea serine protease nucleic molecule corresponding to flea clone 11 (produced using primers cat try #2 and M13 reverse), namely nfSP11$_{307}$, is represented herein as SEQ ID NO:124. SEQ ID NO:38 and SEQ ID NO:98 are within the sequence of the nucleic acid molecule nfSP11$_{307}$. Translation of SEQ ID NO:124 suggests that nucleic acid molecule nfSP11$_{307}$ encodes a non-full-length flea serine protease protein of about 102 amino acids, referred to herein as PfSP11$_{102}$, having amino acid sequence SEQ ID NO:125, assuming the first codon spans from about nucleotide 1 through about nucleotide 3 of SEQ ID NO:124.

C. A nucleic acid sequence of the flea serine protease nucleic molecule corresponding to flea clone 39 (produced using primers cat try #2 and H57), namely nfSP39$_{267}$, is represented herein as SEQ ID NO:164. Translation of SEQ ID NO:164 suggests that nucleic acid molecule nfSP39$_{267}$ encodes a non-full-length flea serine protease protein of about 90 amino acids, referred to herein as PfSP39$_{89}$, having amino acid sequence SEQ ID NO:165, assuming the first codon spans from about nucleotide 1 through about nucleotide 3 of SEQ ID NO:164.

EXAMPLE 26

This example describes the cloning and sequencing of certain flea serine protease nucleic acid molecules.

A. Bovine Blood-Fed Library

Certain flea serine protease cDNA nucleic acid molecules have been isolated in a manner similar to that described in Example 8, using two nucleic acid molecules as probes to screen a bovine blood-fed flea cDNA expression library (produced as described in Example 8), cat-try #1 (SEQ ID NO:11) and cat-try #2 (SEQ ID NO:12). Two clones that hybridized strongly to the probes were isolated and subjected to nucleic acid sequencing using the Sanger dideoxy chain termination method, as described in Sambrook et al., ibid.

1. The nucleic acid sequence of a flea serine protease nucleic molecule correlating to flea clone 8, namely nfSP8$_{436}$ is represented herein as SEQ ID NO:122. SEQ ID NO:92 is within the sequence of the nucleic acid molecule nfSP8$_{436}$. Translation of SEQ ID NO:122 yields a protein of about 145 amino acids, denoted PfSP8$_{145}$, having amino acid sequence SEQ ID NO:123, assuming the first codon spans from about nucleotide 2 through about nucleotide 4 of SEQ ID NO:122. A Genbank homology search revealed most homology between SEQ ID NO:122 and an *Anopheles gambiae* trypsin precursor gene, there being about 48% identity between corresponding regions of the two nucleic acid molecules.

2. The nucleic acid sequence of a flea serine protease nucleic molecule corresponding to flea clone 12, namely nfSP12$_{758}$ is represented herein as SEQ ID NO:126. SEQ ID NO:64 and SEQ ID NO:100 are both contained within the sequence of the nucleic acid molecule nfSP12$_{758}$. Translation of SEQ ID NO:126 yields a protein of about 246 amino acids, denoted PfSP12$_{246}$, having amino acid sequence SEQ ID NO:127, assuming an open reading frame in which the first codon spans from about nucleotide 1 through about nucleotide 3 of SEQ ID NO:126 and a stop codon spanning from about nucleotide 739 through about nucleotide 741 of SEQ ID NO:127. A Genbank homology search revealed most homology between SEQ ID NO:126 and a rat trypsinogen gene, there being about 57% identity between corresponding regions of the two nucleic acid molecules.

B. Cat Blood-Fed Library

Certain flea serine protease cDNA genes have been isolated from a cat blood-fed flea cDNA expression library by screening the library with the cat-try #1 (SEQ ID NO:11) and cat-try #2 (SEQ ID NO:12) probes. The cat blood-fed flea library was produced in a similar manner as the bovine blood-fed flea library (described in Example 8) except the fleas were fed on cat blood. Two clones that hybridized strongly to the probes were isolated and subjected to nucleic acid sequencing using methods described above.

1. The nucleic acid sequence of one of the flea serine protease nucleic molecules, namely nfSP26$_{610}$ is represented herein as SEQ ID NO:140. Translation of SEQ ID NO:140 yields a non-full-length sequence of about 185 amino acids, denoted PfSP26$_{185}$, having amino acid sequence SEQ ID NO:141, assuming the first codon spans from about nucleotide 1 through about nucleotide 3 of SEQ ID NO:140. A Genbank homology search revealed most homology between SEQ ID NO:141 and a *Aedes aegypti* trypsin protein sequence, there being about 48% identity between corresponding regions of the two amino acid sequences.

2. The nucleic acid sequence of a flea serine protease nucleic molecule, namely nfSP27$_{386}$ is represented herein as SEQ ID NO:142. Translation of SEQ ID NO:142 yields a protein of about 128 amino acids, denoted PfSP27$_{128}$, having amino acid sequence SEQ ID NO:143, assuming the first codon spans from about nucleotide 1 through about nucleotide 3 of SEQ ID NO:142.

EXAMPLE 27

This example describes the cloning and sequencing of certain flea serine protease nucleic acid molecules.

Certain serine protease cDNA nucleic acid molecules have been isolated from reverse transcriptase PCR amplification of mRNA isolated from cat blood-fed whole fleas. The mRNA was isolated from fleas gathered over 72 hours after the initiation of feeding on cat blood. As such, the mRNA comprised a mixture of mRNA isolated at different time points over 72 hours. The mRNA was isolated using ground-up fleas, extracting total flea RNA using Tri-Reagent (available from Molecular Research Center, Cincinnati, Ohio) and an Invitrogen Fast Track™ RNA isolation kit (available from Invitrogen, Inc. San Diego, Calif.). cDNA was synthesized using a Stratagene RT-PCR kit (available from Stratagene, Inc, San Diego, Calif.). Primers used for first-strand cDNA synthesis included an equal molar mixture of the following: 5' dT-2VT3' and 5' dT-2VC3' (as provided in a differential display kit, available from Operon Technologies, Inc. Alameda, Calif.).

The actual primers used in the PCR amplification of the cDNA described above included cat-try #2 (SEQ ID NO:12) used in combination with H57 primer (SEQ ID NO:15). The resultant PCR products were gel purified and cloned into the TA Vector™. Six recombinant TA vector clones were isolated and the nucleic acid molecules were subjected to nucleic acid sequencing using analysis as described above.

A. A nucleic acid sequence of one of the flea serine protease nucleic molecules, namely nfSP23$_{423}$, is represented herein as SEQ ID NO:134. Translation of SEQ ID NO:134 suggests that nucleic acid molecule nfSP23$_{423}$ encodes a non-full-length flea serine protease protein of about 141 amino acids, referred to herein as PfSP23$_{141}$, having amino acid sequence SEQ ID NO:135, assuming the first codon spans from about nucleotide 1 through about nucleotide 3 of SEQ ID NO:134. A Genbank homology search revealed most homology between SEQ ID NO:134 and a Homo sapiens plasminogen precursor gene, there being about 51% identity between corresponding regions of the two nucleic acid molecules.

B. Another nucleic acid sequence of a flea serine protease nucleic molecule, namely nfSP24$_{410}$, is represented herein as SEQ ID NO:136. Translation of SEQ ID NO:136 suggests that nucleic acid molecule nfSP24$_{410}$ encodes a non-full-length flea serine protease protein of about 136 amino acids, referred to herein as PfSP24$_{136}$, having amino acid sequence SEQ ID NO:137, assuming the first codon spans from about nucleotide 1 through about nucleotide 3 of SEQ ID NO:136. A Genbank homology search revealed most homology between SEQ ID NO:137 and an *Anopheles gambiae* chymotrypsin protein sequence, there being about 38% identity between corresponding regions of the two amino acid sequences.

C. Another nucleic acid sequence of a flea serine protease nucleic molecule, namely nfSP33$_{426}$, is represented herein as SEQ ID NO:154. Translation of SEQ ID NO:154 suggests that nucleic acid molecule nfSP33$_{426}$ encodes a non-full-length flea serine protease protein of about 142 amino acids, referred to herein as PfSP33$_{142}$, having amino acid sequence SEQ ID NO:155, assuming the first codon spans from about nucleotide 1 through about nucleotide 3 of SEQ ID NO:154. A Genbank homology search revealed most homology between SEQ ID NO:155 and a Drosophila serine protease stubble protein sequence, there being about 45% identity between corresponding regions of the two amino acid sequences.

D. Another nucleic acid sequence of one of the flea serine protease nucleic molecule, namely nfSP36$_{197}$, is represented herein as SEQ ID NO:158. SEQ ID NO:158 represents a partial sequence of a PCR amplified nucleic acid molecule nfSP36$_{500}$. Translation of SEQ ID NO:158 suggests that nucleic acid molecule nfSP36$_{197}$ encodes a non-full-length flea serine protease protein of about 65 amino acids, referred to herein as PfSP36$_{65}$, having amino acid sequence SEQ ID NO:159, assuming the first codon spans from about nucleotide 1 through about nucleotide 3 of SEQ ID NO:158. A Genbank homology search revealed most homology between SEQ ID NO:159 and a *Drosophila melanogaster* easter protein sequence, there being about 42% identity between corresponding regions of the two amino acid sequences.

E. Another nucleic acid sequence of a flea serine protease nucleic molecule, namely nfSP38$_{341}$, is represented herein as SEQ ID NO:162. Translation of SEQ ID NO:162 suggests that nucleic acid molecule nfSP38$_{341}$ encodes a non-full-length flea serine protease protein of about 113 amino acids, referred to herein as PfSP38$_{113}$, having amino acid sequence SEQ ID NO:163, assuming the first codon spans from about nucleotide 3 through about nucleotide 5 of SEQ ID NO:162. A Genbank homology search revealed most homology between SEQ ID NO:163 and a rat trypsinogen protein sequence, there being about 30% identity between corresponding regions of the two amino acid sequences.

F. A nucleic acid sequence of one of the flea serine protease nucleic molecules, namely nfSP34$_{390}$, is represented herein as SEQ ID NO:156. Translation of SEQ ID NO:156 suggests that nucleic acid molecule nfSP4$_{390}$ encodes a non-full-length flea serine protease protein of about 130 amino acids, referred to herein as PfSP34$_{130}$, having amino acid sequence SEQ ID NO:157, assuming the first codon spans from about nucleotide 1 through about nucleotide 3 of SEQ ID NO:156. A Genbank homology search revealed most homology between SEQ ID NO:157 and a *Drosophila melanogaster* Delta precursor protein sequence, there being about 33% identity between corresponding regions of the two amino acid sequences.

EXAMPLE 28

This example describes the cloning and sequencing of a flea serine protease nucleic acid molecule.

A serine protease cDNA nucleic acid molecule was isolated in a manner similar to that described in Example 8. The actual primers used in PCR amplification of the serine protease nucleic acid molecule from a cat blood-fed whole flea cDNA expression library (produced as described in Example 26) included cat-try #2 (SEQ ID NO:12) in combination with M13 reverse primer (SEQ ID NO:13). The resulting PCR product was diluted 1:25 and used as a template in a second PCR reaction using the forward vector primer T3 (SEQ ID NO:15) in combination with the reverse primer (derived from the nucleic acid sequence of nfSP33$_{778}$, described in Example 27) having the nucleic acid sequence 5' ATT CCT CGT GGT TCA GTC GCT C 3', represented herein as SEQ ID NO:188. The resultant PCR product was gel purified and cloned into the TA Vector™. The clones were subjected to nucleic acid sequencing as described above.

A nucleic acid sequence of a flea serine protease nucleic molecule, namely nfSP33$_{778}$ is represented herein as SEQ ID NO:189. As expected, SEQ ID NO:189 includes a portion of SEQ ID NO: 154 Translation of SEQ ID NO:189 suggests that nucleic acid molecule nfSP33$_{778}$ encodes a non-full-length flea serine protease protein of about 259 amino acids, referred to herein as PfSP33$_{259}$, having amino acid sequence SEQ ID NO:190, assuming the first codon spans from about nucleotide 2 through about nucleotide 4 of SEQ ID NO:189. A Genbank homology search revealed most homology between SEQ ID NO:189 and a Drosophila serine protease stubble gene, there being about 54% identity between nucleotides 23–778 of SEQ ID NO:189 and nucleotides 2324–3064 of the Drosophila serine protease stubble gene.

EXAMPLE 29

This example describes the cloning and sequencing of another flea serine protease nucleic acid molecule.

Using the method described in Example 26, a cDNA clone of a flea serine protease was obtained using mRNA isolated from bovine blood-fed whole fleas. The resulting cDNA was used as a template in PCR amplification using the primers cat-try #2 (SEQ ID NO:12) used in combination with H57 primer (SEQ ID NO:15). The resultant PCR products were gel purified and cloned into the TA Vector™. One recombinant TA vector clone was isolated and the flea serine protease nucleic acid molecule and denoted nFS37$_{500}$ was subjected to nucleic acid sequencing as described in Sambrook et al., ibid.

The nucleic acid sequence of part of the flea serine protease nucleic molecule nFS37$_{500}$, namely nfSP37$_{261}$, is represented herein as SEQ ID NO:160. Translation of SEQ ID NO:160 suggests that nucleic acid molecule nfSP37$_{261}$ encodes a non-full-length sequence of a flea serine protease protein of about 87 amino acids, referred to herein as PfSP37$_{87}$, having amino acid sequence SEQ ID NO:161, assuming the first codon spans from about nucleotide 1 through about nucleotide 3 of SEQ ID NO:160. A Genbank homology search revealed most homology between SEQ ID NO:161 and a chicken trypsinogen protein sequence, there being about 31% identity between corresponding regions of the two amino acid sequences.

EXAMPLE 30

This example describes the cloning and sequencing of certain larval flea serine protease nucleic acid molecules.

Certain serine protease cDNA nucleic acid molecules have been isolated from a mixed instar larval cDNA library produced using 1st, 2nd and 3rd instar larvae fed on cat blood, by PCR amplification. The actual primers used in the PCR amplification included either cat-try #2 (SEQ ID NO:12) in combination with either H57 primer (SEQ ID NO:15) or M13 reverse primer (SEQ ID NO:13). The resultant PCR products were gel purified and cloned into the TA Vector™. Three recombinant TA vector clones were isolated containing PCR products using cat-try #2 and M13 reverse as primers and one clone was isolated containing PCR products using cat-try #2 and H57 primers. These newly cloned nucleic acid molecules were subjected to nucleic acid sequencing as described above.

A. A nucleic acid sequence of one of the larval flea serine protease nucleic molecules isolated using cat-try #2 and M13 reverse primers, namely nfSP29$_{612}$ is represented herein as SEQ ID NO:146. Translation of SEQ ID NO:146 suggests that nucleic acid molecule nfSP29$_{612}$ encodes a close to full-length flea serine protease protein of about 204 amino acids, referred to herein as PfSP29$_{204}$, having amino acid sequence SEQ ID NO:147, assuming an open reading frame in which the first codon spans from about nucleotide 10 through about nucleotide 12 of SEQ ID NO:146. A Genbank homology search revealed most homology between SEQ ID NO:146 and a rat trypsinogen gene, there being about 50% identity between corresponding regions of the two nucleic acid molecules.

B. Another nucleic acid sequence of one of the larval flea serine protease nucleic molecules isolated using cat-try #2 and M13 reverse primers, namely nfSP30$_{641}$, is represented herein as SEQ ID NO:148. Translation of SEQ ID NO:148 suggests that nucleic acid molecule nfSP30$_{641}$ encodes a non-full-length flea serine protease protein of about 213 amino acids, referred to herein as PfSP30$_{213}$, having amino acid sequence SEQ ID NO:149, assuming the first codon spans from about nucleotide 3 through about nucleotide 5 of SEQ ID NO:148. A Genbank homology search revealed most homology between SEQ ID NO:148 and a Anopheles gambiae trypsin gene, there being about 52% identity between corresponding regions of the two nucleic acid molecules.

C. Another nucleic acid sequence of one of the larval flea serine protease nucleic molecules isolated using cat-try #2 and M13 reverse primers, namely nfSP31$_{626}$, is represented herein as SEQ ID NO:150. Translation of SEQ ID NO:150 suggests that nucleic acid molecule nfSP31$_{626}$ encodes a non-full-length flea serine protease protein of about 208 amino acids, referred to herein as PfSP31$_{208}$, having amino acid sequence SEQ ID NO:151, a assuming the first residue spans from about nucleotide 3 through about nucleotide 5 or from a putative start codon spanning from about nucleotide 6 to about nucleotide 8 of SEQ ID NO:150. A Genbank homology search revealed homology between SEQ ID NO:150 and an *Anopheles gambiae* trypsin gene, there being about 52% identity between corresponding regions of the two nucleic acid molecules.

D. Another nucleic acid sequence of one of the larval flea serine protease nucleic molecules isolated using cat-try #2 and H57 primers, namely nfSP32$_{433}$, is represented herein as SEQ ID NO:152. Translation of SEQ ID NO:152 suggests that nucleic acid molecule nfSP32$_{433}$ encodes a non-full-length flea serine protease protein of about 144 amino acids, referred to herein as PfSP32$_{144}$, having amino acid sequence SEQ ID NO:153, assuming the first codon spans from about nucleotide 1 through about nucleotide 3 of SEQ ID NO:152. A Genbank homology search revealed most homology between SEQ ID NO:152 and an *Anopheles gambiae* trypsin gene, there being about 52% identity between corresponding regions of the two nucleic acid molecules.

EXAMPLE 31

This example describes the cloning and sequencing of another flea serine protease nucleic acid molecule.

A bovine blood-fed whole flea cDNA library (prepared as described in Example 8) was immunoscreened with antiserum collected from a rabbit that was immunized with a collection of flea salivary gland products referred to as fspN. Immunoscreening was performed as follows. New Zealand White rabbit antiserum developed against fspN flea saliva products was used in the immunoscreening protocols described in the picoBlue™ Immunoscreening Kit instruction manual, available from Stratagene, Inc. The methods for preparation of the cDNA expression libraries for immunoscreening, i.e., expression of the cDNA clones and procedures for transferring lambda phage plaques to membranes for immunoscreening, are described in the ZAP-cDNA Synthesis Kit instruction manual, also available from Stratagene, Inc., La Jolla, Calif.

A nucleotide sequence for a flea serine protease nucleic acid molecule named nfsp15$_{815}$ is denoted as SEQ ID NO:128 and corresponds to SEQ ID NO:70. Translation of SEQ ID NO:128 suggests that nucleic acid molecule nfsp15$_{815}$ encodes a close to full-length flea serine protease protein of about 254 amino acids, referred to herein as Pfsp15$_{254}$, having amino acid sequence SEQ ID NO:129, assuming an open reading frame in which the first codon spans from about nucleotide 1 through about nucleotide 3 of SEQ ID NO:128 and a stop codon spanning from about nucleotide 763 through about nucleotide 765 of SEQ ID NO:128. A Genbank homology search revealed homology between SEQ ID NO:128 and an *Anopheles gambiae* trypsin gene, there being about 52% identity between corresponding regions of the two nucleic acid molecules.

EXAMPLE 32

This example describes the cloning and sequencing of additional flea serine protease nucleic acid molecules.

Certain flea serine protease cDNA nucleic acid molecules have been isolated in a manner similar to that described in Example 8, using two nucleic acid molecules as probes to screen an unfed flea cDNA expression library, nfSP8$_{299}$ (SEQ ID NO:92) and nfSP19$_{359}$ (SEQ ID NO:108). A clone that hybridized strongly to the probes was isolated and subjected to nucleic acid sequencing as described above.

A. The nucleic acid sequence of the flea serine protease nucleic molecule, namely nfSP19$_{855}$, is represented herein as SEQ ID NO:130. SEQ ID NO:108 is within the sequence of the nucleic acid molecule nfSP19$_{855}$. Translation of SEQ ID NO:130 yields an apparent full-length protein of about 253 amino acids, denoted PfSP19$_{253}$, having amino acid sequence SEQ ID NO:131, assuming the first codon, an apparent start codon, spans from about nucleotide 1 through about nucleotide 3 of SEQ ID NO:130. A Genbank homology search revealed most homology between SEQ ID NO:130 and an *Aedes aegypti* trypsin, there being about 53% identity between corresponding regions of both nucleic acid molecules.

B. The nucleic acid sequence of another flea serine protease nucleic molecule, namely nfSP25$_{864}$, is represented herein as SEQ ID NO:138. Translation of SEQ ID NO:138 yields a protein of about 260 amino acids, denoted PfSP25$_{260}$, having amino acid sequence SEQ ID NO:139, assuming the first codon spans from about nucleotide 2 through about nucleotide 4 of SEQ ID NO:138 and a stop codon spanning from about nucleotide 782 through about nucleotide 784 of SEQ ID NO:139. A Genbank homology search revealed most homology between SEQ ID NO:139 and an *Anopheles gambiae* chymotrypsin protein sequence, there being about 34% identity between corresponding regions of the two amino acid sequences.

EXAMPLE 33

This example describes the cloning and sequencing of another flea serine protease nucleic acid molecule.

A flea serine protease cDNA nucleic acid molecule has been isolated in a manner similar to that described in Example 8, using nfSP11$_{252}$ (SEQ ID NO:98) as a probe to screen an bovine blood-fed flea cDNA expression library (produced as described in Example 8). A clone that hybridized strongly to the probe was isolated and subjected to nucleic acid sequencing using the Sanger dideoxy chain termination method, as described in Sambrook et al., ibid.

The nucleic acid sequence of the flea serine protease nucleic molecule, namely nfSP21$_{595}$, is represented herein as SEQ ID NO:132. Translation of SEQ ID NO:132 yields a protein of about 198 amino acids, denoted PfSP21$_{198}$, having amino acid sequence SEQ ID NO:133, assuming the first codon spans from about nucleotide 2 through about nucleotide 4 of SEQ ID NO:132 and a putative stop codon spanning from about nucleotide 596 to about nucleotide 598. A Genbank homology search revealed most homology between SEQ ID NO:133 and *Tachypleus tridentatus* coagulation factor G protein sequence, there being about 45% identity between corresponding regions of the two amino acid sequences.

EXAMPLE 34

This example describes the isolation and characterization of a 31 kD flea serine protease.

Guts from about 1500 fleas that had been fed on cat blood for about 24 hours were dissected in Gut Dissection Buffer (50 mM Tris 8.0, 100 mM CaCl$_2$). The guts were disrupted by freezing and thawing 4 times, followed by sonication. The resulting extracts were clarified by centrifugation for 20 minutes at 14,000 rpm in a microfuge at 4° C. The supernatant was recovered.

The gut supernatant was loaded onto a 3 ml column comprising p-aminobenzamidine cross-linked to Sepharose beads (Sigma), previously equilibrated in Benzamidine Column Buffer (50 mM Tris 8.0, 100 mM CaCl$_2$, 400 mM NaCl). The supernatant was incubated on the column for about 10 min. Unbound protein was slowly washed off the column using Benzamidine Column Buffer until no protein was detectable by Bradford Assay (Bio Rad).

Proteases bound to the benzamidine column were then eluted using 10 ml Benzamidine Column Buffer supplemented with 10 mM p-aminobenzamidine (brought to pH 8.0 with NaOH). Proteases in the eluant were concentrated and diafiltered into a volume of about 0.3 ml Gut Dissection Buffer using a Microcon 3 concentrator (Amicon).

About 120 μl of the concentrated eluant was further concentrated to a volume of about 30 μl. Proteases contained in this concentrate were resolved by gel electrophoresis on a 14% Tris-Glycine electrophoresis gel (15 μl per lane= approximately 300 gut equivalents per lane). After electrophoresis, the separated proteases were blotted onto a PVDF membrane using a CAPS buffer (10 mM CAPS pH 11, 0.5 mM DTT) The membrane was stained with Coomassie Brilliant Blue. A dominant protein band of about 31 kDa was visualized. The membrane was then used for automated N-terminal sequencing (described in Example 7). A partial N-terminal amino acid sequence of the flea protease was determined to be IVGGEDVDISTCGWC (denoted SEQ ID NO:179).

EXAMPLE 35

This example describes the isolation and characterization of a 31 kD flea serine protease contained in a formulation having IgGase activity (i.e., ability to proteolyze immunoglobulin G proteins).

Cat blood-fed flea gut extracts were prepared and selected on a benzamidine column as described above in Example 32. IgG protease activity was assayed by incubating at 37° C., overnight, the benzamidine eluent with cat immunoglobulin G proteins (IgG) purified on Protein A sepharose. The ability of the flea gut benzamidine eluant to digest cat IgG was detected by resolving the samples by gel electrophoresis through a 14% SDS-PAGE gel and silver staining the gel using standard methods. The marked decrease (compared with control samples lacking protease activity) of a 50 kDa band on the silver stained gel, representing cat IgG heavy chain, indicated that the benzamidine eluant contains IgG protease activity.

The benzamidine eluant was then purified on a PolyPropylaspartamide hydrophobic interaction chromatography (HIC) column by applying the eluant to the column in buffer containing 0.1 M $KPO_4$, pH 6.5 and 2 M $(NH_4)_2SO_4$. Proteases bound to the column were eluted using an ammonium sulfate gradient of 2 M to 0 M in HIC column buffer. Column fractions were tested for IgG protease activity using the method described above. Fractions containing IgG protease activity were pooled and applied to a PolyCat cation exchange column in 20 M sodium acetate, pH 6. The proteins were eluted using a sodium chloride gradient of 0 M to 1 M NaCl in 20 M sodium acetate. Fractions eluted from the column were tested for IgG protease activity and then each fraction was resolved by electrophoresis using SDS-PAGE. Fractions having the highest levels of IgG protease activity included a protein band that migrated at about 31 kDa on the SDS-PAGE gel. Weaker protease activity corresponded to an about 28 kDa band.

The 31 kDa protein present on the SDS-PAGE gel was used for N-terminal amino acid sequencing using the blotting method described above. A partial N-terminal amino acid sequence was determined to be IVGGEDVDIST(C)GWQI(S)FQ(S)ENLHF(C)GG(S)IIAPK (denoted herein as SEQ ID NO:184). A comparison of SEQ ID NO:184 and SEQ ID NO:179 (described in Example 34) indicates a single residue difference between the two amino acid sequences at residue 15 of each sequence (i.e., Q and V, respectively). Since SEQ ID NO:184 correlates with IgGase activity, the data suggests that the larval protein containing SEQ ID NO:179 has IgGase activity.

EXAMPLE 36

This example describes the cloning and sequencing of a 31 kDa flea serine protease contained in a formulation having IgGase activity.

A flea protease nucleic acid molecule was isolated from a cat blood-fed whole flea library (described in Example 23) and a bovine blood-fed whole flea library (described in Example 8) by PCR amplification. The actual primers used in the PCR amplification included FP31A primer designed using the N-terminal amino acid sequence SEQ ID NO:179, the primer having the nucleic acid sequence 5' GAA GAT GTW GAT ATT TCW ACA TGT GG 3' (SEQ ID NO:185) used in combination with the M13 universal primer. The resultant PCR products were gel purified and cloned into the TA Vector™ and subjected to nucleic acid sequencing as described above.

A FP31B primer (5' GAA AAT GAA ATC CAC TTA AAC ATT ACG 3', (represented herein as SEQ ID NO:186) was designed using the DNA sequence of a DNA fragment from a bovine blood-fed cDNA library. A flea protease cDNA nucleic acid molecule was isolated by PCR amplification of the cat blood-fed whole flea library and the bovine blood-fed whole flea library described above by PCR amplification. PCR amplification was performed using the FP31B primer in combination with M13 reverse primer. The resulting PCR products were then diluted 1:25, and used as a template for a second PCR reaction using primer FP31C, having the sequence 5' CTC TTA TTG TAC GAG GGA TGC 3' (denoted herein SEQ ID NO:187) in combination with T3 primer (SEQ ID NO:14). The resulting nested PCR product was cloned into TA Vector™ and subjected to DNA sequencing.

The nucleic acid sequence of the resulting flea serine protease nucleic acid molecule, namely $nfSP28_{923}$ is represented herein as SEQ ID NO:144. Translation of SEQ ID NO:144 yields a protein of about 267 amino acids, denoted $PfSP28_{267}$, having amino acid sequence SEQ ID NO: 145, assuming an open reading frame in which the putative start codon spans from about nucleotide 8 through about nucleotide 10 of SEQ ID NO:144 or from about nucleotide 11 through about nucleotide 13, and a stop codon spanning from about nucleotide 803 through about nucleotide 805 of SEQ ID NO:144. SEQ ID NO:145 contains SEQ ID NO:179 except Q is substituted for C, and SEQ ID NO:184 A Genbank homology search revealed most homology between SEQ ID NO: 144 and Bombix mori vitellin-degrading protease gene, there being about 53% identity between corresponding regions of the two nucleic acid sequences.

EXAMPLE 37

This example describes $^3$H-DFP labelling of larval serine proteases.

About 100 unfed larvae, 100 1st instar larvae, and 100 3rd Instar larvae were collected in 100 $\mu$l Gut Dissection Buffer (50 mM Tris 8.0, 100 mM $CaCl_2$). About 400 $\mu$l of water was added to the collected larvae, which were then sonicated. The sonicates were clarified by centrifugation at 15,000 RPM in an SS-34 rotor for 30 minutes at 4° C. The supernatant from each larval sonicate was recovered and concentrated to a volume of about 120 $\mu$l (1.2 $\mu$l per larval equivalent).

Samples containing about 25 larval equivalents (about 30 $\mu$l) were labeled with about 2.5 $\mu$Ci of 3H-diisopropylfluorophosphate (DFP; obtained from New England Nuclear) and incubated at 4° C. for 18 hours. Following the incubation period, 5 larval equivalents of each larval stage (about 6 $\mu$l) were run on a 14% Tris Glycine SDS-PAGE gel. The gel was then soaked in Entensify (obtained from New England Nuclear) to enhance the tritium signal for autoradiography, and dried. The dried gel was then exposed to X-ray film (Kodak Xo-mat) for about 3 days at −70° C.

Figure 12:
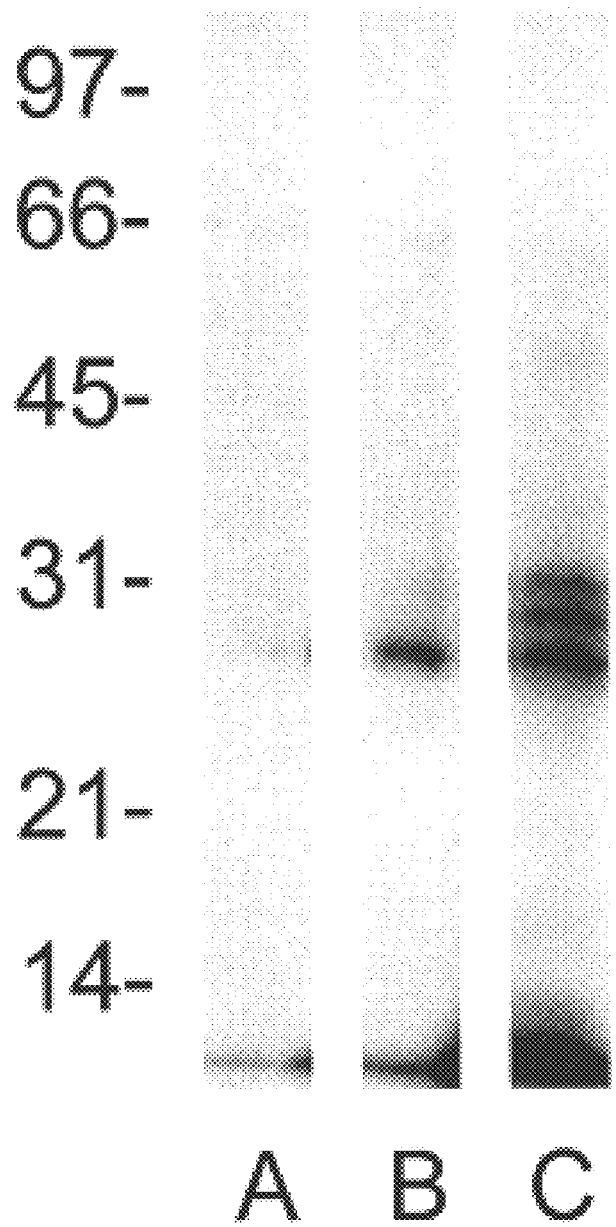
FIG. 12 depicts SDS-PAGE of DFP-labeled larval proteases in unfed larvae, fed 1st instar larvae and fed 3rd instar larvae.

The results indicate that gut extracts from unfed larvae do not contain detectable amounts of serine proteases (FIG. 12, lane A), while both fed 1st instar larvae (FIG. 12, lane B) and fed 3rd instar larvae (FIG. 12, lane C) produce serine proteases. In particular, fed 1st instar larvae primarily produce a serine protease having a molecular weight of about 25 kD; and fed 3rd instar larvae produce about serine proteases having molecular weights of about 25 kD, 28 kD and 31 kD. The approximate size of standard molecular weight protein markers are shown in FIG. 12.

EXAMPLE 38

This example describes the determination of partial N-terminal amino acid sequences for several larval serine proteases.

About 10,300 3rd Instar larvae were collected in Gut Dissection Buffer (50 mM Tris, pH 8.0, 100 mM $CaCl_2$). The larvae were homogenized by sonication and clarified by centrifugation at 15,000 rpm in an SS-34 rotor for 30 min., at 4° C. The supernatant was recovered. The 3rd Instar supernatant was mixed with 5 ml of p-aminobenzamidine cross-linked to Sepharose beads (Sigma) equilibrated in Benzamidine Column Buffer (50 mM Tris pH 8.0, 100 mM $CaCl_2$, 400 mM NaCl). The supernatant was rocked with the beads overnight at 4° C. The beads were washed in about 45 ml Benzamidine Column Buffer to remove unbound protein. The beads were then mixed 2 hours at 4° C. with about 10 ml of Benzamidine Column Buffer containing 100 mM p-aminobenzamidine (pH 8.0 adjusted with NaOH) to elute proteins bound to the beads. The eluted proteins were then collected. The elution process was repeated once more. The eluted protein was concentrated by ultrafiltration with a Centriprep 10 concentrator (Amicon). The concentrate was diluted with Gut Dissection Buffer to a final volume of about 5 ml.

Partial N-terminal amino acid sequence of proteins eluted from the beads was obtained using the method described in Example 32. Two proteins having molecular weights of about 25 kDa and about 26 kDa were identified on the Coomassie Brilliant Blue stained membranes. Partial N-terminal amino acid sequence obtained for the protein having a molecular weight of about 25 kDa is IVGGVSVNINDYGYQLSLQSNGR, denoted herein as SEQ ID NO:181. Partial N-terminal amino acid sequence obtained for the protein having a molecular weight of about 26 kDa is IVGGHDTSIKQHPYQV, denoted herein as SEQ ID NO:180.

EXAMPLE 39

This Example demonstrates the production of certain flea serine protease proteins of the present invention.

A. Flea serine protease protein $PfSP1_{216}$ was in the following manner. Flea serine protease nucleic acid molecule $nfSP1_{670}$, produced as described in Example 20, was digested with XhoI restriction endonuclease, gel purified and subcloned into expression vector $\lambda P_R/T^2ori/S10HIS$-RSET-A9 (the production of which is described in Tripp et al, International PCT Publication No. WO 95/24198, published Sep. 14, 1995; see, in particular, Example 7), that had been digested with XhoI and dephosphorylated. The resultant recombinant molecule, referred to herein as pHisCro-$nfSP1_{670}$, was transformed into $E.\ coli$ HB101 competent cells (available from Gibco BRL) to form recombinant cell $E.\ coli$:pHisCro-$nfSP1_{670}$. The recombinant cell was cultured as described in Example 20. Flea serine protease protein $PfSP1_{216}$ was purified by nickel chelation chromatography followed by reverse phase high performance liquid chromatography (HPLC). Immunoblot analysis of the purified $PfSP1_{216}$ indicated that rabbit anti-flea protease antiserum, produced as described in example 14, selectively bound to $PfSP1_{216}$.

B. Flea serine protease protein $PfSP2_{233}$ was produced in the following manner. Flea serine protease nucleic acid molecule $nfSP2_{715}$, produced as described in Example 20, was digested with XhoI restriction endonuclease, gel purified and subcloned into expression vector $\lambda P_R/T^2ori/S10HIS$-RSET-A9 as described in Example 39A. The resultant recombinant molecule, referred to herein as pHisCro-$nfSP2_{715}$, was transformed into $E.\ coli$ HB101 competent cells (available from Gibco BRL) to form recombinant cell $E.\ coli$:pHisCro-$nfSP2_{715}$. The recombinant cell was cultured as described in Example 20. Flea serine protease protein $PfSP2_{233}$ was purified by nickel chelation chromatography followed by reverse phase HPLC. Immunoblot analysis of the purified $PfSP2_{233}$ indicated that rabbit anti-flea protease antiserum, produced as described in example 14, selectively bound to $PfSP2_{233}$.

C. Flea serine protease protein $PfSP13_{225}$ was produced in the following manner. Flea serine protease nucleic acid molecule $nfSP13_{700}$, produced as described in Example 20, was digested with XhoI restriction endonuclease, gel purified and subcloned into expression vector $\lambda P_R/T^2ori/S10HIS$-RSET-A9 as described in Example 39A. The resultant recombinant molecule, referred to herein as pHisCro-$nfSP13_{700}$, was transformed into $E.\ coli$ HB101 competent cells (available from Gibco BRL) to form recombinant cell $E.\ coli$:pHisCro-$nfSP13_{700}$. The recombinant cell was cultured as described in Example 20. Flea serine protease protein $PfSP13_{225}$ was purified by nickel chelation chromatography followed by reverse phase HPLC. Immunoblot analysis of the purified $PfSP13_{225}$ indicated that rabbit anti-flea protease antiserum, produced as described in example 14, selectively bound to $PfSP13_{225}$.

D. Flea serine protease protein $PfSP20_{222}$ was produced in the following manner. An about 669-bp DNA fragment, referred to herein as $nfSP20_{669}$, and designed to encode an apparently mature serine protease protein, was PCR amplified from flea serine protease clone 20 using the XhoI-site containing primer F27-S (sense) 5' GAG CTC TCG AGA ATC GTA GGA GGA CAC GAT AC 3' (SEQ ID NO:183) and the EcoRI-site containing primer F20-A (antisense) 5' G GAC GAA TTC TTA AAC ACC AGA CAC TTC CTT G 3' (SEQ ID NO:182). The PCR product $nfSP20_{669}$ was digested with XhoI and EcoRI restriction endonucleases, gel purified and subcloned into expression vector $\lambda P_R/T^2ori/S10HIS$-RSET-A9 as described in Example 39A. The resultant recombinant molecule, referred to herein as pHisCro-$nfSP20_{669}$, was transformed into $E.\ coli$ HB101 competent cells (available from Gibco BRL) to form recombinant cell $E.\ coli$:pHisCro-$nfSP20_{669}$. The recombinant cell was cultured as described in Example 20. Immunoblot analysis of recombinant cell $E.\ coli$:pHisCro-$nfSP20_{669}$ lysates using a T7 tag monoclonal antibody (available from Novagen, Inc.) directed against the fusion portion of the recombinant PHISCRO-$PfSP20_{222}$ fusion protein identified a protein of the appropriate size, namely an about 31-kD protein. Flea serine protease protein $PfSP20_{222}$ was purified by nickel chelation chromatography followed by reverse phase HPLC. Immunoblot analysis of the purified $PfSP20_{222}$ indicated that rabbit anti-flea protease antiserum, produced as described in example 14, selectively bound to $PfSP20_{222}$.

EXAMPLE 40

This example describes that various flea serine protease nucleic acid molecules described in the foregoing examples can be obtained from multiple sources.

Nucleic acid molecules corresponding to flea clone 4 have been obtained from a bovine blood-fed whole flea library (described in Example 8), a cat blood-fed whole flea library (described in Example 26), an unfed whole flea library (described in Example 8), and a mixed instar whole flea library (described in Example 30). Nucleic acid molecules corresponding to flea clone 5 have been obtained from a bovine blood-fed whole flea library and a cat blood-fed whole flea library. Nucleic acid molecules corresponding to flea clone 6 have been obtained from a bovine blood-fed whole flea library, a cat blood-fed whole flea library and an unfed whole flea library. Nucleic acid molecule corresponding to flea clone 7 have been obtained from a bovine blood-fed whole flea library, and a cat blood-fed whole flea library. Nucleic acid molecules corresponding to flea clone 8 have been obtained from a bovine blood-fed whole flea library and an unfed whole flea library. Nucleic acid molecules corresponding to flea clone 12 have been obtained from a bovine blood-fed whole flea library and a cat blood-fed whole flea library. Nucleic acid molecules corresponding to flea clone 13 have been obtained from a bovine blood-fed whole flea library, a cat blood-fed whole flea library, and an unfed whole flea library. Nucleic acid molecules corresponding to flea clone 20 have been obtained from a bovine blood-fed whole flea library, a cat blood-fed whole flea library, and an unfed whole flea library. Nucleic acid molecules corresponding to flea clone 28 have been obtained from a bovine blood-fed whole flea library and a cat blood-fed whole flea library.

What is claimed is:

1. An isolated flea leucine aminopeptidase protein selected from the group consisting of:
   a) a protein comprising an amino acid sequence selected from the group consisting of SEQ ID NO:51 and SEQ ID NO:113; and,
   b) a flea protein comprising a homologue of a protein of (a), wherein said homologue comprises at least a 6 contiguous amino acid portion of either one of said amino acid sequences of (a).

2. The protein of claim 1, wherein said leucine aminopeptidase protein comprises an amino acid sequence selected from the group consisting of SEQ ID NO:51 and SEQ ID NO:113.

3. The protein of claim 1, wherein said protein, when administered to an animal elicits an immune response against a flea leucine aminopeptidase protein.

4. The protein of claim 1, wherein said protein has proteolytic activity.

5. The protein of claim 1, wherein said protein is produced by a process comprising culturing an isolated recombinant cell transformed with a nucleic acid molecule encoding said protein to produce said protein.

* * * * *

UNITED STATES PATENT AND TRADEMARK OFFICE
CERTIFICATE OF CORRECTION

PATENT NO. : 6,180,383 B1
DATED : January 30, 2001
INVENTOR(S) : Grieve et al.

It is certified that error appears in the above-identified patent and that said Letters Patent is hereby corrected as shown below:

<u>Title page,</u>
Line 12, after "5,356,622", insert --. Said application No. 08/639,075 is also a continuation-in-part of said application No. 08/326,773 --

Signed and Sealed this

Ninth Day of October, 2001

*Attest:*

NICHOLAS P. GODICI
*Attesting Officer*     *Acting Director of the United States Patent and Trademark Office*